United States Patent
Lee et al.

(10) Patent No.: US 12,037,330 B2
(45) Date of Patent: Jul. 16, 2024

(54) HETEROARYL DERIVATIVE COMPOUNDS, AND USES THEREOF

(71) Applicant: Voronoi Inc., Incheon (KR)

(72) Inventors: Youn Ho Lee, Incheon (KR); Seon Ah Hwang, Incheon (KR); In Seob Shim, Incheon (KR); Hyeon Ho Jeon, Incheon (KR); Woo Mi Do, Incheon (KR); Hee Sun Ryu, Incheon (KR); Jung Beom Son, Incheon (KR); Nam Doo Kim, Incheon (KR); Sung Hwan Kim, Incheon (KR); Hong Ryul Jung, Incheon (KR); Young Yi Lee, Incheon (KR)

(73) Assignee: Voronoi Inc., Incheon (KR)

( * ) Notice: Subject to any disclaimer, the term of this patent is extended or adjusted under 35 U.S.C. 154(b) by 0 days.

(21) Appl. No.: 17/927,324

(22) PCT Filed: May 16, 2022

(86) PCT No.: PCT/KR2022/006994
§ 371 (c)(1),
(2) Date: Nov. 22, 2022

(87) PCT Pub. No.: WO2022/245085
PCT Pub. Date: Nov. 24, 2022

(65) Prior Publication Data
US 2024/0025888 A1 Jan. 25, 2024

(30) Foreign Application Priority Data

May 17, 2021 (KR) .................. 10-2021-0063733

(51) Int. Cl.
| | |
|---|---|
| *C07D 239/48* | (2006.01) |
| *C07D 413/04* | (2006.01) |
| *C07D 413/14* | (2006.01) |
| *C07D 471/04* | (2006.01) |
| *C07D 471/10* | (2006.01) |
| *C07D 487/04* | (2006.01) |
| *C07D 487/08* | (2006.01) |
| *C07D 487/10* | (2006.01) |
| *C07D 498/04* | (2006.01) |
| *C07D 498/08* | (2006.01) |
| *C07F 9/6584* | (2006.01) |

(52) U.S. Cl.
CPC ......... *C07D 413/14* (2013.01); *C07D 413/04* (2013.01); *C07D 471/04* (2013.01); *C07D 471/10* (2013.01); *C07D 487/04* (2013.01); *C07D 487/08* (2013.01); *C07D 487/10* (2013.01); *C07D 498/04* (2013.01); *C07D 498/08* (2013.01); *C07F 9/6584* (2013.01)

(58) Field of Classification Search
CPC .................................................. C07D 239/48
USPC ............................................................ 544/323
See application file for complete search history.

(56) References Cited

U.S. PATENT DOCUMENTS

| | | | |
|---|---|---|---|
| 7,514,445 B2 | 4/2009 | Freyne et al. | |
| 8,552,002 B2 | 10/2013 | Ding et al. | |
| 8,962,834 B2 | 2/2015 | Baumann et al. | |
| 11,440,899 B2 | 9/2022 | Karra et al. | |
| 2017/0313714 A1 | 11/2017 | Wei et al. | |
| 2022/0242870 A1 | 8/2022 | Jo et al. | |

FOREIGN PATENT DOCUMENTS

| | | | |
|---|---|---|---|
| EP | 1761505 B1 | 8/2011 | |
| EP | 2257541 B1 | 8/2013 | |
| KR | 10-2017-0066650 A | 6/2017 | |
| KR | 10-2020-0111644 A | 9/2020 | |
| KR | 10-2020-0133188 A | 11/2020 | |
| WO | 2019-010295 A1 | 1/2019 | |
| WO | WO 2020/190119 A1 * | 9/2020 | ........... A61K 31/407 |
| WO | 2020-235902 A1 | 11/2020 | |

OTHER PUBLICATIONS

Di Fiore et al., "erbB-2 Is a Potent Oncogene When Overexpressed in NIH/3T3 Cells", Science, vol. 237, No. 481, pp. 178-182 (1987).
Hardwick et al., "Immunohistochemical detection of p53 and c-erbB-2 in oesophageal carcinoma; no correlation with prognosis", Eur. J. Surg. Oncol., vol. 23, pp. 30-35 (1997).
Korkaya et al., "HER2 regulates the mammary stem/progenitor cell population driving tumorigenesis and invasion", Oncogene, vol. 27, No. 47, pp. 6120-6130 (2008).
Niederst et al., "The Allelic Context of the C797S Mutation Acquired upon Treatment with Third-Generation EGFR Inhibitors Impacts Sensitivity to Subsequent Treatment Strategies", Clin. Cancer Res., vol. 21, No. 17, pp. 3924-3933 (2015).
Thress et al., "Acquired EGFR C797S mutation mediates resistance to AZD9291 in non-small cell lung cancer harboring EGFR T790M", Nature Medicine, vol. 21, pp. 560-562 (2015).
International Patent Application PCT/KR2022/006994 International Search Report dated Aug. 29, 2022.
International Patent Application PCT/KR2022/006994 Written Opinion dated Aug. 29, 2022.

* cited by examiner

*Primary Examiner* — Charanjit Aulakh
(74) *Attorney, Agent, or Firm* — Nixon & Vanderhye P.C.; Lars H. Genieser

(57) ABSTRACT

The present disclosure relates to a heteroaryl derivative and uses thereof. The heteroaryl derivative of the present disclosure exhibits excellent inhibitory activity against EGFR and/or HER2, and thus may be usefully employed as a therapeutic agent for EGFR- and/or HER2-related diseases.

6 Claims, No Drawings

HETEROARYL DERIVATIVE COMPOUNDS, AND USES THEREOF

CROSS-REFERENCE TO RELATED APPLICATIONS

This application is a Section 371 National Stage of International Application No. PCT/KR2022/006994, filed May 16, 2022, which claims priority under 35 U.S.C. § 119(b) to Republic of Korea Application No. 10-2021-0063733, filed on May 17, 2021, the disclosures of which are incorporated herein by reference in their entireties.

TECHNICAL FIELD

The present disclosure relates to a heteroaryl derivative compound and medicinal uses thereof. Specifically, the present disclosure relates to a heteroaryl derivative compound having EGFR and/or HER2 inhibitory activity.

BACKGROUND ART

Protein kinases are involved in signaling pathways by acting as molecular switches, and the transition between the activity and inactivity of the target protein by kinase in the cell must be smoothly regulated. If the transition between the active and inactive states is abnormally regulated, intracellular signal transmission is excessively activated or deactivated, leading to uncontrollable cell division and proliferation. In particular, abnormal activation by mutation, amplification and/or overexpression of protein kinase genes causes the development and progression of various tumors or plays a decisive role in the onset of various diseases such as inflammatory diseases, degenerative brain diseases, and autoimmune diseases, and the like.

An epidermal growth factor receptor (EGFR), a receptor tyrosine kinase in the ErbB family, is abnormally active in many epithelial cell tumors, including non-small cell lung cancer (NSCLC), breast cancer, glioma, squamous cell carcinoma of the head and neck, colorectal cancer, rectal adenocarcinoma, head and neck cancer, gastric and prostate cancer. It has been known that the activation of the EGFR-tyrosine kinase causes continuous cell proliferation, invasion into surrounding tissues, remote metastasis, and angiogenesis, and increases cell survival.

In addition, EGFR Del19 or EGFR L858R, an EGFR mutation, has been known to be a major cause of non-small cell lung cancer and head and neck cancer, and Iressa and Tarceva, which are therapeutic agents for these mutations, have been developed and are currently being used in clinical practice. However, when these drugs were used in patients, acquired resistance that caused EGFR secondary mutations based on the structure of the drug was observed, and it was also found that this is a real major cause of drug resistance. When the first-generation EGFR inhibitors are used for an average of about 10 months, acquired resistance called the T790M mutation located in the gatekeeper of the EGFR kinase occurs, and thus the first-generation EGFR inhibitors are not effective. In other words, EGFR Del19/T790M or EGFR L858R/T790M double mutation occurs, which prevents existing therapeutic agents from exhibiting drug efficacy. Osimertinib, a third-generation EGFR-TKI target drug that exhibits high reactivity to drug resistance according to EGFR T790M mutation, has been developed, but it has also been reported to cause drug resistance (Niederst M J. et al., Clin Cancer Res, 2015, 17(21):3924-3933). EGFR C797S mutation has been suggested as one of the main mechanisms causing drug resistance to osimertinib, and it has been reported that about 40% of clinical trial patients have EGFR C797S mutation (Thress K S. et al., Nature Medicine, 2015, 21:560-562). Thus, EGFR Del19/C797S (EGFR DC) or EGFR L858R/C797S (EGFR LC) may be the main target.

Further, L861Q, G719A, S768I, L718Q, G724S, or the like, expressing EGFR rare (or uncommon) and drug-resistant mutations may also be potential targets.

Meanwhile, HER2 (human epidermal growth factor receptor 2; also called ErbB2), which is a receptor tyrosine kinase of the ErbB family, forms homodimers or heterodimers with other EGFR receptors, HER1 (EGFR, ErbB1), HER3 (ErbB3) or HER4 (ErbB4), and is activated by autophosphorylation at intracellular tyrosine residues, which plays an important role in cell proliferation, differentiation and survival in normal cells and cancer cells (Di Fiore P P. et al., Science. 1987, 237(481):178-182). HER2 is known to be overexpressed in several carcinomas such as breast, gastric and ovarian cancer (Hardwick R H. et al., Eur. J Surg Oncol. 1997, 23(1):30-35; Korkaya H. et al., Oncogene. 2008, 27(47):6120-6130).

As described above, there is an increasing unmet need for a novel compound that is capable of being usefully employed for the treatment of EGFR- and/or HER2-related diseases by regulating EGFR activities (particularly C797S mutations such as EGFR Del19/C797S and EGFR L858R/C797S, EGFR rare mutations, drug resistance mutations, or the like) and/or HER2.

DISCLOSURE

Technical Problem

An object of the present disclosure is to provide a heteroaryl derivative having a novel structure, an optical isomer thereof, or a pharmaceutically acceptable salt thereof.

Another object of the present disclosure is to provide a method for preparing the heteroaryl derivative compound.

Still another object of the present disclosure is to provide a pharmaceutical use of the heteroaryl derivative compound, and specifically, to a pharmaceutical composition for the treatment or prevention of EGFR- and/or HER2-related diseases comprising the heteroaryl derivative compound as an active ingredient, use of the compound for the treatment or prevention of EGFR- and/or HER2-related diseases, or a method for treating or preventing EGFR- and/or HER2-related diseases comprising administering the compound.

Technical Solution

In order to achieve the above-described objects, the present inventors made efforts to study, and as a result, found that the following heteroaryl derivative compounds represented by Chemical Formula 1 inhibited the proliferation of EGFR- and/or HER2-activated cells, and completed the present disclosure.

Heteroaryl Derivative Compound

The present disclosure provides a compound represented by the following Chemical Formula 1, an optical isomer thereof, or a pharmaceutically acceptable salt thereof:

[Chemical Formula 1]

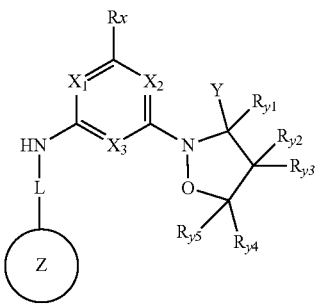

in the Chemical Formula 1, $X_1$ to $X_3$ are each independently CH or N;

$R_X$ is —H, —$C_{1-6}$alkyl, —$C_{1-6}$aminoalkyl, —$NH_2$, —NH(—$C_{1-6}$alkyl), or —N(—$C_{1-6}$alkyl)(—$C_{1-6}$alkyl);

Y is —$C_{1-6}$alkyl, —$(CH_2)_n$aryl, —$(CH_2)_n$hydroaryl, —$(CH_2)_n$heteroaryl, or —$(CH_2)_n$hydroheteroaryl in which at least one H of the —$(CH_2)_n$aryl, —$(CH_2)_n$hydroaryl, —$(CH_2)_n$heteroaryl, or —$(CH_2)_n$hydroheteroaryl ring may be substituted with —$C_{1-6}$alkyl, —$C_{1-6}$aminoalkyl, —$C_{1-6}$hydroxyalkyl, —$C_{1-6}$haloalkyl, —$C_{1-6}$alkyl-O—$C_{1-6}$alkyl, —$C_{1-6}$alkenyl, —$C_{1-6}$alkynyl, —CN, —(C=O)$NR_1R_2$, —(C=O)$OR_3$, —$NR_4R_5$, —$OR_6$, -halo, =O, cycloalkyl, heterocycloalkyl, aryl, or heteroaryl, wherein at least one H of the cycloalkyl, heterocycloalkyl, aryl, or heteroaryl may be substituted with —$C_{1-6}$alkyl, —$C_{1-6}$haloalkyl, or -halo;

n is 0, 1, 2, 3, or 4;

$R_1$ to $R_3$ are each independently —H, —$C_{1-6}$alkyl, or cycloalkyl;

$R_4$ and $R_5$ are each independently —H or —$C_{1-6}$alkyl;

$R_6$ is —H, —$C_{1-6}$alkyl, or phenyl in which at least one H of the phenyl ring may be substituted with —$C_{1-6}$alkyl, —$C_{1-6}$haloalkyl, or halo;

$R_{Y1}$ to $R_{Y5}$ are each independently —H or —$C_{1-6}$alkyl, or $R_{Y2}$ and $R_{Y3}$ may be linked to each other to form cycloalkyl or heterocycloalkyl, $R_{Y4}$ and $R_{Y5}$ may be linked to each other to form cycloalkyl or heterocycloalkyl, and $R_{Y3}$ and $R_{Y4}$ may be linked to each other to form aryl or heteroaryl;

L is —$(CH_2)_m$-, —C(=O)—, or null;

m is 0, 1, 2, 3, or 4;

a ring Z is aryl, heteroaryl, hydroaryl, hydroheteroaryl, cycloalkyl, or heterocycloalkyl in which at least one H of the aryl, heteroaryl, hydroaryl, hydroheteroaryl, cycloalkyl, or heterocycloalkyl ring may be substituted with —$C_{1-6}$alkyl, —$C_{1-6}$cyanoalkyl, —$C_{1-6}$hydroxyalkyl, —$C_{1-6}$aminoalkyl, —$C_{1-6}$haloalkyl, —$C_{1-6}$alkenyl, —$C_{1-6}$alkynyl, —CN, —$NR_7R_8$, —OH, —O—$C_{1-6}$alkyl, —O—$C_{1-6}$haloalkyl, —S—$C_{1-6}$alkyl, —S—$C_{1-6}$haloalkyl, —C(=O)—$C_{1-6}$alkyl, —C(=O)—$C_{1-6}$haloalkyl, —C(=O)O—$C_{1-6}$alkyl, —S(=O)$_2$—$C_{1-6}$alkyl, —C(=N—O—$C_{1-6}$alkyl)($C_{1-6}$ alkyl), =O, -halo, or $Z_1$, or two or more substituents of the aryl, heteroaryl, hydroaryl, hydroheteroaryl, cycloalkyl, or heterocycloalkyl ring may be linked to each other to form a fused ring or a spiro ring, wherein at least one H of the fused ring or spiro ring may be substituted with —$C_{1-6}$alkyl, —$C_{1-6}$haloalkyl, —O—$C_{1-6}$alkyl, -halo, or $Z_1$;

$R_7$ and $R_8$ are each independently —H, —$C_{1-6}$alkyl, —$C_{1-6}$aminoalkyl, —$C_{1-6}$alkyl-NH—$C_{1-6}$alkyl, —$C_{1-6}$alkyl-N($C_{1-6}$alkyl)($C_{1-6}$alkyl), —(C=O)—$C_{1-6}$alkyl, or —(C=O)—$C_{1-6}$haloalkyl;

$Z_1$ is cycloalkyl, heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl in which the heterocycloalkyl, heterobicycloalkyl, heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl ring may be substituted with —$C_{1-6}$alkyl, —$C_{1-6}$aminoalkyl, —$C_{1-6}$haloalkyl, —$C_{1-6}$alkyl-NH—$C_{1-6}$alkyl, —$C_{1-6}$alkyl-N($C_{1-6}$alkyl)($C_{1-6}$alkyl), —$C_{1-6}$alkenyl, —$C_{1-6}$alkynyl, —C(=O)—$C_{1-6}$alkyl, —$C_{1-6}$alkyl-C(=O)—$C_{1-6}$alkyl, —S(=O)$_2$—$C_{1-6}$alkyl, —$C_{1-6}$alkyl-S(=O)$_2$—$C_{1-6}$alkyl, =O, —$NR_9R_{10}$, -halo, cycloalkyl, or $Z_2$;

$R_9$ and $R_{10}$ are each independently —H or —$C_{1-6}$alkyl;

$z_2$ is heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl in which the heterocycloalkyl, heterobicycloalkyl, heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl ring may be substituted with —$C_{1-6}$alkyl, —$C_{1-6}$aminoalkyl, —$C_{1-6}$hydroxyalkyl, —$C_{1-6}$haloalkyl, —$C_{1-6}$alkenyl, —$C_{1-6}$alkynyl, —C(=O)—$C_{1-6}$alkyl, —$C_{1-6}$alkyl-S(=O)$_2$—$C_{1-6}$alkyl, =O, —$NR_{11}R_{12}$, cycloalkyl, or $Z_3$;

$R_{11}$ and $R_{12}$ are each independently —H or —$C_{1-6}$alkyl; and $Z_3$ is heterocycloalkyl, heterobicycloalkyl, heterospiroalkyl, —$C_{1-6}$alkyl-heterocycloalkyl, —(C=O)-heterocycloalkyl, or —NH-heterocycloalkyl in which the heterocycloalkyl, heterobicycloalkyl, heterospiroalkyl —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —$C_{1-6}$alkyl-heterocycloalkyl, —(C=O)-heterocycloalkyl, or —NH-heterocycloalkyl ring may be substituted with —$C_{1-6}$alkyl or cycloalkyl.

According to an embodiment of the present disclosure, the compound represented by Chemical Formula 1 above, an optical isomer thereof, or a pharmaceutically acceptable salt thereof may be included in the following scope:

$X_1$ to $X_3$ are each independently CH or N;

$R_X$ is —H, —$NH_2$, —NH(—$C_{1-6}$alkyl), or —N(—$C_{1-6}$alkyl)(—$C_{1-6}$alkyl);

Y is —$C_{1-6}$alkyl, —$(CH_2)_n$aryl, —$(CH_2)_n$heteroaryl, or —$(CH_2)_n$hydroheteroaryl in which at least one H of the —$(CH_2)_n$aryl, —$(CH_2)_n$heteroaryl, or —$(CH_2)_n$hydroheteroaryl ring may be substituted with —$C_{1-6}$alkyl, —$C_{1-6}$haloalkyl, —$C_{1-6}$alkenyl, —$C_{1-6}$alkynyl, —CN, —(C=O) $NR_1R_2$, —(C=O) $OR_3$, —$NR_4R_5$, —$OR_6$, -halo, =O, heterocycloalkyl, aryl, or heteroaryl, wherein at least one H of the heterocycloalkyl, aryl, or heteroaryl may be substituted with -halo;

n is 0, 1, or 2;

$R_1$ to $R_3$ are each independently —H, —$C_{1-6}$alkyl, or cycloalkyl;

$R_4$ and $R_5$ are each independently —H or —$C_{1-6}$alkyl;

$R_6$ is —$C_{1-6}$alkyl or phenyl in which at least one H of the phenyl ring may be substituted with —$C_{1-6}$alkyl, —$C_{1-6}$ haloalkyl, or halo;

$R_{Y1}$ to $R_{Y5}$ are each independently —H or —$C_{1-6}$alkyl, or $R_{Y2}$ and $R_{Y3}$ may be linked to each other to form cycloalkyl, and $R_{Y3}$ and $R_{Y4}$ may be linked to each other to form aryl;

L is —(CH$_2$)m-, —C(=O)—, or null;

m is 0, 1, or 2;

a ring Z is aryl, heteroaryl, hydroheteroaryl, cycloalkyl, or heterocycloalkyl in which at least one H of the aryl, heteroaryl, hydroheteroaryl, cycloalkyl, or heterocycloalkyl ring may be substituted with —$C_{1-6}$alkyl, —$C_{1-6}$cyanoalkyl, —$C_{1-6}$haloalkyl, —$C_{1-6}$alkenyl, —$C_{1-6}$alkynyl, —CN, —NR$_7$R$_8$, —O—$C_{1-6}$alkyl, —O—$C_{1-6}$haloalkyl, —S—$C_{1-6}$alkyl, —C(=O)—$C_{1-6}$ alkyl, —C(=O)—$C_{1-6}$haloalkyl, —C(=O)O—$C_{1-6}$alkyl, —S(=O)$_2$—$C_{1-6}$alkyl, —C(=N—O—$C_{1-6}$alkyl) ($C_{1-6}$alkyl), =O, -halo, or $Z_1$, or two or more substituents of the aryl, heteroaryl, hydroheteroaryl, cycloalkyl, or heterocycloalkyl ring may be linked to each other to form a fused ring or a spiro ring, wherein at least one H of the fused ring or spiro ring may be substituted with —$C_{1-6}$alkyl or $Z_1$;

$R_7$ and $R_8$ are each independently —H, —$C_{1-6}$alkyl, —$C_{1-6}$alkyl-NH—$C_{1-6}$alkyl, —$C_{1-6}$alkyl-N($C_{1-6}$alkyl) ($C_{1-6}$alkyl), —(C=O)—$C_{1-6}$alkyl, or —(C=O)—$C_{1-6}$haloalkyl;

$Z_1$ is cycloalkyl, heterocycloalkyl, heterobicycloalkyl, heterospiroalkyl, —$C_{1-6}$alkyl-heterocycloalkyl, —(C=O)-heterocycloalkyl, —NH-heterocycloalkyl, or heteroaryl in which the heterocycloalkyl, heterobicycloalkyl, heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —$C_{1-6}$alkyl-heterocycloalkyl, —(C=O)-heterocycloalkyl, —NH-heterocycloalkyl, or heteroaryl ring may be substituted with —$C_{1-6}$alkyl, —$C_{1-6}$aminoalkyl, —$C_{1-6}$haloalkyl, —$C_{1-6}$alkenyl, —$C_{1-6}$alkynyl, —C(=O)—$C_{1-6}$alkyl, —$C_{1-6}$alkyl-S(=O)$_2$—$C_{1-6}$alkyl, =O, —NR$_9$R$_{10}$, -halo, cycloalkyl, or $Z_2$;

$R_9$ and $R_{10}$ are each independently —H or —$C_{1-6}$alkyl;

$Z_2$ is heterocycloalkyl, heterobicycloalkyl, or —NH-heterocycloalkyl in which the heterocycloalkyl, heterobicycloalkyl, or —NH-heterocycloalkyl contains, in the ring, at least one selected from the group consisting of N, O, P, P(=O) and S, and at least one H of the heterocycloalkyl, heterobicycloalkyl, or —NH-heterocycloalkyl ring may be substituted with —$C_{1-6}$alkyl, —$C_{1-6}$hydroxyalkyl, —$C_{1-6}$alkenyl, —$C_{1-6}$alkynyl, —C(=O)—$C_{1-6}$alkyl, —$C_{1-6}$alkyl-S(=O)$_2$—$C_{1-6}$alkyl, =O, —NR$_{11}$R$_{12}$, cycloalkyl, or $Z_3$;

$R_{11}$ and $R_{12}$ are each independently —H or —$C_{1-6}$alkyl; and $Z_3$ is heterocycloalkyl, heterobicycloalkyl, or —$C_{1-6}$alkyl-heterocycloalkyl in which the heterocycloalkyl, heterobicycloalkyl, or —$C_{1-6}$alkyl-heterocycloalkyl contains, in the ring, at least one selected from the group consisting of N, O, P, P(=O) and S, and at least one H of the heterocycloalkyl, heterobicycloalkyl, or —$C_{1-6}$alkyl-heterocycloalkyl ring may be substituted with —$C_{1-6}$alkyl or cycloalkyl.

According to an embodiment of the present disclosure, the compound represented by Chemical Formula 1 above, an optical isomer thereof, or a pharmaceutically acceptable salt thereof may be included in the following scope:

$X_1$ is N;

$X_2$ and $X_3$ are each independently CH or N; and $R_X$ is —H, —NH$_2$, or —NH(—$C_{1-6}$alkyl).

According to an embodiment of the present disclosure, the compound represented by Chemical Formula 1 above, an optical isomer thereof, or a pharmaceutically acceptable salt thereof may be included in the following scope:

Y is —$C_{1-6}$alkyl, —(CH$_2$)$_n$aryl, —(CH$_2$)$_n$heteroaryl, or —(CH$_2$)$_n$hydroheteroaryl in which at least one H of the —(CH$_2$)$_n$aryl, —(CH$_2$)$_n$heteroaryl, or —(CH$_2$)$_n$hydroheteroaryl ring may be substituted with —$C_{1-6}$alkyl, —$C_{1-6}$haloalkyl, —$C_{1-6}$alkynyl, —CN, —(C=O) NH-cycloalkyl, —(C=O) O—$C_{1-6}$alkyl, —N($C_{1-6}$alkyl) ($C_{1-6}$alkyl), —O($C_{1-6}$alkyl), —O-phenyl, -halo, =O, heterocycloalkyl, aryl, or heteroaryl, wherein at least one H of the heterocycloalkyl, aryl, or heteroaryl may be substituted with -halo;

n is 0 or 1; and $R_{Y1}$ to $R_{Y5}$ are each independently —H or —$C_{1-6}$alkyl, or $R_{Y2}$ and $R_{Y3}$ may be linked to each other to form 3- to 6-membered cycloalkyl, and $R_{Y3}$ and $R_{Y4}$ may be linked to each other to form phenyl.

According to an embodiment of the present disclosure, the compound represented by Chemical Formula 1 above, an optical isomer thereof, or a pharmaceutically acceptable salt thereof may be included in the following scope:

L is —(CH$_2$) m-, —C(=O)—, or null;

m is 0 or 1;

a ring Z is aryl, heteroaryl, hydroheteroaryl, 3- to 7-membered cycloalkyl, or 5- to 7-membered heterocycloalkyl in which at least one H of the aryl, heteroaryl, hydroheteroaryl, 3- to 7-membered cycloalkyl, or 5- to 7-membered heterocycloalkyl ring may be substituted with —$C_{1-6}$alkyl, —$C_{1-6}$cyanoalkyl, —$C_{1-6}$haloalkyl, —$C_{1-6}$alkenyl, —$C_{1-6}$alkynyl, —CN, —NR$_7$R$_8$, —O—$C_{1-6}$alkyl, —O—$C_{1-6}$haloalkyl, —S—$C_{1-6}$alkyl, —C(=O)—$C_{1-6}$alkyl, —C(=O)—$C_{1-6}$haloalkyl, —C(=O)O—$C_{1-6}$alkyl, —S(=O)$_2$—$C_{1-6}$alkyl, —C(=N—O—$C_{1-6}$alkyl) ($C_{1-6}$alkyl), =O, -halo, or $Z_1$, wherein at least one H of the aryl, heteroaryl, hydroheteroaryl, 3- to 7-membered cycloalkyl, or 5- to 7-membered heterocycloalkyl ring may be substituted with —$C_{1-6}$alkyl or -halo, or two or more substituents of the aryl, heteroaryl, hydroheteroaryl, 3- to 7-membered cycloalkyl, or 5- to 7-membered heterocycloalkyl ring may be linked to each other to form a fused ring or a spiro ring, wherein at least one H of the fused ring or spiro ring may be substituted with —$C_{1-6}$alkyl or $Z_1$;

$R_7$ and $R_8$ are each independently —H, —$C_{1-6}$alkyl, —$C_{1-6}$alkyl-N($C_{1-6}$alkyl) ($C_{1-6}$alkyl), —(C=O)—$C_{1-6}$alkyl, or —(C=O)—$C_{1-6}$haloalkyl;

$Z_1$ is 3- to 7-membered cycloalkyl, 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, —NH-heterocycloalkyl, or heteroaryl in which the 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, —NH-heterocycloalkyl, or heteroaryl ring may be substituted with —$C_{1-6}$alkyl, —$C_{1-6}$aminoalkyl, —$C_{1-6}$haloalkyl, —$C_{1-6}$alkenyl, —C(=O)—$C_{1-6}$alkyl, —$C_{1-6}$alkyl-S(=O)$_2$—$C_{1-6}$alkyl, =O, —N($C_{1-6}$alkyl) ($C_{1-6}$alkyl), -halo, cycloalkyl, or $Z_2$;

$Z_2$ is 5- to 7-membered heterocycloalkyl, 6- to 10-membered heterobicycloalkyl, or —NH-heterocycloalkyl in which the 5- to 7-membered heterocycloalkyl, 6- to 10-membered heterobicycloalkyl, or —NH-heterocycloalkyl contains, in the ring, at least one selected from the group consisting of N, O, and S, and at least one H of the 5- to 7-membered heterocycloalkyl, 6- to 10-membered heterobicycloalkyl, or —NH-heterocycloalkyl ring may be substituted with —$C_{1-6}$alkyl, —$C_{1-6}$hydroxyalkyl, —$C_{1-6}$alkenyl, —$C_{1-6}$alkynyl, —C(=O)—$C_{1-6}$alkyl, —$C_{1-6}$alkyl-S(=O)$_2$—$C_{1-6}$alkyl, =O, —N($C_{1-6}$alkyl) ($C_{1-6}$alkyl), 3- to 7-membered cycloalkyl, or $Z_3$; and $Z_3$ is 5- to 7-membered heterocycloalkyl, 6- to 10-membered heterobicycloalkyl, or —$C_{1-6}$alkyl-heterocycloalkyl in which the 5- to 7-membered heterocycloalkyl, 6- to 10-membered heterobicycloalkyl, or —$C_{1-6}$alkyl-heterocycloalkyl contains, in the ring, at least one selected from the group consisting of N, O, and S, and at least one H of the 5- to 7-membered heterocycloalkyl, 6- to 10-membered heterobicycloalkyl, or —$C_{1-6}$alkyl-heterocycloalkyl ring may be substituted with —$C_{1-6}$alkyl or 3- to 7-membered cycloalkyl.

According to an embodiment of the present disclosure, the compound represented by Chemical Formula 1 above may be selected from the group consisting of compounds listed in Table 1 below.

In the present disclosure, unless otherwise specified, the term "alkyl" may refer to a straight or branched chain acyclic, cyclic, or saturated hydrocarbon to which they are bonded. For example, "$C_{1-6}$alkyl" may indicate an alkyl containing 1 to 6 carbon atoms. As an example, acyclic alkyl may include, but is not limited to, methyl, ethyl, n-propyl, n-butyl, isopropyl, sec-butyl, isobutyl, tert-butyl, or the like. Cyclic alkyl may be used interchangeably with "cycloalkyl" as used herein, and as an example, may include, but is not limited to, cyclopropyl, cyclobutyl, cyclopentyl, cyclohexyl, cycloheptyl, cyclooctyl, or the like.

In the present disclosure, "alkoxy" may indicate —(O-alkyl) as an alkyl ether group, wherein alkyl is the same as defined above. For example, "$C_{1-6}$alkoxy" may mean alkoxy containing $C_{1-6}$alkyl, that is, —(O—$C_{1-6}$alkyl), and as an example, may include, but is not limited to, methoxy, ethoxy, n-propoxy, isopropoxy, n-butoxy, isobutoxy, sec-butoxy, tert-butoxy, or the like.

In the present disclosure, "halo" may be F, Cl, Br, or I.

As used herein, "haloalkyl" may mean a straight or branched chain alkyl (hydrocarbon) having one or more halo-substituted carbon atoms as defined herein. Examples of the haloalkyl may include, but are not limited to, methyl, ethyl, propyl, isopropyl, isobutyl or n-butyl independently substituted with one or more halogens, such as F, Cl, Br, or I.

As used herein, "hydroxyalkyl" may indicate a straight or branched chain alkyl (hydrocarbon) having a carbon atom substituted with hydroxy (OH). Examples of the hydroxyalkyl may include, but are not limited to, methyl, ethyl, propyl, isopropyl, isobutyl or n-butyl independently substituted with one or more —OH.

As used herein, "aminoalkyl" may mean a straight or branched chain alkyl (hydrocarbon) having a carbon atom substituted with amino (NR'R"). Here, R' and R" may be each independently selected from the group consisting of hydrogen and $C_{1-6}$alkyl, and the selected R' and R" may be each independently substituted or unsubstituted.

As used herein, "cyanoalkyl" may indicate a straight or branched alkyl (hydrocarbon) having a carbon atom substituted with cyano (CN).

In the present disclosure, "heterocycloalkyl" may mean a ring containing at least one selected from N, O, P, P(=O), and S in the ring, and may be saturated or partially unsaturated. Here, when unsaturated, it may be referred to as a heterocycloalkene. Unless otherwise stated, heterocycloalkyl may be a single ring or a multiple ring such as a spiro ring, a bridged ring or a fused ring. In addition, "3- to 12-membered heterocycloalkyl" may indicate a heterocycloalkyl containing 3 to 12 atoms forming a ring.

As an example, the heterocycloalkyl may include, but is not limited to, pyrrolidine, piperidine, imidazolidine, pyrazolidine, butyrolactam, valerolactam, imidazolidinone, hydantoin, dioxolane, phthalimide, piperidine, pyrimidin-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, or (1R,4R)-2-oxa-5-azabicyclo[2.2.2]octane, and the like.

In the present disclosure, "arene" may mean an aromatic hydrocarbon ring. The arene may be a monocyclic arene or a polycyclic arene. The number of ring-forming carbons in the arene may be 5 or more and 30 or less, 5 or more and 20 or less, or 5 or more and 15 or less. Examples of the arene may include, but are not limited to, benzene, naphthalene, fluorene, anthracene, phenanthrene, bibenzene, terbenzene, quaterbenzene, quinquebenzene, sexibenzene, triphenylene, pyrene, benzofluoranthene, chrysene, and the like. In the present specification, the residue obtained by removing one hydrogen atom from "arene" is referred to as "aryl".

In the present disclosure, "heteroarene" may be a ring containing at least one of 0, N, P, Si, and S as a heterogeneous element. The number of ring-forming carbons in the heteroarene may be 2 or more and 30 or less, or 2 or more and 20 or less. The heteroarene may be a monocyclic heteroarene or a polycyclic heteroarene. The polycyclic heteroarene may have, for example, a bicyclic or tricyclic structure. Examples of the heteroarene may include thiophene, purine, pyrrole, pyrazole, imidazole, thiazole, oxazole, isothiazole, oxadiazole, triazole, pyridine, bipyridyl, triazine, acridyl, pyridazine, pyrazine, quinoline, quinazoline, quinoxaline, phenoxazine, phthalazine, pyrimidine, pyridopyrimidine, pyridopyrazine, pyrazinopyrazine, isoquinoline, indole, carbazole, imidazopyridazine, imidazopyridine, imidazopyrimidine, pyrazolopyrimidine, imidazopyrazine or pyrazolopyridine, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, isoxazole, oxadiazole, thiadiazole, benzothiazole, tetrazole, phenothiazine, dibenzosilole, dibenzofuran, and the like, but are not limited thereto. In an embodiment of the present disclosure, heteroarene may also include bicyclic heterocyclo-arene containing heteroarene fused to an arene ring or a cycloalkyl ring fused to heterocycloalkyl rings. In the present specification, the residue obtained by removing one hydrogen atom from the "heteroarene" is referred to as "heteroaryl".

In the present disclosure, "hydroaryl" means that one or more double bonds present in "aryl" are substituted with a single bond.

In the present disclosure, "hydroheteroaryl" means that one or more double bonds present in "heteroaryl" are substituted with a single bond.

In the present disclosure, the term "optical isomers (enantiomers)" mean compounds of the present disclosure or salts thereof that have the same chemical formula or molecular formula but are different in stereostructure.

Each of these enantiomers and mixtures thereof are also included within the scope of the present disclosure. Unless otherwise specified, the straight solid-line bond (–) connecting an asymmetric carbon atom may include a wedge-shaped solid-line bond '╱' or a wedge-shaped dashed-line bond indicating the absolute configuration of the stereocenter.

In the present disclosure, the term "cis" refers to a case in which the binding directions of two substituents in a ring are the same, and the term "trans" refers to a case in which the binding directions of two substituents in the ring are different.

The compound of Chemical Formula 1 of the present disclosure may exist in the form of a "pharmaceutically acceptable salt". As the salt, an acid addition salt formed by a pharmaceutically acceptable free acid is useful. The term "pharmaceutically acceptable salt" as used herein means any and all organic or inorganic acid addition salts of the compound represented by Chemical Formula 1 of which side effects caused by the salt do not reduce the beneficial efficacy of the compound at concentrations having an effective action that is relatively non-toxic and harmless to a patient.

Acid addition salts are prepared by conventional methods, for example by dissolving the compound in an excess of aqueous acid solution and precipitating the salt using a water-miscible organic solvent such as methanol, ethanol, acetone or acetonitrile. An acid or alcohol in an equimolar amount of the compound and water may be heated, and the mixture may then be evaporated to dryness, or the precipitated salt may be filtered off with suction.

Here, an organic acid and an inorganic acid may be used as the free acid, wherein the inorganic acid may be hydrochloric acid, phosphoric acid, sulfuric acid, nitric acid, or the like, and the organic acid may be methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, or the like. However, the present disclosure is not limited thereto.

In addition, it is possible to prepare a pharmaceutically acceptable metal salt using a base. The alkali metal salt or alkaline earth metal salt is obtained, for example, by dissolving a compound in an excess of alkali metal hydroxide or alkaline earth metal hydroxide solution, filtering the undissolved compound salt, and then evaporating and drying the filtrate. Here, it is pharmaceutically suitable to prepare a sodium, potassium, or calcium salt as the metal salt, but the present disclosure is not limited thereto. Further, the corresponding silver salt may be obtained by reacting an alkali metal or alkaline earth metal salt with a suitable silver salt (for example, silver nitrate).

Unless otherwise indicated, the pharmaceutically acceptable salt of the present disclosure includes salts of acidic or basic groups that may be present in the compound of Chemical Formula 1. For example, the pharmaceutically acceptable salt may include sodium, calcium and potassium salts of hydroxyl groups, and the like, and as other pharmaceutically acceptable salts of amino groups, may include hydrobromide, sulfate, hydrogen sulfate, phosphate, hydrogen phosphate, dihydrogen phosphate, acetate, succinate, citrate, tartrate, lactate, mandelate, methanesulfonate(mesylate), and p-toluenesulfonate (tosylate) salts, and the like, and may be prepared by a method for preparing a salt known in the art.

Use of Heteroaryl Derivative Compound

The present disclosure provides use of a compound represented by the following Chemical Formula 1, an optical isomer thereof, or a pharmaceutically acceptable salt thereof:

[Chemical Formula 1]

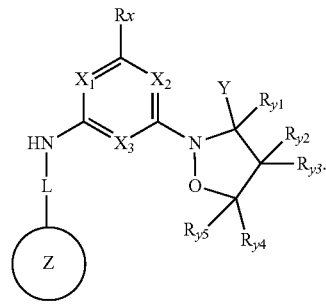

The compound represented by Chemical Formula 1 of the present disclosure, an optical isomer thereof, or a pharmaceutically acceptable salt thereof exhibits inhibitory activity against various kinases.

According to an embodiment of the present disclosure, the heteroaryl derivative represented by Chemical Formula 1 exhibits excellent inhibitory activity against EGFR and/or HER2 kinase, and thus may be usefully employed for the treatment or prevention of EGFR- and/or HER2-related diseases, in particular, cancer. Specifically, the compound of Chemical Formula 1 is able to inhibit EGFR and/or HER2 wild-type or mutant kinase, which is supported by the Experimental Examples to be described below. The EGFR mutation may be a C797S mutation such as EGFR Del19/C797S (EGFR DC) or EGFR L858R/C797S (EGFR LC), but is not limited thereto. In addition, the EGFR mutation may be EGFR L861Q, EGFR G719A, EGFR S768I, EGFR L718Q, or EGFR G724S, but is not limited thereto. Further, the EGFR mutation may be EGFR d746-750, EGFR d746-750/C797A, EGFR d746-750/C797S, EGFR d746-750/T790M/C797S, EGFR D761Y, EGFR G719C, EGFR G719D, EGFR G719S, EGFR L747S, EGFR L792F, EGFR L858R, or EGFR L792F/L858R, but is not limited thereto.

In the present disclosure, the cancer includes any cancer capable of exhibiting therapeutic or prophylactic efficacy due to inhibition of EGFR and/or HER2 kinase activity, and may be a solid cancer or a hematologic cancer. As a non-limiting example, the cancer may be one or more selected from the group consisting of pseudomyxoma, intrahepatic biliary tract cancer, hepatoblastoma, liver cancer, thyroid cancer, colon cancer, testicular cancer, myelodysplastic syndrome, glioblastoma, oral cancer, labial cancer, mycosis fungoides, acute myeloid leukemia, acute lymphocytic leukemia, basal cell cancer, ovarian epithelial cancer, ovarian germ cell cancer, male breast cancer, brain cancer, pituitary adenoma, multiple myeloma, gallbladder cancer, biliary tract cancer, colorectal cancer, chronic myelogenous leukemia, chronic lymphocytic leukemia, retinoblastoma, choroidal melanoma, ampulla of vater cancer, bladder cancer, peritoneal cancer, parathyroid cancer, adrenal cancer, sinus cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvic cancer, kidney cancer, heart cancer, duodenal cancer, malignant soft tissue cancer, malignant bone cancer, malignant lymphoma, malignant mesothelioma, malignant melanoma, eye cancer, vulvar cancer, ureter cancer, urethral cancer, cancer of unknown primary site, gastric lymphoma, gastric cancer, gastric carcinoma, gastrointestinal stromal cancer, Wilms cancer, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoma, vaginal cancer, spinal cord cancer, acoustic tumor, pancreatic cancer, salivary gland cancer, Kaposi's sarcoma, Paget's disease, tonsil cancer, squamous cell carcinoma, lung adenocarcinoma, lung cancer, lung squamous cell carcinoma, skin cancer, anal cancer, rhabdomyosarcoma, laryngeal cancer, pleural cancer, blood cancer, and thymus cancer. The cancer includes not only primary cancer but also metastatic cancer.

According to an embodiment of the present disclosure, the present disclosure provides a pharmaceutical composition for treatment or prevention of EGFR- and/or HER2-related diseases containing the compound represented by Chemical Formula 1, an optical isomer thereof, or a pharmaceutically acceptable salt thereof as an active ingredient. Specifically, the EGFR- and/or HER2-related disease may be cancer. The types of cancer are the same as described above.

The pharmaceutical composition of the present disclosure may further include one or more active ingredients exhibiting the same or similar drug efficacy in addition to the compound represented by Chemical Formula 1 above, the optical isomer thereof, or the pharmaceutically acceptable salt thereof.

The pharmaceutical composition of the present disclosure may be used in clinical administration, and may be prepared to be administered in various oral and parenteral formulations.

Further, according to an embodiment of the present disclosure, there is provided a method for treating or preventing EGFR- and/or HER2-related diseases, comprising: administering to a subject in need thereof a therapeutically effective amount of the compound represented by Chemical Formula 1, an optical isomer thereof, or a pharmaceutically acceptable salt thereof. The subject may be a mammal including a human.

The term "therapeutically effective amount" as used herein refers to an amount of the compound represented by Chemical Formula 1 that is effective for the treatment or prevention of EGFR- and/or HER2-related diseases. Specifically, "therapeutically effective amount" indicates an amount sufficient to treat a disease with a reasonable benefit/risk ratio applicable to medical treatment, and the effective dose level may be determined depending on factors including the subject type and severity, age, sex, type of disease, drug activity, drug sensitivity, administration time, administration route and excretion rate, treatment period, drugs used at the same time, and other factors well-known in medical fields. The pharmaceutical composition of the present disclosure may be administered as an individual therapeutic agent or may be administered in combination with other therapeutic agents, and may be administered sequentially or simultaneously with commercially available therapeutic agents. In addition, the pharmaceutical composition of the present disclosure may be administered in a single dose or multiple doses. It is important to administer the minimum amount capable of obtaining the maximum effect without side effects in consideration of all of the above factors, and the amount may be readily determined by those skilled in the art. The dosage of the pharmaceutical composition of the present disclosure may be determined by a medical specialist according to various factors such as the patient's condition, age, sex, complications, and the like. Since the active ingredient of the pharmaceutical composition of the present disclosure has excellent safety, it may be used at a dose higher than the determined dosage.

Further, according to an embodiment of the present disclosure, the present disclosure provides use of the compound represented by Chemical Formula 1, the optical isomer thereof, or the pharmaceutically acceptable salt thereof for use in preparation of a medicament to treat or prevent EGFR- and/or HER2-related diseases. The compound represented by Chemical Formula 1 for preparing the medicament may be mixed with acceptable adjuvants, diluents, carriers, and the like, and may have a synergistic effect of active ingredients by being prepared as a complex formulation with other active agents.

Matters mentioned in the uses, compositions and treatment methods of the present disclosure are applied equally except to the extent that they are inconsistent with each other.

Advantageous Effects

The heteroaryl derivative compound of the present disclosure exhibits excellent inhibitory activity against EGFR and/or HER2, and thus may be usefully employed for the treatment or prevention of EGFR- and/or HER2-related diseases.

BEST MODE

Hereinafter, the present disclosure will be described in more detail through Examples and Experimental Examples. However, the following Examples and Experimental Examples are merely presented to illustrate the present disclosure, and the content of the present disclosure is not limited thereto.

<Analysis and Purification Conditions>

Compounds synthesized in the Examples of the present disclosure were purified by the following HPLC conditions or subjected to structural analysis.

1. HPLC Conditions
Analytical HPLC Condition (ACQUITY UPLC H-Class Core System)

Waters UPLC system (ACQUITY UPLC PDA Detector) equipped with a mass QDa detector manufactured by Waters corporation was used. The column used was Waters ACQUITY UPLC® BEH C18 (1.7 μl, 2.1×50 mm), and performed at 30° C.

Water containing 0.1% formic acid was used as the mobile phase A and acetonitrile containing 0.1% formic acid was used as the mobile phase B.

Gradient conditions (10-100% B over 3 minutes and flow rate=0.6 ml/min)

Prep-LCMS for Purification (Preparative-Liquid Chromatography Mass Spectrometry)

Waters Autopurification HPLC system (2767 sample manager, 2545 binary gradient module, 2998 Photodiode Array Detector) equipped with a mass QDa detector manufactured by Waters corporation was used. The column used was Waters SunFire®Prep C18 OBD™ (5 μm, 19×50 mm), and performed at room temperature.

Water containing 0.035% trifluoroacetic acid was used as the mobile phase A and methanol containing 0.035% trifluoroacetic acid was used as the mobile phase B.

Gradient conditions (15-100% B over 10 minutes and flow rate=25 ml/min)

Prep-150 LC System for Purification (Preparative-Liquid Chromatography UV Spectrometry)

Waters Prep 150 LC system (2545 Quaternary gradient module, 2998 Photodiode Array Detector, Fraction collector III) was used. The column used was Waters XTERRA®Prep RP18 OBD™ (10 μm, 30×300 mm) and performed at room temperature.

Gradient conditions (3-100% B over 120 minutes and flow rate=40 ml/min)

Preparative HPLC System for Purification (Preparative-Liquid Chromatography UV Spectrometry)

Teledyne ACCQPrep HP150 was used. The column used was Waters XTERRA®Prep RP18 OBD™ (10 μm, 30×300 mm) and performed at room temperature.

Gradient conditions (10-100% B over 120 minutes and flow rate=42 ml/min)

2. MM Analysis

NMR analysis was performed using AVANCE III 400 or AVANCE III 400 HD manufactured by Bruker, and data are expressed in parts per million (δ) (ppm).

Commercially available reagents were used without further purification. In the present disclosure, room temperature or ordinary temperature refers to a temperature of about 5° C. to 40° C., for example, 10° C. to 30° C., as another example, 20° C. to 27° C., which is not strictly limited to the above scope. Concentration under reduced pressure or solvent distillation was performed using a rotary evaporator.

<Preparation Example 1> Preparation of (S)-3-phenylisoxazolidine

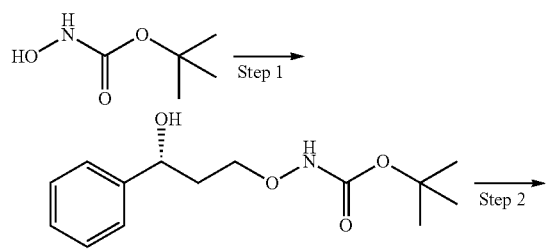

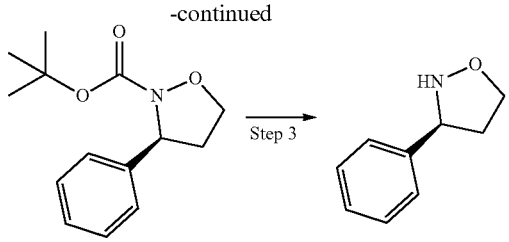

Step 1: Preparation of tert-butyl (R)-(3-hydroxy-3-phenylpropoxy)carbamate

Tert-butyl hydroxycarbamate (7.8 g, 58.6 mmol) was dissolved in dimethylformamide (140 ml), then sodium hydride (2.58 g, 64.5 mmol) was added at 0° C. and the reaction mixture was reacted for 30 min. Next, (R)-3-chloro-1-phenylpropan-1-ol (5 g, 29.3 mmol) dissolved in dimethylformamide (DMF; 10 ml) was slowly added dropwise at 0° C. for 10 min, and stirred at room temperature for 72 hours. The reaction was terminated by adding an aqueous ammonium chloride solution to the reaction mixture, followed by extraction with ethyl acetate and brine to combine the organic layers. The organic layer was dried over sodium sulfate and concentrated under reduced pressure. The title compound (2.8 g, 68%) was obtained by purification using medium pressure liquid chromatography (ethyl acetate/n-hexane).

MS (m/z): 150.17 [M+1]$^+$, UPLC r.t. (min): 1.51

Step 2: Preparation of tert-butyl (S)-3-phenylisoxazolidin-2-carboxylate

Tert-Butyl (R)-(3-hydroxy-3-phenylpropoxy)carbamate (2.55 g, 9.54 mmol) obtained in Step 1 above and triethylamine (3.13 ml, 22.44 mmol) were dissolved in dichloromethane (250 ml) and then cooled to 0° C. Next, methanesulfonyl chloride (1 ml, 13 mmol) was added dropwise and the reaction mixture was reacted at 0° C. for 2 hours. The reaction mixture was extracted with brine and dichloromethane, and the organic layers were combined. The organic layer was dried over sodium sulfate and concentrated under reduced pressure to obtain the title compound, which was used in the next reaction without purification.

MS (m/z): 194.13 [M+1]$^+$, UPLC r.t. (min): 1.69

Step 3: Preparation of (S)-3-phenylisoxazolidine

Tert-butyl (S)-3-phenylisoxazolidin-2-carboxylate (2.3 g) obtained in Step 2 was dissolved in dichloromethane (90 ml), then trifluoroacetic acid (14 ml) was added and the reaction mixture was reacted at room temperature for 1 hour. The reaction mixture was neutralized with aqueous sodium bicarbonate solution, and then the organic layers were combined. The organic layer was dried over sodium sulfate, followed by concentration under reduced pressure. The title compound (1.3 g, 94%) was obtained by purification using medium pressure liquid chromatography (tetrahydrofuran/n-hexane).

MS (m/z): 150.08 [M+1]$^+$, UPLC r.t. (min): 0.72

<Preparation Example 2> Preparation of (R)-3-phenylisoxazolidine

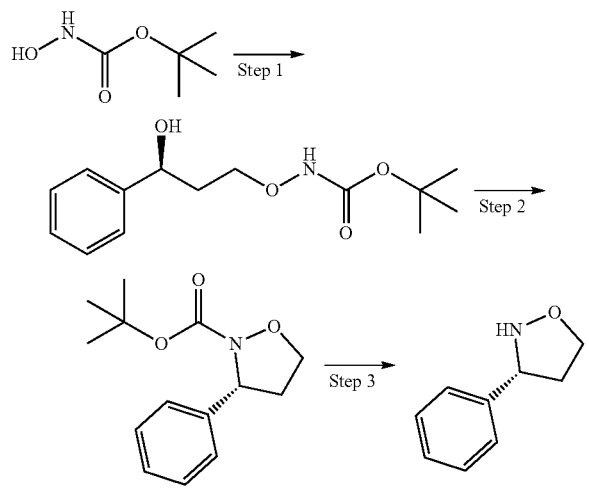

A compound of Preparation Example 2 was prepared in a manner similar to that of Preparation Example 1, and was used for the synthesis of the Example compound shown in Table 1 below.

MS (m/z): 150.08 [M+1]$^+$, UPLC r.t. (min): 0.72

<Preparation Example 3> Preparation of (R)-3-(3-fluorophenyl)isoxazolidine

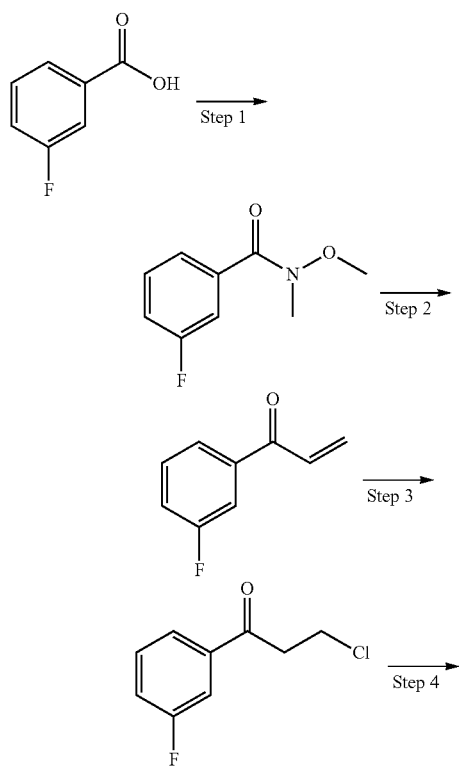

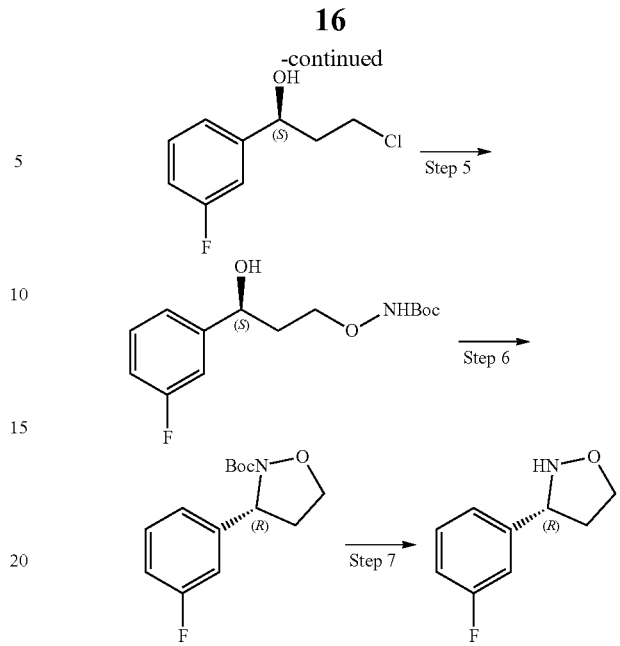

Step 1: Preparation of 3-fluoro-N-methoxy-N-methylbenzamide

3-Fluorobenzoic acid (90 g, 642.35 mmol, 1 eq.) was dissolved in pyridine (150 mL), and N-methoxy methanamine (75.19 g, 770.81 mmol, 1.2 eq, HCl) was added thereto. Then, 1-ethyl-3-(3-dimethylaminopropyl)carbodiimide (EDCI; 147.77 g, 770.81 mmol, 1.2 eq.) was added at 15° C. The reaction mixture was stirred at 50° C. for 30 min. As a result of TLC analysis (petroleum ether (PE):ethyl acetate (EA)=3:1), all of the starting materials disappeared, and a new spot with low polarity was detected. The pyridine solvent was removed by concentration under reduced pressure, and the organic layer was extracted using dichloromethane (DCM; 500 mL), hydrochloric acid (500 mL, 2N), and brine (200 mL). The organic layer was dried over sodium sulfate and concentrated under reduced pressure to obtain the title compound as a yellow oil (110 g, 600.50 mmol, 93.49% yield).

$^1$H NMR (400 MHz, CHLOROFORM-d) δ 7.47-7.40 (m, 1H), 7.39-7.38 (m, 2H), 7.14-7.13 (m, 1H), 3.54 (s, 3H), 3.45 (s, 3H).

Step 2: Preparation of 1-(3-fluorophenyl)prop-2-en-1-one

3-Fluoro-N-methoxy-N-methyl-benzamide (110 g, 600.50 mmol, 1 eq.) obtained in Step 1 above was dissolved in tetrahydrofuran (THF; 1 L), then bromo(vinyl)magnesium (1M, 630.53 mL, 1.05 eq.) was added dropwise at 0° C. Next, the reaction mixture was stirred at 0° C. for 30 min. As a result of TLC analysis (petroleum ether (PE):ethyl acetate (EA)=4:1), all of the starting materials disappeared, and a new spot with low polarity was detected. The reaction was terminated by adding hydrochloric acid (4N, 500 mL), and the organic layer was extracted using methyl tert-butyl ether (MTBE; 2000 mL) and brine (500 mL). The organic layer was dried over sodium sulfate, followed by concentration under reduced pressure. The concentrated compound was purified by chromatography (petroleum ether/ethyl acetate=30/1) to obtain the title compound as a yellow oil (80 g, 532.80 mmol, 88.73% yield).

¹H NMR (400 MHz, CHLOROFORM-d) δ 7.65 (m, 1H), 7.58-7.52 (m, 1H), 7.39 (m, 1H), 7.24-7.17 (m, 1H), 7.04 (dd, J=17.2, 10.4 Hz, 1H), 6.39 (dd, J=17.2, 1.6 Hz, 1H), 5.90 (dd, J=10.4, 1.6 Hz, 1H).

Step 3: Preparation of 3-chloro-1-(3-fluorophenyl)propan-1-one 1-(3-Fluorophenyl)prop-2-en-1-one (71 g, 472.86 mmol, 1.0 eq.) obtained in Step 2 above was dissolved in dichloromethane (DCM; 71 mL), and HCl/dioxane (4M, 295.54 mL, 2.5 eq.) was added at 0° C. Next, the reaction mixture was stirred at 15° C. for 1.5 hours. As a result of TLC analysis (petroleum ether (PE):ethyl acetate (EA)=10:1), all of the starting materials disappeared, and the title compound was detected. The reaction mixture was concentrated under reduced pressure, and dichloromethane (DCM; 450 mL) and water (200 mL*5) were added to extract the organic layer. The organic layer was dried over sodium sulfate and concentrated under reduced pressure to obtain the title compound as a yellow solid (73 g, 391.19 mmol, 82.73% yield).

¹H NMR (400 MHz, CHLOROFORM-d) δ 7.78-7.72 (m, 1H), 7.69-7.60 (m, 1H), 7.53-7.44 (m, 1H), 7.37-7.24 (m, 1H), 3.93 (t, J=6.8 Hz, 2H), 3.46 (t, J=6.8 Hz, 2H).

Step 4: Preparation of (S)-3-chloro-1-(3-fluorophenyl)propan-1-ol (3aR)-1-methyl-3,3-diphenyl-3a,4,5,6-tetrahydropyrrolo[1,2-c][1,3,2]oxazabolol (1M, 32.15 mL, 0.1 eq.) was dissolved in tetrahydrofuran (THF; 1.2 L), then borane tetrahydrofuran (BH$_3$·THF; 1M, 186.48 mL, 0.6 eq.) was added dropwise at 0° C. under a nitrogen atmosphere. The reaction mixture was stirred at 0° C. for 30 min. Next, 3-chloro-1-(3-fluorophenyl)propan-1-one (60 g, 309.02 mmol, 1 eq.) obtained in Step 3 above diluted in tetrahydrofuran was added dropwise to the reaction mixture at 0° C. The reaction mixture was stirred at 0° C. for 30 min. As a result of TLC analysis (petroleum ether (PE):ethyl acetate (EA)=5:1), all of the starting materials disappeared, and a spot of the title compound was detected. The reaction was terminated by adding methanol (100 mL) at 0° C., and then the solvent was distilled off under reduced pressure. The organic layer was extracted from the concentrated compound using dichloromethane (DCM; 100 mL*3) and ammonium chloride (NH$_4$Cl) solution (300 mL). The organic layer was dried over sodium sulfate, followed by concentration under reduced pressure. The concentrated compound was purified using silica gel chromatography (petroleum ether (PE):ethyl acetate (EA)=50:1 to 5:1) to obtain the title compound as a colorless oil (140 g, 664.2 mmol, 71.65% yield, 89.49% purity, 65.5% e.e).

¹H NMR (400 MHz, CHLOROFORM-d) δ 7.33 (m, 1H), 7.16-7.07 (m, 2H), 7.02-6.96 (m, 1H), 4.96 (m, 1H), 3.75 (m, 1H), 3.57 (m, 1H), 2.26-2.15 (m, 2H).

Step 5: Preparation of tert-butyl (S)-(3-(3-fluorophenyl)-3-hydroxypropoxy)carbamate Tert-butyl hydroxycarbamate (50.4 g, 378.52 mmol, 1.05 eq.) was dissolved in dimethylformamide (DMF; 500 mL), and then sodium hydride (NaH; 15.86 g, 396.55 mmol, 60% purity, 1.1 eq.) was added at 0° C. under a nitrogen atmosphere. The reaction mixture was stirred at 10° C. for 1 hour, and (S)-3-chloro-1-(3-fluorophenyl)propan-1-ol (68 g, 360.5 mmol, 1 eq.) obtained in step 4 above diluted in dimethylformamide (DMF; 180 mL) was added dropwise at 0° C. and stirred at 10° C. for 16 hours. As a result of TLC analysis (petroleum ether (PE):ethyl acetate (EA)=2:1), all of the starting materials disappeared, and the title compound was detected. After the reaction was terminated by adding an aqueous ammonium chloride solution (3 L), the organic layer was extracted using ethyl acetate (2000 mL) and brine (2000 mL). The organic layer was dried over sodium sulfate and concentrated under reduced pressure to obtain the title compound as a light yellow solid (176 g, 616.87 mmol, 85.56% yield).

¹H NMR (400 MHz, CHLOROFORM-d) δ 7.67-7.64 (m, 1H), 7.23-7.17 (m, 1H), 7.08-7.03 (m, 2H), 6.88-6.81 (m, 1H), 4.99-4.84 (m, 1H), 4.02-3.97 (m, 1H), 3.96-3.89 (m, 1H), 1.95-1.89 (m, 1H), 1.88-1.78 (m, 1H), 1.42-1.39 (m, 9H).

Step 6: Preparation of tert-butyl (R)-3-(3-fluorophenyl)isoxazolidin-2-carboxylate Tert-butyl (S)-(3-(3-fluorophenyl)-3-hydroxypropoxy)carbamate (88 g, 308.44 mmol, 1 eq.) obtained in step 5 above and triethylamine (93.63 g, 925.31 mmol, 128.79 mL, 3 eq.) were dissolved in dichloromethane (DCM; 1 L), and then methanesulfonic anhydride (80.59 g, 462.65 mmol, 1.5 eq.) was added slowly at 0° C. The reaction mixture was stirred at 20° C. for 12 hours. As a result of TLC analysis (petroleum ether (PE):ethyl acetate (EA)=3:1), all of the starting materials disappeared, and a new spot was detected. After the reaction was terminated by adding water (2000 mL), the organic layer was extracted using dichloromethane (DCM; 200 mL*3). The organic layer was dried over sodium sulfate, followed by concentration under reduced pressure. The concentrated compound was purified by chromatography (petroleum ether (PE):ethyl acetate (EA)=50:1 to 5:1) to extract 88 g of the title compound having an 82.5% e.e value. The title compound was purified through SFC (column: DAICEL CHIRALPAK AD (250 mm*50 mm, 10 µm); mobile phase: [Neu-MeOH]; B %: 15%-15%, 3.4 min; 380 min) to obtain the title compound as a white solid (51 g, 189.66 mmol, 30.74% yield, 99.4% purity).

The purity of the optical isomer of tert-butyl (R)-3-(3-fluorophenyl)isoxazolidin-2-carboxylate obtained in step 6 above was analyzed under SFC conditions as follows.

Instrument: CAS-WH-ANA-SFC-C(SHIMADZU LC-30ADsf)

Column: Amycoat 50×4.6 mm I.D., 3 um

Mobile phase: Phase A for $CO_2$, and Phase B for MeOH (0.05% DEA);

Gradient elution: MeOH (0.05% DEA) in $CO_2$ from 5% to 40%

Flow rate: 3 mL/min; Detector: PDA;

Column Temp: 35° C.; Back Pressure: 100 Bar

When the purity of the optical isomer of tert-butyl (R)-3-(3-fluorophenyl)isoxazolidin-2-carboxylate obtained in step 6 was low, the desired optical isomer as a yellow liquid was obtained by performing purification under SFC conditions as follows.

Column: DAICEL CHIRALPAK AD-H (250 mm*30 mm, 5 um);

Mobile phase: [0.1% NH$_3$H$_2$O MeOH]; B %: 15%-15%, 3.8 min; 600 min

Step 7: Preparation of (R)-3-(3-fluorophenyl)isoxazolidine

Tert-butyl (R)-3-(3-fluorophenyl)isoxazolidin-2-carboxylate (50 g, 185.94 mmol, 1 eq.) obtained in step 6 above was dissolved in ethyl acetate (EA; 200 mL), and then HCl/EtOAc (4M, 300 mL, 6.45 eq.) was added at 0° C. Next, the reaction mixture was stirred at 10° C. for 1 hour. As a result of LCMS analysis, all of the starting materials disappeared and the reaction mixture was concentrated under reduced pressure to obtain a solid to thereby yield the title compound as a white solid (32 g, 150.26 mmol, 80.81% yield, 95.62% purity, 100% e.e. HCl).

MS: m/z 168.2 [M+H]$^+$ $^1$H NMR (400 MHz, DMSO-d$_6$) δ 7.53-7.43 (m, 2H), 7.39 (d, J=7.8 Hz, 1H), 7.30-7.23 (m, 1H), 5.01 (t, J=8.0 Hz, 1H), 4.47 (m, 1H), 4.27 (m, 1H), 2.87 (m, 1H), 2.62-2.52 (m, 1H).

The following conditions were employed for purification or analysis of optical isomers of the compound in step 7 above.

Instrument: CAS-WH-ANA-SFC-C(SHIMADZU LC-30ADsf)
Column: Chiralpak AY-3 50×4.6 mm I.D., 3 um;
Mobile phase: Phase A for CO$_2$, and Phase B for IPA (0.05% DEA);
Gradient elution: B in A from 5% to 40%;
Flow rate: 3 mL/min; Detector: PDA;
Column Temp: 35° C.; Back Pressure: 100 Bar Preparation Examples 4 to 44

The following compounds of Preparation Examples 4 to 44 were prepared in a manner similar to those of Preparation Examples 1 to 3 above, and the compounds of Preparation Examples 1 to 44 were employed to prepare the Example compounds of the present disclosure.

<Preparation Example 4> Preparation of (R)-3-(3,5-difluorophenyl)isoxazolidine

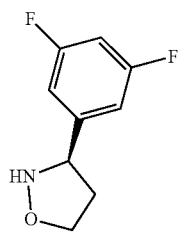

$^1$H NMR (400 MHz, DMSO-d$_6$) δ 7.36-7.27 (m, 3H), 5.04-4.98 (t, J=7.6 Hz, 1H), 4.46-4.36 (m, 1H), 4.25-4.19 (dd, J=7.6, 15.2 Hz, 1H), 2.90-2.78 (m, 1H), 2.56-2.51 (m, 1H).

<Preparation Example 5> Preparation of (R)-3-(2,5-difluorophenyl)isoxazolidine

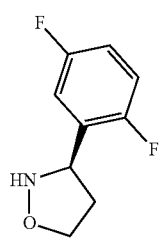 [SMILES: Fc1ccc(F)c([C@H]2CCON2)c1]

<Preparation Example 6> Preparation of (R)-3-(4-fluorophenyl)isoxazolidine

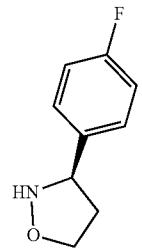

<Preparation Example 7> Preparation of (R)-3-(3-chloro-4-fluorophenyl)isoxazolidine

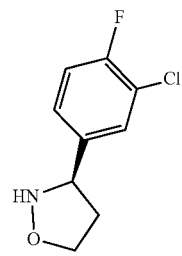 [SMILES: Fc1ccc([C@H]2CCON2)cc1Cl]

$^1$H NMR (400 MHz, DMSO-d$_6$) δ 7.82-7.89 (dd, J=2, 7.2, 1H), 7.56-7.51 (s, J=15.6, 2H), 5.00-4.96 (m, 1H), 4.46-4.40 (m, 1H), 4.24-4.20 (m, 1H), 2.85-2.82 (m, 1H), 2.54-2.52 (m, 1H).

<Preparation Example 8> Preparation of (R)-3-(3-chloro-2-fluorophenyl)isoxazolidine

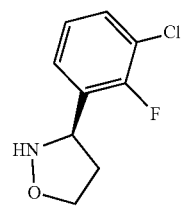 [SMILES: Fc1c(Cl)cccc1[C@H]1CCON1]

$^1$H NMR (400 MHz, DMSO-d$_6$) δ 7.49-7.42 (m, 2H), 7.20-7.16 (m, 1H), 6.56 (s, 1H), 4.66-4.65 (m, 1H), 3.96-3.91 (m, 1H), 3.67-3.65 (m, 1H), 2.66-2.61 (m, 1H), 2.08-2.01 (m, 1H).

<Preparation Example 9> Preparation of (R)-3-(3-methoxyphenyl)isoxazolidine

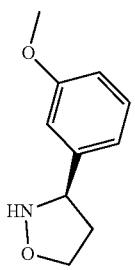

¹H NMR (400 MHz, Chloroform-d) δ 7.25-7.20 (m, 2H), 7.11-7.09 (m, 1H), 6.88-6.86 (m, 1H), 4.80-4.76 (m, 1H), 4.46-4.44 (m, 1H), 4.17-4.15 (m, 1H), 3.76 (s, 3H), 2.69-2.66 (m, 2H).

<Preparation Example 10> Preparation of (R)-3-(6-methylpyridin-3-yl)isoxazolidine

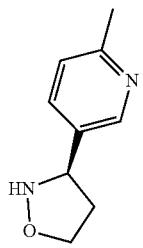

<Preparation Example 11> Preparation of (R)-3-(3-ethynylphenyl)isoxazolidine

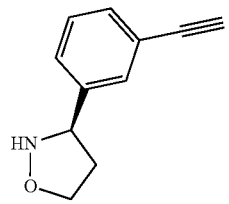

¹H NMR (400 MHz, DMSO-d₆) δ 7.49 (s, 1H), 7.43-7.37 (m, 1H), 7.36-7.29 (m, 2H), 6.41 (s, 1H), 4.38 (s, 1H), 4.15 (s, 1H), 3.90 (m, 1H), 3.71 (s, 1H), 2.65-2.53 (m, 1H), 2.11-2.00 (m, 1H).

<Preparation Example 12> Preparation of (R)-3-methyl-3-phenylisoxazolidine

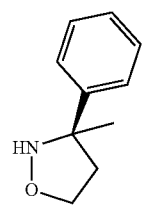

¹H NMR (400 MHz, DMSO-d₆) δ 12.88 (br s, 1H), 7.56-7.46 (m, 2H), 7.44-7.36 (m, 2H), 7.34-7.26 (m, 1H), 3.74-3.62 (m, 1H), 3.46-3.28 (m, 1H), 2.72-2.54 (m, 2H), 1.64 (s, 3H).

<Preparation Example 13> Preparation of (R)-3-(2,4-difluorophenyl)isoxazolidine

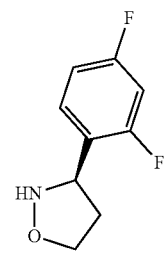

¹H NMR (400 MHz, CHLOROFORM-d) δ 7.52-7.47 (m, 1H), 6.87-6.75 (m, 2H), 5.30 (s, 1H), 4.71-4.68 (m, 1H), 4.09-4.04 (m, 1H), 3.91-3.85 (m, 1H), 2.73-2.64 (3, 1H), 2.24-2.20 (m, 1H).

<Preparation Example 14> Preparation of (R)-3-(naphthalen-1-yl)isoxazolidine

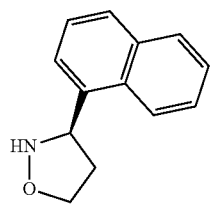 [SMILES: c1ccc2c([C@H]3CCON3)cccc2c1]

¹H NMR (400 MHz, CHLOROFORM-d) δ 8.13 (br s, 1H), 7.89-7.88 (m, 1H), 7.87-7.78 (m, 2H), 7.55-7.48 (m, 3H), 5.54 (br s, 1H), 5.23-5.20 (m, 1H, J=6.4 Hz), 4.15-4.03 (m, 2H), 2.90-2.81 (m, 1H), 2.44-2.41 (m, 1H).

<Preparation Example 15> Preparation of (R)-3-(thiophen-2-yl)isoxazolidine

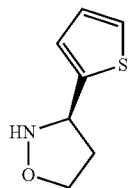

¹H NMR (400 MHz, CHLOROFORM-d) δ 7.23 (d, J=5.0 Hz, 1H), 7.04-6.94 (m, 2H), 4.97-4.58 (m, 2H), 4.11-3.96 (m, 2H), 2.75-2.58 (m, 1H), 2.44-2.33 (m, 1H).

<Preparation Example 16> Preparation of (R)-3-(3-(trifluoromethyl)phenyl)isoxazolidine

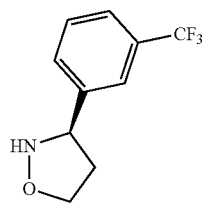

¹H NMR (400 MHz, CHLOROFORM-d) δ 7.65 (s, 1H), 7.59 (d, J=7.7 Hz, 1H), 7.53 (d, J=7.8 Hz, 1H), 7.46 (t, J=7.7 Hz, 1H), 5.64-5.19 (m, 1H), 4.58 (t, J=7.2 Hz, 1H), 4.11 (td, J=8.2, 5.2 Hz, 1H), 3.94 (s, 1H), 2.80-2.67 (m, 1H), 2.36-2.23 (m, 1H).

<Preparation Example 17> Preparation of (R)-3-(naphthalen-2-yl)isoxazolidine

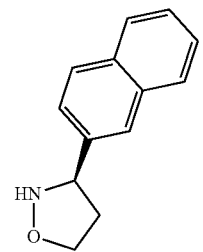 [SMILES: c1ccc2cc([C@H]3CCON3)ccc2c1]

¹H NMR (400 MHz, CHLOROFORM-d) δ 7.91-7.81 (m, 4H), 7.56-7.46 (m, 3H), 5.80-5.00 (m, 1H), 4.68 (t, J=7.2 Hz, 1H), 4.19-3.99 (m, 2H), 2.80-2.72 (m, 1H), 2.45-2.37 (m, 1H).

<Preparation Example 18> Preparation of (R)-3-(3,4-difluorophenyl)isoxazolidine

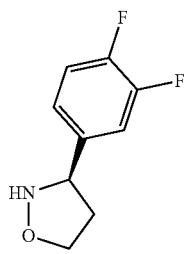 [SMILES: Fc1ccc([C@H]2CCON2)cc1F]

¹H NMR (400 MHz, CHLOROFORM-d) δ 7.24-7.19 (m, 1H), 7.12-7.06 (m, 2H), 5.24 (s, 1H), 4.46 (dd, J1=8.4 Hz, J2=5.6 Hz, 1H), 4.05 (dt, J1=8.0 Hz, J2=5.2 Hz, 1H), 3.91-3.85 (m, 1H), 2.70-2.61 (m, 1H), 2.25-2.17 (m, 1H).

<Preparation Example 19> Preparation of (R)-3-(2,3-difluorophenyl)isoxazolidine

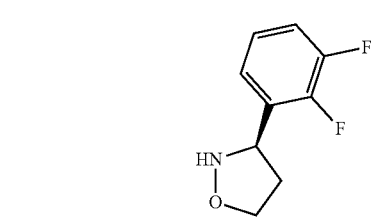 [SMILES: Fc1cccc([C@H]2CCON2)c1F]

¹H NMR (CHLOROFORM-d, 400 MHz) δ 7.29-7.27 (m, 1H), 7.06-7.02 (m, 2H), 5.44 (br s, 1H), 4.75 (dd, J1=4.4 Hz, J2=8.4 Hz, 1H), 4.08 (dt, J1=5.2 Hz, J2=8.0 Hz, 1H), 3.86 (q, J=8.0 Hz, 1H), 2.76-2.66 (m, 1H), 2.27-2.19 (m, 1H).

<Preparation Example 20> Preparation of (R)-3-(3-chloro-2,4-difluorophenyl)isoxazolidine

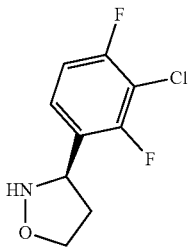

¹H NMR (DMSO-d6, 400 MHz) δ 7.51 (dt, J=6.8, 8.4 Hz, 1H), 7.28 (dt, J=2.0, 8.8 Hz, 1H), 6.60 (br s, 1H), 4.64 (br s, 1H), 3.94 (dt, J=5.2, 8.0 Hz, 1H), 3.76-3.57 (m, 1H), 2.68-2.61 (m, 1H), 2.10-2.01 (m, 1H).

<Preparation Example 21> Preparation of (R)-3-(4-chloro-2-fluorophenyl)isoxazolidine

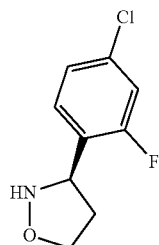

¹H NMR (400 MHz, DEUTERIUM OXIDE) δ 7.48-7.38 (m, 1H), 7.34-7.22 (m, 2H), 5.29-5.20 (m, 1H), 4.58-4.50 (m, 1H), 4.36-4.27 (m, 1H), 2.96-2.84 (m, 1H), 2.79-2.66 (m, 1H).

<Preparation Example 22> Preparation of (R)-3-(4-chloro-3-fluorophenyl)isoxazolidine

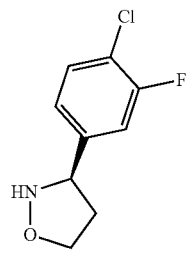

<Preparation Example 23> Preparation of (R)-3-(isoxazolidin-3-yl)-N,N-dimethylaniline

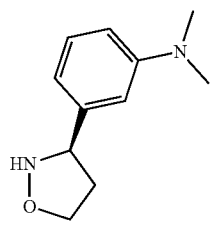

<Preparation Example 24> Preparation of (S)-3-(5-fluoropyridin-3-yl)isoxazolidine

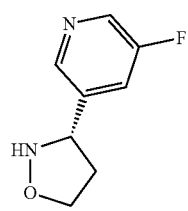

<Preparation Example 25> Preparation of (R)-3-(5-fluoropyridin-3-yl)isoxazolidine

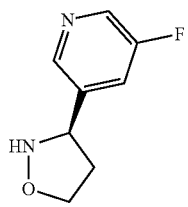 [SMILES: Fc1cncc([C@H]2CCON2)c1]

<Preparation Example 26> Preparation of (R)-3-fluoro-5-(isoxazolidin-3-yl)benzonitrile

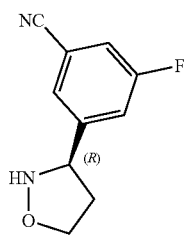

<Preparation Example 27> Preparation of (S)-3-fluoro-5-(isoxazolidin-3-yl)benzonitrile

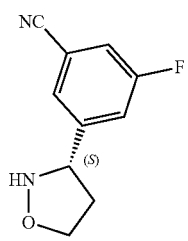

<Preparation Example 28> Preparation of (R)-3-(1-methyl-1H-pyrazol-4-yl)isoxazolidine

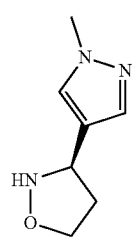

<Preparation Example 29> Preparation of (R)-3-(furan-2-yl)isoxazolidine

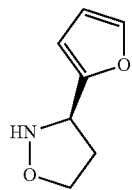

<Preparation Example 30> Preparation of (R)-3-(5-chloropyridin-3-yl)isoxazolidine

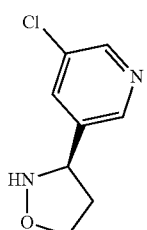

<Preparation Example 31> Preparation of (S)-3-(5-chloropyridin-3-yl)isoxazolidine

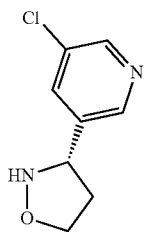 [SMILES: Clc1cncc([C@@H]2CCON2)c1]

<Preparation Example 32> Preparation of (R)-3-(3-difluoromethyl)phenyl)isoxazolidine

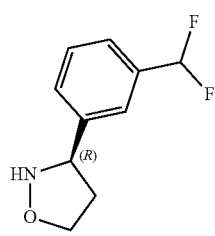

<Preparation Example 33> Preparation of (S)-3-(3-(difluoromethyl)phenyl)isoxazolidine

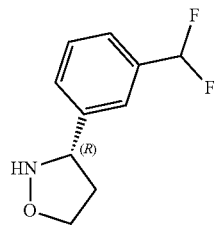

<Preparation Example 34> Preparation of (R)-3-(2-fluoro-3-(trifluormethyl)phenyl)isoxazolidine

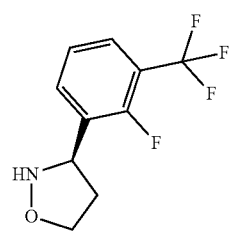 [SMILES: Fc1c([C@H]2CCON2)cccc1C(F)(F)F]

<Preparation Example 35> Preparation of (S)-3-benzylisoxazolidine

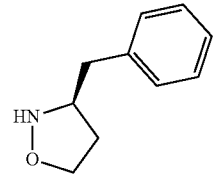 [SMILES: c1ccc(C[C@H]2CCON2)cc1]

$^1$H NMR (400 MHz, CHLOROFORM-d) δ 12.7-12.4 (m, 1H), 7.28-7.18 (m, 5H), 4.42-4.32 (m, 1H), 4.25-4.10 (m, 2H), 3.50 (dd, J=4.8, 13.6 Hz, 1H), 3.03 (dd, J=10.4, 13.2 Hz, 1H), 2.44-2.33 (m, 1H), 2.32-2.20 (m, 1H).

<Preparation Example 36> Preparation of isopropyl (R)-3-(isoxazolidin-3-yl)benzoate

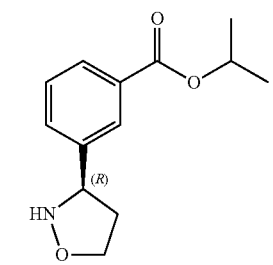

The desired title compound was prepared in a manner similar to that of <Preparation Example 3> using 3-(isopropoxycarbonyl)benzoic acid prepared in <Preparation Example 36-1> below as an intermediate.

<Preparation Example 36-1> Preparation of 3-(isopropoxycarbonyl)benzoic acid

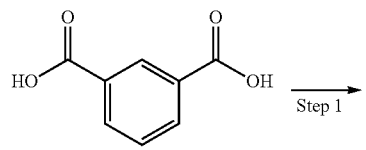

Step 1: Preparation of 3-(isopropoxycarbonyl)benzoic acid

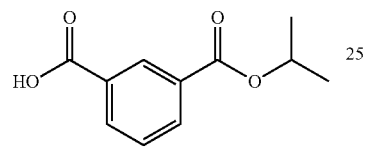

Isophthalic acid (40 g, 1 eq.) was dissolved in isopropyl alcohol (150 mL) and tetrahydrofuran (THF; 450 mL), and then sulfuric acid (concentrated $H_2SO_4$; 38.5 mL, 3 eq.) was added. The reaction mixture was stirred at 75° C. for 48 hours. After the reaction was completed, the organic solvent was subjected to concentration under reduced pressure, and the organic layer was extracted using ethyl acetate (EA; 500 mL) and water (200 mL). The organic layer was dried over sodium sulfate, followed by concentration under reduced pressure. The concentrated compound was purified by chromatography (dichloromethane/methanol=8/1) to obtain the title compound as a clear oil (23.25 g, 46.5% yield).

<Preparation Example 37> Preparation of (R)-3-(isoxazolidin-3-yl)benzoic acid

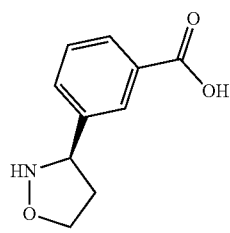 [SMILES: O=C(O)c1cccc([C@H]2CCON2)c1]

The desired title compound was prepared by hydrolyzing the isopropyl (R)-3-(isoxazolidin-3-yl)benzoate obtained in <Preparation Example 36> with an aqueous base solution.

<Preparation Example 38> Preparation of (R)—N-cyclohexyl-3-(isoxazolidin-3-yl)benzamide

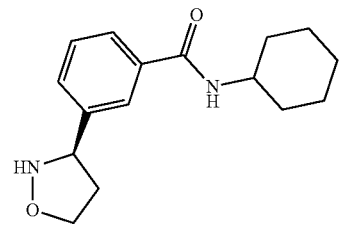

The desired title compound was prepared by introducing an amide functional group by a method such as HATU employing the (R)-3-(isoxazolidin-3-yl)benzoic acid obtained in <Preparation Example 37>.

<Preparation Example 39> Preparation of (R)-3-(3-(benzyloxy)phenyl)isoxazolidine

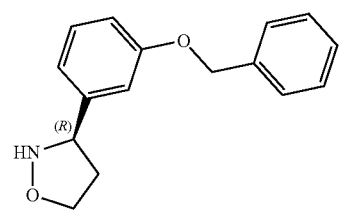

The desired title compound was prepared in a manner similar to that of <Preparation Example 3> using 3-(benzyloxy)-N-methoxy-N-methylbenzamide prepared in <Preparation Example 39-1> below as an intermediate.

<Preparation Example 39-1> Preparation of 3-(benzyloxy)-N-methoxy-N-methylbenzamide

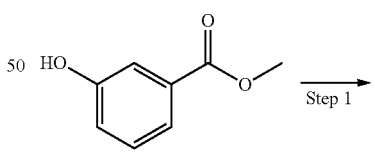

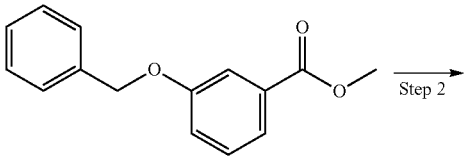

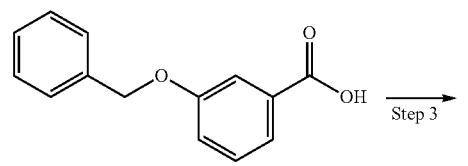

-continued

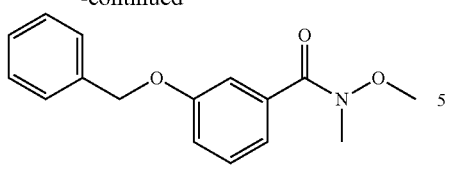

Step 1: Preparation of methyl 3-(benzyloxy)benzoate

Methyl 3-hydroxybenzoate (20 g, 1.0 eq.) was dissolved in acetone (260 mL), and then (bromomethyl)benzene (18.76 ml 1.2 eq.) and potassium carbonate (54.5 g, 3 eq.) were added. The reaction mixture was stirred at 60° C. for 16 hours. As a result of TLC analysis (hexane:ethyl acetate=3:2), all of the starting materials disappeared and the title compound was detected. The reaction mixture was concentrated under reduced pressure, dichloromethane (DCM; 300 mL*2) and water (200 mL) were added to extract the organic layer. The organic layer was dried over sodium sulfate, and then concentrated under reduced pressure. The concentrated compound was recrystallized using hexane to obtain the title compound as a white solid (29.27 g, 92% yield).

Step 2: Preparation of 3-(benzyloxy)benzoic acid

Methyl 3-(benzyloxy)benzoate (29 g, 1.0 eq.) obtained in step 1 was dissolved in methanol (MeOH; 300 ml), and potassium hydroxide (KOH; 6M, 4.5 eq.) was added. Next, the reaction mixture was stirred at 80° C. for 3 hours. As a result of TLC analysis (hexane:ethyl acetate=7:3), all of the starting materials disappeared and a new spot with low polarity was detected. The reaction mixture was concentrated under reduced pressure, water (100 ml) was added and hydrochloric acid (3N) was added dropwise to acidify the reaction solution to pH 1. The resulting precipitate was filtered under reduced pressure and dried to obtain the title compound as a white solid (27 g, 99% yield).

Step 3: Preparation of 3-(benzyloxy)-N-methoxy-N-methylbenzamide 3-(Benzyloxy)benzoic acid (20 g, 1.0 eq.) obtained in step 2 was dissolved in dichloromethane (DCM; 700 ml), and 1,1-carboxyldiimidazole (9.40 g, 1.1 eq.) was slowly added. The reaction mixture was stirred at room temperature for 2 hours, then N,O-dimethylhydroxylamine hydrochloride (15.63 g, 1.1 eq.) was added and the resulting mixture was stirred at 40° C. for 18 hours. UPLC/MS analysis was performed, and as a result, all of the starting material disappeared, and the title compound was detected. The reaction mixture was washed with hydrochloric acid (1N, 500 ml) and a saturated aqueous sodium hydrogen carbonate solution (500 ml), dried over sodium sulfate, and then concentrated under reduced pressure to obtain the title compound as a pale yellow oil (90 g, 85% yield).

<Preparation Example 40> Preparation of (R)-3-(3-phenoxyphenyl)isoxazolidine

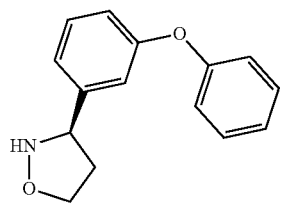 [SMILES: c1ccc(Oc2cccc([C@H]3CCON3)c2)cc1]

The desired title compound was prepared in a manner similar to that of <Preparation Example 39>.

<Preparation Example 41> Preparation of (R)-3-(3-bromo-5-fluorophenyl)isoxazolidine hydrochloride

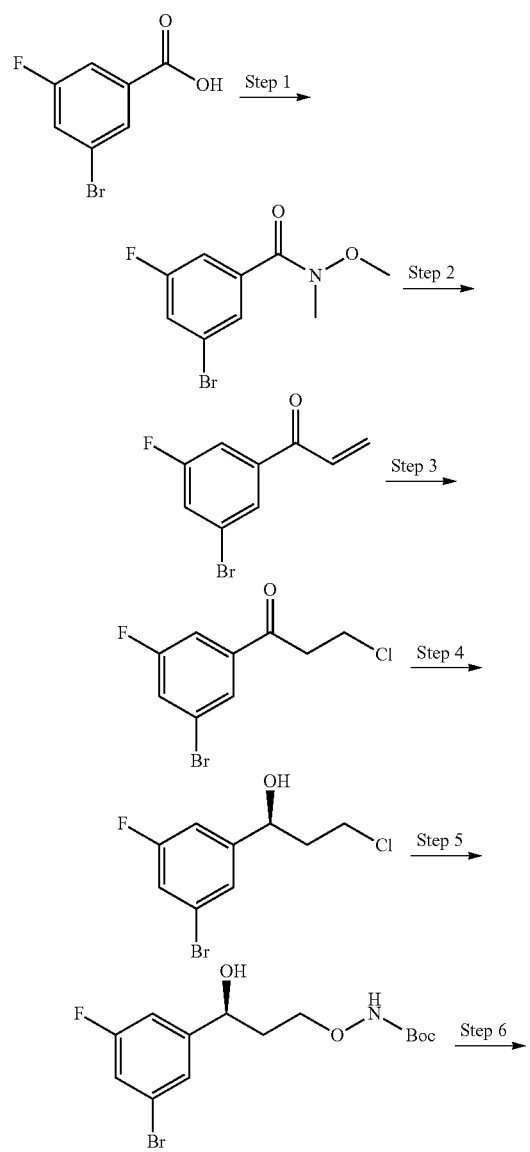

-continued

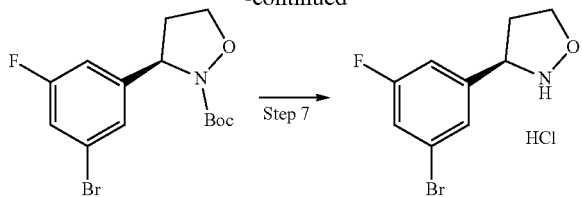

Step 1: Preparation of 3-bromo-5-fluoro-N-methoxy-N-methylbenzamide

3-Bromo-5-fluorobenzoic acid (10 g, 1 eq.) was dissolved in dichloromethane (110 mL), and then N,O-dimethylhydroxylamine hydrochloride (5.4 g, 1.2 eq.), triethylamine (TEA; 5.7 mL, 0.9 eq.), and 1-ethyl-3-(3-dimethylaminopropyl)carbodiimide (EDCI; 11.5 g, 1.2 eq.) were added sequentially at room temperature. The reaction mixture was stirred at room temperature for 3 hours. As a result of TLC analysis (dichloromethane), all of the starting materials disappeared and a new spot with low polarity was detected. The organic layer was extracted using ethyl acetate (EA; 300 mL) and a saturated aqueous sodium hydrogen carbonate solution (400 mL*2). The organic layer was dried over sodium sulfate and concentrated under reduced pressure to obtain the title compound as a yellow oil (11.2 g, 94.0% yield).

Step 2: Preparation of 1-(3-bromo-5-fluorophenyl)prop-2-en-1-one

3-Bromo-5-fluoro-N-methoxy-N-methylbenzamide (11.2 g, 1 eq.) obtained in step 1 was dissolved in tetrahydrofuran (THF; 220 mL), and then bromo(vinyl)magnesium (0.7M, 93 mL, 1.5 eq.) was added dropwise at 0° C. Next, the reaction mixture was stirred at 0° C. for 1 hour. As a result of TLC analysis (hexane:dichloromethane=1:1), all of the starting materials disappeared and a new spot with low polarity was detected. The reaction was terminated by adding hydrochloric acid (1N, 50 mL), and then the organic layer was extracted using ethyl acetate (EA; 300 mL) and hydrochloric acid (1N, 400 mL*2). The organic layer was dried over sodium sulfate, and then concentrated under reduced pressure. The concentrated compound was purified by chromatography (hexane:dichloromethane=1:1) to obtain the title compound as a colorless oil (7.9 g, 76% yield).

Step 3: Preparation of 1-(3-bromo-5-fluorophenyl)-3-chloropropan-1-one 1-(3-Bromo-5-fluorophenyl)prop-2-en-1-one (7.9 g, 1.0 eq.) obtained in Step 2 was dissolved in dichloromethane (DCM; 13 mL), and then HCl/dioxane (4M, 13 mL, 1.2 eq.) was added at 0° C. Then, the reaction mixture was stirred at room temperature for 12 hours. As a result of TLC analysis (hexane:dichloromethane=1:1), all of the starting materials disappeared, and the title compound was detected. The reaction mixture was concentrated under reduced pressure, and ethyl acetate (EA; 300 mL) and a saturated aqueous sodium hydrogen carbonate solution (400 mL*2) were added to extract the organic layer. The organic layer was dried over sodium sulfate and concentrated under reduced pressure to obtain the title compound as a yellow oil (8.9 g, 97% yield).

Step 4: Preparation of (S)-1-(3-bromo-5-fluorophenyl)-3-chloropropan-1-ol (3aR)-1-methyl-3,3-diphenyl-3a,4,5,6-tetrahydropyrrolo[1,2-c][1,3,2]oxazabolol (1M, 6.7 mL, 0.2 eq.) was dissolved in tetrahydrofuran (THF; 84 mL), and then borane dimethylsulfide ($BH_3 \cdot Me_2S$; 1M, 21.8 mL, 1.3 eq.) was added dropwise at 0° C. under a nitrogen atmosphere. The reaction mixture was stirred at 0° C. for 30 min, and then 1-(3-bromo-5-fluorophenyl)-3-chloropropan-1-one (8.9 g, 1 eq.) obtained in step 3 and diluted in tetrahydrofuran was added dropwise at 0° C. The reaction mixture was stirred at 0° C. for 2 hours. As a result of TLC analysis (hexane:dichloromethane=1:1), all of the starting materials disappeared, and a spot of the title compound was detected. The reaction was terminated by adding methanol (20 mL) at 20° C., and then the solvent was distilled off under reduced pressure. The concentrated compound was treated with ethyl acetate (EA; 300 mL) and hydrochloric acid (1N, 400 mL*2) to extract the organic layer. The organic layer was dried over sodium sulfate and concentrated under reduced pressure to obtain the title compound as a yellow oil (8.5 g, 95% yield).

Step 5: Preparation of tert-butyl (S)-(3-(3-bromo-5-fluorophenyl)-3-hydroxypropoxy)carbamate Tert-butyl hydroxycarbamate (9.3 g, 2.2 eq.) was dissolved in dimethylformamide (DMF; 80 mL), and then sodium hydride (NaH; 3.1 g, 60% purity, 2.4 eq.) was added at 0° C. under a nitrogen atmosphere. The reaction mixture was stirred at 0° C. for 30 min. (S)-1-(3-bromo-5-fluorophenyl)-3-chloropropan-1-ol (8.5 g, 1 eq.) obtained in step 4 and diluted in dimethylformamide (DMF; 10 mL) was added dropwise at 0° C. and stirred at room temperature for 12 hours. As a result of TLC analysis (dichloromethane:EA=9:1), all of the starting materials disappeared, and the title compound was detected. The reaction was terminated by adding brine (50 mL), and then the organic layer was extracted using ethyl acetate (EA; 300 mL) and a saturated aqueous sodium hydrogen carbonate solution (400 mL*3). The organic layer was dried over sodium sulfate and concentrated under reduced pressure to obtain the title compound as a yellow oil (9.2 g, 79% yield).

Step 6: Preparation of tert-butyl (R)-3-(3-bromo-5-fluorophenyl)isoxazolidin-2-carboxylate Tert-butyl (S)-(3-(3-bromo-5-fluorophenyl)-3-hydroxypropoxy)carbamate (9.2 g, 1 eq.) obtained in step 5 and triphenylphosphine ($Ph_3P$; 8.6 g, 1.3 eq.) were dissolved in dichloromethane (DCM; 110 mL), and then diisopropyl azodicarboxylate (DIAD; 6.6 g, 1.3 eq.) diluted in dichloromethane (DCM; 20 mL) was added slowly at 0° C. The reaction mixture was stirred at 0° C. for 2 hours. As a result of TLC analysis (dichloromethane (DCM):ethyl acetate (EA)=9:1), all of the starting materials disappeared, and a new spot was detected. The reaction mixture was concentrated under reduced pressure, and the concentrated compound was purified by chromatography (dichloromethane:ethyl acetate=10:0 to 9:1) to obtain the title compound as a yellow oil (7.7 g, 88% yield).

Step 7: Preparation of (R)-3-(3-bromo-5-fluorophenyl)isoxazolidine hydrochloride Tert-butyl (R)-3-(3-bromo-5-fluorophenyl)isoxazolidin-2-carboxylate (7.7 g, 1 eq.) obtained in step 6 was dissolved in dichloromethane (DCM; 40 mL), and then HCl/dioxane (4M, 28 mL, 5 eq.) was added at room temperature. Then, the reaction mixture was stirred at room temperature for 2 hours. As a result of LCMS analysis, all of the starting materials disappeared, diethyl ether (200 mL) was added to obtain a solid, and the resulting precipitate was filtered and dried to obtain the title compound as a white solid (5.3 g, 84% yield).

The following conditions were employed for purification or analysis of optical isomers of the compound in step 7 above.

Instrument: CAS-WH-ANA-SFC-C(SHIMADZU LC-30ADsf)
Column: Chiralpak AY-3 50×4.6 mm I.D., 3 um;
Mobile phase: Phase A for $CO_2$, and Phase B for IPA (0.05% DEA);
Gradient elution: B in A from 5% to 40%;
Flow rate: 3 mL/min; Detector: PDA;
Column Temp: 35° C.; Back Pressure: 100 Bar
(R)-3-(3-Bromo-5-fluorophenyl)isoxazolidine hydrochloride (5.3 g) obtained in step 7 was purified under SFC conditions as follows to obtain the desired optical isomer (100% purity, 100% e.e.).
Column: DAICEL CHIRALPAK AD-H (250 mm*30 mm, 5 um);
Mobile phase: [0.1% $NH_3H_2O$ MeOH]; B %: 15%-15%, 3.8 min; 600 min
$^1H$ NMR (400 MHz, DMSO-d6) δ 7.62-7.58 (m, 2H), 7.43 (dt, J=9.8, 2.0 Hz, 1H), 4.93 (t, J=7.4 Hz, 1H), 4.36 (td, J=8.1, 4.4 Hz, 1H), 4.12 (q, J=7.8 Hz, 1H), 2.81 (dtd, J=12.4, 7.9, 4.4 Hz, 1H), 2.49-2.41 (m, 1H).

<Preparation Example 42> Preparation of (R)-3-(3',5-difluoro-[1,1'-biphenyl]-3-yl)isoxazolidine hydrochloride

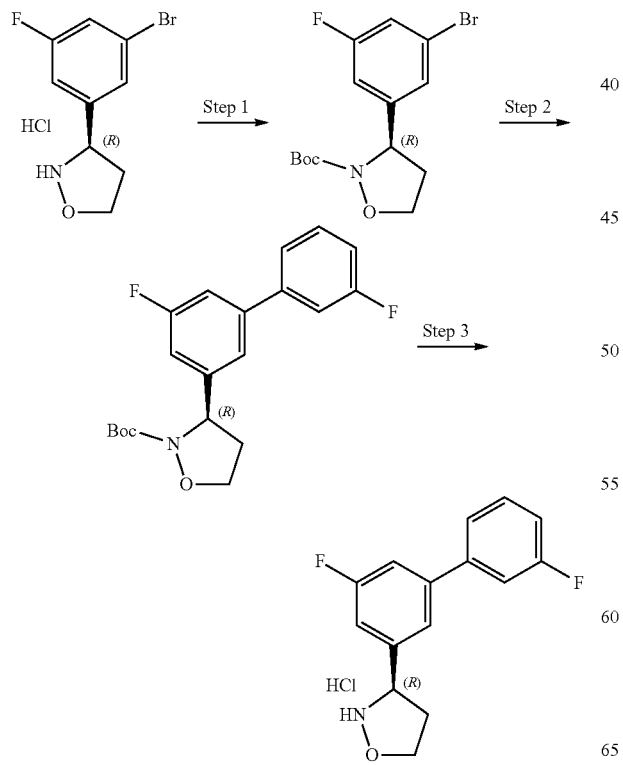

Step 1: Preparation of tert-butyl (R)-3-(3-bromo-5-fluorophenyl)isoxazolidin-2-carboxylate (R)-3-(3-Bromo-5-fluorophenyl)isoxazolidine hydrochloride (1 g, 1 eq.) obtained in <Preparation Example 41> and triethylamine (TEA; 1.5 mL, 3 eq.) were dissolved in tetrahydrofuran (7 mL), and then di-tert-butyl dicarbonate ($Boc_2O$; 1.0 mL, 1.2 eq.) was slowly added at 0° C. Next, the reaction mixture was stirred at 50° C. for 2 hours. As a result of TLC analysis (DCM), all of the starting materials disappeared and a new spot with different polarity was detected. The organic layer was extracted using ethyl acetate (EA; 70 mL) and a saturated aqueous sodium hydrogen carbonate solution (100 mL*2). The organic layer was dried over sodium sulfate and concentrated under reduced pressure to obtain the title compound as a pale yellow oil (1.1 g, 95% yield).

Step 2: Preparation of tert-butyl (R)-3-(3',5-difluoro-[1,1'-biphenyl]-3-yl)isoxazolidin-2-carboxylate Tert-butyl (R)-3-(3-bromo-5-fluorophenyl)isoxazolidin-2-carboxylate obtained in step 1 (350 mg, 1 eq.), (3-fluorophenyl)boronic acid (170 mg, 1.2 eq.), and $K_2CO_3$ (280 mg, 2 eq.) were dissolved in 1,4-dioxane (5 mL) at room temperature under a nitrogen atmosphere. Next, tetrakis (triphenylphosphine)palladium(0) (110 mg, 0.1 eq.) was added to the reaction mixture at 80° C. and stirred for 3 hours. As a result of TLC analysis (DCM), all of the starting materials disappeared and a new spot with different polarity was detected. The organic layer was extracted using ethyl acetate (EA; 70 mL) and a saturated aqueous sodium hydrogen carbonate solution (100 mL*2). The organic layer was dried over sodium sulfate, and then concentrated under reduced pressure. The concentrated compound was purified by chromatography (hexane:dichloromethane=5:5 to 0:10) to obtain the title compound as a colorless oil (320 mg, 88% yield).

Step 3: Preparation of (R)-3-(3',5-difluoro-[1,1'-biphenyl]-3-yl)isoxazolidine hydrochloride Tert-butyl (R)-3-(3',5-difluoro-[1,1'-biphenyl]-3-yl)isoxazolidin-2-carboxylate (320 mg, 1 eq.) obtained in step 2 was dissolved in dichloromethane (DCM; 40 mL), and then HCl/dioxane (4M, 1 mL, 5 eq.) was added at room temperature. Then, the reaction mixture was stirred at room temperature for 2 hours. As a result of LCMS analysis, all of the starting materials disappeared, diethyl ether (10 mL) was added to obtain a solid, and the resulting precipitate was filtered and dried to obtain the title compound as a white solid (240 mg, 91% yield).

<Preparation Example 43> Preparation of (R)-3-(3-([1,2,4]triazolo[1,5-a]pyridin-7-yl)phenyl)isoxazolidine

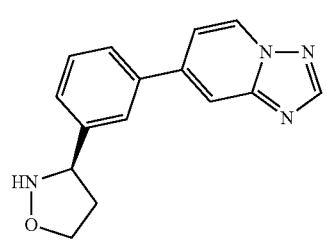 [SMILES: c1cc(-c2ccn3ncnc3c2)cc([C@H]2CCON2)c1]

The desired title compound was prepared in a manner similar to that of <Preparation Example 42>.

<Preparation Example 44> Preparation of (R)-3-(3-fluoro-5-thiomorpholinophenyl)isoxazolidine

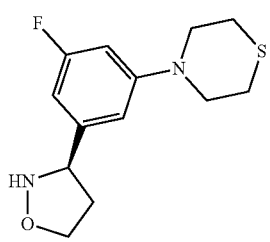 [SMILES: Fc1cc([C@H]2CCON2)cc(N2CCSCC2)c1]

A compound was prepared by a method such as $S_NAr$, or the like, using the compound of <Preparation Example 41>.

<Example 1> Preparation of (R)—N-(4-(4-methylpiperazin-1-yl)phenyl)-6-(3-phenylisoxazolidin-2-yl)pyrimidin-4-amine

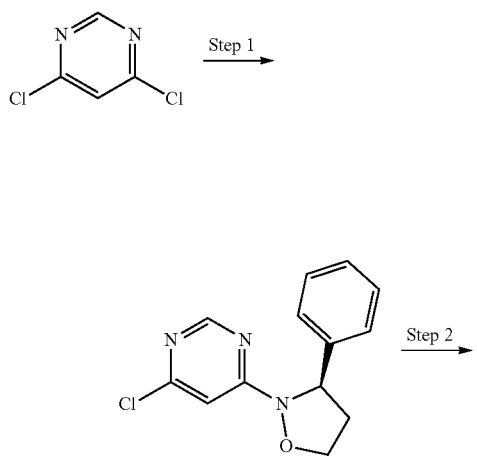

Step 1: Preparation of (R)-2-(6-chloropyrimidin-4-yl)-3-phenylisoxazolidine 4,6-Dichloropyrimidine (600 mg, 1 eq.) and (R)-3-phenylisoxazolidine (631 mg, 1.05 eq.) were dissolved in dimethyl sulfoxide (DMSO, 7 ml), and then N,N-diisopropylethylamine (DIPEA; 1.41 mL, 2 eq.) was added. The reaction solution was stirred at 60° C. for 30 min. After the reaction was completed, the reaction solution was extracted using ethyl acetate and water. The combined organic layers were washed with brine, dried over anhydrous sodium sulfate, concentrated under reduced pressure, and purified by MPLC (ethyl acetate/hexane) to obtain the title compound (810 mg, 77% yield) as a clear liquid.

Step 2: Preparation of (R)—N-(4-(4-methylpiperazin-1-yl)phenyl)-6-(3-phenylisoxazolidin-2-yl)pyrimidin-4-amine (R)-2-(6-chloropyrimidin-4-yl)-3-phenylisoxazolidine (139 mg, 1 eq.) obtained in step 1, 4-(4-methylpiperazin-1-yl)aniline (152 mg, 1.5 eq.), and potassium carbonate (220 mg, 3 eq.) were added to and dissolved in sec-butanol (1.8 ml), followed by sonication for 5 min under nitrogen to degas. Tris(dibenzylideneacetone)dipalladium(0) ($Pd_2(dba)_3$; 47 mg, 0.1 eq.) and Xphos (51 mg, 0.2 eq.) were added to the reaction mixture and stirred at 100 for 1 hour. After the reaction was completed, the mixture was filtered through celite and washed with dichloromethane. The resulting filtrate was concentrated and purified by Prep-HPLC to obtain the title compound (71 mg, 32%).

$^1$H NMR (400 MHz, Chloroform-d) δ 8.23 (s, 1H), 7.42 (d, J=7.4 Hz, 2H), 7.34 (dd, J=8.4, 6.7 Hz, 2H), 7.20-7.16 (m, 2H), 6.97-6.91 (m, 2H), 6.38 (s, 1H), 5.64 (dd, J=8.6, 4.7 Hz, 1H), 4.10 (td, J=7.8, 4.5 Hz, 1H), 3.85 (q, J=7.8 Hz, 1H), 3.23 (t, J=5.1 Hz, 4H), 2.71 (dtd, J=12.2, 7.9, 4.4 Hz, 1H), 2.64 (t, J=5.0 Hz, 4H), 2.38 (s, 3H), 2.37-2.32 (m, 1H), 2.04 (s, 1H).

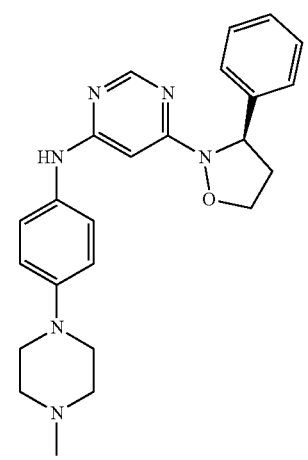

Examples 2 to 237

All of the Example compounds (Example compounds Nos. 1 to 237) of the present disclosure were prepared in a manner similar to that of Example 1. The compound names, chemical structures, and NMR and LCMS analysis results of the respective Example compounds are summarized and shown in Table 1 below.

TABLE 1

| Example Compound | Structure | Compound Name | ¹H NMR; MS [M + H]⁺ |
|---|---|---|---|
| 1 | 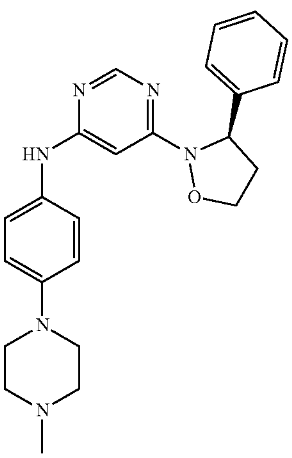 [SMILES: CN1CCN(c2ccc(Nc3cc(N4OCC[C@@H]4c4ccccc4)ncn3)cc2)CC1] | (R)-N-(4-(4-methylpiperazin-1-yl)phenyl)-6-(3-phenylisoxazolidin-2-yl)pyrimidin-4-amine | ¹H NMR (400 MHz, Chloroform-d) δ 8.23 (s, 1H), 7.42 (d, J = 7.4 Hz, 2H), 7.34 (dd, J = 8.4, 6.7 Hz, 2H), 7.20-7.16 (m, 2H), 6.97-6.91 (m, 2H), 6.38 (s, 1H), 5.64 (dd, J = 8.6, 4.7 Hz, 1H), 4.10 (td, J = 7.8, 4.5 Hz, 1H), 3.85 (q, J = 7.8 Hz, 1H), 3.23 (t, J = 5.1 Hz, 4H), 2.71 (dtd, J = 12.2, 7.9, 4.4 Hz, 1H), 2.64 (t, J = 5.0 Hz, 4H), 2.38 (s, 3H), 2.37-2.32 (m, 1H), 2.04 (s, 1H); 417.4 [M + H]⁺ |
| 2 | 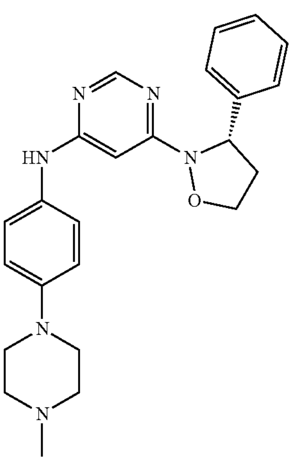 [SMILES: CN1CCN(c2ccc(Nc3cc(N4OCC[C@H]4c4ccccc4)ncn3)cc2)CC1] | (S)-N-(4-(4-methylpiperazin-1-yl)phenyl)-6-(3-phenylisoxazolidin-2-yl)pyrimidin-4-amine | ¹H NMR (400 MHz, Chloroform-d) δ 8.23 (s, 1H), 7.42 (d, J = 7.4 Hz, 2H), 7.34 (dd, J = 8.4, 6.7 Hz, 2H), 7.20-7.16 (m, 2H), 6.97-6.91 (m, 2H), 6.38 (s, 1H), 5.64 (dd, J = 8.6, 4.7 Hz, 1H), 4.10 (td, J = 7.8, 4.5 Hz, 1H), 3.85 (q, J = 7.8 Hz, 1H), 3.23 (t, J = 5.1 Hz, 4H), 2.71 (dtd, J = 12.2, 7.9, 4.4 Hz, 1H), 2.64 (t, J = 5.0 Hz, 4H), 2.38 (s, 3H), 2.37-2.32 (m, 1H), 2.04 (s, 1H); 417.3 [M + H]⁺ |
| 3 | 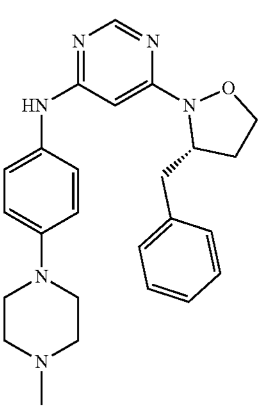 [SMILES: CN1CCN(c2ccc(Nc3cc(N4OCC[C@@H]4Cc4ccccc4)ncn3)cc2)CC1] | (S)-6-(3-benzylisoxazolidin-2-yl)-N-(4-(4-methylpiperazin-1-yl)phenyl)pyrimidin-4-amine | 431.4 [M + H]⁺ |

TABLE 1-continued

| Example Compound | Structure | Compound Name | ¹H NMR; MS [M + H]⁺ |
|---|---|---|---|
| 4 | 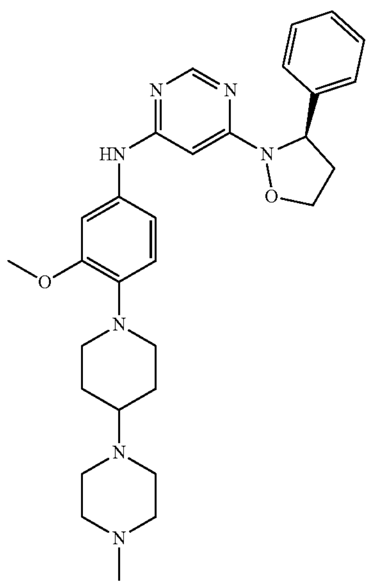 [SMILES: COc1cc(Nc2cc(N3OCC[C@@H]3c3ccccc3)ncn2)ccc1N1CCC(N2CCN(C)CC2)CC1] | (R)-N-(3-methoxy-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.30-8.26 (m, 1H), 7.46-7.41 (m, 2H), 7.34 (t, J = 7.7 Hz, 2H), 7.26-7.22 (m, 1H), 6.96-6.90 (m, 2H), 6.85-6.80 (m, 2H), 6.47-6.43 (m, 1H), 5.66 (dd, J = 8.7, 4.6 Hz, 1H), 4.11 (td, J = 7.8, 4.4 Hz, 1H), 3.89-3.82 (m, 4H), 3.54 (d, J = 11.2 Hz, 2H), 2.76-2.65 (m, 4H), 2.63-2.33 (m, 9H), 2.30 (s, 3H), 1.92 (d, J = 12.3 Hz, 2H), 1.85-1.75 (m, 2H); 530.4 [M + H]⁺ |
| 5 | 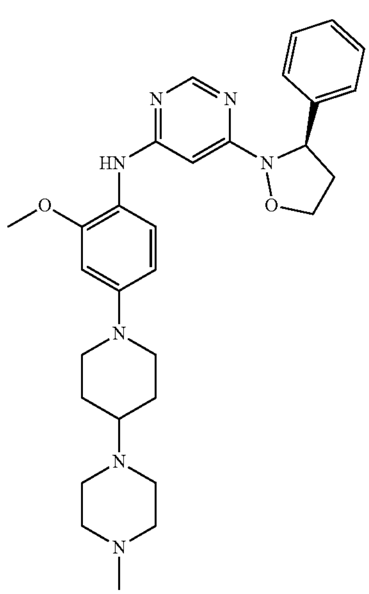 [SMILES: COc1cc(N2CCC(N3CCN(C)CC3)CC2)ccc1Nc1cc(N2OCC[C@@H]2c2ccccc2)ncn1] | (R)-N-(2-methoxy-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.30 (s, 1H), 7.51 (d, J = 8.5 Hz, 1H), 7.45 (d, J = 7.6 Hz, 2H), 7.34 (t, J = 7.5 Hz, 2H), 7.26-7.23 (m, 1H), 6.70 (s, 1H), 6.57-6.51 (m, 2H), 6.41 (s, 1H), 5.68 (dd, J = 8.7, 4.5 Hz, 1H), 4.11 (td, J = 7.8, 4.3 Hz, 1H), 3.92-3.87 (m, 1H), 3.84 (s, 3H), 3.71 (d, J = 12.0 Hz, 2H), 2.78-2.64 (m, 7H), 2.58-2.47 (m, 3H), 2.44-2.35 (m, 3H), 2.32 (s, 3H), 1.96 (d, J = 12.0 Hz, 2H), 1.74-1.67 (m, 2H); 530.4 [M + H]⁺ |

TABLE 1-continued

| Example Compound | Structure | Compound Name | ¹H NMR; MS [M + H]⁺ |
|---|---|---|---|
| 6 | 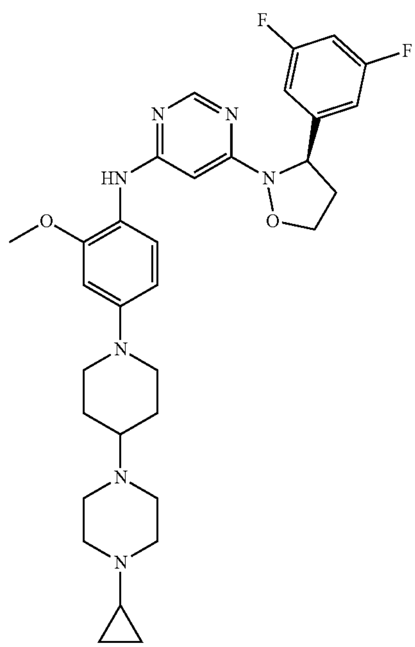 [SMILES: COc1cc(N2CCC(N3CCN(C4CC4)CC3)CC2)ccc1Nc1cc(N2OCC[C@@H]2c2cc(F)cc(F)c2)ncn1] | (R)-N-(4-(4-(4-cyclopropylpiperazin-1-yl)piperidin-1-yl)-2-methoxyphenyl)-6-(3-(3,5-difluorophenyl)isoxazolidin-2-yl)pyrimidin-4-amine | 592.3 [M + H]⁺ |
| 7 | 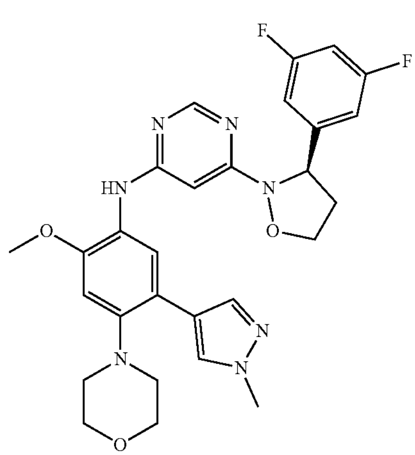 [SMILES: COc1cc(N2CCOCC2)c(-c2cnn(C)c2)cc1Nc1cc(N2OCC[C@@H]2c2cc(F)cc(F)c2)ncn1] | (R)-6-(3-(3,5-difluorophenyl)isoxazolidin-2-yl)-N-(2-methoxy-5-(1-methyl-1H-pyrazol-4-yl)-4-morpholinophenyl)pyrimidin-4-amine | ¹H NMR (400 MHz, Methanol-d4) δ 8.47 (s, 1H), 8.39 (s, 1H), 8.22 (s, 1H), 7.47 (s, 1H), 7.06-6.99 (m, 3H), 6.94 (s, 1H), 5.56 (s, 1H), 4.44 (dt, J = 7.6, 3.8 Hz, 1H), 4.21 (s, 1H), 4.14 (s, 3H), 3.94 (s, 3H), 3.88-3.82 (m, 4H), 3.56-3.51 (m, 1H), 3.11-3.00 (m, 5H), 2.54-2.44 (m, 1H); 550.4 [M + H]⁺ |

TABLE 1-continued

| Example Compound | Structure | Compound Name | 1H NMR; MS [M + H]+ |
|---|---|---|---|
| 8 | 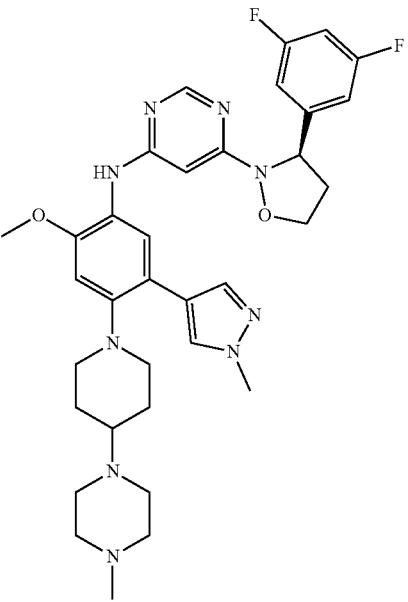 [SMILES: COc1cc(N2CCC(N3CCN(C)CC3)CC2)c(-c2cnn(C)c2)cc1Nc1cc(N2OCC[C@@H]2c2cc(F)cc(F)c2)ncn1] | (R)-6-(3-(3,5-difluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine | 1H NMR (400 MHz, Methanol-d4) δ 8.50 (s, 1H), 8.31 (s, 1H), 8.19 (s, 1H), 7.45 (s, 1H), 7.01 (dt, J = 6.8, 2.1 Hz, 2H), 6.96-6.88 (m, 1H), 6.00 (s, 1H), 5.52 (d, J = 10.1 Hz, 1H), 4.42 (d, J = 4.4 Hz, 1H), 4.17 (s, 4H), 4.06 (s, 1H), 3.91 (s, 5H), 3.81-3.47 (m, 7H), 3.37 (s, 2H), 3.07 (s, 4H), 2.84 (t, J = 11.8 Hz, 2H), 2.48 (d, J = 5.9 Hz, 1H), 2.32 (d, J = 11.7 Hz, 2H), 2.13 (d, J = 9.4 Hz, 2H); 646.5 [M + H]+ |
| 9 | 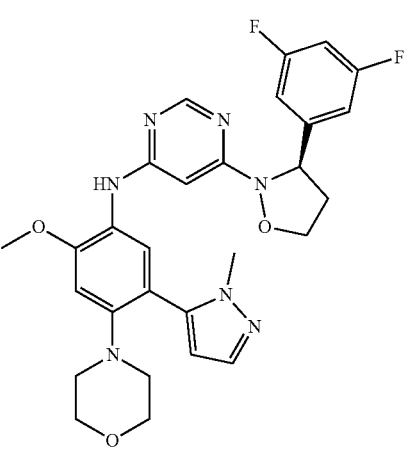 [SMILES: COc1cc(N2CCOCC2)c(-c2ccnn2C)cc1Nc1cc(N2OCC[C@@H]2c2cc(F)cc(F)c2)ncn1] | (R)-6-(3-(3,5-difluorophenyl)isoxazolidin-2-yl)-N-(2-methoxy-5-(1-methyl-1H-pyrazol-5-yl)-4-morpholinophenyl)pyrimidin-4-amine | 550.4 [M + H]+ |

TABLE 1-continued

| Example Compound | Structure | Compound Name | ¹H NMR; MS [M + H]⁺ |
|---|---|---|---|
| 10 | 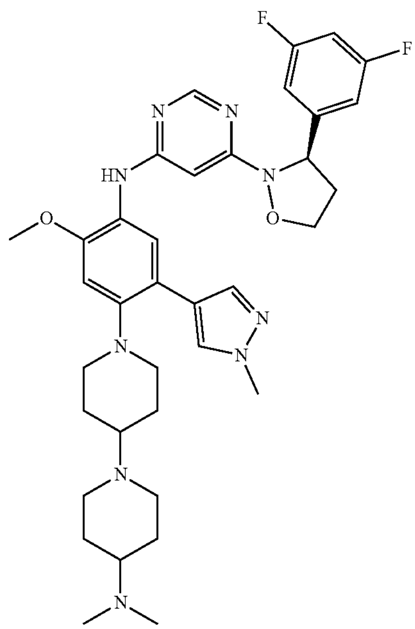 [SMILES: COc1cc(N2CCC(N3CCC(N(C)C)CC3)CC2)c(-c2cnn(C)c2)cc1Nc1cc(N2OCC[C@@H]2c2cc(F)cc(F)c2)ncn1] | (R)-1'-(4-((6-(3-(3,5-difluorophenyl)isoxazolidin-2-yl)pyrimidin-4-yl)amino)-5-methoxy-2-(1-methyl-1H-pyrazol-4-yl)phenyl)-N,N-dimethyl-[1,4'-bipiperidin]-4-amine | 674.6 [M + H]⁺ |
| 11 | 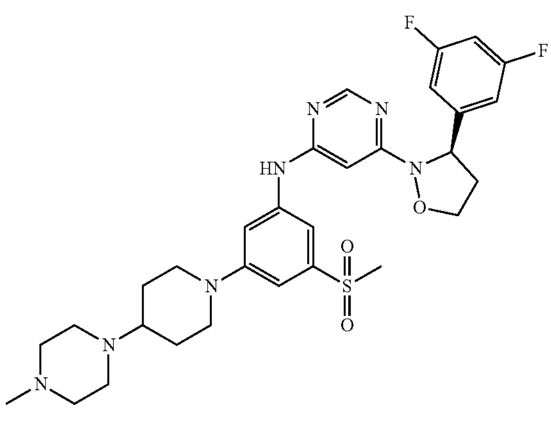 [SMILES: CN1CCN(C2CCN(c3cc(Nc4cc(N5OCC[C@@H]5c5cc(F)cc(F)c5)ncn4)cc(S(C)(=O)=O)c3)CC2)CC1] | (R)-6-(3-(3,5-difluorophenyl)isoxazolidin-2-yl)-N-(3-(4-(4-methylpiperazin-1-yl)piperidin-1-yl)-5-(methylsulfonyl)phenyl)pyrimidin-4-amine | 614.3 [M + H]⁺ |
| 12 | 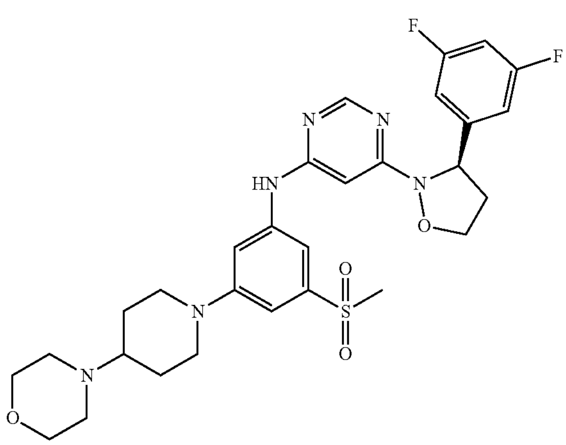 [SMILES: CS(=O)(=O)c1cc(Nc2cc(N3OCC[C@@H]3c3cc(F)cc(F)c3)ncn2)cc(N2CCC(N3CCOCC3)CC2)c1] | (R)-6-(3-(3,5-difluorophenyl)isoxazolidin-2-yl)-N-(3-(methylsulfonyl)-5-(4-morpholinopiperidin-1-yl)phenyl)pyrimidin-4-amine | 601.3 [M + H]⁺ |

TABLE 1-continued

| Example Compound | Structure | Compound Name | ¹H NMR; MS [M + H]⁺ |
|---|---|---|---|
| 13 | 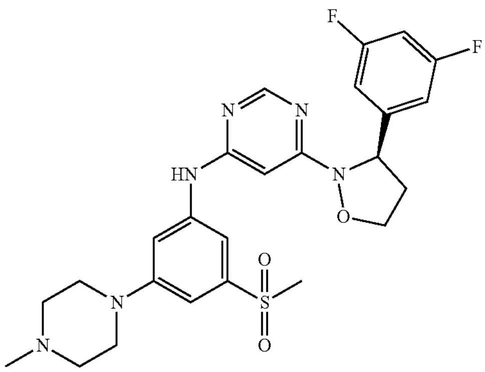 [SMILES: CN1CCN(c2cc(Nc3cc(N4OCC[C@@H]4c4cc(F)cc(F)c4)ncn3)cc(S(C)(=O)=O)c2)CC1] | (R)-6-(3-(3,5-difluorophenyl)isoxazolidin-2-yl)-N-(3-(4-methylpiperazin-1-yl)-5-(methylsulfonyl)phenyl)pyrimidin-4-amine | 531.3 [M + H]⁺ |
| 14 | 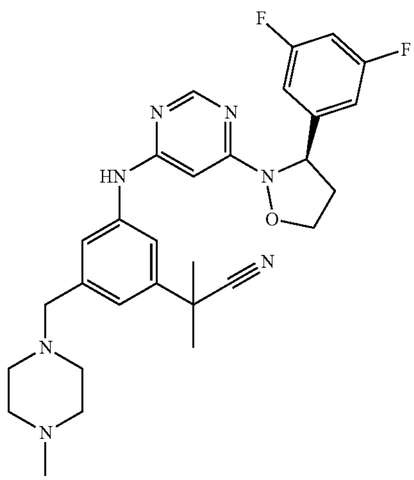 [SMILES: CN1CCN(Cc2cc(Nc3cc(N4OCC[C@@H]4c4cc(F)cc(F)c4)ncn3)cc(C(C)(C)C#N)c2)CC1] | (R)-2-(3-((6-(3-(3,5-difluorophenyl)isoxazolidin-2-yl)pyrimidin-4-yl)amino)-5-((4-methylpiperazin-1-yl)methyl)phenyl)-2-methylpropanenitrile | 534.3 [M + H]⁺ |
| 15 | 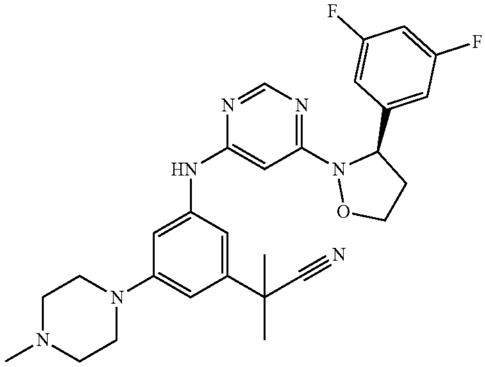 [SMILES: CN1CCN(c2cc(Nc3cc(N4OCC[C@@H]4c4cc(F)cc(F)c4)ncn3)cc(C(C)(C)C#N)c2)CC1] | (R)-2-(3-((6-(3-(3,5-difluorophenyl)isoxazolidin-2-yl)pyrimidin-4-yl)amino)-5-(4-methylpiperazin-1-yl)phenyl)-2-methylpropanenitrile | 520.3 [M + H]⁺ |

TABLE 1-continued

| Example Compound | Structure | Compound Name | ¹H NMR; MS [M + H]⁺ |
|---|---|---|---|
| 16 | 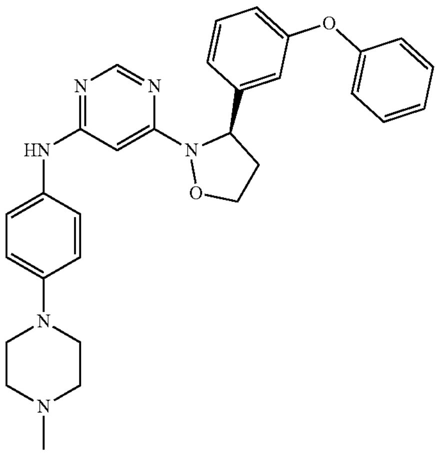 [SMILES: CN1CCN(c2ccc(Nc3cc(N4OCC[C@@H]4c4cccc(Oc5ccccc5)c4)ncn3)cc2)CC1] | (R)-N-(4-(4-methylpiperazin-1-yl)phenyl)-6-(3-(3-phenoxyphenyl)isoxazolidin-2-yl)pyrimidin-4-amine | ¹H NMR (400 MHz, Chloroform-d) δ 8.25 (d, J = 1.1 Hz, 1H), 7.12 (dt, J = 4.1, 2.0 Hz, 2H), 7.11-7.05 (m, 3H), 7.01 (dt, J = 5.3, 1.8 Hz, 3H), 7.00-6.98 (m, 1H), 6.96-6.92 (m, 3H), 6.90-6.85 (m, 2H), 5.63 (dt, J = 8.6, 5.6 Hz, 2H), 4.22 (td, J = 7.8, 4.2 Hz, 1H), 3.93-3.79 (m, 2H), 3.24-3.20 (m, 4H), 2.61 (t, J = 5.0 Hz, 4H), 2.48-2.41 (m, 1H), 2.37 (s, 3H), 2.33 (dd, J = 7.8, 4.4 Hz, 1H); 509.4 [M + H]⁺ |
| 17 | 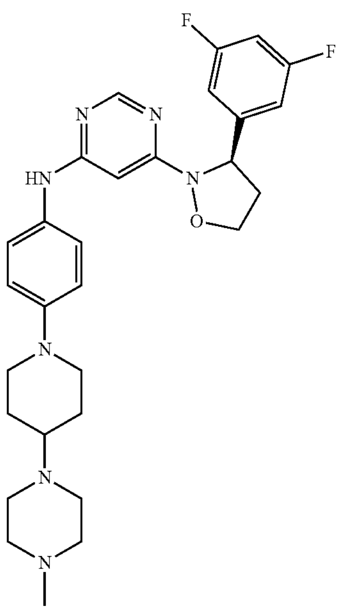 [SMILES: CN1CCN(C2CCN(c3ccc(Nc4cc(N5OCC[C@@H]5c5cc(F)cc(F)c5)ncn4)cc3)CC2)CC1] | (R)-6-(3-(3,5-difluorophenyl)isoxazolidin-2-yl)-N-(4-(4-(4-methylpiperazin-1-yl)piperidin-1-yl)phenyl)pyrimidin-4-amine | ¹H NMR (400 MHz, Chloroform-d) δ 8.20 (s, 1H), 8.17 (d, J = 1.0 Hz, 1H), 7.20-7.14 (m, 2H), 6.99-6.92 (m, 4H), 6.69 (tt, J = 8.8, 2.4 Hz, 1H), 6.38 (d, J = 1.0 Hz, 1H), 5.61 (dd, J = 8.8, 4.7 Hz, 1H), 4.10 (td, J = 7.9, 4.2 Hz, 1H), 3.83 (q, J = 8.0 Hz, 1H), 3.77-3.69 (m, 2H), 2.82 (s, 7H), 2.77-2.69 (m, 4H), 2.54 (tt, J = 11.5, 3.6 Hz, 1H), 2.45 (s, 3H), 2.36-2.27 (m, 1H), 2.01-1.94 (m, 2H), 1.76-1.64 (m, 2H); 536.4 [M + H]⁺ |
| 18 | 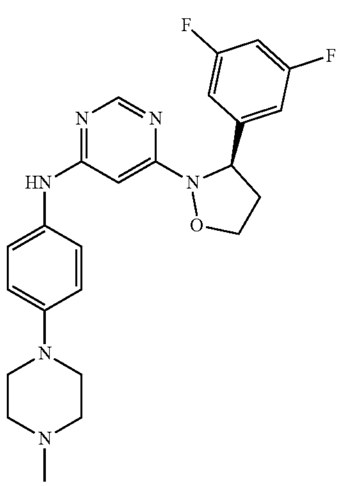 [SMILES: CN1CCN(c2ccc(Nc3cc(N4OCC[C@@H]4c4cc(F)cc(F)c4)ncn3)cc2)CC1] | (R)-6-(3-(3,5-difluorophenyl)isoxazolidin-2-yl)-N-(4-(4-methylpiperazin-1-yl)phenyl)pyrimidin-4-amine | ¹H NMR (400 MHz, Chloroform-d) δ 8.18 (s, 1H), 8.11 (s, 1H), 7.19 (d, J = 8.8 Hz, 2H), 6.99-6.92 (m, 4H), 6.69 (tt, J = 8.9, 2.4 Hz, 1H), 6.39 (d, J = 1.0 Hz, 1H), 5.62 (dd, J = 8.8, 4.8 Hz, 1H), 4.10 (td, J = 7.9, 4.2 Hz, 1H), 3.83 (q, J = 7.9 Hz, 1H), 3.31-3.23 (m, 4H), 2.75 (t, J = 5.2 Hz, 5H), 2.43 (s, 3H), 2.33 (ddd, J = 12.4, 8.3, 4.7 Hz, 1H); 453.3 [M + H]⁺ |

TABLE 1-continued

| Example Compound | Structure | Compound Name | $^1$H NMR; MS [M + H]$^+$ |
|---|---|---|---|
| 19 | 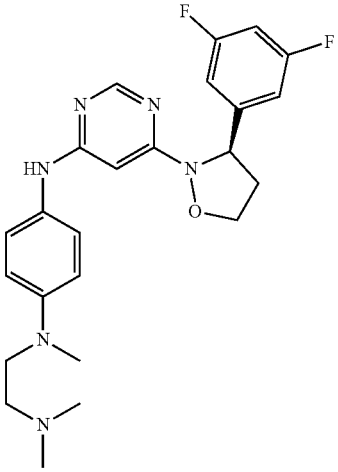 [SMILES: CN(C)CCN(C)c1ccc(Nc2cc(N3OCC[C@@H]3c3cc(F)cc(F)c3)ncn2)cc1] | (R)-N$^1$-(6-(3-(3,5-difluorophenyl)isoxazolidin-2-yl)pyrimidin-4-yl)-N$^4$-(2-(dimethylamino)ethyl)-N$^4$-methylbenzene-1,4-diamine | $^1$H NMR (400 MHz, Chloroform-d) δ 8.20 (s, 1H), 7.52 (s, 1H), 7.17-7.10 (m, 2H), 7.00-6.92 (m, 2H), 6.75-6.66 (m, 3H), 6.33-6.31 (m, 1H), 5.63 (dd, J = 8.8, 4.7 Hz, 1H), 4.08 (td, J = 7.9, 4.2 Hz, 1H), 3.83 (q, J = 7.9 Hz, 1H), 3.57-3.52 (m, 2H), 2.98 (s, 3H), 2.78-2.62 (m, 3H), 2.40 (s, 6H), 2.36-2.27 (m, 1H); 455.3 [M + H]$^+$ |
| 20 | 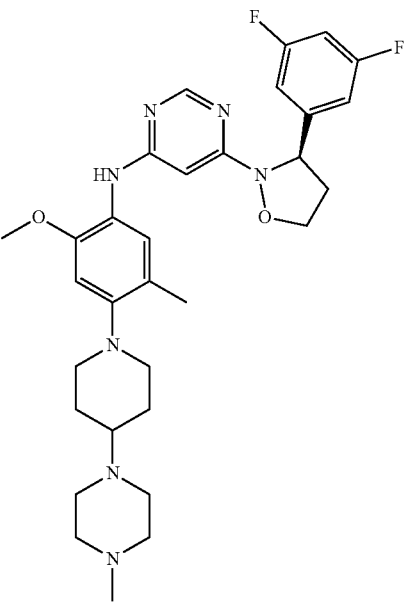 [SMILES: COc1cc(N2CCC(N3CCN(C)CC3)CC2)c(C)cc1Nc1cc(N2OCC[C@@H]2c2cc(F)cc(F)c2)ncn1] | (R)-6-(3-(3,5-difluorophenyl)isoxazolidin-2-yl)-N-(2-methoxy-5-methyl-4-(4-(4-methylpiperazin-1-yl)piperidin-1-yl)phenyl)pyrimidin-4-amine | $^1$H NMR (400 MHz, Chloroform-d) δ 8.51 (s, 1H), 8.26 (d, J = 1.0 Hz, 1H), 7.42 (s, 1H), 7.01-6.95 (m, 2H), 6.69 (tt, J = 8.9, 2.4 Hz, 1H), 6.62 (s, 1H), 6.40-6.37 (m, 1H), 5.64 (dd, J = 8.8, 4.7 Hz, 1H), 4.11 (td, J = 7.9, 4.2 Hz, 1H), 3.90-3.84 (m, 1H), 3.83 (s, 3H), 3.19 (d, J = 11.3 Hz, 2H), 2.86 (s, 7H), 2.78-2.62 (m, 4H), 2.61-2.52 (m, 1H), 2.45 (s, 3H), 2.39-2.28 (m, 1H), 2.24 (s, 3H), 1.97 (d, J = 12.4 Hz, 2H), 1.74 (qd, J = 11.9, 3.8 Hz, 2H); 580.4 [M +H]$^+$ |

TABLE 1-continued

| Example Compound | Structure | Compound Name | ¹H NMR; MS [M + H]⁺ |
|---|---|---|---|
| 21 | 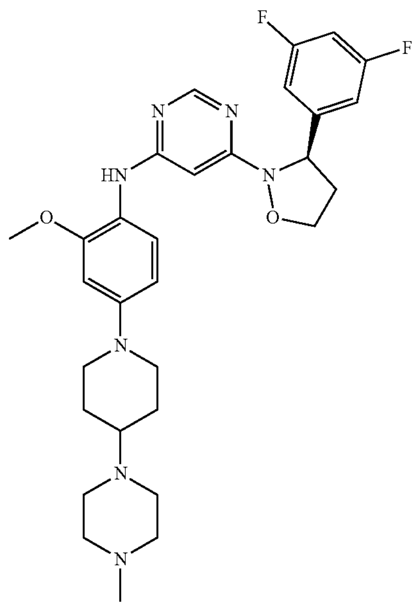 [SMILES: COc1cc(N2CCC(N3CCN(C)CC3)CC2)ccc1Nc1cc(N2OCC[C@@H]2c2cc(F)cc(F)c2)ncn1] | (R)-6-(3-(3,5-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.28 (s, 1H), 7.48 (d, J = 9.1 Hz, 1H), 7.01-6.95 (m, 2H), 6.93 (s, 1H), 6.73-6.65 (m, 1H), 6.57-6.52 (m, 2H), 6.39 (s, 1H), 5.65 (dd, J = 8.8, 4.7 Hz, 1H), 4.13-4.06 (m, 1H), 3.90-3.81 (m, 4H), 3.74-3.68 (m, 2H), 2.78-2.67 (m, 8H), 2.66-2.57 (m, 3H), 2.49-2.40 (m, 1H), 2.38-2.28 (m, 4H), 2.01-1.93 (m, 2H), 1.77-1.65 (m, 2H); 566.5 [M + H]⁺ |
| 22 | 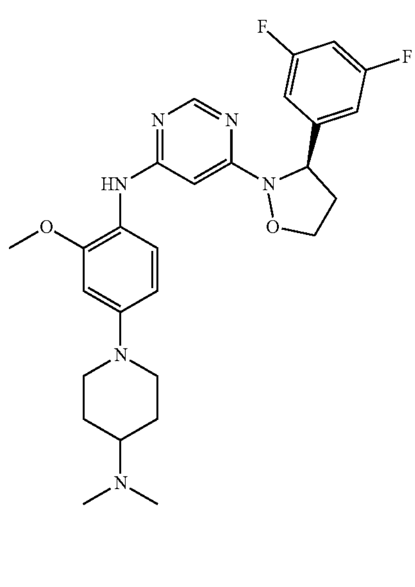 [SMILES: COc1cc(N2CCC(N(C)C)CC2)ccc1Nc1cc(N2OCC[C@@H]2c2cc(F)cc(F)c2)ncn1] | (R)-6-(3-(3,5-difluorophenyl)isoxazolidin-2-yl)-N-(4-(4-(dimethylamino)piperidin-1-yl)-2-methoxyphenyl)pyrimidin-4-amine | ¹H NMR (400 MHz, Chloroform-d) δ 8.30 (s, 1H), 7.52 (d, J = 9.3 Hz, 1H), 7.02-6.96 (m, 2H), 6.81 (s, 1H), 6.72-6.66 (m, 1H), 6.58-6.53 (m, 2H), 6.41 (s, 1H), 5.65 (dd, J = 8.8, 4.7 Hz, 1H), 4.14-4.07 (m, 1H), 3.90-3.82 (m, 4H), 3.74-3.68 (m, 2H), 2.79-2.68 (m, 3H), 2.48-2.28 (m, 8H), 2.02-1.96 (m, 2H), 1.77-1.65 (m, 2H); 511.5 [M + H]⁺ |

TABLE 1-continued

| Example Compound | Structure | Compound Name | ¹H NMR; MS [M + H]⁺ |
|---|---|---|---|
| 23 | 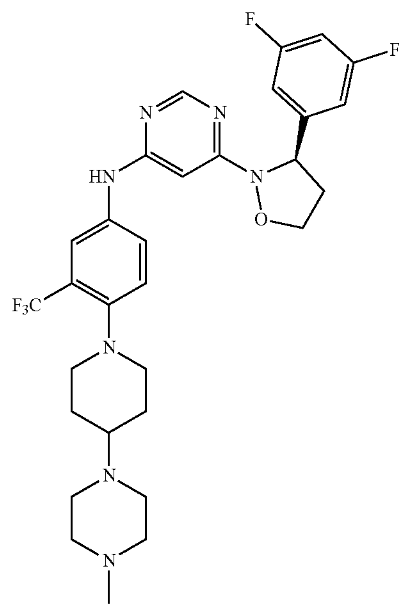 [SMILES: CN1CCN(C2CCN(c3ccc(Nc4cc(N5OCC[C@@H]5c5cc(F)cc(F)c5)ncn4)cc3C(F)(F)F)CC2)CC1] | (R)-6-(3-(3,5-difluorophenyl)isoxazolidin-2-yl)-N-(4-(4-(4-methylpiperazin-1-yl)piperidin-1-yl)-3-(trifluoromethyl)phenyl)pyrimidin-4-amine | ¹H NMR (400 MHz, Chloroform-d) δ 8.57 (s, 1H), 8.25-8.22 (m, 1H), 7.55 (d, J = 2.6 Hz, 1H), 7.49 (dd, J = 8.6, 2.6 Hz, 1H), 7.33 (d, J = 8.6 Hz, 1H), 7.00-6.92 (m, 2H), 6.70 (tt, J = 8.8, 2.3 Hz, 1H), 6.50-6.48 (m, 1H), 5.62 (dd, J = 8.7, 4.8 Hz, 1H), 4.19-4.13 (m, 1H), 3.88 (q, J = 8.0 Hz, 1H), 3.48 (s, 3H), 3.16-3.08 (m, 2H), 2.88 (s, 5H), 2.81-2.71 (m, 3H), 2.66-2.55 (m, 1H), 2.48 (s, 3H), 2.40-2.30 (m, 1H), 1.96-1.88 (m, 2H), 1.75 (tt, J = 11.9, 6.0 Hz, 2H); 604.4 [M + H]⁺ |
| 24 | 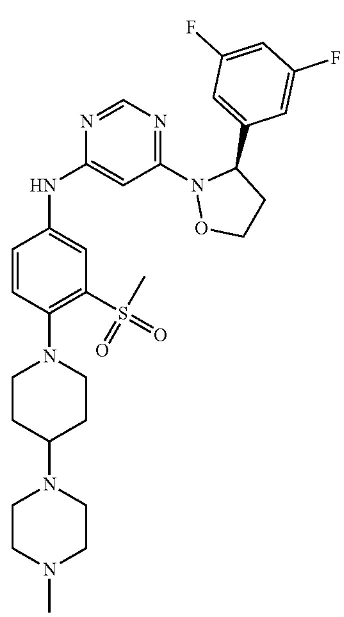 [SMILES: CN1CCN(C2CCN(c3ccc(Nc4cc(N5OCC[C@@H]5c5cc(F)cc(F)c5)ncn4)cc3S(C)(=O)=O)CC2)CC1] | (R)-6-(3-(3,5-difluorophenyl)isoxazolidin-2-yl)-N-(4-(4-(4-methylpiperazin-1-yl)piperidin-1-yl)-3-(methylsulfonyl)phenyl)pyrimidin-4-amine | ¹H NMR (400 MHz, Chloroform-d) δ 8.30-8.26 (m, 1H), 8.02 (s, 1H), 7.98 (d, J = 2.7 Hz, 1H), 7.70 (dd, J = 8.6, 2.7 Hz, 1H), 7.37 (d, J = 8.6 Hz, 1H), 7.00-6.94 (m, 2H), 6.70 (tt, J = 8.8, 2.4 Hz, 1H), 6.53-6.51 (m, 1H), 5.63 (dd, J = 8.7, 4.8 Hz, 1H), 4.17 (td, J = 7.9, 4.2 Hz, 1H), 3.93 (q, J = 8.0 Hz, 1H), 3.35-3.28 (m, 4H), 2.82-2.70 (m, 9H), 2.53-2.44 (m, 1H), 2.41 (s, 3H), 2.40-2.32 (m, 1H), 2.05 (s, 3H), 2.00 (d, J = 12.7 Hz, 2H), 1.75 (q, J = 11.9 Hz, 2H); 614.4 [M + H]⁺ |

TABLE 1-continued

| Example Compound | Structure | Compound Name | ¹H NMR; MS [M + H]⁺ |
|---|---|---|---|
| 25 | 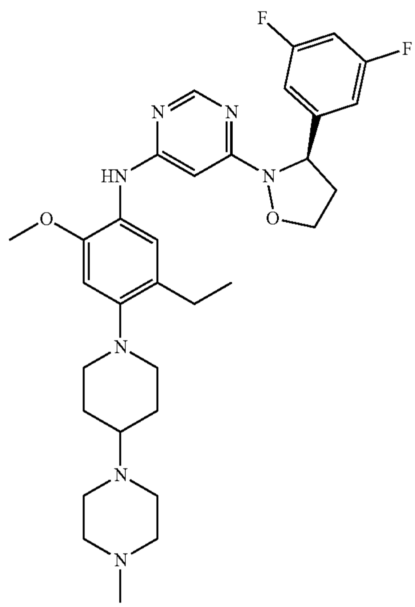 [SMILES: CCc1cc(Nc2cc(N3OCC[C@@H]3c3cc(F)cc(F)c3)ncn2)c(OC)cc1N1CCC(N2CCN(C)CC2)CC1] | (R)-6-(3-(3,5-difluorophenyl)isoxazolidin-2-yl)-N-(5-methyl-2-methoxy-4-(4-(4-methylpiperazin-1-yl)piperidin-1-yl)phenyl)pyrimidin-4-amine | ¹H NMR (400 MHz, Chloroform-d) δ 8.29 (s, 1H), 7.49 (s, 1H), 7.12 (s, 1H), 7.02-6.95 (m, 2H), 6.72-6.67 (m, 2H), 6.49 (s, 1H), 5.65 (dd, J = 8.8, 4.7 Hz, 1H), 4.11 (td, J = 7.9, 4.1 Hz, 1H), 3.90-3.79 (m, 7H), 3.13 (d, J = 11.4 Hz, 2H), 2.79-2.62 (m, 12H), 2.51-2.44 (m, 1H), 2.39 (s, 3H), 2.36-2.30 (m, 1H), 2.17 (s, 1H), 1.96 (d, J = 12.2 Hz, 2H), 1.73 (qd, J = 11.5, 3.2 Hz, 2H); 594.4 [M + H]⁺ |
| 26 | 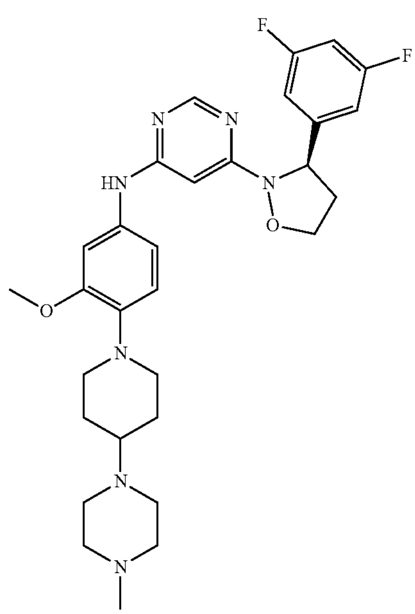 [SMILES: COc1cc(Nc2cc(N3OCC[C@@H]3c3cc(F)cc(F)c3)ncn2)ccc1N1CCC(N2CCN(C)CC2)CC1] | (R)-6-(3-(3,5-difluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, Chloroform-d) δ 8.25-8.20 (m, 1H), 7.65-7.60 (m, 1H), 7.00-6.89 (m, 3H), 6.86-6.78 (m, 2H), 6.69 (tt, J = 8.7, 2.4 Hz, 1H), 6.46 (d, J = 0.9 Hz, 1H), 5.62 (dd, J = 8.8, 4.8 Hz, 1H), 4.10 (td, J = 7.9, 4.2 Hz, 1H), 3.87 (s, 3H), 3.86-3.82 (m, 1H), 3.55 (d, J = 11.4 Hz, 2H), 2.82-2.65 (m, 8H), 2.64-2.47 (m, 4H), 2.38 (s, 3H), 2.37-2.31 (m, 1H), 1.94 (d, J = 12.2 Hz, 2H), 1.82 (tt, J = 12.0, 6.0 Hz, 2H); 566.4 [M + H]⁺ |

TABLE 1-continued

| Example Compound | Structure | Compound Name | $^1$H NMR; MS [M + H]$^+$ |
|---|---|---|---|
| 27 | 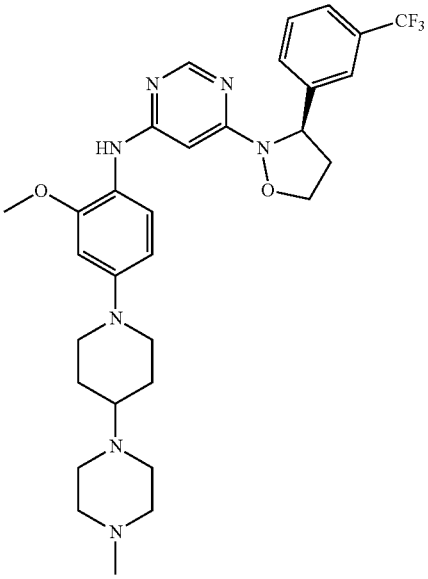 [SMILES: COc1cc(N2CCC(N3CCN(C)CC3)CC2)ccc1Nc1cc(N2OCC[C@@H]2c2cccc(C(F)(F)F)c2)ncn1] | (R)-N-(2-methoxy-4-(4-(4-methylpiperazin-1-yl)piperidin-1-yl)phenyl)-6-(3-(3-(trifluoromethyl)phenyl)isoxazolidin-2-yl)pyrimidin-4-amine | $^1$H NMR (400 MHz, Chloroform-d) δ 8.28 (s, 1H), 7.71 (s, 1H), 7.64 (d, J = 7.5 Hz, 1H), 7.48 (dt, J = 15.8, 7.7 Hz, 3H), 6.95 (s, 1H), 6.59-6.49 (m, 2H), 6.41 (s, 1H), 5.74 (dd, J = 8.8, 4.6 Hz, 1H), 4.11 (q, J = 8.0 Hz, 1H), 3.93-3.80 (m, 4H), 3.71 (d, J = 12.5 Hz, 2H), 2.81-2.67 (m, 7H), 2.62 (s, 4H), 2.48-2.31 (m, 5H), 1.97 (d, J = 12.4 Hz, 2H), 1.74-1.66 (m, 2H); 598.44 [M + H]$^+$ |
| 28 | 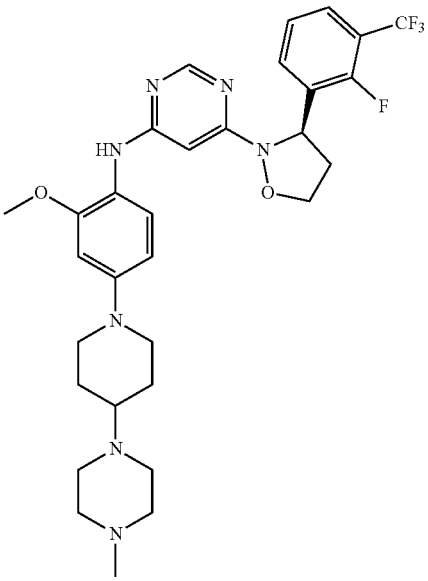 [SMILES: COc1cc(N2CCC(N3CCN(C)CC3)CC2)ccc1Nc1cc(N2OCC[C@@H]2c2cccc(C(F)(F)F)c2F)ncn1] | (R)-6-(3-(2-fluoro-3-(trifluoromethyl)phenyl)isoxazolidin-2-yl)-N-(2-methoxy-4-(4-(4-methylpiperazin-1-yl)piperidin-1-yl)phenyl)pyrimidin-4-amine | $^1$H NMR (400 MHz, Chloroform-d) δ 8.28 (s, 1H), 7.79 (t, J = 7.4 Hz, 1H), 7.51 (t, J = 9.5 Hz, 2H), 7.21 (t, J = 7.9 Hz, 1H), 6.99 (s, 1H), 6.55 (d, J = 7.5 Hz, 2H), 6.42 (s, 1H), 5.93 (dd, J = 8.8, 4.6 Hz, 1H), 4.12-4.05 (m, 1H), 3.92-3.81 (m, 4H), 3.72 (d, J = 12.2 Hz, 2H), 2.84 (d, J = 8.7 Hz, 1H), 2.80-2.51 (m, 10H), 2.50-2.41 (m, 1H), 2.36 (s, 3H), 2.32-2.25 (m, 1H), 1.97 (d, J = 12.6 Hz, 2H), 1.71 (q, J = 11.4, 10.9 Hz, 2H); 616.35 [M + H]$^+$ |

TABLE 1-continued

| Example Compound | Structure | Compound Name | ¹H NMR; MS [M + H]⁺ |
|---|---|---|---|
| 29 | 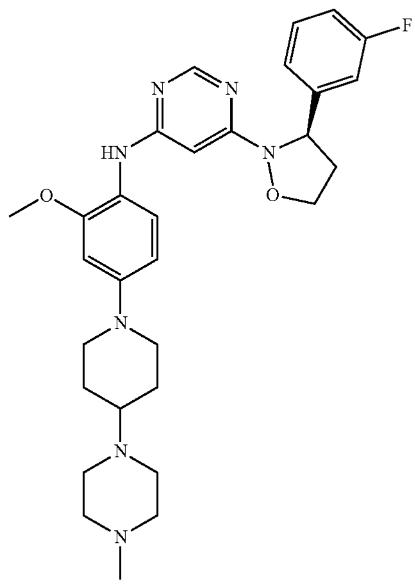 | (R)-6-(3-(3-fluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.30 (s, 1H), 7.50 (d, J = 8.9 Hz, 1H), 7.34-7.28 (m, 1H), 7.19 (dd, J = 13.5, 8.8 Hz, 2H), 6.94 (td, J = 8.4, 1.9 Hz, 1H), 6.80 (s, 1H), 6.57-6.51 (m, 2H), 6.40 (d, J = 1.1 Hz, 1H), 5.67 (dd, J = 8.7, 4.6 Hz, 1H), 4.10 (td, J = 7.8, 4.2 Hz, 1H), 3.91-3.82 (m, 4H), 3.71 (d, J = 12.2 Hz, 2H), 2.78-2.53 (m, 11H), 2.41-2.38 (m, 1H), 2.37-2.34 (m, 1H), 2.32 (d, J = 1.3 Hz, 3H), 1.96 (d, J = 12.7 Hz, 2H), 1.70 (dt, J = 11.5, 7.9 Hz, 2H); 548.39 [M + H]⁺ |
| 30 | 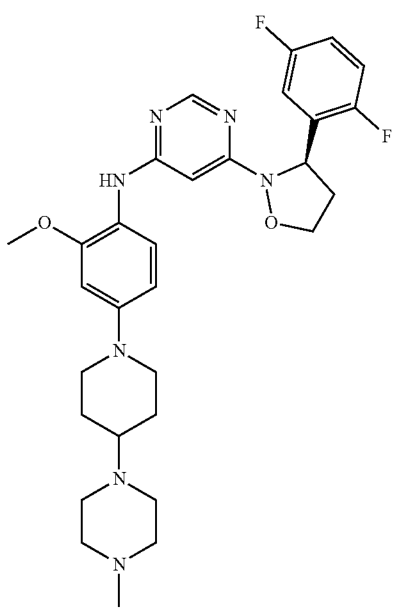 [SMILES: COc1cc(N2CCC(N3CCN(C)CC3)CC2)ccc1Nc1cc(N2OCC[C@@H]2c2cc(F)ccc2F)ncn1] | (R)-6-(3-(2,5-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.30 (s, 1H), 7.51 (d, J = 8.9 Hz, 1H), 7.30 (d, J = 3.3 Hz, 1H), 7.00 (td, J = 9.0, 4.0 Hz, 1H), 6.94-6.86 (m, 1H), 6.83 (s, 1H), 6.58-6.52 (m, 2H), 6.43 (s, 1H), 5.87 (dd, J = 8.7, 4.4 Hz, 1H), 4.10-4.05 (m, 1H), 3.85 (s, 4H), 3.71 (d, J = 12.3 Hz, 2H), 2.80-2.66 (m, 7H), 2.56 (s, 4H), 2.42 (t, J = 11.6 Hz, 1H), 2.33 (s, 3H), 2.31-2.23 (m, 1H), 2.05-2.01 (m, 2H), 1.70 (dd, J = 20.7, 11.3 Hz, 2H); 566.36 [M + H]⁺ |

TABLE 1-continued

| Example Compound | Structure | Compound Name | ¹H NMR; MS [M + H]⁺ |
|---|---|---|---|
| 31 | 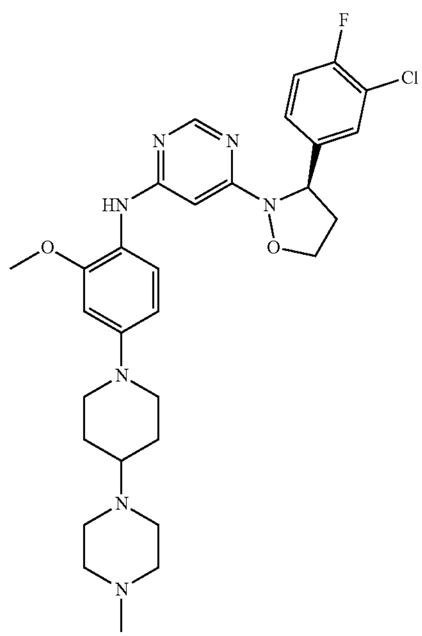 [SMILES: COc1cc(N2CCC(N3CCN(C)CC3)CC2)ccc1Nc1cc(N2OCC[C@@H]2c2ccc(F)c(Cl)c2)ncn1] | (R)-6-(3-(3-chloro-4-fluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.28 (s, 1H), 7.50 (t, J = 7.4 Hz, 2H), 7.33-7.28 (m, 1H), 7.10 (t, J = 8.6 Hz, 1H), 6.87 (s, 1H), 6.54 (d, J = 7.8 Hz, 2H), 6.39 (s, 1H), 5.63 (dd, J = 8.3, 4.5 Hz, 1H), 4.15-4.06 (m, 1H), 3.86 (d, J = 11.0 Hz, 4H), 3.71 (d, J = 12.0 Hz, 2H), 2.78-2.68 (m, 5H), 2.58 (s, 6H), 2.46-2.40 (m, 1H), 2.37-2.26 (m, 4H), 1.97 (d, J = 12.4 Hz, 2H), 1.70 (dd, J = 22.3, 10.3 Hz, 2H); 582.36 [M + H]⁺ |
| 32 | 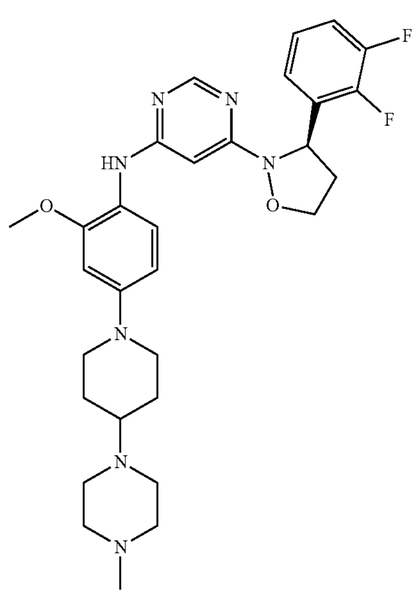 | (R)-6-(3-(2,3-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.27 (s, 1H), 7.47 (d, J = 8.5 Hz, 1H), 7.31 (t, J = 7.0 Hz, 1H), 7.12-7.01 (m, 3H), 6.54 (d, J = 7.3 Hz, 2H), 6.39 (d, J = 1.0 Hz, 1H), 5.90 (dd, J = 8.8, 4.7 Hz, 1H), 4.09 (dt, J = 7.8, 3.8 Hz, 1H), 3.90-3.85 (m, 1H), 3.84 (s, 3H), 3.71 (d, J = 12.3 Hz, 2H), 2.86-2.60 (m, 11H), 2.51-2.44 (m, 1H), 2.38 (s, 3H), 2.34-2.28 (m, 1H), 1.97 (d, J = 12.6 Hz, 2H), 1.76-1.65 (m, 2H); 566.31 [M + H]⁺ |

TABLE 1-continued

| Example Compound | Structure | Compound Name | ¹H NMR; MS [M + H]⁺ |
|---|---|---|---|
| 33 | 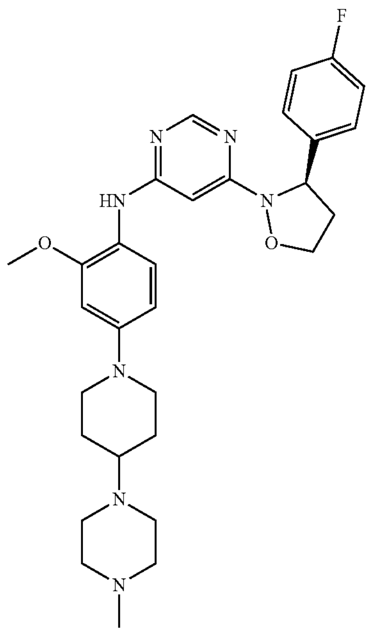 [SMILES: COc1cc(N2CCC(N3CCN(C)CC3)CC2)ccc1Nc1cc(N2OCC[C@@H]2c2ccc(F)cc2)ncn1] | (R)-6-(3-(4-fluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.27 (d, J = 1.0 Hz, 1H), 7.46 (d, J = 8.3 Hz, 1H), 7.43-7.37 (m, 2H), 7.06 (s, 1H), 7.02 (t, J = 8.7 Hz, 2H), 6.53 (d, J = 8.1 Hz, 2H), 6.36 (d, J = 1.0 Hz, 1H), 5.64 (dd, J = 8.5, 4.6 Hz, 1H), 4.11 (dt, J = 7.9, 4.0 Hz, 1H), 3.91-3.83 (m, 4H), 3.71 (d, J = 12.3 Hz, 2H), 2.88-2.55 (m, 11H), 2.50-2.43 (m, 1H), 2.42-2.29 (m, 4H), 1.97 (d, J = 12.4 Hz, 2H), 1.76-1.65 (m, 2H); 548.31 [M + H]⁺ |
| 34 | 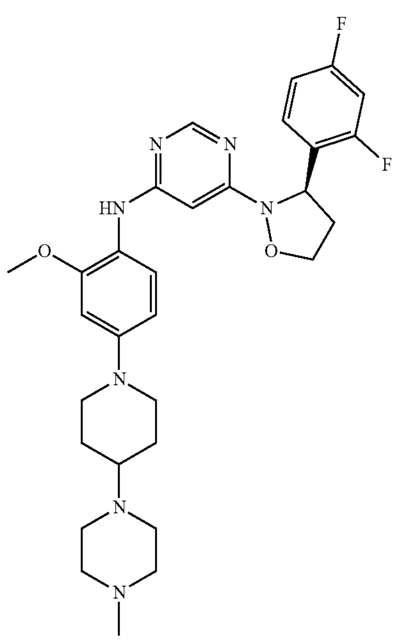 [SMILES: COc1cc(N2CCC(N3CCN(C)CC3)CC2)ccc1Nc1cc(N2OCC[C@@H]2c2ccc(F)cc2F)ncn1] | (R)-6-(3-(2,4-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, DMSO-d6) δ 8.44 (s, 1H), 8.11 (d, J = 1.0 Hz, 1H), 7.49 (q, J = 8.6, 8.1 Hz, 1H), 7.34-7.22 (m, 2H), 7.07 (t, J = 8.8 Hz, 1H), 6.62 (d, J = 2.7 Hz, 1H), 6.49 (dd, J = 8.8, 2.6 Hz, 1H), 6.17 (s, 1H), 5.68 (dd, J = 8.7, 4.7 Hz, 1H), 4.16-4.10 (m, 1H), 3.83-3.75 (m, 4H), 3.72 (d, J = 12.1 Hz, 2H), 3.43-3.36 (m, 5H), 2.80-2.72 (m, 1H), 2.67 (t, J = 12.1 Hz, 2H), 2.38-2.25 (m, 4H), 2.21-2.09 (m, 4H), 1.83 (d, 2H), 1.51 (q, J = 11.4 Hz, 2H); 566.27 [M + H]⁺ |

TABLE 1-continued

| Example Compound | Structure | Compound Name | $^1$H NMR; MS [M + H]$^+$ |
|---|---|---|---|
| 35 | 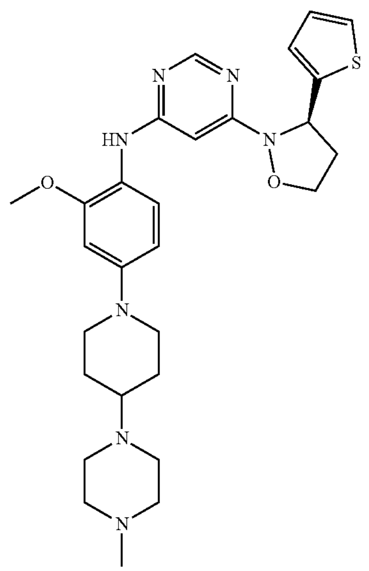 [SMILES: COc1cc(N2CCC(N3CCN(C)CC3)CC2)ccc1Nc1cc(N2OCC[C@@H]2c2cccs2)ncn1] | (R)-N-(2-methoxy-4-(4-(4-methylpiperazin-1-yl)piperidin-1-yl)phenyl)-6-(3-(thiophen-2-yl)isoxazolidin-2-yl)pyrimidin-4-amine | $^1$H NMR (400 MHz, Chloroform-d) δ 8.32 (d, J = 1.0 Hz, 1H), 7.50 (d, J = 8.5 Hz, 1H), 7.20 (dd, J = 5.0, 1.2 Hz, 1H), 7.08-7.04 (m, 1H), 7.02-6.94 (m, 2H), 6.55-6.49 (m, 2H), 6.38 (d, J = 1.1 Hz, 1H), 5.98 (dd, J = 8.3, 3.5 Hz, 1H), 4.17 (td, J = 7.9, 5.2 Hz, 1H), 3.93 (q, J = 7.8 Hz, 1H), 3.84 (s, 3H), 3.75-3.67 (m, 2H), 2.93 (s, 6H), 2.75 (td, J = 12.2, 2.3 Hz, 3H), 2.69-2.62 (m, 2H), 2.60 (s, 3H), 2.55-2.44 (m, 2H), 1.98 (d, J = 12.4 Hz, 2H), 1.79-1.66 (m, 2H); 536.4 [M + H]$^+$ |
| 36 | 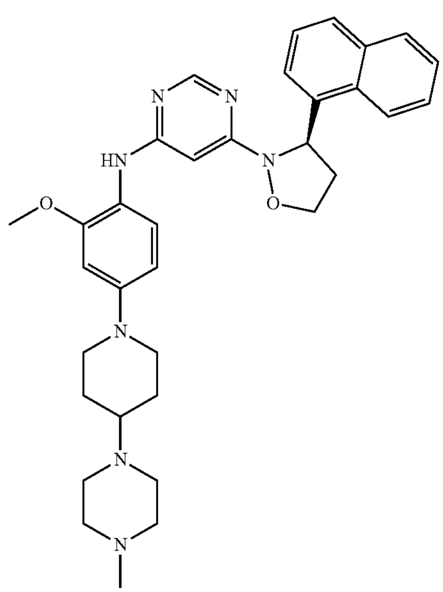 [SMILES: COc1cc(N2CCC(N3CCN(C)CC3)CC2)ccc1Nc1cc(N2OCC[C@@H]2c2cccc3ccccc23)ncn1] | (R)-N-(2-methoxy-4-(4-(4-methylpiperazin-1-yl)piperidin-1-yl)phenyl)-6-(3-(naphthalen-1-yl)isoxazolidin-2-yl)pyrimidin-4-amine | 1H NMR (400 MHz, Chloroform-d) δ 8.28 (s, 1H), 8.12 (d, J = 8.3 Hz, 1H), 7.89 (d, J = 8.0 Hz, 1H), 7.78 (d, J = 8.2 Hz, 1H), 7.73 (d, J = 7.2 Hz, 1H), 7.58-7.43 (m, 4H), 6.54 (d, J = 8.0 Hz, 2H), 6.45 (s, 1H), 6.39 (dd, J = 8.7, 4.0 Hz, 1H), 4.16-4.09 (m, 1H), 4.00 (q, J = 7.8 Hz, 1H), 3.86 (s, 3H), 3.71 (d, J = 12.3 Hz, 2H), 2.97-2.87 (m, 4H), 2.76 (t, J = 12.0 Hz, 3H), 2.63 (s, 4H), 2.45-2.35 (m, 2H), 2.08 (s, 3H), 1.97 (d, 2H), 1.75 (ddd, 2H); 580.39 [M + H]$^+$ |

TABLE 1-continued

| Example Compound | Structure | Compound Name | ¹H NMR; MS [M + H]⁺ |
|---|---|---|---|
| 37 | 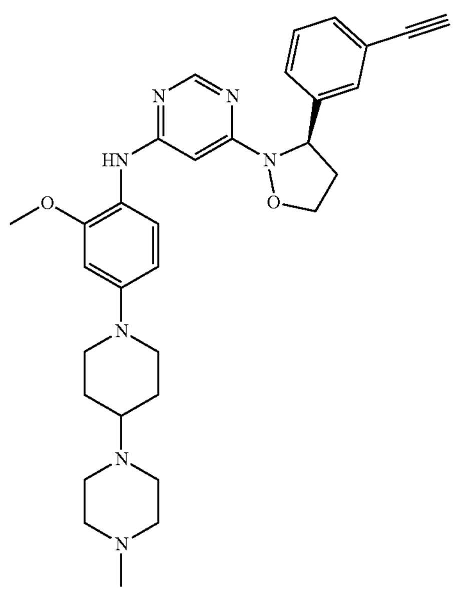 [SMILES: C#Cc1cccc([C@H]2CCON2c2cc(Nc3ccc(N4CCC(N5CCN(C)CC5)CC4)cc3OC)ncn2)c1] | (R)-6-(3-(3-ethynylphenyl)isoxazolidin-2-yl)-N-(2-methoxy-4-(4-(4-methylpiperazin-1-yl)piperidin-1-yl)phenyl)pyrimidin-4-amine | 554.3 [M + H]⁺ |
| 38 | 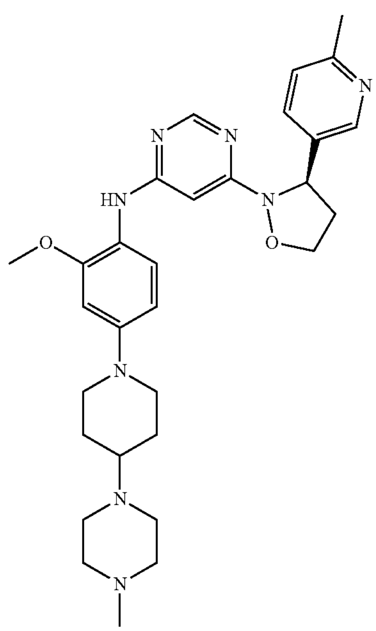 [SMILES: COc1cc(N2CCC(N3CCN(C)CC3)CC2)ccc1Nc1cc(N2OCC[C@@H]2c2ccc(C)nc2)ncn1] | (R)-N-(2-methoxy-4-(4-(4-methylpiperazin-1-yl)piperidin-1-yl)phenyl)-6-(3-(6-methylpyridin-3-yl)isoxazolidin-2-yl)pyrimidin-4-amine | ¹H NMR (400 MHz, DMSO-d$_6$) δ 8.75-8.49 (m, 2H), 8.22-8.12 (m, 1H), 8.08-7.94 (m, 1H), 7.57-7.27 (m, 2H), 6.68 (s, 1H), 6.61-6.50 (m, 1H), 6.25-6.12 (m, 1H), 5.65-5.53 (m, 1H), 4.20-4.13 (m, 1H), 3.99-3.93 (m, 1H), 3.91-3.67 (m, 6H), 3.50-3.27 (m, 4H), 3.19-3.14 (m, 2H), 2.83-2.66 (m, 6H), 2.60-2.55 (m, 2H), 2.38-2.19 (m, 2H), 2.04-1.92 (m, 2H), 1.92-1.79 (m, 2H), 1.68-1.50 (m, 2H); 545.4 [M + H]⁺ |

TABLE 1-continued

| Example Compound | Structure | Compound Name | ¹H NMR; MS [M + H]⁺ |
|---|---|---|---|
| 39 | 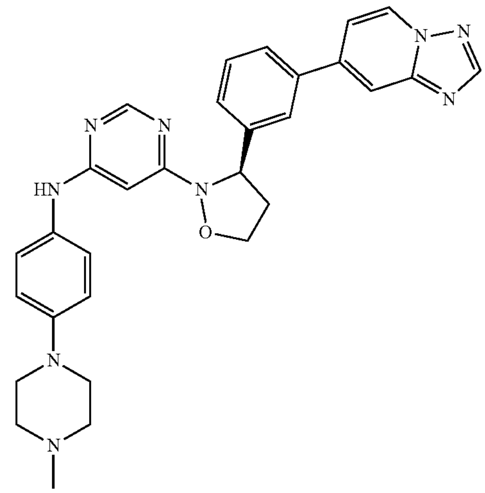 [SMILES: CN1CCN(c2ccc(Nc3cc(N4OCC[C@@H]4c4cccc(-c5ccn6ncnc6c5)c4)ncn3)cc2)CC1] | (R)-6-(3-(3-([1,2,4]triazolo[1,5-a]pyridin-7-yl)phenyl)isoxazolidin-2-yl)-N-(4-(4-methylpiperazin-1-yl)phenyl)pyrimidin-4-amine | 534.3 [M + H]⁺ |
| 40 | 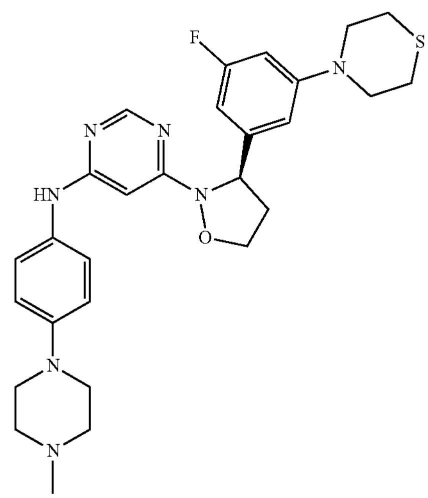 [SMILES: CN1CCN(c2ccc(Nc3cc(N4OCC[C@@H]4c4cc(F)cc(N5CCSCC5)c4)ncn3)cc2)CC1] | (R)-6-(3-(3-fluoro-5-thiomorpholinophenyl)isoxazolidin-2-yl)-N-(4-(4-methylpiperazin-1-yl)phenyl)pyrimidin-4-amine | 536.3 [M + H]⁺ |
| 41 | 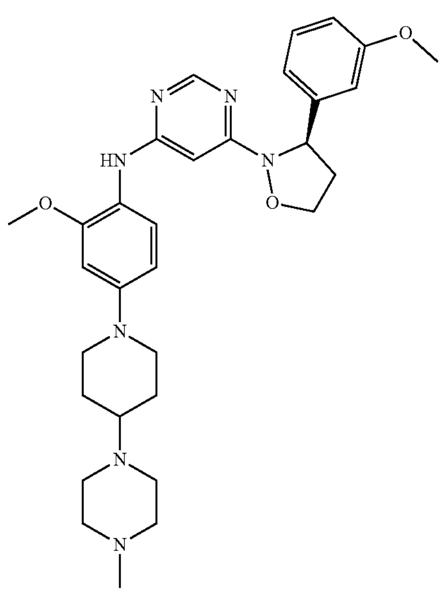 | (R)-N-(2-methoxy-4-(4-(4-methylpiperazin-1-yl)piperidin-1-yl)phenyl)-6-(3-(3-methoxyphenyl)isoxazolidin-2-yl)pyrimidin-4-amine | ¹H NMR (400 MHz, Chloroform-d) δ 10.83 (s, 1H), 8.04 (s, 1H), 7.31-7.26 (m, 1H), 7.15 (d, J = 8.5 Hz, 1H), 6.89-6.79 (m, 3H), 6.62-6.52 (m, 2H), 5.75 (s, 1H), 5.54 (dd, J = 8.6, 4.5 Hz, 1H), 4.24 (td, J = 7.5, 5.5 Hz, 1H), 4.03 (q, J = 7.5 Hz, 1H), 3.89-3.77 (m, 8H), 3.66 (s, 8H), 3.34-3.22 (m, 1H), 2.94-2.81 (m, 6H), 2.49-2.37 (m, 1H), 2.26-2.15 (m, 2H), 2.05-1.93 (m, 2H); 560.4 [M + H]⁺ |

TABLE 1-continued

| Example Compound | Structure | Compound Name | ¹H NMR; MS [M + H]⁺ |
|---|---|---|---|
| 42 | 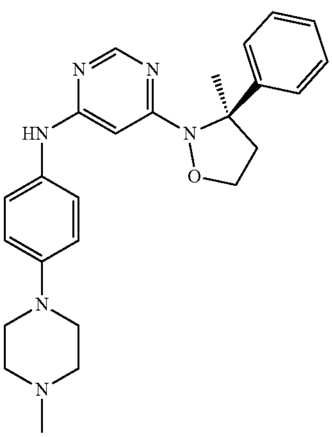 [SMILES: CN1CCN(c2ccc(Nc3cc(N4OCC[C@]4(C)c4ccccc4)ncn3)cc2)CC1] | (R)-6-(3-methyl-3-phenylisoxazolidin-2-yl)-N-(4-(4-methylpiperazin-1-yl)phenyl)pyrimidin-4-amine | 431.3 [M + H]⁺ |
| 43 | 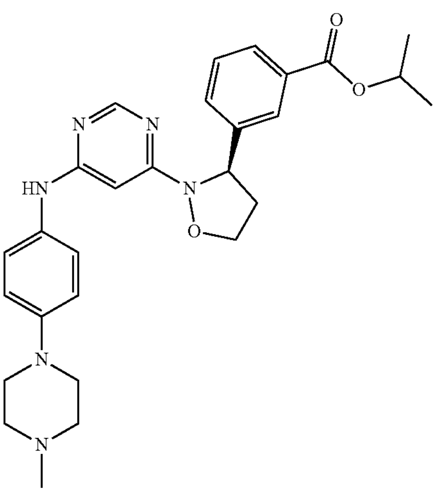 [SMILES: CC(C)OC(=O)c1cccc([C@H]2CCON2c2cc(Nc3ccc(N4CCN(C)CC4)cc3)ncn2)c1] | isopropyl (R)-3-(2-(6-((4-(4-methylpiperazin-1-yl)phenyl)amino)pyrimidin-4-yl)isoxazolidin-3-yl)benzoate | 503.3 [M + H]⁺ |
| 44 | 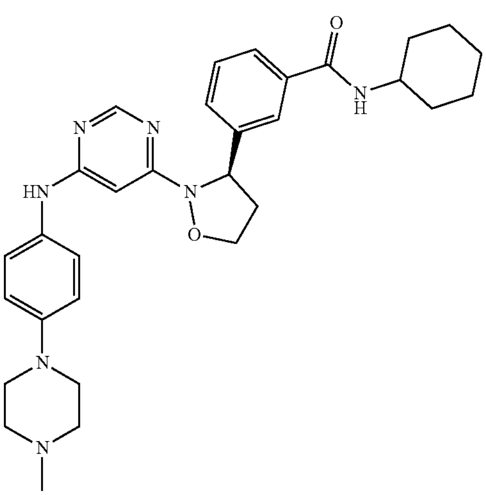 [SMILES: CN1CCN(c2ccc(Nc3cc(N4OCC[C@@H]4c4cccc(C(=O)NC5CCCCC5)c4)ncn3)cc2)CC1] | (R)-N-cyclohexyl-3-(2-(6-((4-(4-methylpiperazin-1-yl)phenyl)amino)pyrimidin-4-yl)isoxazolidin-3-yl)benzamide | 542.3 [M + H]⁺ |

TABLE 1-continued

| Example Compound | Structure | Compound Name | $^1$H NMR; MS [M + H]$^+$ |
|---|---|---|---|
| 45 | 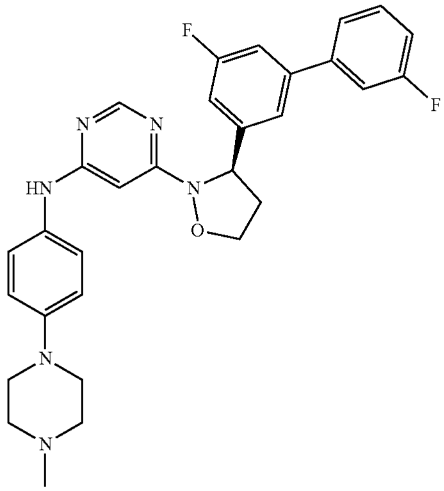 [SMILES: CN1CCN(c2ccc(Nc3cc(N4OCC[C@@H]4c4cc(F)cc(-c5cccc(F)c5)c4)ncn3)cc2)CC1] | (R)-6-(3-(3',5-difluoro-[1,1'-biphenyl]-3-yl)isoxazolidin-2-yl)-N-(4-(4-methylpiperazin-1-yl)phenyl)pyrimidin-4-amine | $^1$H NMR (400 MHz, Chloroform-d) δ 8.27 (d, J = 1.0 Hz, 1H), 7.45-7.10 (m, 9H), 7.09-6.90 (m, 3H), 6.40 (d, J = 1.0 Hz, 1H), 5.71 (dd, J = 8.7, 4.7 Hz, 1H), 4.11 (td, J = 7.9, 4.1 Hz, 1H), 3.85 (q, J = 7.9 Hz, 1H), 3.26-3.19 (m, 4H), 2.76 (dtt, J = 12.2, 7.6, 4.2 Hz, 1H), 2.63-2.54 (m, 4H), 2.44-2.31 (m, 4H); 529.4 [M + H]$^+$ |
| 46 | 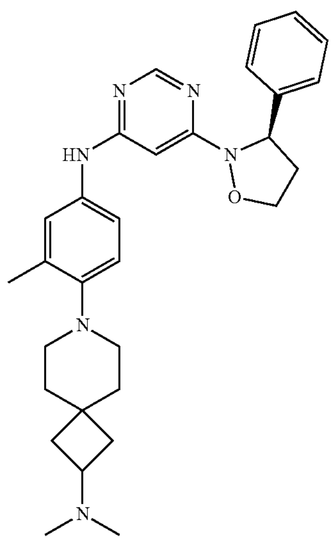 [SMILES: Cc1cc(Nc2cc(N3OCC[C@@H]3c3ccccc3)ncn2)ccc1N1CCC2(CC1)CC(N(C)C)C2] | (R)-N,N-dimethyl-7-(2-methyl-4-((6-(3-phenylisoxazolidin-2-yl)pyrimidin-4-yl)amino)phenyl)-7-azaspiro[3.5]nonan-2-amine | 499.3 [M + H]$^+$ |
| 47 | 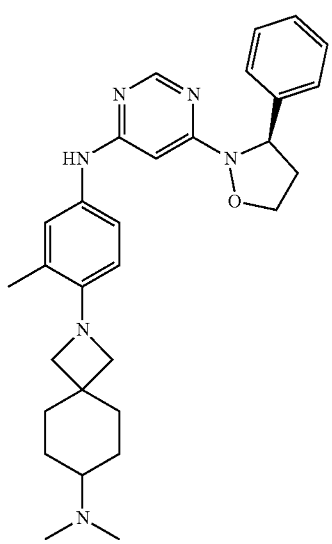 [SMILES: Cc1cc(Nc2cc(N3OCC[C@@H]3c3ccccc3)ncn2)ccc1N1CC2(CCC(N(C)C)CC2)C1] | (R)-N,N-dimethyl-2-(2-methyl-4-((6-(3-phenylisoxazolidin-2-yl)pyrimidin-4-yl)amino)phenyl)-2-azaspiro[3.5]nonan-7-amine | 499.3 [M + H]$^+$ |

TABLE 1-continued

| Example Compound | Structure | Compound Name | ¹H NMR; MS [M + H]⁺ |
|---|---|---|---|
| 48 | 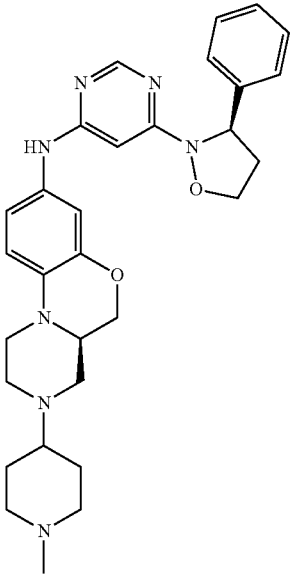 [SMILES: CN1CCC(N2CCN3c4ccc(Nc5cc(N6OCC[C@@H]6c6ccccc6)ncn5)cc4OC[C@H]3C2)CC1] | (R)-3-(1-methylpiperidin-4-yl)-N-(6-((R)-3-phenylisoxazolidin-2-yl)pyrimidin-4-yl)-1,2,3,4,4a,5-hexahydrobenzo[b]pyrazino[1,2-d][1,4]oxazin-8-amine | ¹H NMR (400 MHz, Chloroform-d) δ 8.17 (d, J = 1.0 Hz, 1H), 8.07 (s, 1H), 7.44-7.40 (m, 2H), 7.35 (t, J = 7.6 Hz, 2H), 7.26-7.22 (m, 1H), 6.79-6.69 (m, 3H), 6.42 (d, J = 1.0 Hz, 1H), 5.64 (dd, J = 8.6, 4.6 Hz, 1H), 4.20 (dd, J = 10.6, 2.7 Hz, 1H), 4.12 (td, J = 7.8, 4.5 Hz, 1H), 4.01 (dd, J = 10.6, 8.9 Hz, 1H), 3.88 (q, J = 7.8 Hz, 1H), 3.68 (dt, J = 11.6, 2.8 Hz, 1H), 3.30 (d, J = 11.5 Hz, 2H), 3.16 (ddt, J = 11.5, 9.4, 2.9 Hz, 1H), 3.02 (d, J = 11.2 Hz, 1H), 2.88 (dt, J = 10.5, 2.6 Hz, 1H), 2.80 (td, J = 11.8, 3.4 Hz, 1H), 2.73 (ddt, J = 8.8, 7.6, 4.5 Hz, 1H), 2.54 (s, 3H), 2.47 (ddt, J = 11.6, 8.9, 3.8 Hz, 3H), 2.38 (dtd, J = 12.4, 7.9, 4.7 Hz, 1H), 2.07 (s, 1H), 2.02 (s, 1H), 1.98-1.86 (m, 4H); 528.37 [M + H]⁺ |
| 49 | 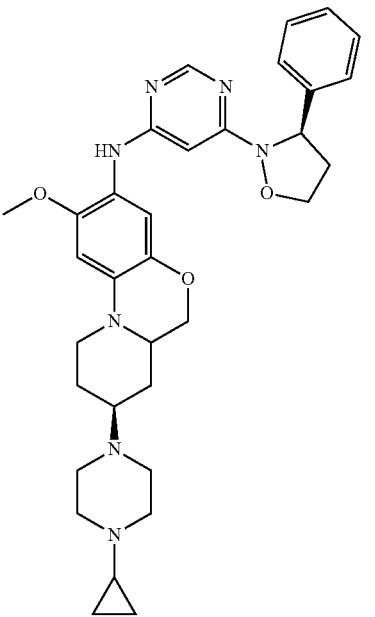 [SMILES: COc1cc2c(cc1Nc1cc(N3OCC[C@@H]3c3ccccc3)ncn1)OCC1C[C@@H](N3CCN(C4CC4)CC3)CCN21] | (6aR,8S)-8-(4-cyclopropylpiperazin-1-yl)-2-methoxy-N-(6-((R)-3-phenylisoxazolidin-2-yl)pyrimidin-4-yl)-6,6a,7,8,9,10-hexahydrobenzo[b]pyrido[1,2-d][1,4]oxazin-3-amine | ¹H NMR (400 MHz, Chloroform-d) δ 8.29 (d, J = 1.1 Hz, 1H), 7.45 (d, J = 7.4 Hz, 2H), 7.35 (t, J = 7.6 Hz, 2H), 7.24 (t, J = 7.1 Hz, 1H), 7.20 (s, 1H), 6.80 (s, 1H), 6.45 (s, 1H), 6.41 (d, J = 1.1 Hz, 1H), 5.68 (dd, J = 8.6, 4.5 Hz, 1H), 4.20-4.07 (m, 2H), 3.98 (dd, J = 10.8, 8.2 Hz, 1H), 3.90 (q, J = 8.0 Hz, 2H), 3.79 (s, 3H), 3.02 (dd, J = 11.4, 8.4 Hz, 1H), 2.79-2.47 (m, 10H), 2.43-2.34 (m, 1H), 2.07-1.99 (m, 2H), 1.88-1.83 (m, 1H), 1.69-1.61 (m, 7H); 584.45 [M + H]⁺ |

TABLE 1-continued
| Example Compound | Structure | Compound Name | ¹H NMR; MS [M + H]⁺ |
|---|---|---|---|
| 50 | 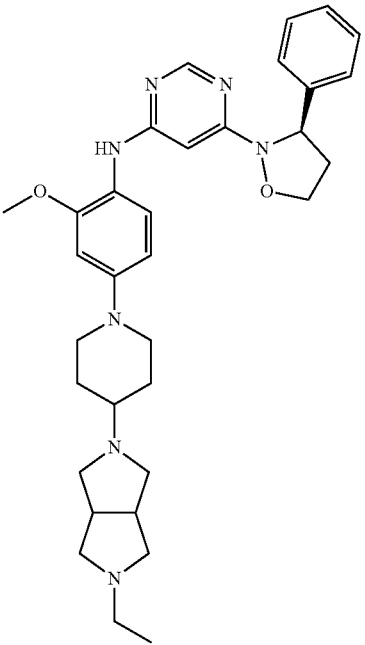 [SMILES: CCN1CC2CN(C3CCN(c4ccc(Nc5cc(N6OCC[C@@H]6c6ccccc6)ncn5)c(OC)c4)CC3)CC2C1] | N-(4-(4-(5-ethylhexahydropyrrolo[3,4-c]pyrrol-2(1H)-yl)piperidin-1-yl)-2-methoxyphenyl)-6-((R)-3-phenylisoxazolidin-2-yl)pyrimidin-4-amine | 570.3 [M + H]⁺ |
| 51 | 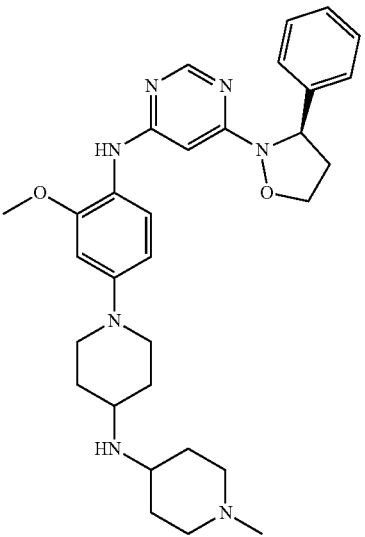 [SMILES: COc1cc(N2CCC(NC3CCN(C)CC3)CC2)ccc1Nc1cc(N2OCC[C@@H]2c2ccccc2)ncn1] | (R)-N-(2-methoxy-4-(4-((1-methylpiperidin-4-yl)amino)piperidin-1-yl)phenyl)-6-(3-phenylisoxazolidin-2-yl)pyrimidin-4-amine | 544.3 [M + H]⁺ |

TABLE 1-continued

| Example Compound | Structure | Compound Name | ¹H NMR; MS [M + H]⁺ |
|---|---|---|---|
| 52 | 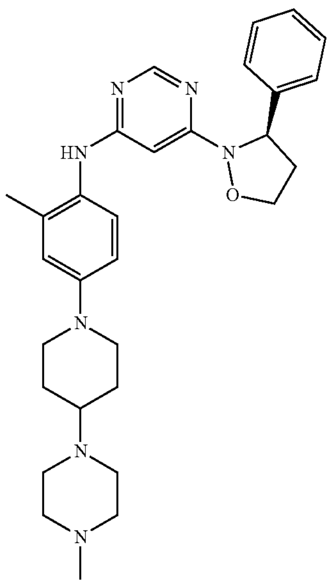 [SMILES: Cc1cc(N2CCC(N3CCN(C)CC3)CC2)ccc1Nc1cc(N2OCC[C@@H]2c2ccccc2)ncn1] | (R)-N-(2-methyl-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.40 (s, 1H), 8.14 (s, 1H), 7.40-7.31 (m, 4H), 7.24 (s, 1H), 7.13 (d, J = 8.6 Hz, 1H), 6.85-6.73 (m, 2H), 5.97 (s, 1H), 5.62 (dd, J = 8.7, 4.7 Hz, 1H), 4.10 (td, J = 7.8, 4.5 Hz, 1H), 3.85 (q, J = 7.8 Hz, 1H), 3.76 (d, J = 12.2 Hz, 2H), 3.02 (d, J = 30.2 Hz, 8H), 2.81-2.66 (m, 4H), 2.63 (s, 3H), 2.42-2.31 (m, 1H), 2.22 (s, 3H), 1.98 (d, J = 12.4 Hz, 2H), 1.72 (qd, J = 12.1, 4.0 Hz, 2H); 514.34 [M + H]⁺ |
| 53 | 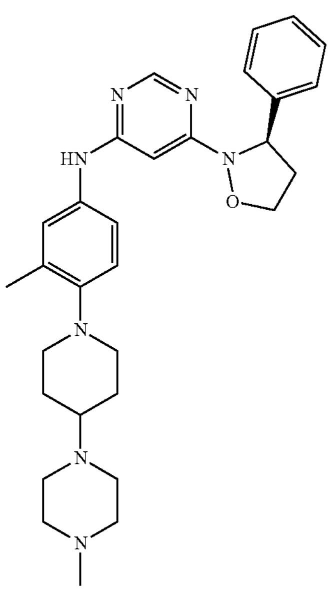 [SMILES: Cc1cc(Nc2cc(N3OCC[C@@H]3c3ccccc3)ncn2)ccc1N1CCC(N2CCN(C)CC2)CC1] | (R)-N-(3-methyl-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.29-8.26 (m, 1H), 7.46-7.42 (m, 2H), 7.37-7.31 (m, 2H), 7.26-7.23 (m, 1H), 7.12-7.06 (m, 2H), 7.02-6.98 (m, 1H), 6.63 (s, 1H), 6.45-6.43 (m, 1H), 5.67 (dd, J = 8.6, 4.6 Hz, 1H), 4.11 (td, J = 7.9, 4.5 Hz, 1H), 3.91-3.83 (m, 1H), 3.21-3.13 (m, 2H), 2.83-2.61 (m, 8H), 2.60-2.45 (m, 3H), 2.43-2.36 (m, 2H), 2.34 (s, 3H), 2.29 (s, 3H), 1.97 (d, J = 12.2 Hz, 2H), 1.75-1.69 (m, 2H); 514.3 [M + H]⁺ |

TABLE 1-continued

| Example Compound | Structure | Compound Name | ¹H NMR; MS [M + H]⁺ |
|---|---|---|---|
| 54 | 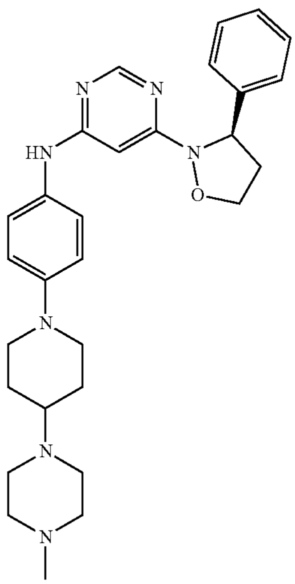 [SMILES: CN1CCN(C2CCN(c3ccc(Nc4cc(N5OCC[C@@H]5c5ccccc5)ncn4)cc3)CC2)CC1] | (R)-N-(4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.20 (s, 1H), 7.61 (s, 1H), 7.42 (d, J = 7.5 Hz, 2H), 7.34 (t, J = 7.5 Hz, 2H), 7.26-7.22 (m, 1H), 7.19-7.12 (m, 2H), 6.94 (d, J = 8.8 Hz, 2H), 6.37 (s, 1H), 5.65 (dd, J = 8.7, 4.6 Hz, 1H), 4.10 (td, J = 7.8, 4.4 Hz, 1H), 3.86 (q, J = 7.8 Hz, 1H), 3.73 (d, J = 12.2 Hz, 2H), 2.79-2.63 (m, 11H), 2.48-2.39 (m, 2H), 2.37 (s, 3H), 1.97 (d, J = 12.5 Hz, 2H), 1.69 (qd, J = 12.1, 4.0 Hz, 2H); 500.3 [M + H]⁺ |
| 55 | 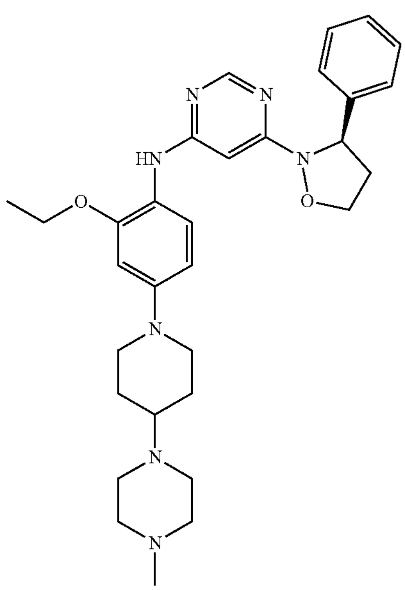 [SMILES: CCOc1cc(N2CCC(N3CCN(C)CC3)CC2)ccc1Nc1cc(N2OCC[C@@H]2c2ccccc2)ncn1] | (R)-N-(2-ethoxy-4-(4-(4-methylpiperazin-1-yl)piperidin-1-yl)phenyl)-6-(3-phenylisoxazolidin-2-yl)pyrimidin-4-amine | 544.3 [M + H]⁺ |

TABLE 1-continued

| Example Compound | Structure | Compound Name | ¹H NMR; MS [M + H]⁺ |
|---|---|---|---|
| 56 | 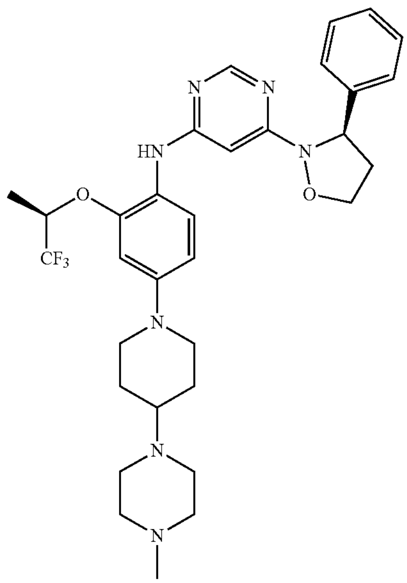 [SMILES: C[C@@H](Oc1cc(N2CCC(N3CCN(C)CC3)CC2)ccc1Nc1cc(N2OCC[C@@H]2c2ccccc2)ncn1)C(F)(F)F] | N-(4-(4-(4-methylpiperazin-1-yl)piperidin-1-yl)-2-((R)-1,1,1-trifluoropropan-2-yl)oxy)phenyl)-6-((R)-3-phenylisoxazolidin-2-yl)pyrimidin-4-amine | ¹H NMR (400 MHz, Chloroform-d) δ 8.31 (d, J = 1.0 Hz, 1H), 7.57 (d, J = 8.8 Hz, 1H), 7.47-7.42 (m, 2H), 7.35 (dd, J = 8.4, 6.9 Hz, 2H), 7.26-7.23 (m, 1H), 6.70 (s, 1H), 6.67 (dd, J = 8,9, 2.6 Hz, 1H), 6.58 (d, J = 2.6 Hz, 1H), 6.37 (d, J = 1.0 Hz, 1H), 5.67 (dd, J = 8.6, 4.6 Hz, 1H), 4.56 (p, J = 6.3 Hz, 1H), 4.13 (td, J = 7.8, 4.4 Hz, 1H), 3.68 (d, J = 12.1 Hz, 2H), 2.84-2.46 (m, 11H), 2.40 (ddd, J = 12.5, 8.3, 4.5 Hz, 2H), 2.32 (s, 3H), 1.96 (s, 2H), 1.68 (qd, J = 12.2, 4.0 Hz, 2H), 1.49-1.46 (m, 3H), 1.33-1.27 (m, 1H); 612.38 [M + H]⁺ |
| 57 | 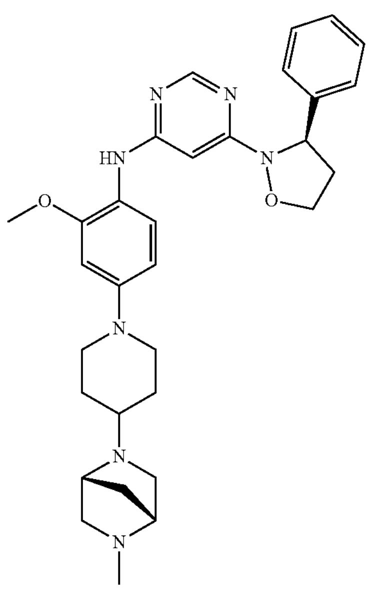 [SMILES: COc1cc(N2CCC(N3C[C@H]4C[C@@H]3CN4C)CC2)ccc1Nc1cc(N2OCC[C@@H]2c2ccccc2)ncn1] | N-(2-methoxy-4-(4-((1R,4R)-5-methyl-2,5-diazabicyclo[2.2.1]heptan-2-yl)piperidin-1-yl)phenyl)-6-((R)-3-phenylisoxazolidin-2-yl)pyrimidin-4-amine | ¹H NMR (400 MHz, Chloroform-d) δ 10.95 (s, 1H), 8.01 (s, 1H), 7.35 (d, J = 7.2 Hz, 2H), 7.29 (d, J = 7.4 Hz, 3H), 7.15 (d, J = 8.5 Hz, 1H), 6.62 (s, 1H), 6.57 (d, J = 8.7 Hz, 1H), 5.75 (s, 1H), 5.57 (dd, J = 8.7, 4.6 Hz, 1H), 4.32 (s, 1H), 4.25 (q, J = 7.0 Hz, 1H), 4.09 (s, 1H), 4.03 (q, J = 7.6 Hz, 1H), 3.82 (s, 3H), 3.77-3.69 (m, 2H), 3.59 (s, 2H), 3.16 (s, 2H), 2.95-2.81 (m, 7H), 2.45-2.39 (m, 2H), 2.31 (d, J = 11.9 Hz, 1H), 2.05 (s, 1H), 1.94 (s, 3H); 542.40 [M + H]⁺ |

TABLE 1-continued

| Example Compound | Structure | Compound Name | ¹H NMR; MS [M + H]⁺ |
|---|---|---|---|
| 58 | 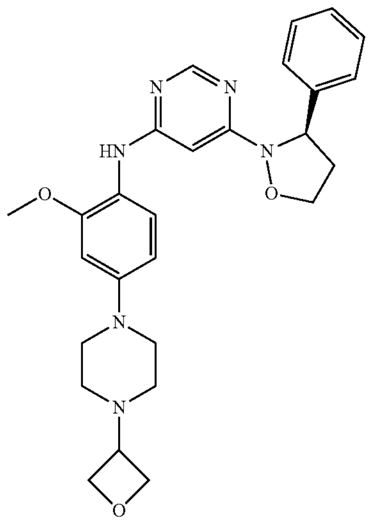 [SMILES: COc1cc(N2CCN(C3COC3)CC2)ccc1Nc1cc(N2OCC[C@@H]2c2ccccc2)ncn1] | (R)-N-(2-methoxy-4-(4-(oxetan-3-yl)piperazin-1-yl)phenyl)-6-(3-phenylisoxazolidin-2-yl)pyrimidin-4-amine | 489.3 [M + H]⁺ |
| 59 | 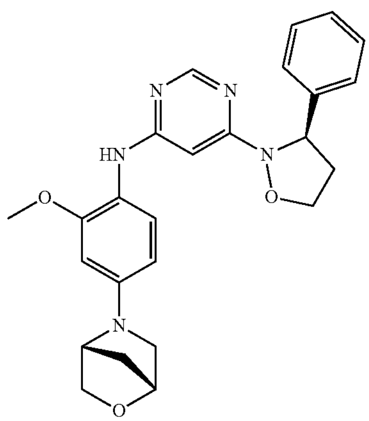 [SMILES: COc1cc(N2C[C@H]3C[C@@H]2CO3)ccc1Nc1cc(N2OCC[C@@H]2c2ccccc2)ncn1] | N-(4-((1R,4R)-2-oxa-5-azabicyclo[2.2.1]heptan-5-yl)-2-methoxyphenyl)-6-((R)-3-phenylisoxazolidin-2-yl)pyrimidin-4-amine | ¹H NMR (400 MHz, Chloroform-d) δ 8.28 (d, J = 1.0 Hz, 1H), 7.47-7.37 (m, 2H), 7.34 (t, J = 7.6 Hz, 2H), 7.25-7.21 (m, 2H), 6.58 (s, 1H), 6.35 (d, J = 1.0 Hz, 1H), 6.20 (dd, J = 8.6, 2.5 Hz, 1H), 6.16 (d, J = 2.5 Hz, 1H), 5.68 (dd, J = 8.7, 4.5 Hz, 1H), 4.67 (s, 1H), 4.40 (s, 1H), 4.14-4.07 (m, 1H), 3.97 (d, J = 7.4 Hz, 1H), 3.92-3.85 (m, 2H), 3.83 (s, 3H), 3.58 (dd, J = 9.0, 1.6 Hz, 1H), 3.20 (d, J = 9.1 Hz, 1H), 2.76-2.66 (m, 1H), 2.43-2.33 (m, 1H), 2.07-1.96 (m, 2H); 446.3 [M +H]⁺ |
| 60 | 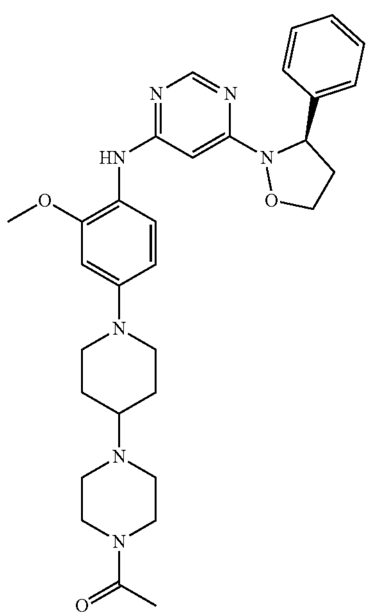 [SMILES: COc1cc(N2CCC(N3CCN(C(C)=O)CC3)CC2)ccc1Nc1cc(N2OCC[C@@H]2c2ccccc2)ncn1] | (R)-1-(4-(1-(3-methoxy-4-((6-(3-phenylisoxazolidin-2-yl)pyrimidin-4-yl)amino)phenyl)piperidin-4-yl)piperazin-1-yl)ethan-1-one | 558.3 [M + H]⁺ |

TABLE 1-continued

| Example Compound | Structure | Compound Name | ¹H NMR; MS [M + H]⁺ |
|---|---|---|---|
| 61 | 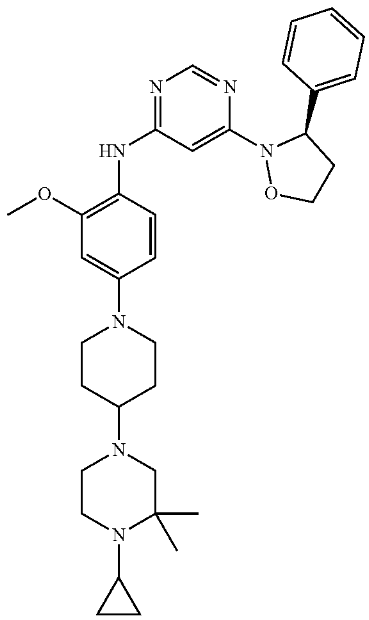 [SMILES: COc1cc(N2CCC(N3CCN(C4CC4)C(C)(C)C3)CC2)ccc1Nc1cc(N2OCC[C@@H]2c2ccccc2)ncn1] | (R)-N-(4-(4-(4-cyclopropyl-3,3-dimethylpiperazin-1-yl)piperidin-1-yl)-2-methoxyphenyl)-6-(3-phenylisoxazolidin-2-yl)pyrimidin-4-amine | ¹H NMR (400 MHz, Chloroform-d) δ 8.23 (s, 1H), 7.71 (s, 1H), 7.47-7.39 (m, 3H), 7.38-7.31 (m, 2H), 7.29-7.25 (m, 1H), 6.55-6.48 (m, 2H), 6.27 (s, 1H), 5.65 (dd, J = 8.6, 4.6 Hz, 1H), 4.13 (td, J = 7.7, 4.6 Hz, 1H), 3.91 (q, J = 7.8 Hz, 1H), 3.83 (s, 3H), 3.70 (d, J = 12.4 Hz, 2H), 3.20 (s, 3H), 3.08-2.86 (m, 3H), 2.82-2.63 (m, 6H), 2.46-2.32 (m, 2H), 2.14 (s, 1H), 2.06 (s, 1H), 2.03-1.94 (m, 2H), 1.73 (d, J = 12.3 Hz, 2H), 1.44 (s, 6H); 584.5 [M + H]⁺ |
| 62 | 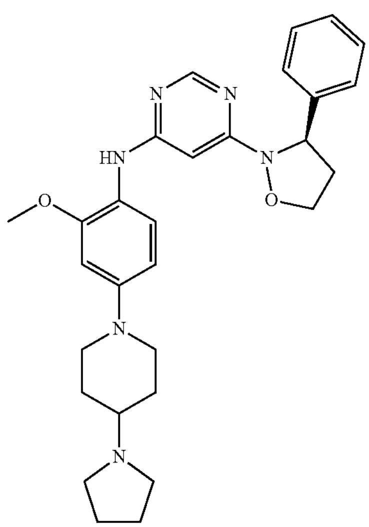 [SMILES: COc1cc(N2CCC(N3CCCC3)CC2)ccc1Nc1cc(N2OCC[C@@H]2c2ccccc2)ncn1] | (R)-N-(2-methoxy-4-(4-(pyrrolidin-1-yl)piperidin-1-yl)phenyl)-6-(3-phenylisoxazolidin-2 yl)pyrimidin-4-amine | ¹H NMR (400 MHz, Chloroform-d) δ 12.12 (s, 1H), 10.75 (s, 1H), 8.02 (s, 1H), 7.39-7.27 (m, 4H), 7.14 (d, J = 8.5 Hz, 1H), 6.67-6.54 (m, 2H), 5.75 (s, 1H), 5.57 (dd, J = 8.6, 4.6 Hz, 1H), 4.71 (s, 1H), 4.29-4.21 (m, 1H), 4.04 (q, J = 7.5 Hz, 1H), 3.93-3.35 (m, 7H), 3.28-3.13 (m, 1H), 3.00-2.80 (m, 4H), 2.48-2.39 (m, 1H), 2.25-1.89 (m, 8H); 501.3 [M + H]⁺ |

TABLE 1-continued

| Example Compound | Structure | Compound Name | ¹H NMR; MS [M + H]⁺ |
|---|---|---|---|
| 63 | 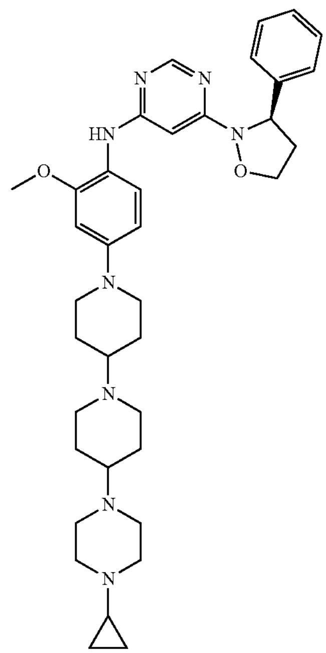 [SMILES: COc1cc(N2CCC(N3CCC(N4CCN(C5CC5)CC4)CC3)CC2)ccc1Nc1cc(N2OCC[C@@H]2c2ccccc2)ncn1] | (R)-N-(4-(4-(4-cyclopropylpiperazin-1-yl)-(1,4'-bipiperidin]-1'-yl)-2-methoxyphenyl)-6-(3-phenylisoxazolidin-2-yl)pyrimidin-4-amine | ¹H NMR (400 MHz, Chloroform-d) δ 8.22 (s, 1H), 7.71 (s, 1H), 7.43 (d, J = 7.6 Hz, 2H), 7.35 (t, J = 7.5 Hz, 2H), 7.24 (s, 1H), 6.91 (d, J = 8.2 Hz, 1H), 6.82 (d, J = 7.6 Hz, 2H), 6.46 (s, 1H), 5.64 (dd, J = 8.7, 4.7 Hz, 1H), 4.12 (td, J = 7.8, 4.3 Hz, 1H), 3.86 (s, 4H), 3.55 (d, J = 11.2 Hz, 2H), 3.17 (d, J = 11.0 Hz, 2H), 2.75-2.55 (m, 12H), 2.49-2.35 (m, 5H), 1.98-1.63 (m, 12H); 639.56 [M + H]⁺ |
| 64 | 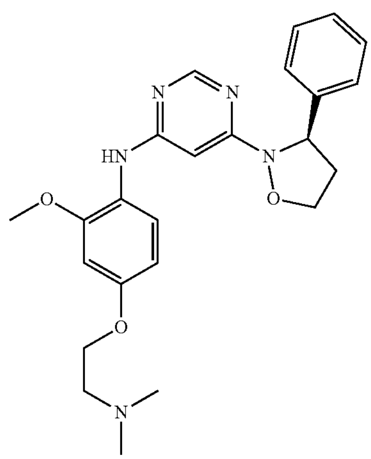 [SMILES: COc1cc(OCCN(C)C)ccc1Nc1cc(N2OCC[C@@H]2c2ccccc2)ncn1] | (R)-N-(4-(2-(dimethylamino)ethoxy)-2-methoxyphenyl)-6-(3-phenylisoxazolidin-2-yl)pyrimidin-4-amine | ¹H NMR (400 MHz, Chloroform-d) δ 8.30 (d, J = 1.0 Hz, 1H), 7.55 (d, J = 8.6 Hz, 1H), 7.47-7.40 (m, 2H), 7.35 (t, J = 8.4, 6.9 Hz, 2H), 7.26-7.23 (m, 1H), 6.90 (s, 1H), 6.58 (d, J = 2.6 Hz, 1H), 6.51 (dd, J = 8.7, 2.6 Hz, 1H), 6.38 (d, J = 1.0 Hz, 1H), 5.67 (dd, J = 8.6, 4.5 Hz, 1H), 4.17-4.07 (m, 3H), 3.89 (q, J = 7.9 Hz, 1H), 3.83 (s, 3H), 2.81 (t, J = 5.6 Hz, 2H), 2.72 (tdd, J = 8.7, 7.9, 4.4 Hz, 1H), 2.43-2.32 (m, 7H); 436.24 [M + H]⁺ |
| 65 | 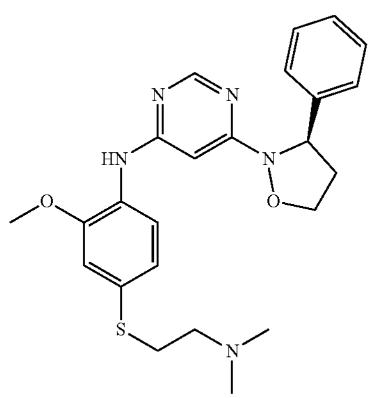 [SMILES: COc1cc(SCCN(C)C)ccc1Nc1cc(N2OCC[C@@H]2c2ccccc2)ncn1] | (R)-N-(4-((2-(dimethylamino)ethyl)thio)-2-methoxyphenyl)-6-(3-phenylisoxazolidin-2-yl)pyrimidin-4-amine | ¹H NMR (400 MHz, Chloroform-d) δ 8.36 (d, J = 1.0 Hz, 1H), 7.89 (d, J = 8.3 Hz, 1H), 7.46 (d, J = 7.3 Hz, 2H), 7.36 (t, J = 7.6 Hz, 2H), 7.29-7.25 (m, 1H), 7.10 (s, 1H), 7.02 (dd, J = 8.3, 2.0 Hz, 1H), 6.96 (d, J = 2.0 Hz, 1H), 6.52 (d, J = 1.0 Hz, 1H), 5.68 (dd, J = 8.6, 4.7 Hz, 1H), 4.16 (td, J = 7.8, 4.4 Hz, 1H), 3.96-3.87 (m, 4H), 3.06-2.98 (m, 2H), 2.81-2.70 (m, 1H), 2.62-2.55 (m, 2H), 2.46-2.36 (m, 1H), 2.29 (s, 6H); 452.21 [M + H]⁺ |

TABLE 1-continued

| Example Compound | Structure | Compound Name | ¹H NMR; MS [M + H]⁺ |
|---|---|---|---|
| 66 | 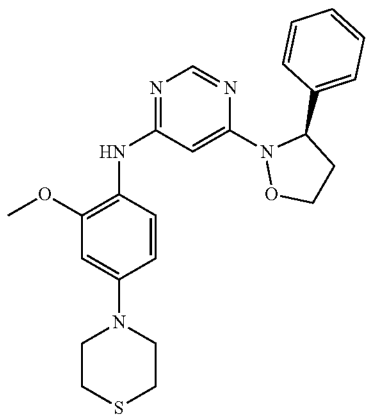 [SMILES: COc1cc(N2CCSCC2)ccc1Nc1cc(N2OCC[C@@H]2c2ccccc2)ncn1] | (R)-N-(2-methoxy-4-thiomorpholino-phenyl)-6-(3-phenylisoxazolidin-2-yl)pyrimidin-4-amine | ¹H NMR (400 MHz, Chloroform-d) δ 8.30 (d, J = 1.0 Hz, 1H), 7.56 (d, J = 8.3 Hz, 1H), 7.45 (d, J = 7.5 Hz, 2H), 7.35 (t, J = 7.6 Hz, 2H), 7.26-7.23 (m, 1H), 6.89 (s, 1H), 6.56-6.48 (m, 2H), 6.42 (d, J = 1.0 Hz, 1H), 5.68 (dd, J = 8.6, 4.6 Hz, 1H), 4.12 (td, J = 7.8, 4.4 Hz, 1H), 3.89 (q, J = 7.8 Hz, 1H), 3.85 (s, 3H), 3.53-3.49 (m, 4H), 2.81-2.67 (m, 5H), 2.44-2.34 (m, 1H); 450.22 [M + H]⁺ |
| 67 | 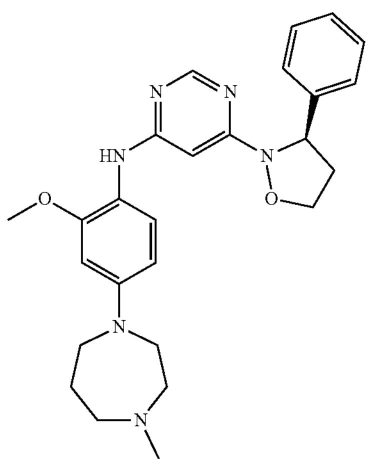 [SMILES: COc1cc(N2CCCN(C)CC2)ccc1Nc1cc(N2OCC[C@@H]2c2ccccc2)ncn1] | (R)-N-(2-methoxy-4-(4-methyl-1,4-diazepan-1-yl)phenyl)-6-(3-phenylisoxazolidin-2-yl)pyrimidin-4-amine | ¹H NMR (400 MHz, Chloroform-d) δ 8.26 (d, J = 1.0 Hz, 1H), 7.47-7.42 (m, 2H), 7.34 (td, J = 6.9, 6.3, 3.0 Hz, 3H), 7.24 (t, J = 7.2 Hz, 1H), 6.88 (s, 1H), 6.32 (d, J = 1.0 Hz, 1H), 6.31-6.23 (m, 2H), 5.68 (dd, J = 8.6, 4.5 Hz, 1H), 4.10 (td, J = 7.8, 4.4 Hz, 1H), 3.88 (q, J = 7.9 Hz, 1H), 3.83 (s, 3H), 3.67-3.62 (m, 2H), 3.50 (t, J = 6.4 Hz, 2H), 2.91-.286 (m, 2H), 2.78-2.68 (m, 4H), 2.48 (s, 3H), 2.42-2.33 (m, 1H), 2.13 (p, J = 6.2 Hz, 1H); 461.21 [M +H]⁺ |
| 68 | 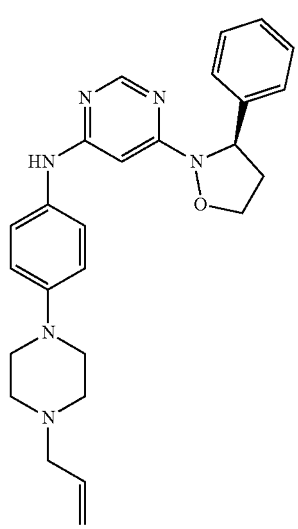 [SMILES: C=CCN1CCN(c2ccc(Nc3cc(N4OCC[C@@H]4c4ccccc4)ncn3)cc2)CC1] | (R)-N-(4-(4-allylpiperazin-1-yl)phenyl)-6-(3-phenylisoxazolidin-2-yl)pyrimidin-4-amine | ¹H NMR (400 MHz, Chloroform-d) δ 8.81 (s, 1H), 8.15 (s, 1H), 7.44-7.31 (m, 4H), 7.29-7.17 (m, 3H), 6.97-6.91 (m, 2H), 6.26 (s, 1H), 6.03-6.91 (m, 1H), 5.62 (dd, J = 8.6, 4.6 Hz, 1H), 5.47-5.36 (m, 2H), 4.17 (td, J = 7.7, 4.9 Hz, 1H), 3.94 (q, J = 7.7 Hz, 1H), 3.45 (d, J = 7.0 Hz, 2H), 3.39 (t, J = 5.1 Hz, 4H), 3.04 (t, J = 5.0 Hz, 4H), 2.83-2.73 (m, 1H), 2.45-2.35 (m, 1H); 443.3 [M + H]⁺ |

TABLE 1-continued

| Example Compound | Structure | Compound Name | ¹H NMR; MS [M + H]⁺ |
|---|---|---|---|
| 69 | 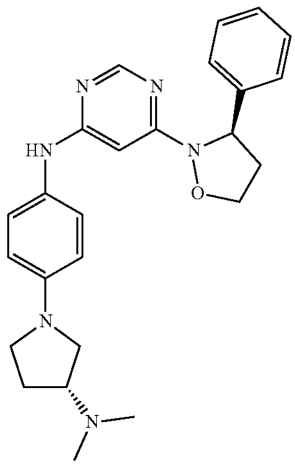 [SMILES: CN(C)[C@@H]1CCN(c2ccc(Nc3cc(N4OCC[C@@H]4c4ccccc4)ncn3)cc2)C1] | N-(4-((R)-3-(dimethylamino)pyrrolidin-1-yl)phenyl)-6-((R)-3-phenylisoxazolidin-2-yl)pyrimidin-4-amine | ¹H NMR (400 MHz, Chloroform-d) δ 10.89 (s, 1H), 8.01 (s, 1H), 7.39-7.27 (m, 6H), 7.18-7.13 (m, 2H), 6.60 (d, J = 8.7 Hz, 1H), 6.02 (s, 1H), 5.58 (dd, J = 8.7, 4.5 Hz, 1H), 4.29-4.20 (m, 1H), 4.04 (q, J = 7.5 Hz, 1H), 3.90-3.83 (m, 1H), 3.75-3.55 (m, 3H), 3.38 (q, J = 8.3 Hz, 1H), 2.86 (s, 3H), 2.68 (s, 3H), 2.50-2.34 (m, 4H); 431.3 [M + H]⁺ |
| 70 | 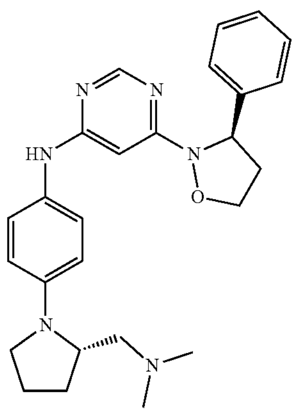 [SMILES: CN(C)C[C@@H]1CCCN1c1ccc(Nc2cc(N3OCC[C@@H]3c3ccccc3)ncn2)cc1] | N-(4-((S)-2-((dimethylamino)methyl)pyrrolidin-1-yl)phenyl)-6-((R)-3-phenylisoxazolidin-2-yl)pyrimidin-4-amine | 445.3 [M + H]⁺ |
| 71 | 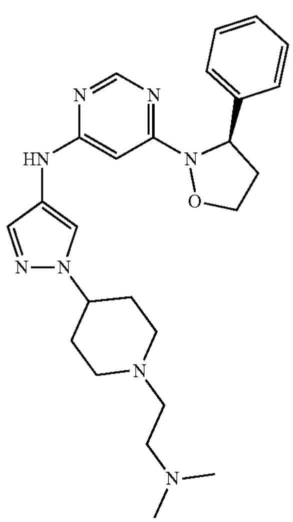 [SMILES: CN(C)CCN1CCC(n2cc(Nc3cc(N4OCC[C@@H]4c4ccccc4)ncn3)cn2)CC1] | (R)-N-(1-(1-(2-(dimethylamino)ethyl)piperidin-4-yl)-1H-pyrazol-4-yl)-6-(3-phenylisoxazolidin-2-yl)pyrimidin-4-amine | 463.3 [M + H]⁺ |

TABLE 1-continued

| Example Compound | Structure | Compound Name | ¹H NMR; MS [M + H]⁺ |
|---|---|---|---|
| 72 | 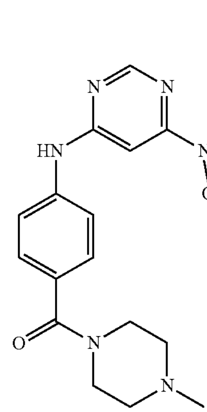 | (R)-(4-methylpiperazin-1-yl)(4-((6-(3-phenylisoxazolidin-2-yl)pyrimidin-4-yl)amino)phenyl)methanone | ¹H NMR (400 MHz, Chloroform-d) δ 8.66 (s, 1H), 8.24 (s, 1H), 7.47-7.40 (m, 4H), 7.39-7.33 (m, 4H), 7.31-7.27 (m, 1H), 6.57 (s, 1H), 5.63 (dd, J = 8.7, 4.8 Hz, 1H), 4.20 (td, J = 7.7, 4.5 Hz, 1H), 3.93 (q, J = 7.8 Hz, 1H), 3.74 (s, 4H), 2.83-2.74 (m, 1H), 2.63 (s, 4H), 2.48-2.37 (m, 4H); 445.24 [M + H]⁺ |
| 73 | 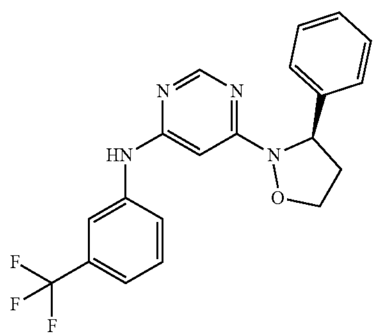 [SMILES: FC(F)(F)c1cccc(Nc2cc(N3OCC[C@@H]3c3ccccc3)ncn2)c1] | (R)-6-(3-phenylisoxazolidin-2-yl)-N-(3-(trifluoromethyl)phenyl)pyrimidin-4-amine | ¹H NMR (400 MHz, Chloroform-d) δ 8.36 (s, 1H), 7.65 (s, 1H), 7.58 (d, J = 8.5 Hz, 1H), 7.48 (t, J = 8.8 Hz, 1H), 7.45 (d, J = 7.4 Hz, 2H), 7.36 (t, J = 7.7 Hz, 3H), 7.28 (d, J = 7.7 Hz, 1H), 6.94 (s, 1H), 6.52 (d, J = 1.0 Hz, 1H), 5.67 (dd, J = 8.7, 4.8 Hz, 1H), 4.18 (td, J = 7.8, 4.4 Hz, 1H), 3.91 (q, J = 7.9 Hz, 1H), 2.77 (dtd, J = 12.2, 8.0, 4.4 Hz, 1H), 2.46-2.36 (m, 1H); 387.17 [M + H]⁺ |
| 74 | 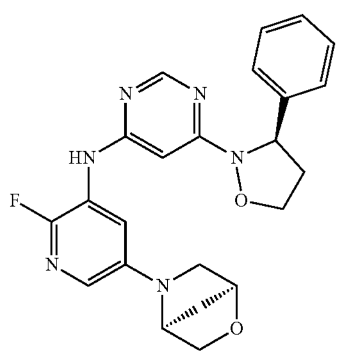 [SMILES: Fc1ncc(N2C[C@@H]3C[C@H]2CO3)cc1Nc1cc(N2OCC[C@@H]2c2ccccc2)ncn1] | N-(5-((1S,4S)-2-oxa-5-azabicyclo[2.2.1]heptan-5-yl)-2-fluoropyridin-3-yl)-6-((R)-3-phenylisoxazolidin-2-yl)pyrimidin-4-amine | ¹H NMR (400 MHz, Chloroform-d) δ 8.37 (d, J = 1.0 Hz, 1H), 7.92 (dd, J = 8.6, 2.9 Hz, 1H), 7.48-7.41 (m, 2H), 7.37 (t, J = 7.6 Hz, 2H), 7.30-7.27 (m, 1H), 7.17-7.09 (m, 1H), 6.90 (s, 1H), 6.46 (d, J = 0.8 Hz, 1H), 5.66 (dd, J = 8.6, 4.8 Hz, 1H), 4.67 (d, J = 2.2 Hz, 1H), 4.38 (s, 1H), 4.19 (td, J = 7.8, 4.4 Hz, 1H), 3.97-3.86 (m, 3H), 3.59 (dd, J = 9.1, 1.6 Hz, 1H), 3.18 (d, J = 9.2 Hz, 1H), 2.78 (dddd, J = 12.0, 8.6, 7.5, 4.4 Hz, 1H), 2.43 (dtd, J = 12.5, 7.9, 4.7 Hz, 1H), 2.02 (ddd, J = 22.7, 9.8, 2.4 Hz, 2H); 435.27 [M + H]⁺ |
| 75 | 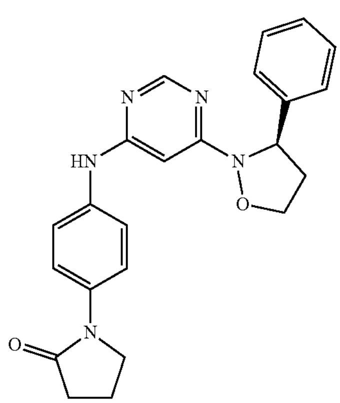 [SMILES: O=C1CCCN1c1ccc(Nc2cc(N3OCC[C@@H]3c3ccccc3)ncn2)cc1] | (R)-1-(4-((6-(3-phenylisoxazolidin-2-yl)pyrimidin-4-yl)amino)phenyl)pyrrolidin-2-one | ¹H NMR (400 MHz, Chloroform-d) δ 8.26 (s, 1H), 7.63 (d, J = 8.7 Hz, 2H), 7.50 (s, 1H), 7.44 (d, J = 7.7 Hz, 2H), 7.39-7.27 (m, 5H), 6.49 (d, J = 1.1 Hz, 1H), 5.65 (dd, J = 8.7, 4.8 Hz, 1H), 4.14 (td, J = 7.8, 4.4 Hz, 1H), 3.88 (q, J = 7.2 Hz, 3H), 2.75 (dtd, J = 12.5, 8.0, 4.3 Hz, 1H), 2.64 (t, J = 8.1 Hz, 2H), 2.44-2.35 (m, 1H), 2.20 (dd, J = 13.7, 6.3 Hz, 2H); 402.21 [M + H]⁺ |

TABLE 1-continued

| Example Compound | Structure | Compound Name | ¹H NMR; MS [M + H]⁺ |
|---|---|---|---|
| 76 | 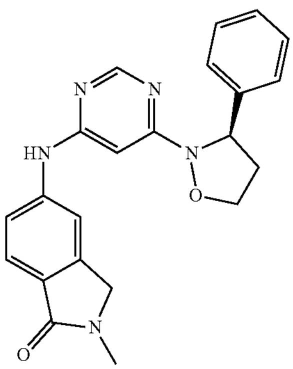 [SMILES: CN1Cc2cc(Nc3cc(N4OCC[C@@H]4c4ccccc4)ncn3)ccc2C1=O] | (R)-2-methyl-5-((6-(3-phenylisoxazolidin-2-yl)pyrimidin-4-yl)amino)isoindolin-1-one | ¹H NMR (400 MHz, Chloroform-d) δ 8.32 (d, J = 1.0 Hz, 1H), 7.81 (d, J = 8.2 Hz, 1H), 7.71 (s, 1H), 7.59 (d, J = 1.2 Hz, 1H), 7.47-7.41 (m, 2H), 7.37 (td, J = 6.9, 1.6 Hz, 2H), 7.33-7.27 (m, 2H), 6.58 (d, J = 1.0 Hz, 1H), 5.65 (dd, J = 8.6, 4.8 Hz, 1H), 4.38 (s, 2H), 4.18 (td, J = 7.8, 4.5 Hz, 1H), 3.91 (q, J = 7.9 Hz, 1H), 3.20 (s, 3H), 2.83-2.74 (m, 1H), 2.42 (dtd, J = 12.5, 7.9, 4.8 Hz, 1H); 388.23 [M + H]⁺ |
| 77 | 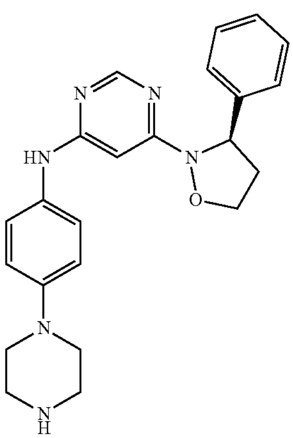 [SMILES: c1ccc([C@H]2CCON2c2cc(Nc3ccc(N4CCNCC4)cc3)ncn2)cc1] | (R)-6-(3-phenylisoxazolidin-2-yl)-N-(4-(piperazin-1-yl)phenyl)pyrimidin-4-amine | 1H NMR (400 MHz, Chloroform-d) δ 8.19 (d, J = 1.0 Hz, 1H), 7.97 (s, 1H), 7.44-7.40 (m, 2H), 7.35 (dd, J = 8.5, 6.8 Hz, 2H), 7.28-7.24 (m, 1H), 7.22-7.17 (m, 2H), 6.98-6.90 (m, 2H), 6.39 (d, J = 1.1 Hz, 1H), 5.64 (dd, J = 8.6, 4.7 Hz, 1H), 4.12 (td, J = 7.7, 4.4 Hz, 1H), 3.87 (q, J = 7.9 Hz, 1H), 3.25 (dd, J = 6.5, 3.5 Hz, 4H), 3.17 (dd, J = 6.5, 3.5 Hz, 4H), 2.74 (dddd, J = 12.1, 8.7, 7.6, 4.5 Hz, 1H), 2.38 (dtd, J = 12.4, 7.9, 4.7 Hz, 1H); 403.23 [M + H]⁺ |
| 78 | 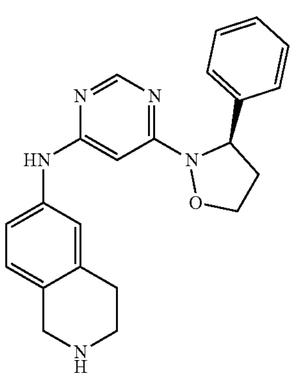 [SMILES: c1ccc([C@H]2CCON2c2cc(Nc3ccc4c(c3)CCNC4)ncn2)cc1] | (R)-N-(6-(3-phenylisoxazolidin-2-yl)pyrimidin-4-yl)-1,2,3,4-tetrahydroisoquinolin-6-amine | ¹H NMR (400 MHz, Chloroform-d) δ 8.23 (s, 1H), 7.81 (s, 1H), 7.46-7.30 (m, 4H), 7.26-7.22 (m, 1H), 7.20-7.12 (m, 2H), 7.04 (d, J = 8.1 Hz, 1H), 6.46 (s, 1H), 5.61 (dd, J = 8.6, 4.8 Hz, 1H), 5.13 (s, 1H), 4.23 (s, 2H), 4.14 (td, J = 7.8, 4.4 Hz, 1H), 3.88 (q, J = 7.8 Hz, 1H), 3.43-3.33 (m, 2H), 3.09-2.98 (m, 2H), 2.80-2.67 (m, 1H), 2.43-2.33 (m, 1H); 374.2 [M + H]⁺ |

TABLE 1-continued

| Example Compound | Structure | Compound Name | ¹H NMR; MS [M + H]⁺ |
|---|---|---|---|
| 79 | 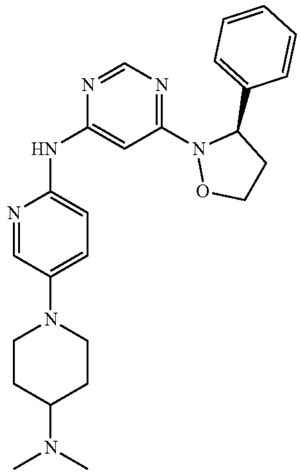 [SMILES: CN(C)C1CCN(c2ccc(Nc3cc(N4OCC[C@@H]4c4ccccc4)ncn3)nc2)CC1] | (R)-N-(5-(4-(dimethylamino)piperidin-1-yl)pyridin-2-yl)-6-(3-phenylisoxazolidin-2-yl)pyrimidin-4-amine | ¹H NMR (400 MHz, Chloroform-d) δ 8.76 (s, 1H), 8.30 (d, J = 1.0 Hz, 1H), 7.96 (d, J = 3.0 Hz, 1H), 7.47 (dd, J = 9.0, 7.1 Hz, 3H), 7.36 (dd, J = 8.4, 6.8 Hz, 2H), 7.32-7.28 (m, 1H), 7.26-7.24 (m, 2H), 5.67 (dd, J = 8.6, 4.7 Hz, 1H), 4.21 (td, J = 7.9, 4.6 Hz, 1H), 3.99 (q, J = 7.8 Hz, 2H), 3.66 (d, J = 12.1 Hz, 2H), 2.87-2.71 (m, 4H), 2.55 (s, 6H), 2.42 (ddt, J = 11.5, 7.5, 3.8 Hz, 1H), 2.07 (s, 2H), 1.80 (qd, J = 12.1, 4.1 Hz, 1H); 446.30 [M + H]⁺ |
| 80 | 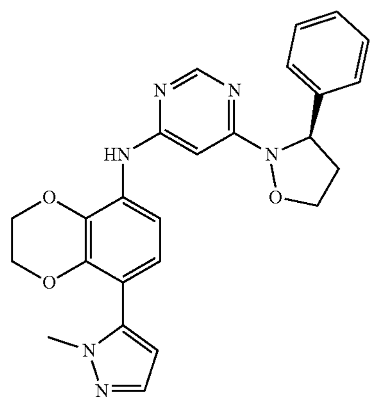 [SMILES: Cn1nccc1-c1ccc(Nc2cc(N3OCC[C@@H]3c3ccccc3)ncn2)c2c1OCCO2] | (R)-N-(8-(1-methyl-1H-pyrazol-5-yl)-2,3-dihydrobenzo[b][1,4]dioxin-5-yl)-6-(3-phenylisoxazolidin-2-yl)pyrimidin-4-amine | ¹H NMR (400 MHz, Chloroform-d) δ 8.39 (d, J = 1.0 Hz, 1H), 7.63 (d, J = 8.4 Hz, 1H), 7.53 (d, J = 1.9 Hz, 1H), 7.48-7.44 (m, 2H), 7.39-7.33 (m, 2H), 7.30-7.27 (m, 1H), 7.01 (s, 1H), 6.86 (d, J = 8.4 Hz, 1H), 6.61 (d, J = 1.0 Hz, 1H), 6.27 (d, J = 1.9 Hz, 1H), 5.69 (dd, J = 8.6, 4.7 Hz, 1H), 4.40-4.29 (m, 4H), 4.24-4.15 (m, 1H), 3.95 (q, J = 7.8 Hz, 1H), 3.79 (s, 3H), 2.84-2.71 (m, 1H), 2.48-2.37 (m, 1H); 457.2 [M + H]⁺ |
| 81 | 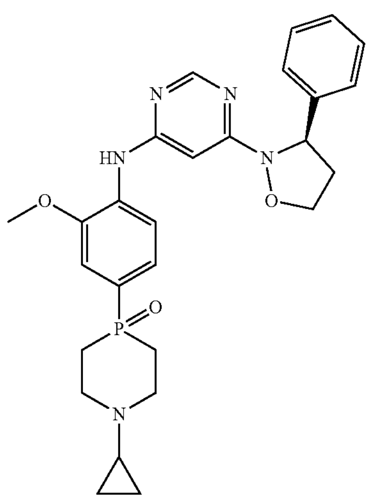 [SMILES: COc1cc(P2(=O)CCN(C3CC3)CC2)ccc1Nc1cc(N2OCC[C@@H]2c2ccccc2)ncn1] | (R)-1-cyclopropyl-4-(3-methoxy-4-((6-(3-phenylisoxazolidin-2-yl)pyrimidin-4-yl)amino)phenyl)-1,4-azaphosphinane 4-oxide | ¹H NMR (400 MHz, Chloroform-d) δ 10.67 (s, 1H), 8.13 (s, 1H), 7.68-7.60 (m, 1H), 7.53-7.43 (m, 2H), 7.41-7.25 (m, 5H), 6.03 (s, 1H), 5.61 (dd, J = 8.6, 4.6 Hz, 1H), 4.32-4.25 (m, 1H), 4.08 (q, J = 7.5 Hz, 1H), 4.03-3.79 (m, 7H), 3.03 (td, J = 14.7, 4.9 Hz, 2H), 2.94-2.82 (m, 1H), 2.64-2.57 (m, 1H), 2.50-2.40 (m, 1H), 2.18 (t, J = 17.1 Hz, 2H), 1.42-1.34 (m, 2H), 1.00-0.91 (m, 2H); 506.3 [M + H]⁺ |

TABLE 1-continued

| Example Compound | Structure | Compound Name | ¹H NMR; MS [M + H]⁺ |
|---|---|---|---|
| 82 | 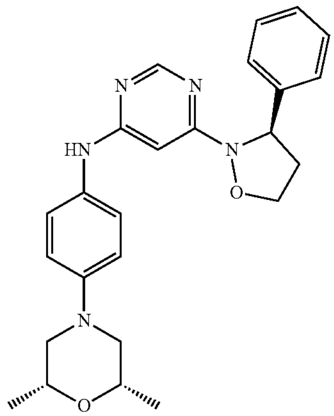 [SMILES: C[C@@H]1CN(c2ccc(Nc3cc(N4OCC[C@@H]4c4ccccc4)ncn3)cc2)C[C@H](C)O1] | N-(4-((2R,6S)-2,6-dimethylmorpholino)phenyl)-6-((R)-3-phenylisoxazolidin-2-yl)pyrimidin-4-amine | 432.3 [M + H]⁺ |
| 83 | 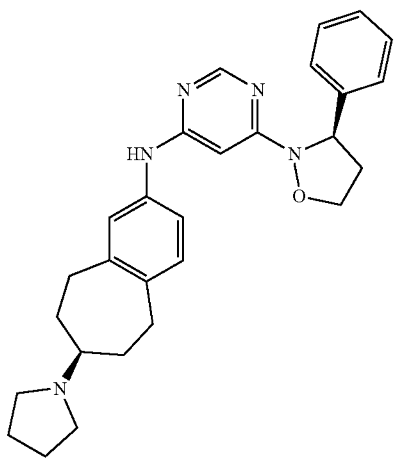 [SMILES: c1ccc([C@H]2CCON2c2cc(Nc3ccc4c(c3)CC[C@H](N3CCCC3)CC4)ncn2)cc1] | 6-((R)-3-phenylisoxazolidin-2-yl)-N-((R)-7-(pyrrolidin-1-yl)-6,7,8,9-tetrahydro-5H-benzo[7]annulen-2-yl)pyrimidin-4-amine | ¹H NMR (400 MHz, Chloroform-d) δ 12.65 (s, 1H), 11.67 (s, 1H), 8.01 (s, 1H), 7.40-7.29 (m, 4H), 7.20-7.04 (m, 3H), 6.15 (s, 1H), 5.59 (dd, J = 8.6, 4.4 Hz, 1H), 4.29 (q, J = 7.0 Hz, 1H), 4.11 (q, J = 7.4 Hz, 1H), 3.83-3.70 (m, 2H), 3.41 (t, J = 11.7 Hz, 1H), 2.98-2.87 (m, 5H), 2.78 (t, J = 13.1 Hz, 2H), 2.51-2.36 (m, 3H), 2.22-2.10 (m, 2H), 2.05-1.95 (m, 2H), 1.70-1.56 (m, 2H); 456.3 [M + H]⁺ |
| 84 | 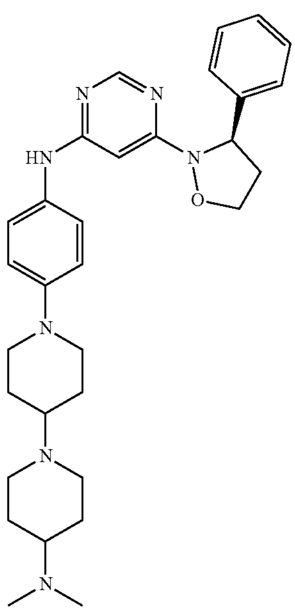 [SMILES: CN(C)C1CCN(C2CCN(c3ccc(Nc4cc(N5OCC[C@@H]5c5ccccc5)ncn4)cc3)CC2)CC1] | (R)-N,N-dimethyl-1'-(4-((6-(3-phenylisoxazolidin-2-yl)pyrimidin-4-yl)amino)phenyl)-[1,4'-bipiperidin]-4-amine | ¹H NMR (400 MHz, Chloroform-d) δ 8.27 (d, J = 1.0 Hz, 1H), 7.46-7.40 (m, 2H), 7.38-7.31 (m, 2H), 7.24 (d, J = 7.2 Hz, 1H), 7.19-7.15 (m, 2H), 6.94 (d, J = 8.9 Hz, 2H), 6.53 (s, 1H), 6.36 (d, J = 1.1 Hz, 1H), 5.67 (dd, J = 8.6, 4.6 Hz, 1H), 4.14-4.06 (m, 1H), 3.86 (q, J = 7.9 Hz, 1H), 3.74 (d, J = 12.1 Hz, 2H), 3.05 (d, J = 11.3 Hz, 2H), 2.78-2.67 (m, 3H), 2.52-2.35 (m, 3H), 2.33 (s, 6H), 2.29-2.19 (m, 3H), 1.98-1.83 (m, 5H), 1.72 (d, J = 3.7 Hz, 2H); 528.3 [M + H]⁺ |

TABLE 1-continued

| Example Compound | Structure | Compound Name | ¹H NMR; MS [M + H]⁺ |
|---|---|---|---|
| 85 | 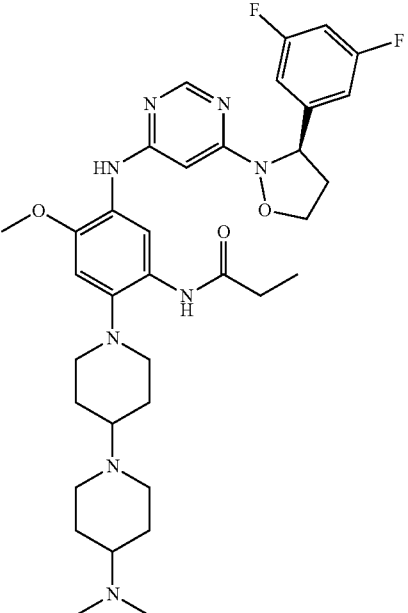 [SMILES: CCC(=O)Nc1cc(Nc2cc(N3OCC[C@@H]3c3cc(F)cc(F)c3)ncn2)c(OC)cc1N1CCC(N2CCC(N(C)C)CC2)CC1] | (R)-N-(5-((6-(3-(3,5-difluorophenyl)isoxazolidin-2-yl)pyrimidin-4-yl)amino)-2-(4-(dimethylamino)-[1,4'-bipiperidin]-1'-yl)-4-methoxyphenyl)propionamide | ¹H NMR (400 MHz, Chloroform-d) δ 8.77 (s, 1H), 8.35 (s, 1H), 8.30 (s, 1H), 7.04-6.96 (m, 2H), 6.94 (s, 1H), 6.75-6.64 (m, 3H), 5.71-5.61 (m, 1H), 4.19-4.11 (m, 1H), 4.05 (q, J = 8.1 Hz, 1H), 3.83 (s, 3H), 3.17-3.01 (m, 4H), 2.82-2.66 (m, 3H), 2.46-2.29 (m, 11H), 2.24-2.16 (m, 3H), 1.94-1.86 (m, 2H), 1.75-1.54 (m, 5H), 1.31-1.23 (m, 3H); 665.6 [M + H]⁺ |
| 86 | 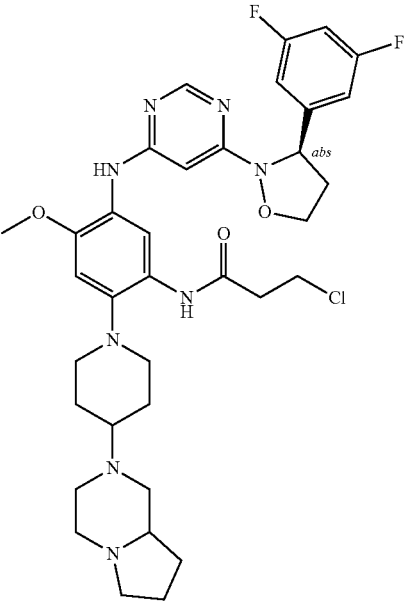 [SMILES: COc1cc(N2CCC(N3CCN4CCCC4C3)CC2)c(NC(=O)CCCl)cc1Nc1cc(N2OCC[C@@H]2c2cc(F)cc(F)c2)ncn1] | 3-chloro-N-(5-((6-((R)-3-(3,5-difluorophenyl)isoxazolidin-2-yl)pyrimidin-4-yl)amino)-2-(4-(hexahydropyrrolo[1,2-a]pyrazin-2(1H)-yl)piperidin-1-yl)-4-methoxyphenyl)propanamide | 698.3 [M + H]⁺ |

TABLE 1-continued

| Example Compound | Structure | Compound Name | ¹H NMR; MS [M + H]⁺ |
|---|---|---|---|
| 87 | 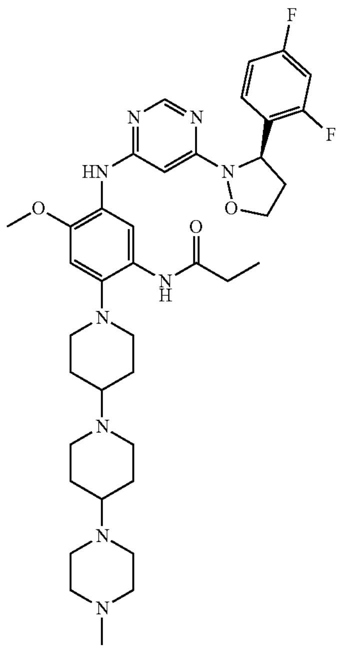 [SMILES: CCC(=O)Nc1cc(Nc2cc(N3OCC[C@@H]3c3ccc(F)cc3F)ncn2)c(OC)cc1N1CCC(N2CCC(N3CCN(C)CC3)CC2)CC1] | (R)-N-(5-((6-(3-(2,4-difluorophenyl)isoxazolidin-2-yl)pyrimidin-4-yl)amino)-4-methoxy-2-(4-(4-methylpiperazin-1-yl)-[1,4'-bipiperidin]-1'-yl)phenyl)propanionamide | ¹H NMR (400 MHz, Chloroform-d) δ 8.72 (s, 1H), 8.36-8.24 (m, 2H), 7.55 (q, J = 7.9 Hz, 1H), 6.85-6.77 (m, 2H), 6.71 (d, J = 10.1 Hz, 2H), 5.86 (dd, J = 8.8, 4.4 Hz, 1H), 4.14-4.00 (m, 3H), 3.85-3.80 (m, 3H), 3.21 (d, J = 11.1 Hz, 2H), 3.11-2.99 (m, 3H), 2.82-2.66 (m, 11H), 2.63-2.53 (m, 2H), 2.48-2.41 (m, 3H), 2.39 (s, 3H), 2.35-2.22 (m, 4H), 1.96-1.88 (m, 3H), 1.81-1.63 (m, 5H); 720.7 [M + H]⁺ |
| 88 | 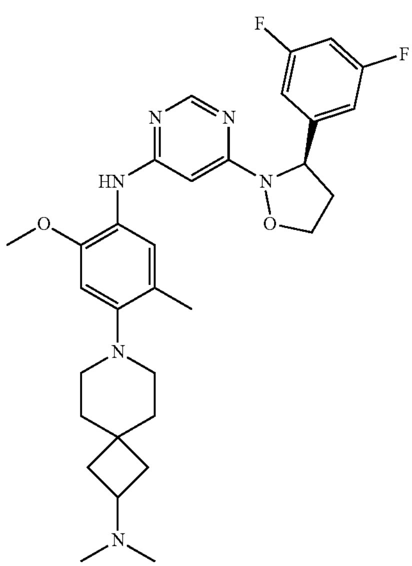 [SMILES: COc1cc(N2CCC3(CC2)CC(N(C)C)C3)c(C)cc1Nc1cc(N2OCC[C@@H]2c2cc(F)cc(F)c2)ncn1] | (R)-7-(5-methoxy-2-methyl-4-((6-(3-phenylisoxazolidin-2-yl)pyrimidin-4-yl)amino)phenyl)-N,N-dimethyl-7-azaspiro[3.5]nonan-2-amine | ¹H NMR (400 MHz, Chloroform-d) δ 8.29-8.27 (m, 1H), 7.44 (s, 1H), 7.11 (s, 1H), 7.03-6.96 (m, 2H), 6.73-6.65 (m, 1H), 6.61 (s, 1H), 6.43-6.39 (m, 1H), 5.65 (dd, J = 8.8, 4.6 Hz, 1H), 4.11 (td, J = 7.9, 4.1 Hz, 1H), 3.90-3.84 (m, 1H), 3.83 (s, 3H), 3.43-3.34 (m, 5H), 3.02-2.92 (m, 1H), 2.83-2.70 (m, 5H), 2.35 (s, 6H), 2.24 (s, 3H), 2.15-2.10 (m, 2H), 2.03-1.98 (m, 2H); 565.3 [M + H]⁺ |

TABLE 1-continued

| Example Compound | Structure | Compound Name | ¹H NMR; MS [M + H]⁺ |
|---|---|---|---|
| 89 | 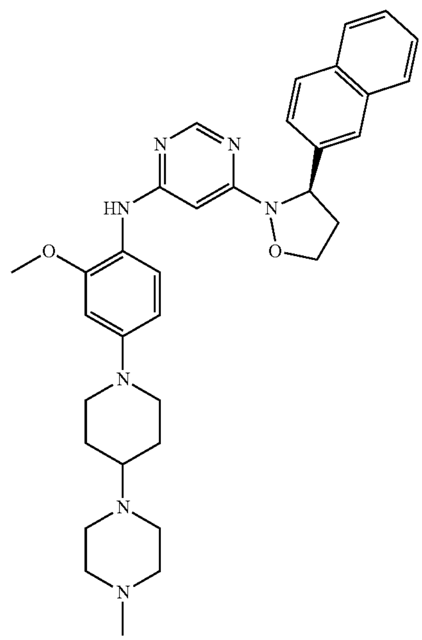 [SMILES: COc1cc(N2CCC(N3CCN(C)CC3)CC2)ccc1Nc1cc(N2OCC[C@@H]2c2ccc3ccccc3c2)ncn1] | (R)-N-(2-methoxy-4-(4-(4-methylpiperazin-1-yl)piperidin-1-yl)phenyl)-6-(3-(naphthalen-2-yl)isoxazolidin-2-yl)pyrimidin-4-amine | ¹H NMR (400 MHz, Chloroform-d) δ 8.28 (s, 1H), 7.91 (d, J = 1.6 Hz, 1H), 7.86-7.78 (m, 3H), 7.54 (dd, J = 8.5, 1.8 Hz, 1H), 7.49-7.41 (m, 3H), 7.08 (s, 1H), 6.57-6.48 (m, 2H), 6.40 (s, 1H), 5.82 (dd, J = 8.6, 4.7 Hz, 1H), 4.15 (td, J = 7.8, 4.5 Hz, 1H), 3.93 (q, J = 7.9 Hz, 1H), 3.84 (s, 3H), 3.71 (d, J = 12.2 Hz, 2H), 2.76 (dt, J = 19.9, 12.4 Hz, 11H), 2.51-2.42 (m, 2H), 2.39 (s, 3H), 1.97 (d, J = 12.5 Hz, 2H), 1.71 (ddd, J = 24.0, 12.1, 3.8 Hz, 2H); 580.44 [M + H]⁺ |
| 90 | 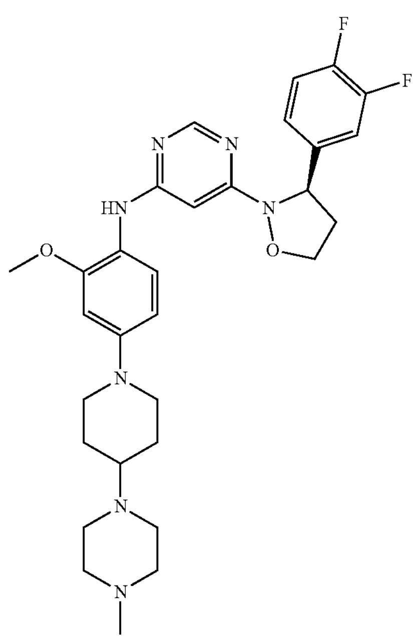 [SMILES: COc1cc(N2CCC(N3CCN(C)CC3)CC2)ccc1Nc1cc(N2OCC[C@@H]2c2ccc(F)c(F)c2)ncn1] | (R)-6-(3-(3,4-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.29 (s, 1H), 7.49 (d, J = 8.8 Hz, 1H), 7.32-7.27 (m, 1H), 7.18-7.08 (m, 2H), 6.84 (s, 1H), 6.54 (d, J = 7.2 Hz, 2H), 6.39 (d, J = 1.1 Hz, 1H), 5.63 (dd, J = 8.7, 4.6 Hz, 1H), 4.10 (td, J = 7.9, 4.3 Hz, 1H), 3.92-3.80 (m, 4H), 3.71 (d, J = 12.3 Hz, 2H), 2.84-2.47 (m, 11H), 2.42 (dq, J = 11.5, 3.4 Hz, 1H), 2.34 (s, 4H), 1.97 (d, J = 14.1 Hz, 2H), 1.75-1.65 (m, 2H); 566.31 [M + H]⁺ |

TABLE 1-continued

| Example Compound | Structure | Compound Name | ¹H NMR; MS [M + H]⁺ |
|---|---|---|---|
| 91 | 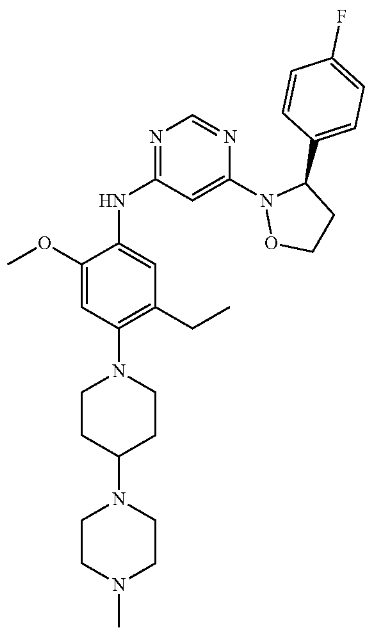 [SMILES: CCc1cc(Nc2cc(N3OCC[C@@H]3c3ccc(F)cc3)ncn2)c(OC)cc1N1CCC(N2CCN(C)CC2)CC1] | (R)-N-(5-ethyl-2-methoxy-4-(4-(4-methylpiperazin-1-yl)piperidin-1-yl)phenyl)-6-(3-(4-fluorophenyl)isoxazolidin-2-yl)pyrimidin-4-amine | ¹H NMR (400 MHz, Chloroform-d) δ 8.29 (d, J = 2.9 Hz, 1H), 7.48 (d, J = 2.9 Hz, 1H), 7.42 (ddd, J = 8.5, 5.3, 2.8 Hz, 2H), 7.16 (s, 1H), 7.03 (td, J = 8.7, 2.9 Hz, 2H), 6.67 (d, J = 3.0 Hz, 1H), 6.48 (d, J = 2.9 Hz, 1H), 5.65 (dd, J = 8.4, 4.5 Hz, 1H), 4.11 (td, J = 7.8, 4.1 Hz, 1H), 3.92-3.86 (m, 1H), 3.83 (d, J = 2.9 Hz, 3H), 3.13 (d, J = 11.3 Hz, 2H), 2.84-2.59 (m, 13H), 2.50 (d, J = 12.7 Hz, 1H), 2.40 (d, J = 2.9 Hz, 3H), 2.35 (dt, J = 8.0, 4.3 Hz, 1H), 1.96 (d, J = 12.1 Hz, 2H), 1.78-1.68 (m, 2H), 1.22 (t, J = 7.5 Hz, 3H); 576.42 [M + H]⁺ |
| 92 | 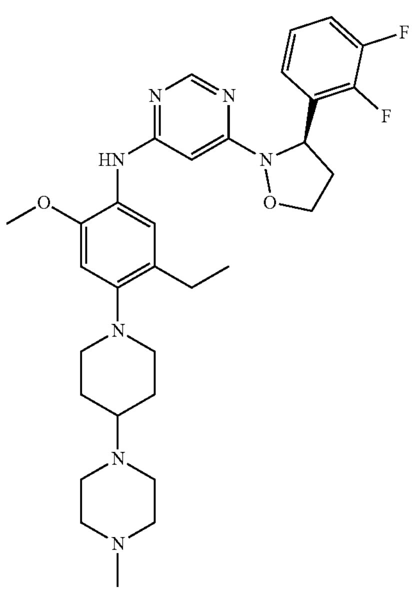 [SMILES: CCc1cc(Nc2cc(N3OCC[C@@H]3c3cccc(F)c3F)ncn2)c(OC)cc1N1CCC(N2CCN(C)CC2)CC1] | (R)-6-(3-(2,3-difluorophenyl)isoxazolidin-2-yl)-N-(5-ethyl-2-methoxy-4-(4-(4-methylpiperazin-1-yl)piperidin-1-yl)phenyl)pyrimidin-4-amine | ¹H NMR (400 MHz, Chloroform-d) δ 8.31 (s, 1H), 7.52 (s, 1H), 7.33 (t, J = 7.4 Hz, 1H), 7.05 (t, J = 6.2 Hz, 2H), 6.91 (s, 1H), 6.67 (s, 1H), 6.53 (s, 1H), 5.91 (dd, J = 8.8, 4.7 Hz, 1H), 4.10 (dq, J = 7.6, 4.2 Hz, 1H), 3.89 (q, J = 8.2, 7.8 Hz, 1H), 3.84 (s, 3H), 3.13 (d, J = 11.4 Hz, 2H), 2.88-2.49 (m, 13H), 2.43-2.36 (m, 1H), 2.33 (s, 3H), 2.32-2.27 (m, 1H), 1.95 (d, J = 13.0 Hz, 2H), 1.78-1.68 (m, 2H), 1.25-1.21 (m, 3H); 594.33 [M +H]⁺ |

TABLE 1-continued

| Example Compound | Structure | Compound Name | ¹H NMR; MS [M + H]⁺ |
|---|---|---|---|
| 93 | 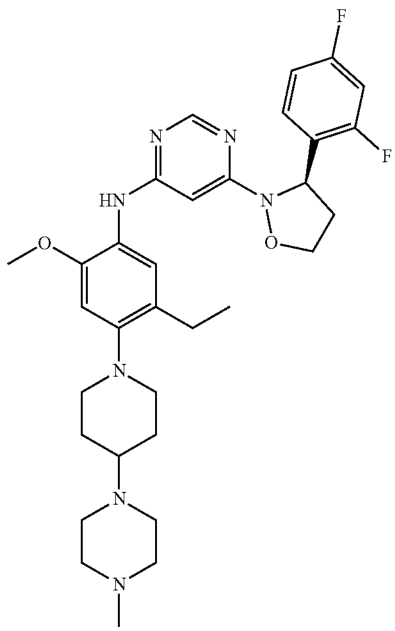 [SMILES: CCc1cc(Nc2cc(N3OCC[C@@H]3c3ccc(F)cc3F)ncn2)c(OC)cc1N1CCC(N2CCN(C)CC2)CC1] | (R)-6-(3-(2,4-difluorophenyl)isoxazolidin-2-yl)-N-(5-ethyl-2-methoxy-4-(4-(4-methylpiperazin-1-yl)piperidin-1-yl)phenyl)pyrimidin-4-amine | ¹H NMR (400 MHz, Chloroform-d) δ 8.32 (d, J = 1.0 Hz, 1H), 7.58-7.50 (m, 2H), 6.88-6.78 (m, 3H), 6.67 (s, 1H), 6.54 (d, J = 1.0 Hz, 1H), 5.85 (dd, J = 8.7, 4.5 Hz, 1H), 4.08 (td, J = 7.9, 4.4 Hz, 1H), 3.90 (q, J = 7.9 Hz, 1H), 3.84 (s, 3H), 3.13 (d, J = 11.5 Hz, 2H), 2.82-2.50 (m, 12H), 2.40-2.24 (m, 5H), 1.96 (d, J = 12.1 Hz, 2H), 1.72 (qd, J = 12.0, 3.8 Hz, 3H), 1.23 (t, J = 7.5 Hz, 3H); 594.33 [M + H]⁺ |
| 94 | 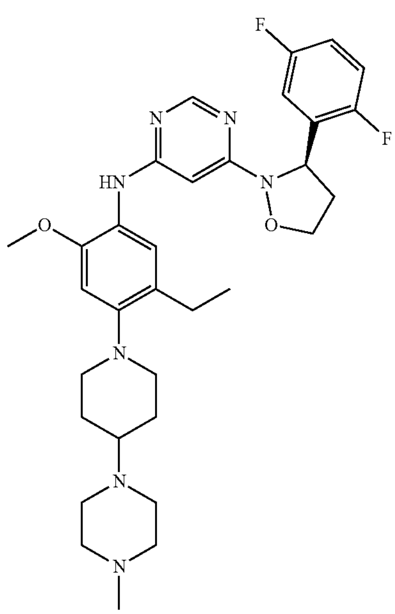 [SMILES: CCc1cc(Nc2cc(N3OCC[C@@H]3c3cc(F)ccc3F)ncn2)c(OC)cc1N1CCC(N2CCN(C)CC2)CC1] | (R)-6-(3-(2,5-difluorophenyl)isoxazolidin-2-yl)-N-(5-ethyl-2-methoxy-4-(4-(4-methylpiperazin-1-yl)piperidin-1-yl)phenyl)pyrimidin-4-amine | ¹H NMR (400 MHz, Chloroform-d) δ 8.30 (d, J = 1.0 Hz, 1H), 7.49 (s, 1H), 7.29 (td, J = 6.0, 3.0 Hz, 1H), 7.17 (s, 1H), 7.00 (td, J = 9.1, 4.3 Hz, 1H), 6.96-6.85 (m, 1H), 6.67 (s, 1H), 6.51 (d, J = 1.1 Hz, 1H), 5.87 (dd, J = 9.0, 4.5 Hz, 1H), 4.08 (td, J = 7.9, 4.2 Hz, 1H), 3.88 (q, J = 7.9 Hz, 1H), 3.84 (s, 3H), 3.13 (d, J = 11.6 Hz, 2H), 2.90-2.59 (m, 13H), 2.54-2.44 (m, 1H), 2.40 (s, 3H), 2.34-2.24 (m, 1H), 1.96 (d, J = 12.1 Hz, 2H), 1.73 (qd, J = 11.8, 3.7 Hz, 2H), 1.23 (t, J = 7.5 Hz, 3H); 594.28 [M + H]⁺ |

TABLE 1-continued

| Example Compound | Structure | Compound Name | ¹H NMR; MS [M + H]⁺ |
|---|---|---|---|
| 95 | 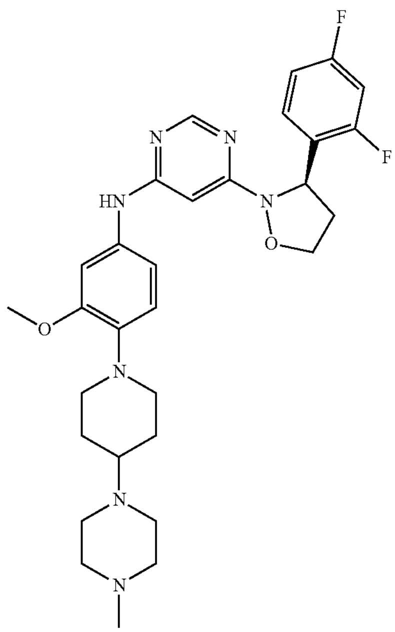 [SMILES: COc1cc(Nc2cc(N3OCC[C@@H]3c3ccc(F)cc3F)ncn2)ccc1N1CCC(N2CCN(C)CC2)CC1] | (R)-6-(3-(2,4-difluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, DMSO-d₆) δ 9.26 (s, 1H), 8.24 (s, 1H), 7.50 (dd, J = 8.8, 6.6 Hz, 1H), 7.27 (ddd, J = 11.2, 9.2, 2.6 Hz, 1H), 7.16 (d, J = 2.4 Hz, 1H), 7.07 (ddt, J = 11.0, 5.5, 2.4 Hz, 2H), 6.84 (d, J = 8.5 Hz, 1H), 6.43 (d, J = 1.0 Hz, 1H), 5.70 (dd, J = 8.7, 4.9 Hz, 1H), 4.18 (td, J = 7.9, 3.9 Hz, 1H), 3.89 (t, J = 8.1 Hz, 1H), 3.76 (s, 3H), 2.77 (dq, J = 8.1, 4.1 Hz, 1H), 2.38-2.18 (m, 6H), 2.15 (s, 3H), 1.80 (d, J = 12.1 Hz, 2H), 1.76-1.64 (m, 1H), 1.54 (dt, J = 12.1, 5.9 Hz, 2H), 1.32-1.21 (m, 2H), 1.19-0.98 (m, 1H), 0.95-0.80 (m, 2H); 566.4 [M + H]⁺ |
| 96 | 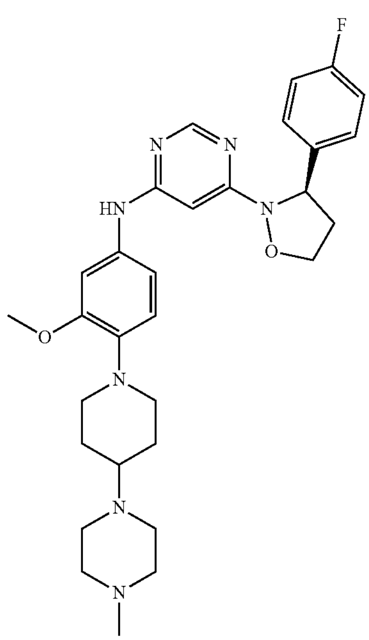 [SMILES: COc1cc(Nc2cc(N3OCC[C@@H]3c3ccc(F)cc3)ncn2)ccc1N1CCC(N2CCN(C)CC2)CC1] | (R)-6-(3-(4-fluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, DMSO-d₆) δ 9.22 (s, 1H), 8.23 (d, J = 1.0 Hz, 1H), 7.44 (ddd, J = 8.8, 5.6, 2.6 Hz, 2H), 7.21-7.12 (m, 3H), 7.05 (dd, J = 8.5, 2.3 Hz, 1H), 6.84 (d, J = 8.5 Hz, 1H), 6.40 (d, J = 1.1 Hz, 1H), 5.53 (dd, J = 8.6, 5.0 Hz, 1H), 4.16 (td, J = 7.9, 4.0 Hz, 1H), 3.85 (d, J = 8.1 Hz, 1H), 3.76 (s, 3H), 2.75 (dq, J = 8.3, 4.3 Hz, 1H), 2.46 (s, 2H), 2.37-2.22 (m, 6H), 2.15 (s, 3H), 2.09 (d, J = 1.0 Hz, 1H), 1.80 (d, J = 12.0 Hz, 2H), 1.54 (dt, J = 11.6, 5.9 Hz, 2H), 1.25 (d, J = 3.4 Hz, 2H), 1.05-0.80 (m, 2H); 548.3 [M + H]⁺ |

| Example Compound | Structure | Compound Name | ¹H NMR; MS [M + H]⁺ |
|---|---|---|---|
| 97 | 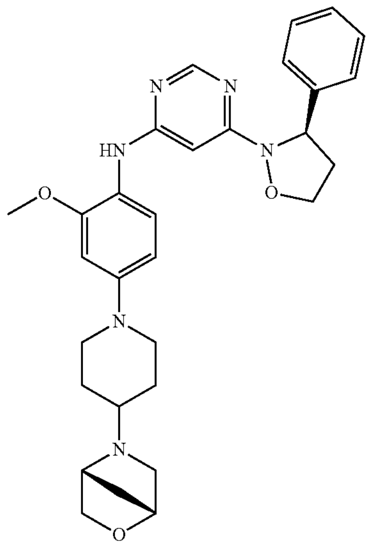 [SMILES: COc1cc(N2CCC(N3C[C@H]4C[C@@H]3CO4)CC2)ccc1Nc1cc(N2OCC[C@@H]2c2ccccc2)ncn1] | N-(4-(4-((1R,4R)-2-oxa-5-azabicyclo[2.2.1]heptan-5-yl)piperidin-1-yl)-2-methoxyphenyl)-6-((R)-3-phenylisoxazolidin-2-yl)pyrimidin-4-amine | ¹H NMR (400 MHz, Chloroform-d) δ 8.24 (s, 1H), 7.46 (d, J = 8.5 Hz, 1H), 7.42 (d, J = 7.3 Hz, 2H), 7.35 (t, J = 7.6 Hz, 2H), 7.28 (d, J = 1.2 Hz, 1H), 7.24 (t, J = 1.4 Hz, 1H), 6.55 (d, J = 2.5 Hz, 1H), 6.51 (dd, J = 8.6, 2.5 Hz, 1H), 6.29 (s, 1H), 5.65 (dd, J = 8.7, 4.6 Hz, 1H), 4.61 (s, 1H), 4.45 (s, 1H), 4.22-4.09 (m, 2H), 3.90 (q, J = 7.8 Hz, 1H), 3.84 (s, 4H), 3.72 (d, J = 12.3 Hz, 3H), 2.98 (s, 2H), 2.74 (ddd, J = 11.9, 7.9, 3.9 Hz, 4H), 2.39 (ddt, J = 11.7, 7.7, 3.9 Hz, 2H), 2.29 (d, J = 11.1 Hz, 1H), 2.16-2.10 (m, 2H), 1.99 (d, J = 12.8 Hz, 1H); 529.39 [M + H]⁺ |
| 98 | 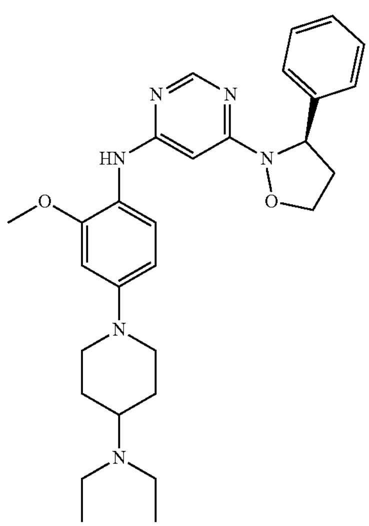 [SMILES: CCN(CC)C1CCN(c2ccc(Nc3cc(N4OCC[C@@H]4c4ccccc4)ncn3)c(OC)c2)CC1] | (R)-N-(4-(4-(diethylamino)piperidin-1-yl)-2-methoxyphenyl)-6-(3-phenylisoxazolidin-2-yl)pyrimidin-4-amine | ¹H NMR (400 MHz, Chloroform-d) δ 8.26 (d, J = 1.0 Hz, 1H), 7.50 (d, J = 8.3 Hz, 1H), 7.45-7.41 (m, 2H), 7.35 (dd, J = 8.4, 6.7 Hz, 3H), 7.27-7.22 (m, 1H), 6.52 (d, J = 8.6 Hz, 2H), 6.35 (d, J = 1.0 Hz, 1H), 5.66 (dd, J = 8.6, 4.6 Hz, 1H), 4.12 (td, J = 7.8, 4.5 Hz, 1H), 3.89 (q, J = 7.8 Hz, 1H), 3.84 (s, 3H), 3.76 (d, J = 13.3 Hz, 2H), 3.39 (tt, J = 12.2, 3.7 Hz, 1H), 3.16 (q, J = 7.3 Hz, 4H), 2.80 (t, J = 11.3 Hz, 2H), 2.72 (tt, J = 8.0, 4.4 Hz, 1H), 2.43-2.32 (m, 1H), 2.16 (d, J = 9.3 Hz, 2H), 1.98 (qd, J = 12.4, 4.1 Hz, 2H), 1.39 (t, J = 7.3 Hz, 6H); 503.40 [M + H]⁺ |

TABLE 1-continued

| Example Compound | Structure | Compound Name | ¹H NMR; MS [M + H]⁺ |
|---|---|---|---|
| 99 | 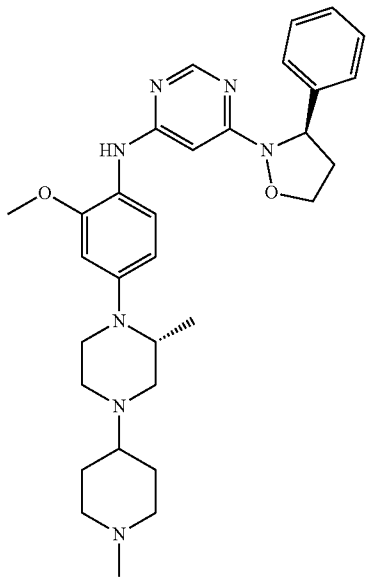 [SMILES: COc1cc(N2CCN(C3CCN(C)CC3)C[C@H]2C)ccc1Nc1cc(N2OCC[C@@H]2c2ccccc2)ncn1] | N-(2-methoxy-4-((R)-2-methyl-4-(1-methylpiperidin-4-yl)piperazin-1-yl)phenyl)-6-((R)-3-phenylisoxazolidin-2-yl)pyrimidin-4-amine | 1H NMR (400 MHz, Chloroform-d) δ 8.27 (s, 1H), 7.54 (d, J = 6.6 Hz, 1H), 7.43 (d, J = 7.6 Hz, 2H), 7.35 (t, J = 7.6 Hz, 2H), 7.28-7.24 (m, 1H), 6.56 (d, J = 6.1 Hz, 2H), 6.34 (s, 1H), 5.66 (dd, J = 8.6, 4.6 Hz, 1H), 4.14 (td, J = 7.8, 4.5 Hz, 1H), 3.91 (q, J = 7.7 Hz, 1H), 3.84 (s, 3H), 3.74 (s, 1H), 3.25-3.10 (m, 3H), 2.89-2.84 (m, 1H), 2.80-2.70 (m, 5H), 2.67-2.61 (m, 2H), 2.44-2.35 (m, 2H), 2.24-2.19 (m, 1H), 2.08 (s, 3H), 2.03-1.98 (m, 2H), 1.31 (s, 1H), 1.06 (d, J = 6.1 Hz, 3H), 0.87-0.80 (m, 1H); 544.39 [M + H]⁺ |
| 100 | 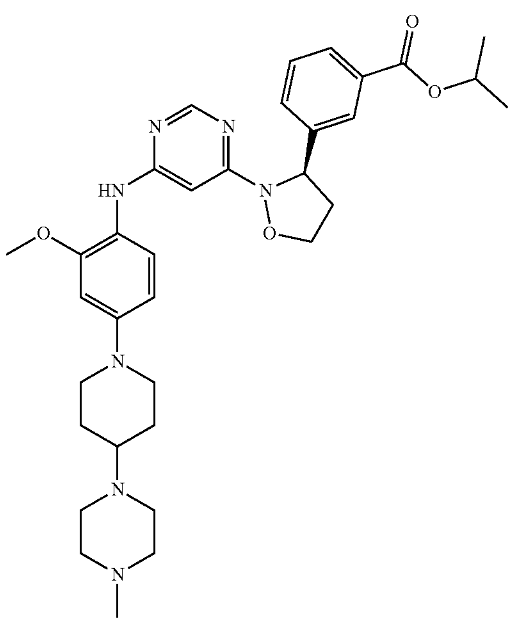 [SMILES: COc1cc(N2CCC(N3CCN(C)CC3)CC2)ccc1Nc1cc(N2OCC[C@@H]2c2cccc(C(=O)OC(C)C)c2)ncn1] | isopropyl (R)-3-(2-(6-((2-methoxy-4-(4-(4-methylpiperazin-1-yl)piperidin-1-yl)phenyl)amino)pyrimidin-4-yl)isoxazolidin-3-yl)benzoate | 616.4 [M + H]⁺ |

TABLE 1-continued

| Example Compound | Structure | Compound Name | ¹H NMR; MS [M + H]⁺ |
|---|---|---|---|
| 101 | 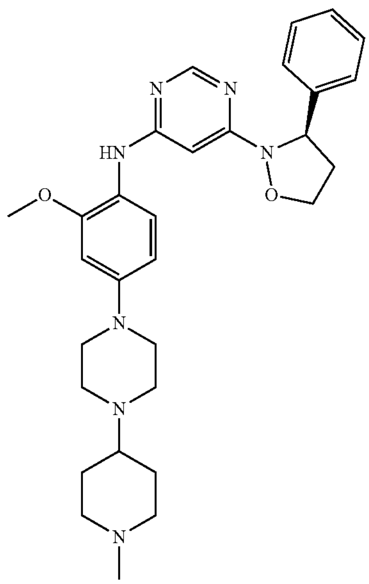 [SMILES: COc1cc(N2CCN(C3CCN(C)CC3)CC2)ccc1Nc1cc(N2OCC[C@@H]2c2ccccc2)ncn1] | (R)-N-(2-methoxy-4-(4-(1-methylpiperidin-4-yl)piperazin-1-yl)phenyl)-6-(3-phenylisoxazolidin-2-yl)pyrimidin-4-amine | ¹H NMR (400 MHz, Chloroform-d) δ 8.21 (s, 1H), 8.00 (s, 1H), 7.44-7.31 (m, 5H), 7.29-7.26 (m, 1H), 6.55-6.49 (m, 2H), 6.24 (s, 1H), 5.64 (dd, J = 8.6, 4.6 Hz, 1H), 4.18-4.09 (m, 1H), 3.90 (q, J = 7.8 Hz, 1H), 3.84 (s, 3H), 3.50 (s, 2H), 3.24 (t, J = 4.8 Hz, 4H), 2.89-2.76 (m, 5H), 2.75 (s, 3H), 2.74-2.61 (m, 2H), 2.44-2.34 (m, 1H), 2.18-2.06 (m, 5H); 530.4 [M + H]⁺ |
| 102 | 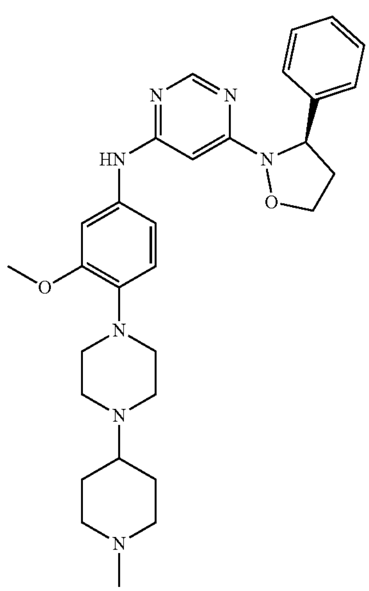 [SMILES: COc1cc(Nc2cc(N3OCC[C@@H]3c3ccccc3)ncn2)ccc1N1CCN(C2CCN(C)CC2)CC1] | (R)-N-(3-methoxy-4-(4-(1-methylpiperidin-4-yl)piperazin-1-yl)phenyl)-6-(3-phenylisoxazolidin-2-yl)pyrimidin-4-amine | ¹H NMR (400 MHz, Chloroform-d) δ 8.29 (d, J = 1.0 Hz, 1H), 7.46-7.41 (m, 2H), 7.38-7.31 (m, 2H), 7.26-7.22 (m, 1H), 6.95-6.90 (m, 1H), 6.86-6.80 (m, 2H), 6.60 (s, 1H), 6.45 (d, J = 1.0 Hz, 1H), 5.66 (dd, J = 8.7, 4.6 Hz, 1H), 4.16-4.07 (m, 1H), 3.91-3.82 (m, 4H), 3.11 (s, 4H), 2.98 (d, J = 11.2 Hz, 2H), 2.82-2.76 (m, 4H), 2.71 (s, 1H), 2.44-2.34 (m, 2H), 2.32 (s, 3H), 2.11-1.96 (m, 2H), 1.88 (d, J = 12.4 Hz, 2H), 1.76-1.68 (m, 2H); 530.3 [M + H]⁺ |

TABLE 1-continued

| Example Compound | Structure | Compound Name | ¹H NMR; MS [M + H]⁺ |
|---|---|---|---|
| 103 | 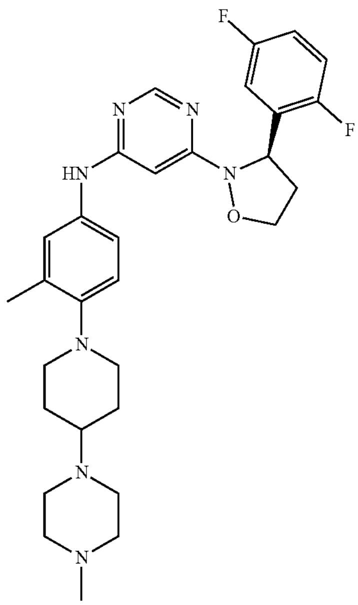 [SMILES: Cc1cc(Nc2cc(N3OCC[C@@H]3c3cc(F)ccc3F)ncn2)ccc1N1CCC(N2CCN(C)CC2)CC1] | (R)-6-(3-(2,5-difluorophenyl)isoxazolidin-2-yl)-N-(3-methyl-4-(4-(4-methylpiperazin-1-yl)piperidin-1-yl)phenyl)pyrimidin-4-amine | 550.44 [M + H]⁺ |
| 104 | 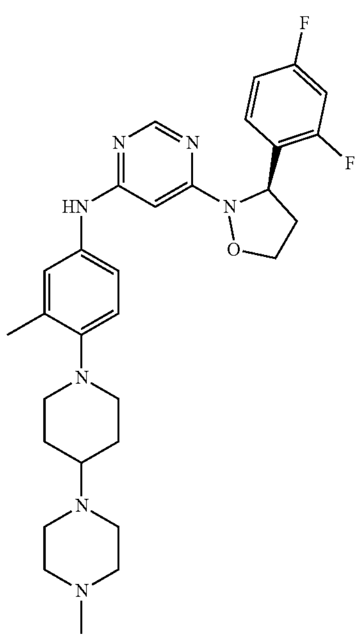 [SMILES: Cc1cc(Nc2cc(N3OCC[C@@H]3c3ccc(F)cc3F)ncn2)ccc1N1CCC(N2CCN(C)CC2)CC1] | (R)-6-(3-(2,4-difluorophenyl)isoxazolidin-2-yl)-N-(3-methyl-4-(4-(4-methylpiperazin-1-yl)piperidin-1-yl)phenyl)pyrimidin-4-amine | ¹H NMR (400 MHz, Chloroform-d) δ 8.23 (d, J = 1.0 Hz, 1H), 7.51 (q, J = 8.3 Hz, 1H), 7.41 (s, 1H), 7.12-7.06 (m, 2H), 7.00 (d, J = 9.2 Hz, 1H), 6.88-6.77 (m, 2H), 6.47 (d, J = 1.0 Hz, 1H), 5.83 (dd, J = 8.7, 4.6 Hz, 1H), 4.08 (td, J = 7.9, 4.4 Hz, 1H), 3.86 (q, J = 7.9 Hz, 1H), 3.18 (d, J = 11.7 Hz, 2H), 2.78-2.69 (m, 11H), 2.44 (dtd, J = 11.7, 7.6, 3.8 Hz, 1H), 2.37 (s, 3H), 2.30 (s, 3H), 2.28-2.23 (m, 1H), 1.96 (d, J = 12.2 Hz, 2H), 1.72 (qd, J = 12.2, 3.3 Hz, 2H); 550.44 [M + H]⁺ |

TABLE 1-continued

| Example Compound | Structure | Compound Name | ¹H NMR; MS [M + H]⁺ |
|---|---|---|---|
| 105 | 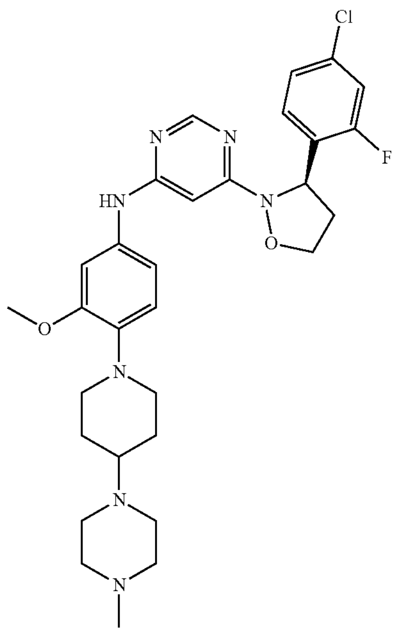 [SMILES: COc1cc(Nc2cc(N3OCC[C@@H]3c3ccc(Cl)cc3F)ncn2)ccc1N1CCC(N2CCN(C)CC2)CC1] | (R)-6-(3-(4-chloro-2-fluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, Chloroform-d) δ 8.26 (s, 1H), 7.73 (s, 1H), 7.49 (t, J = 8.4 Hz, 1H), 7.13-7.04 (m, 2H), 6.92 (d, J = 8.9 Hz, 1H), 6.86-6.79 (m, 2H), 6.48 (s, 1H), 5.82 (dd, J = 8.7, 4.6 Hz, 1H), 4.06 (td, J = 7.9, 4.3 Hz, 1H), 3.86 (s, 3H), 3.85-3.79 (m, 1H), 3.55 (d, J = 11.1 Hz, 2H), 2.83-2.75 (m, 1H), 2.72-2.39 (m, 11H), 2.31 (s, 3H), 2.29-2.18 (m, 1H), 1.96-1.88 (m, 2H), 1.80 (qd, J = 12.0, 3.7 Hz, 2H); 582.3 [M + H]⁺ |
| 106 | 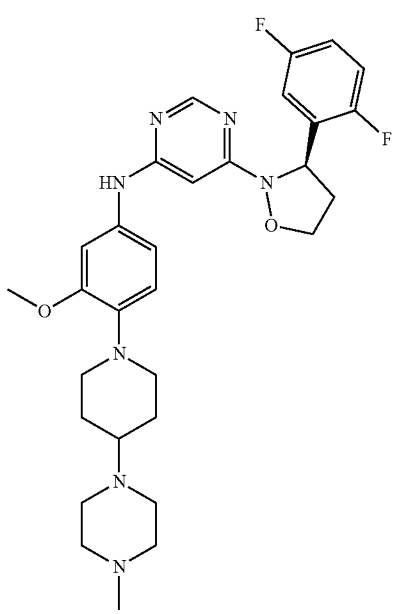 [SMILES: COc1cc(Nc2cc(N3OCC[C@@H]3c3cc(F)ccc3F)ncn2)ccc1N1CCC(N2CCN(C)CC2)CC1] | (R)-6-(3-(2,5-difluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, Chloroform-d) δ 8.28 (d, J = 1.1 Hz, 1H), 7.29 (dd, J = 5.9, 3.2 Hz, 1H), 7.05-6.80 (m, 6H), 6.48 (d, J = 1.1 Hz, 1H), 5.85 (dd, J = 8.8, 4.6 Hz, 1H), 4.07 (td, J = 7.8, 4.2 Hz, 1H), 3.87 (s, 3H), 3.85-3.81 (m, 1H), 3.55 (d, J = 11.6 Hz, 2H), 2.86-2.76 (m, 1H), 2.73-2.55 (m, 7H), 2.54-2.39 (m, 4H), 2.31 (s, 3H), 2.30-2.21 (m, 1H), 1.92 (d, J = 12.3 Hz, 2H), 1.81 (qd, J = 11.9, 3.8 Hz, 2H); 566.4 [M + H]⁺ |

TABLE 1-continued

| Example Compound | Structure | Compound Name | ¹H NMR; MS [M + H]⁺ |
|---|---|---|---|
| 107 | 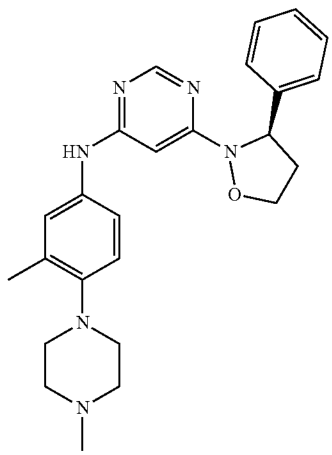 [SMILES: Cc1cc(Nc2cc(N3OCC[C@@H]3c3ccccc3)ncn2)ccc1N1CCN(C)CC1] | (R)-N-(3-methyl-4-(4-methylpiperazin-1-yl)phenyl)-6-(3-phenylisoxazolidin-2-yl)pyrimidin-4-amine | ¹H NMR (400 MHz, Chloroform-d) δ 8.29 (d, J = 1.1 Hz, 1H), 7.44 (d, J = 7.3 Hz, 2H), 7.35 (t, J = 7.7 Hz, 2H), 7.25-7.22 (m, 1H), 7.14-7.02 (m, 3H), 6.59 (s, 1H), 6.45 (d, J = 1.1 Hz, 1H), 5.67 (dd, J = 8.7, 4.7 Hz, 1H), 4.12 (td, J = 7.8, 4.4 Hz, 1H), 3.88 (q, J = 7.8 Hz, 1H), 3.06-2.95 (m, 4H), 2.80-2.59 (m, 5H), 2.43 (s, 3H), 2.42-2.37 (m, 1H), 2.31 (s, 3H); 431.3 [M + H]⁺ |
| 108 | 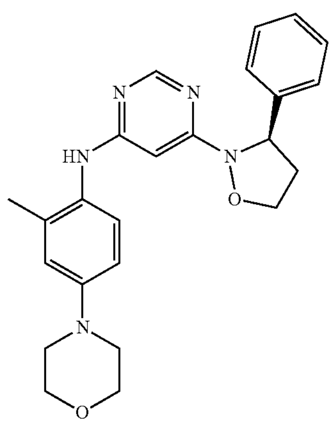 [SMILES: Cc1cc(N2CCOCC2)ccc1Nc1cc(N2OCC[C@@H]2c2ccccc2)ncn1] | (R)-N-(2-methyl-4-morpholinophenyl)-6-(3-phenylisoxazolidin-2-yl)pyrimidin-4-amine | ¹H NMR (400 MHz, Chloroform-d) δ 8.26 (s, 1H), 7.46-7.30 (m, 4H), 7.25-7.22 (m, 2H), 6.84-6.76 (m, 2H), 6.36 (s, 1H), 6.04 (d, J = 1.2 Hz, 1H), 5.66 (dd, J = 8.6, 4.6 Hz, 1H), 4.07 (td, J = 7.9, 4.4 Hz, 1H), 3.87 (q, J = 7.0, 5.9 Hz, 4H), 3.84-3.79 (m, 1H), 3.18 (t, J = 4.9 Hz, 4H), 2.78-2.65 (m, 1H), 2.42-2.30 (m, 1H), 2.23 (s, 3H); 418.3 [M + H]⁺ |
| 109 | 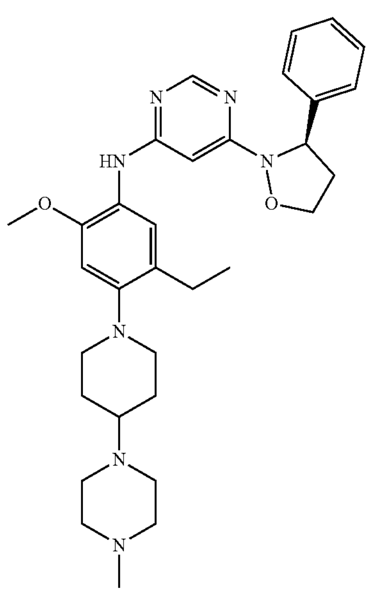 [SMILES: CCc1cc(Nc2cc(N3OCC[C@@H]3c3ccccc3)ncn2)c(OC)cc1N1CCC(N2CCN(C)CC2)CC1] | (R)-N-(5-ethyl-2-methoxy-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 10.93 (s, 1H), 8.07-8.02 (m, 1H), 7.41-7.27 (m, 5H), 7.11 (s, 1H), 6.65 (s, 1H), 5.88-5.80 (m, 1H), 5.59 (dd, J = 8.6, 4.6 Hz, 1H), 4.24 (td, J = 7.6, 5.3 Hz, 1H), 4.02 (q, J = 7.5 Hz, 1H), 3.80 (s, 3H), 3.40 (s, 7H), 3.22 (d, J = 11.7 Hz, 2H), 3.10-2.98 (m, 1H), 2.91-2.82 (m, 1H), 2.79 (s, 3H), 2.77-2.69 (m, 2H), 2.59 (q, J = 7.5 Hz, 2H), 2.49-2.39 (m, 1H), 2.13-2.05 (m, 3H), 1.95-1.83 (m, 2H), 1.20 (t, J = 7.5 Hz, 3H); 558.4 [M + H]⁺ |

TABLE 1-continued

| Example Compound | Structure | Compound Name | ¹H NMR; MS [M + H]⁺ |
|---|---|---|---|
| 110 | 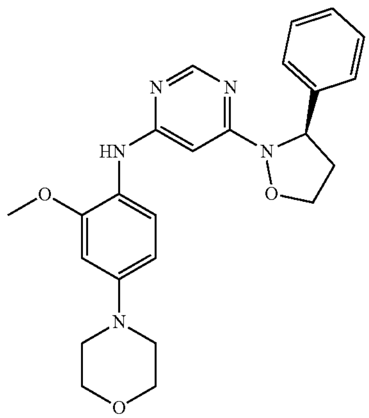 [SMILES: COc1cc(N2CCOCC2)ccc1Nc1cc(N2OCC[C@@H]2c2ccccc2)ncn1] | (R)-N-(2-methoxy-4-morpholinophenyl)-6-(3-phenylisoxazolidin-2-yl)pyrimidin-4-amine | ¹H NMR (400 MHz, Chloroform-d) δ 8.29 (d, J = 1.0 Hz, 1H), 7.54 (d, J = 9.3 Hz, 1H), 7.44 (d, J = 7.5 Hz, 2H), 7.35 (dd, J = 8.4, 6.8 Hz, 2H), 7.27-7.24 (m, 1H), 6.98 (s, 1H), 6.53 (dd, J = 6.3, 2.6 Hz, 2H), 6.40 (d, J = 1.0 Hz, 1H), 5.67 (dd, J = 8.7, 4.6 Hz, 1H), 4.12 (td, J = 7.8, 4.4 Hz, 1H), 3.93-3.86 (m, 5H), 3.85 (s, 3H), 3.20-3.11 (m, 4H), 2.72 (dtd, J = 12.3, 8.0, 4.4 Hz, 1H), 2.39 (ddt, J = 11.7, 7.7, 3.9 Hz, 1H); 434.25 [M + H]⁺ |
| 111 | 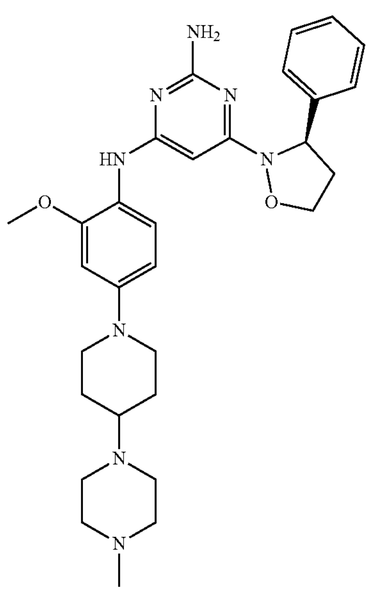 [SMILES: COc1cc(N2CCC(N3CCN(C)CC3)CC2)ccc1Nc1cc(N2OCC[C@@H]2c2ccccc2)nc(N)n1] | (R)-N4-(2-methoxy-4-(4-(4-methylpiperazin-1-yl)piperidin-1-yl)phenyl)-6-(3-phenylisoxazolidin-2-yl)pyrimidin-2,4-diamine | ¹H NMR (400 MHz, Chloroform-d) δ 7.44-7.39 (m, 3H), 7.34 (dd, J = 8.4, 6.7 Hz, 2H), 7.24 (d, J = 7.2 Hz, 2H), 7.15 (s, 1H), 6.55-6.47 (m, 2H), 5.61 (dd, J = 8.6, 4.4 Hz, 1H), 5.07 (s, 2H), 4.06 (td, J = 7.8, 4.6 Hz, 1H), 3.86 (q, J = 7.9 Hz, 1H), 3.83 (s, 3H), 3.70 (d, J = 12.2 Hz, 2H), 2.80-2.61 (m, 11H), 2.38 (s, 3H), 2.33-2.30 (m, 2H), 1.97 (d, J = 12.5 Hz, 2H), 1.72 (q, J = 13.1, 9.2 Hz, 2H); 545.40 [M + H]⁺ |

TABLE 1-continued

| Example Compound | Structure | Compound Name | $^1$H NMR; MS [M + H]$^+$ |
|---|---|---|---|
| 112 | 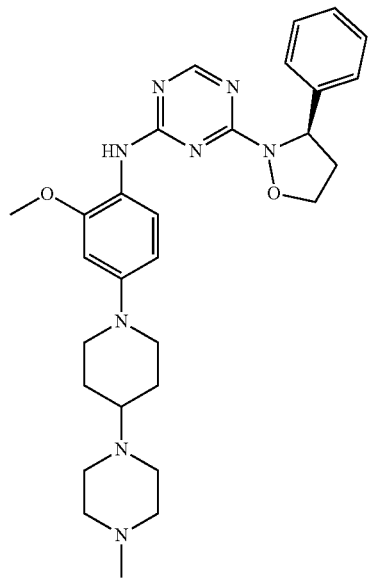 [SMILES: COc1cc(N2CCC(N3CCN(C)CC3)CC2)ccc1Nc1ncnc(N2OCC[C@@H]2c2ccccc2)n1] | (R)-N-(2-methoxy-4-(4-(4-methylpiperazin-1-yl)piperidin-1-yl)phenyl)-4-(3-phenylisoxazolidin-2-yl)-1,3,5-triazin-2-amine | $^1$H NMR (400 MHz, Chloroform-d) δ 8.33 (s, 1H), 7.59-7.28 (m, 7H), 6.55-6.45 (m, 1H), 6.26 (s, 1H), 5.69-5.45 (m, 1H), 4.31 (s, 1H), 4.07 (q, J = 7.7 Hz, 1H), 3.83 (s, 3H), 3.64 (d, J = 11.9 Hz, 2H), 2.91-2.83 (m, 1H), 2.69 (t, J = 11.4 Hz, 6H), 2.58 (s, 3H), 2.47-2.37 (m, 3H), 2.34 (s, 3H), 1.95 (d, J = 12.5 Hz, 2H), 1.78-1.68 (m, 2H); 531.3 [M + H]$^+$ |
| 113 | 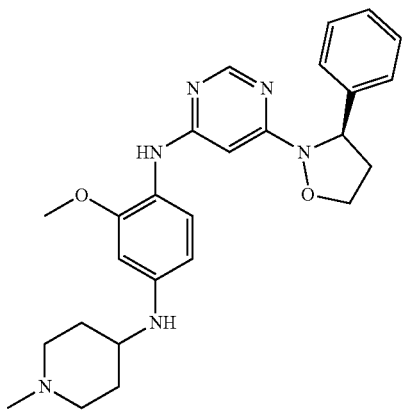 [SMILES: COc1cc(NC2CCN(C)CC2)ccc1Nc1cc(N2OCC[C@@H]2c2ccccc2)ncn1] | (R)-2-methoxy-N4-(1-methylpiperidin-4-yl)-N1-(6-(3-phenylisoxazolidin-2-yl)pyrimidin-4-yl)benzene-1,4-diamine | $^1$H NMR (400 MHz, Chloroform-d) δ 12.30 (s, 1H), 10.70-10.51 (m, 1H), 8.02-7.96 (m, 1H), 7.40-7.26 (m, 5H), 6.99 (d, J = 8.4 Hz, 1H), 6.32-6.18 (m, 1H), 5.71 (s, 1H), 5.56 (dd, J = 8.6, 4.6 Hz, 1H), 4.24 (q, J = 7.1 Hz, 1H), 4.03 (q, J = 7.5 Hz, 1H), 3.79-3.68 (m, 3H), 3.67-3.49 (m, 3H), 3.36 (d, J = 12.3 Hz, 1H), 3.25-3.12 (m, 1H), 2.95-2.75 (m, 5H), 2.48-2.37 (m, 1H), 2.24 (d, J = 14.3 Hz, 2H), 1.99 (q, J = 13.8, 11.8 Hz, 2H); 461.3 [M + H]$^+$ |

TABLE 1-continued

| Example Compound | Structure | Compound Name | ¹H NMR; MS [M + H]⁺ |
|---|---|---|---|
| 114 | 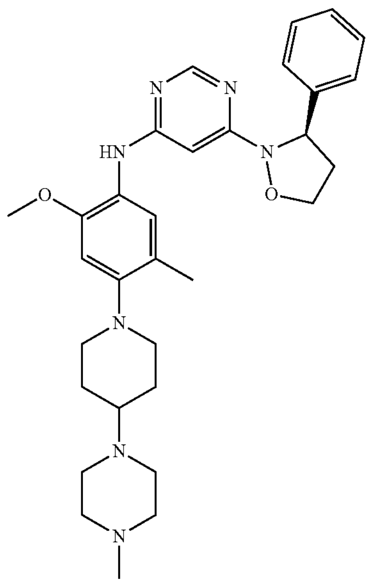 [SMILES: COc1cc(N2CCC(N3CCN(C)CC3)CC2)c(C)cc1Nc1cc(N2OCC[C@@H]2c2ccccc2)ncn1] | (R)-N-(2-methoxy-5-methyl-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 9.13 (s, 1H), 8.15 (s, 1H), 7.39-7.17 (m, 6H), 6.61 (s, 1H), 6.08 (s, 1H), 5.62 (dd, J = 8.6, 4.6 Hz, 1H), 4.21-4.12 (m, 1H), 3.95 (q, J = 7.7 Hz, 1H), 3.81 (s, 3H), 3.42-3.19 (m, 3H), 3.09 (s, 5H), 2.86-2.57 (m, 7H), 2.46-2.36 (m, 1H), 2.21 (s, 3H), 2.09-1.97 (m, 4H), 1.85-1.72 (m, 2H); 544.4 [M + H]⁺ |
| 115 | 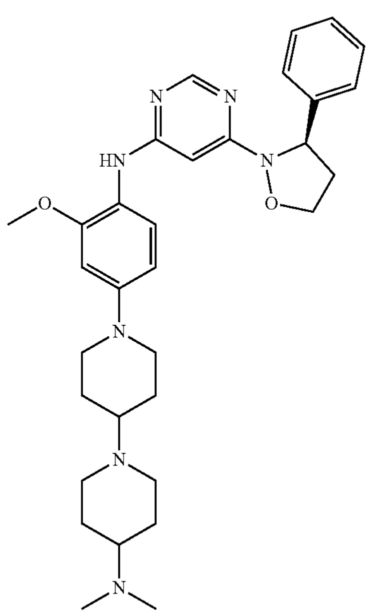 [SMILES: COc1cc(N2CCC(N3CCC(N(C)C)CC3)CC2)ccc1Nc1cc(N2OCC[C@@H]2c2ccccc2)ncn1] | (R)-1'-(3-methoxy-4-((6-(3-phenylisoxazolidin-2-yl)pyrimidin-4-yl)amino)phenyl)-N,N-dimethyl-[1,4'-bipiperidin]-4-amine | ¹H NMR (400 MHz, DMSO-d₆) δ 10.21 (s, 1H), 9.83 (s, 1H), 9.07 (s, 1H), 8.19 (d, J = 0.9 Hz, 1H), 7.38-7.35 (m, 3H), 7.29-7.26 (m, 1H), 6.69 (d, J = 2.5 Hz, 1H), 6.57 (dd, J = 8.8, 2.5 Hz, 1H), 6.05 (s, 1H), 5.51 (dd, J = 8.6, 5.2 Hz, 1H), 4.20 (td, J = 7.7, 4.2 Hz, 1H), 3.97-3.87 (m, 3H), 3.79 (s, 3H), 3.69 (d, J = 12.0 Hz, 2H), 3.48-3.35 (m, 2H), 3.11-2.99 (m, 2H), 2.88-2.70 (m, 8H), 2.50 (s, 6H), 2.32-2.24 (m, 2H), 2.14-2.08 (m, 2H); 558.5 [M + H]⁺ |

TABLE 1-continued

| Example Compound | Structure | Compound Name | ¹H NMR; MS [M + H]⁺ |
|---|---|---|---|
| 116 | 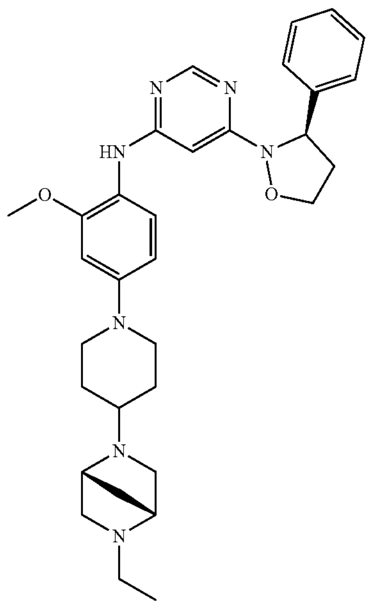 [SMILES: CCN1C[C@H]2C[C@@H]1CN2C1CCN(c2ccc(Nc3cc(N4OCC[C@@H]4c4ccccc4)ncn3)c(OC)c2)CC1] | N-(4-(4-((1R,4R)-5-ethyl-2,5-diazabicyclo[2.2.1]heptan-2-yl)piperidin-1-yl)-2-methoxyphenyl)-6-((R)-3-phenylisoxazolidin-2-yl)pyrimidin-4-amine | ¹H NMR (400 MHz, Chloroform-d) δ 7.98 (s, 1H), 7.37-6.98 (m, 7H), 6.64-6.44 (m, 2H), 5.73 (s, 1H), 5.56-5.40 (m, 1H), 4.65-4.54 (m, 1H), 4.44-4.30 (m, 1H), 4.23 (q, J = 7.1 Hz, 1H), 4.13-3.93 (m, 2H), 3.91-3.56 (m, 6H), 3.54-3.04 (m, 5H), 2.95-2.69 (m, 3H), 2.57-2.25 (m, 3H), 2.19-1.74 (m, 5H), 1.34-1.23 (m, 2H); 556.4 [M +H]⁺ |
| 117 | 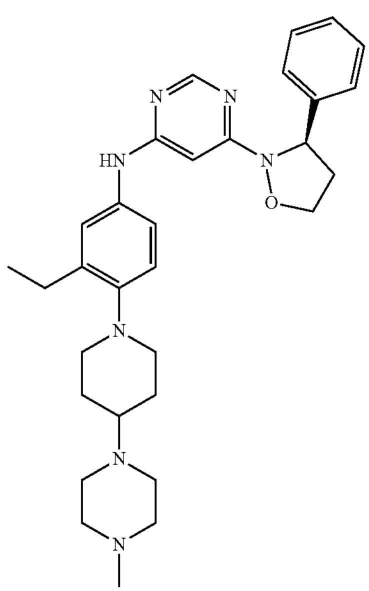 [SMILES: CCc1cc(Nc2cc(N3OCC[C@@H]3c3ccccc3)ncn2)ccc1N1CCC(N2CCN(C)CC2)CC1] | (R)-N-(3-ethyl-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.20 (d, J = 1.0 Hz, 1H), 8.10 (s, 1H), 7.45-7.39 (m, 2H), 7.35 (dd, J = 8.5, 6.8 Hz, 2H), 7.26-7.22 (m, 1H), 7.12 (d, J = 2.4 Hz, 1H), 7.10-7.02 (m, 2H), 6.49 (d, J = 1.0 Hz, 1H), 5.65 (dd, J = 8.6, 4.7 Hz, 1H), 4.13 (td, J = 7.8, 4.4 Hz, 1H), 3.88 (q, J = 7.9 Hz, 1H), 3.12 (d, J = 12.0 Hz, 2H), 2.87 (s, 6H), 2.71 (dqd, J = 26.2, 8.1, 7.3, 4.3 Hz, 7H), 2.60-2.52 (m, 1H), 2.48 (s, 3H), 2.39 (dtd, J = 12.5, 7.9, 4.7 Hz, 1H), 1.99-1.92 (m, 2H), 1.74 (qd, J = 11.7, 3.7 Hz, 2H), 1.23 (t, J = 7.5 Hz, 3H); 528.42 [M + H]⁺ |

TABLE 1-continued

| Example Compound | Structure | Compound Name | ¹H NMR; MS [M + H]⁺ |
|---|---|---|---|
| 118 | 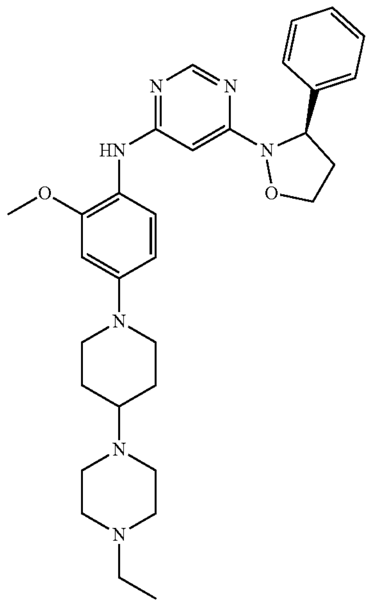 [SMILES: CCN1CCN(C2CCN(c3ccc(Nc4cc(N5OCC[C@@H]5c5ccccc5)ncn4)c(OC)c3)CC2)CC1] | (R)-N-(4-(4-(4-ethylpiperazin-1-yl)piperidin-1-yl)-2-methoxyphenyl)-6-(3-phenylisoxazolidin-2-yl)pyrimidin-4-amine | $^1$H NMR (400 MHz, Chloroform-d) δ 8.30 (s, 1H), 7.51 (d, J = 8.5 Hz, 1H), 7.45 (d, J = 7.6 Hz, 2H), 7.34 (t, J = 7.6 Hz, 2H), 7.25-7.22 (m, 1H), 6.70 (s, 1H), 6.57-6.52 (m, 2H), 6.41 (s, 1H), 5.68 (dd, J = 8.7, 4.5 Hz, 1H), 4.16-4.07 (m, 1H), 3.92-3.86 (m, 1H), 3.84 (s, 3H), 3.71 (d, J = 12.2 Hz, 2H), 2.78-2.65 (m, 6H), 2.54 (s, 2H), 2.51-2.35 (m, 5H), 1.97 (d, J = 12.6 Hz, 2H), 1.75-1.68 (m, 4H), 1.11 (t, J = 7.2 Hz, 3H); 544.3 [M + H]⁺ |
| 119 | 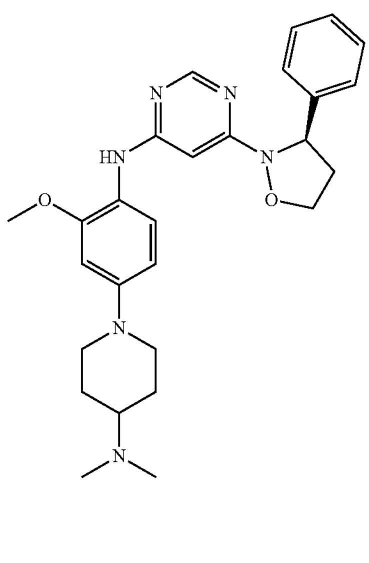 [SMILES: COc1cc(N2CCC(N(C)C)CC2)ccc1Nc1cc(N2OCC[C@@H]2c2ccccc2)ncn1] | (R)-N-(4-(4-(dimethylamino)piperidin-1-yl)-2-methoxyphenyl)-6-(3-phenylisoxazolidin-2-yl)pyrimidin-4-amine | $^1$H NMR (400 MHz, Chloroform-d) δ 8.23 (s, 1H), 7.83 (s, 1H), 7.48 (d, J = 8.6 Hz, 1H), 7.43-7.38 (m, 2H), 7.34 (td, J = 8.4, 7.9, 2.8 Hz, 2H), 7.27-7.23 (m, 1H), 6.55-6.47 (m, 2H), 6.26 (d, J = 2.8 Hz, 1H), 5.64 (dd, J = 8.6, 4.5 Hz, 1H), 4.14 (td, J = 7.7, 4.5 Hz, 1H), 3.95-3.88 (m, 1H), 3.83 (s, 3H), 3.80-3.73 (m, 2H), 3.30-3.18 (m, 1H), 2.86-2.71 (m, 9H), 2.45-2.34 (m, 1H), 2.19-2.12 (m, 2H), 1.90 (qd, J = 12.2, 3.8 Hz, 2H); 475.3 [M + H]⁺ |

| Example Compound | Structure | Compound Name | ¹H NMR; MS [M + H]⁺ |
|---|---|---|---|
| 120 | 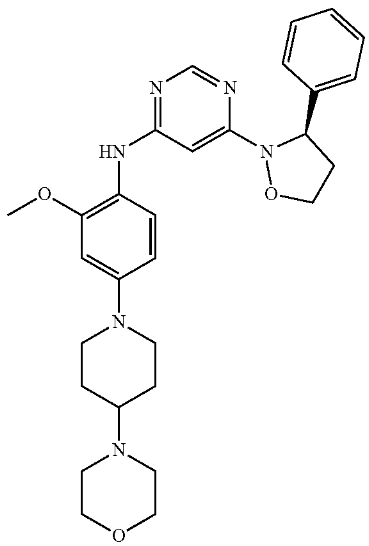 [SMILES: COc1cc(N2CCC(N3CCOCC3)CC2)ccc1Nc1cc(N2OCC[C@@H]2c2ccccc2)ncn1] | (R)-N-(2-methoxy-4-(4-morpholinopiperidin-1-yl)phenyl)-6-(3-phenylisoxazolidin-2-yl)pyrimidin-4-amine | ¹H NMR (400 MHz, Chloroform-d) δ 8.28 (s, 1H), 7.50-7.41 (m, 3H), 7.34 (t, J = 7.7 Hz, 2H), 7.26-7.22 (m, 1H), 6.98 (s, 1H), 6.57-6.51 (m, 2H), 6.40-6.36 (m, 1H), 5.67 (dd, J = 8.7, 4.5 Hz, 1H), 4.11 (td, J = 7.8, 4.5 Hz, 1H), 3.92-3.86 (m, 1H), 3.84 (s, 3H), 3.76 (t, J = 4.6 Hz, 3H), 3.71 (d, J = 12.1 Hz, 2H), 2.79-2.70 (m, 3H), 2.63 (t, J = 4.7 Hz, 3H), 2.43-2.34 (m, 3H), 2.07 (s, 1H), 1.98 (d, J = 12.4 Hz, 2H), 1.70 (qd, J = 12.1, 3.9 Hz, 2H); 517.3 [M +H]⁺ |
| 121 | 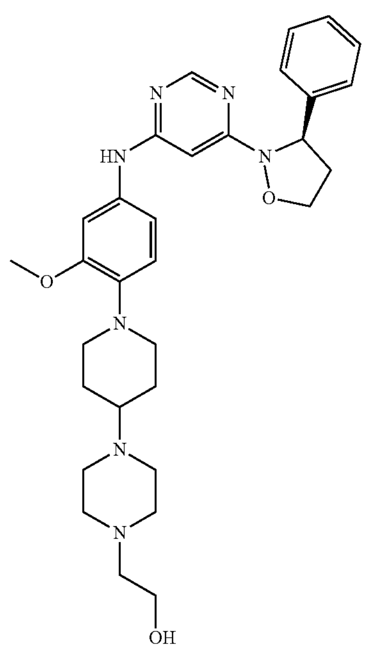 [SMILES: COc1cc(Nc2cc(N3OCC[C@@H]3c3ccccc3)ncn2)ccc1N1CCC(N2CCN(CCO)CC2)CC1] | (R)-2-(4-(1-(2-methoxy-4-((6-(3-phenylisoxazolidin-2-yl)pyrimidin-4-yl)amino)phenyl)piperidin-4-yl)piperazin-1-yl)ethan-1-ol | 560.4 [M + H]⁺ |

TABLE 1-continued

| Example Compound | Structure | Compound Name | ¹H NMR; MS [M + H]⁺ |
|---|---|---|---|
| 122 | 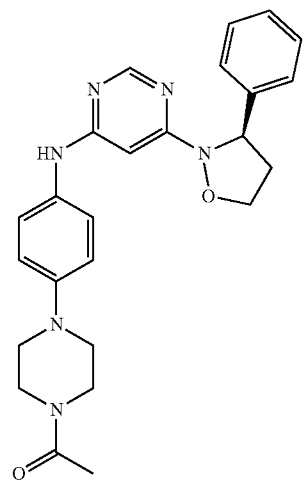 [SMILES: CC(=O)N1CCN(c2ccc(Nc3cc(N4OCC[C@@H]4c4ccccc4)ncn3)cc2)CC1] | (R)-1-(4-(4-((6-(3-phenylisoxazolidin-2-yl)pyrimidin-4-yl)amino)phenyl)piperazin-1-yl)ethan-1-one | ¹H NMR (400 MHz, Chloroform-d) δ 8.21-8.10 (m, 2H), 7.45-7.38 (m, 2H), 7.34 (t, J = 7.5 Hz, 2H), 7.26-7.17 (m, 3H), 6.94 (d, J = 8.8 Hz, 2H), 6.39 (d, J = 1.1 Hz, 1H), 5.64 (dd, J = 8.7, 4.7 Hz, 1H), 4.16-4.07 (m, 1H), 3.87 (q, J = 7.8 Hz, 1H), 3.79 (t, J = 5.3 Hz, 2H), 3.64 (t, J = 5.2 Hz, 2H), 3.22-3.11 (m, 4H), 2.80-2.67 (m, 1H), 2.44-2.32 (m, 1H), 2.15 (s, 3H); 445.3 [M + H]⁺ |
| 123 | 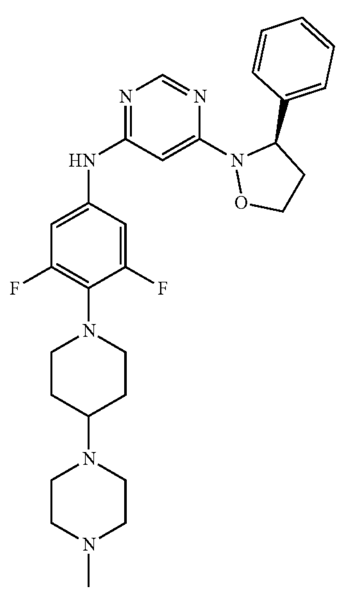 [SMILES: CN1CCN(C2CCN(c3c(F)cc(Nc4cc(N5OCC[C@@H]5c5ccccc5)ncn4)cc3F)CC2)CC1] | (R)-N-(3,5-difluoro-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.27 (s, 1H), 7.66 (s, 1H), 7.46-7.33 (m, 4H), 7.31-7.26 (m, 1H), 6.92 (d, J = 9.9 Hz, 2H), 6.40 (s, 1H), 5.65 (dd, J = 8.7, 4.7 Hz, 1H), 4.25-4.17 (m, 1H), 3.97 (q, J = 7.7 Hz, 1H), 3.27 (d, J = 11.9 Hz, 3H), 3.12 (t, J = 11.8 Hz, 4H), 2.90 (s, 3H), 2.85-2.75 (m, 3H), 2.66 (s, 3H), 2.48-2.38 (m, 2H), 1.99-1.84 (m, 4H); 536.3 [M + H]⁺ |

TABLE 1-continued

| Example Compound | Structure | Compound Name | ¹H NMR; MS [M + H]⁺ |
|---|---|---|---|
| 124 | 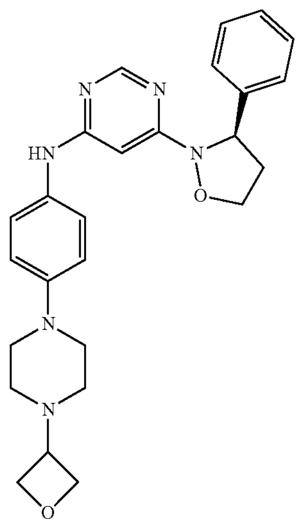 [SMILES: c1ccc([C@H]2CCON2c2cc(Nc3ccc(N4CCN(C5COC5)CC4)cc3)ncn2)cc1] | (R)-N-(4-(4-(oxetan-3-yl)piperazin-1-yl)phenyl)-6-(3-phenylisoxazolidin-2-yl)pyrimidin-4-amine | ¹H NMR (400 MHz, Chloroform-d) δ 10.52 (s, 1H), 8.48 (s, 1H), 8.04 (s, 1H), 7.36-7.27 (m, 4H), 7.22-7.13 (m, 2H), 6.97-6.87 (m, 2H), 6.14 (s, 1H), 5.58 (dd, J = 8.6, 4.6 Hz, 1H), 4.74-4.64 (m, 4H), 4.25-4.15 (m, 1H), 4.04-3.95 (m, 1H), 3.66-3.56 (m, 1H), 3.27 (t, J = 5.1 Hz, 4H), 2.88-2.77 (m, 1H), 2.57 (t, J = 5.0 Hz, 4H), 2.45-2.35 (m, 1H); 459.3 [M + H]⁺ |
| 125 | 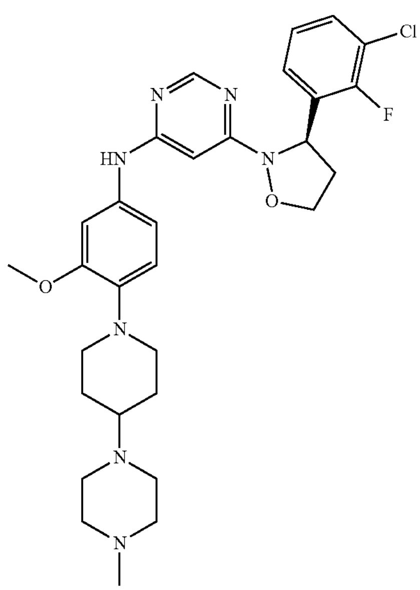 [SMILES: COc1cc(Nc2cc(N3OCC[C@@H]3c3cccc(Cl)c3F)ncn2)ccc1N1CCC(N2CCN(C)CC2)CC1] | (R)-6-(3-(3-chloro-2-fluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, Chloroform-d) δ 8.27 (s, 1H), 7.50-7.41 (m, 1H), 7.34-7.25 (m, 2H), 7.05 (t, J = 7.9 Hz, 1H), 6.93 (d, J = 9.0 Hz, 1H), 6.87-6.79 (m, 2H), 6.48 (d, J = 1.1 Hz, 1H), 5.87 (dd, J = 8.9, 4.8 Hz, 1H), 4.07 (tt, J = 9.3, 4.6 Hz, 1H), 3.86-3.81 (m, 4H), 3.55 (d, J = 11.1 Hz, 2H), 2.87-2.77 (m, 1H), 2.74-2.54 (m, 7H), 2.43 (ddt, J = 11.1, 7.3, 3.8 Hz, 4H), 2.31 (s, 3H), 2.29-2.23 (m, 1H), 1.92 (d, J = 12.2 Hz, 2H), 1.81 (qd, J = 12.0, 3.8 Hz, 2H); 582.3 [M + H]⁺ |

TABLE 1-continued

| Example Compound | Structure | Compound Name | ¹H NMR; MS [M + H]⁺ |
|---|---|---|---|
| 126 | 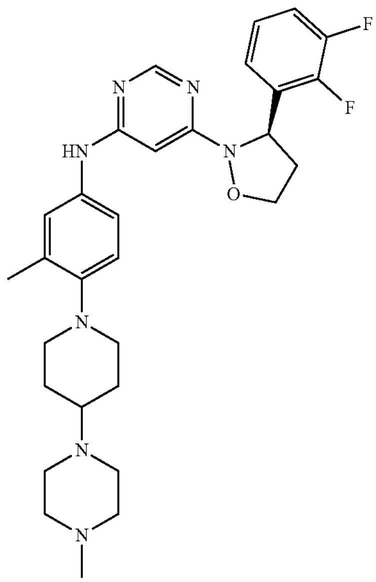 [SMILES: Cc1cc(Nc2cc(N3OCC[C@@H]3c3cccc(F)c3F)ncn2)ccc1N1CCC(N2CCN(C)CC2)CC1] | (R)-6-(3-(2,3-difluorophenyl)isoxazolidin-2-yl)-N-(3-methyl-4-(4-(4-methylpiperazin-1-yl)piperidin-1-yl)phenyl)pyrimidin-4-amine | 550.39 [M + H]⁺ |
| 127 | 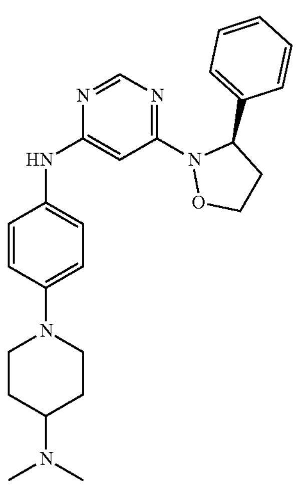 [SMILES: CN(C)C1CCN(c2ccc(Nc3cc(N4OCC[C@@H]4c4ccccc4)ncn3)cc2)CC1] | (R)-N-(4-(4-(dimethylamino)piperidin-1-yl)phenyl)-6-(3-phenylisoxazolidin-2-yl)pyrimidin-4-amine | ¹H NMR (400 MHz, Chloroform-d) δ 8.27 (d, J = 1.1 Hz, 1H), 7.46-7.41 (m, 2H), 7.35 (dd, J = 8.4, 6.8 Hz, 2H), 7.28 (t, J = 1.5 Hz, 1H), 7.23-7.19 (m, 2H), 6.97-6.92 (m, 2H), 6.37 (d, J = 1.1 Hz, 1H), 5.67 (dd, J = 8.7, 4.7 Hz, 1H), 4.12 (td, J = 7.8, 4.5 Hz, 1H), 3.88 (q, J = 7.9 Hz, 1H), 3.79 (d, J = 12.6 Hz, 2H), 3.23-3.09 (m, 1H), 2.85-2.67 (m, 9H), 2.44-2.33 (m, 1H), 2.15 (d, J = 11.6 Hz, 2H), 1.89 (qd, J = 12.1, 4.1 Hz, 3H); 445.24 [M + H]⁺ |

TABLE 1-continued

| Example Compound | Structure | Compound Name | ¹H NMR; MS [M + H]⁺ |
|---|---|---|---|
| 128 | 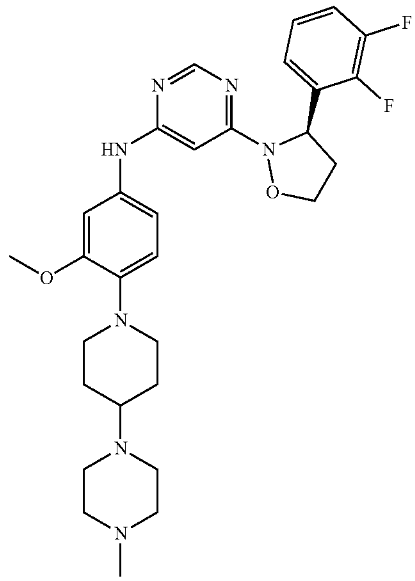 [SMILES: COc1cc(Nc2cc(N3OCC[C@@H]3c3cccc(F)c3F)ncn2)ccc1N1CCC(N2CCN(C)CC2)CC1] | (R)-6-(3-(2,3-difluorophenyl)isoxazolidin-2-yl)-N-(3-methoxy-4-(4-(4-methylpiperazin-1-yl)piperidin-1-yl)phenyl)pyrimidin-4-amine | ¹H NMR (400 MHz, Chloroform-d) δ 8.28 (d, J = 1.0 Hz, 1H), 7.35-7.28 (m, 1H), 7.13-7.01 (m, 2H), 7.00-6.90 (m, 1H), 6.89-6.79 (m, 3H), 6.47 (d, J = 1.1 Hz, 1H), 5.89 (dd, J = 8.8, 4.8 Hz, 1H), 4.09 (td, J = 7.9, 4.2 Hz, 1H), 3.87 (s, 3H), 3.86-3.81 (m, 1H), 3.55 (d, J = 11.3 Hz, 2H), 2.86-2.77 (m, 1H), 2.75-2.51 (m, 9H), 2.49-2.40 (m, 2H), 2.33 (s, 3H), 2.30-2.27 (m, 1H), 1.93 (d, J = 12.3 Hz, 2H), 1.81 (qd, J = 11.9, 3.8 Hz, 2H); 566.4 [M + H]⁺ |
| 129 | 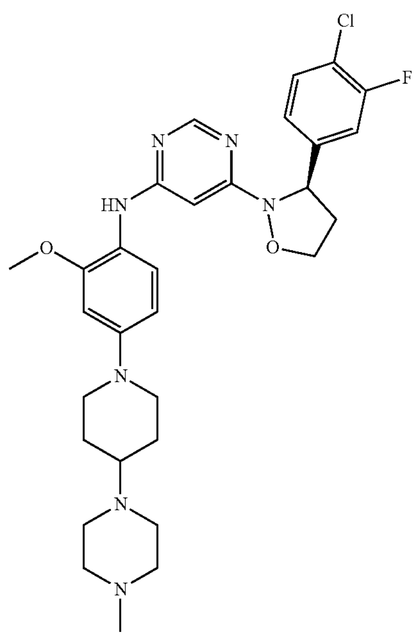 | (R)-6-(3-(4-chloro-3-fluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.27 (s, 1H), 7.47 (d, J = 8.5 Hz, 1H), 7.36 (t, J = 7.8 Hz, 1H), 7.28 (d, J = 1.8 Hz, 1H), 7.16 (dd, J = 8.3, 1.9 Hz, 1H), 6.95 (s, 1H), 6.54 (d, J = 7.3 Hz, 2H), 6.37 (s, 1H), 5.63 (dd, J = 8.8, 4.7 Hz, 1H), 4.09 (td, J = 7.9, 4.2 Hz, 1H), 3.90-3.80 (m, 4H), 3.71 (d, J = 12.2 Hz, 2H), 2.78-2.65 (m, 10H), 2.48-2.40 (m, 2H), 2.37-2.25 (m, 4H), 1.97 (d, J = 12.5 Hz, 2H), 1.70 (ddd, J = 24.4, 12.4, 3.3 Hz, 2H); 582.28 [M + H]⁺ |

TABLE 1-continued

| Example Compound | Structure | Compound Name | ¹H NMR; MS [M + H]⁺ |
|---|---|---|---|
| 130 | 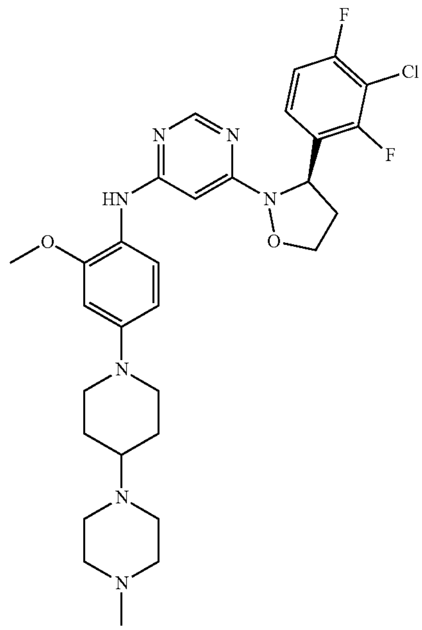 [SMILES: COc1cc(N2CCC(N3CCN(C)CC3)CC2)ccc1Nc1cc(N2OCC[C@@H]2c2ccc(F)c(Cl)c2F)ncn1] | (R)-6-(3-(3-chloro-2,4-difluorophenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.26 (s, 1H), 7.45 (td, J = 8.8, 5.6 Hz, 2H), 7.14 (s, 1H), 6.95 (td, J = 8.6, 1.8 Hz, 1H), 6.54 (d, J = 7.8 Hz, 2H), 6.38 (s, 1H), 5.83 (dd, J = 8.9, 4.7 Hz, 1H), 4.08 (td, J = 8.0, 4.1 Hz, 1H), 3.84 (s, 4H), 3.73 (s, 2H), 2.77 (td, J = 16.1, 12.7, 6.9 Hz, 11H), 2.49 (ddt, J = 11.5, 7.5, 3.6 Hz, 1H), 2.40 (s, 3H), 2.25 (dtd, J = 12.7, 8.0, 4.8 Hz, 1H), 1.98 (d, J = 12.7 Hz, 2H), 1.71 (qd, J = 12.1, 3.9 Hz, 2H); 600.28 [M + H]⁺ |
| 131 | 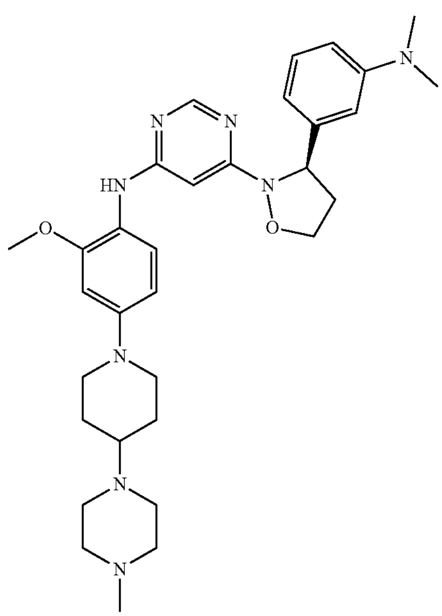 | (R)-6-(3-(3-(dimethylamino)phenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, Chloroform-d) δ 8.26 (s, 1H), 7.44 (d, J = 8.3 Hz, 1H), 7.21 (t, J = 7.9 Hz, 1H), 7.16 (s, 1H), 6.82 (t, J = 2.1 Hz, 1H), 6.77 (d, J = 7.5 Hz, 1H), 6.63 (dd, J = 8.3, 2.6 Hz, 1H), 6.55-6.48 (m, 2H), 6.35 (s, 1H), 5.59 (dd, J = 8.6, 4.6 Hz, 1H), 4.11 (td, J = 7.8, 4.5 Hz, 1H), 3.89-3.81 (m, 4H), 3.70 (d, J = 11.9 Hz, 2H), 2.95 (s, 6H), 2.83-2.65 (m, 11H), 2.52-2.45 (m, 1H), 2.40 (s, 4H), 1.97 (d, J = 12.7 Hz, 2H), 1.71 (qd, J = 12.0, 4.0 Hz, 2H); 573.42 [M + H]⁺ |

TABLE 1-continued

| Example Compound | Structure | Compound Name | ¹H NMR; MS [M + H]⁺ |
|---|---|---|---|
| 132 | 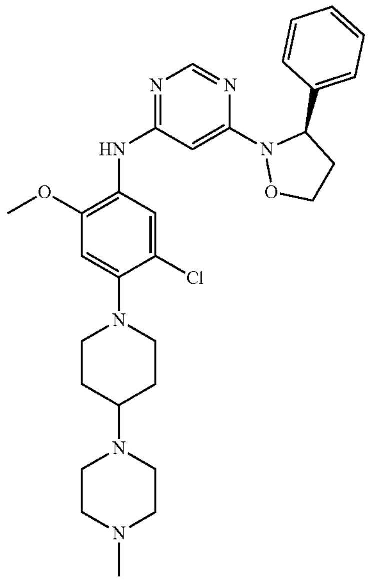 [SMILES: COc1cc(N2CCC(N3CCN(C)CC3)CC2)c(Cl)cc1Nc1cc(N2OCC[C@@H]2c2ccccc2)ncn1] | (R)-N-(5-chloro-2-methoxy-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 8.36 (d, J = 1.0 Hz, 1H), 7.98 (s, 1H), 7.47-7.43 (m, 2H), 7.35 (t, J = 7.6 Hz, 2H), 7.24 (s, 1H), 6.80 (s, 1H), 6.62 (s, 1H), 6.43 (d, J = 1.0 Hz, 1H), 5.68 (dd, J = 8.6, 4.6 Hz, 1H), 4.16 (td, J = 7.9, 4.5 Hz, 1H), 3.92 (q, J = 7.8 Hz, 1H), 3.86 (s, 3H), 3.44 (d, J = 11.4 Hz, 2H), 2.80-2.61 (m, 7H), 2.51 (s, 3H), 2.46-2.35 (m, 3H), 2.31 (s, 3H), 1.94 (d, J = 12.2 Hz, 2H), 1.85-1.74 (m, 2H); 564.3 [M + H]⁺ |
| 133 | 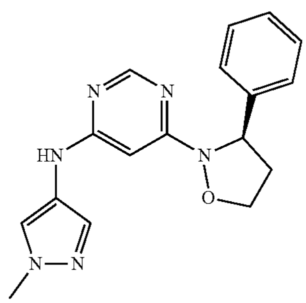 [SMILES: Cn1cc(Nc2cc(N3OCC[C@@H]3c3ccccc3)ncn2)cn1] | (R)-N-(1-methyl-1H-pyrazol-4-yl)-6-(3-phenylisoxazolidin-2-yl)pyrimidin-4-amine | ¹H NMR (400 MHz, Chloroform-d) δ 11.36 (s, 1H), 7.98 (s, 1H), 7.49 (d, J = 26.4 Hz, 2H), 7.41-7.26 (m, 5H), 6.03 (s, 1H), 5.59 (dd, J = 8.7, 4.5 Hz, 1H), 4.30 (q, J = 6.8 Hz, 1H), 4.10 (q, J = 7.4 Hz, 1H), 3.92 (s, 3H), 2.96-2.85 (m, 1H), 2.52-2.41 (m, 1H); 323.2 [M + H]⁺ |
| 134 | 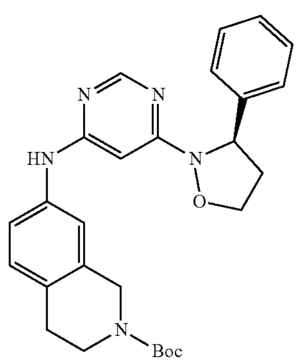 [SMILES: CC(C)(C)OC(=O)N1CCc2ccc(Nc3cc(N4OCC[C@@H]4c4ccccc4)ncn3)cc2C1] | tert-butyl (R)-7-((6-(3-phenylisoxazolidin-2-yl)pyrimidin-4-yl)amino)-3,4-dihydroisoquinoline-2(1H)-carboxylate | ¹H NMR (400 MHz, Chloroform-d) δ 11.65 (s, 1H), 8.04-7.97 (m, 1H), 7.37 (dt, J = 7.9, 4.5 Hz, 2H), 7.34-7.27 (m, 3H), 7.25-6.98 (m, 3H), 6.19-6.09 (m, 1H), 5.63-5.54 (m, 1H), 4.59 (s, 1H), 4.32-4.25 (m, 1H), 4.16-4.07 (m, 1H), 3.75-3.54 (m, 2H), 3.18-3.00 (m, 1H), 2.97-2.76 (m, 3H), 2.50-2.40 (m, 1H), 1.67-1.20 (m, 9H); 474.3 [M + H]⁺ |

TABLE 1-continued

| Example Compound | Structure | Compound Name | ¹H NMR; MS [M + H]⁺ |
|---|---|---|---|
| 135 | 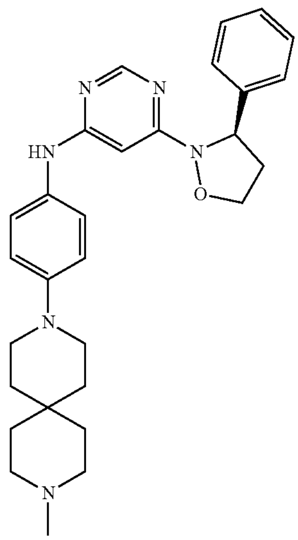 [SMILES: CN1CCC2(CC1)CCN(c1ccc(Nc3cc(N4OCC[C@@H]4c4ccccc4)ncn3)cc1)CC2] | (R)-N-(4-(9-methyl-3,9-diazaspiro[5.5]undecan-3-yl)phenyl)-6-(3-phenylisoxazolidin-2-yl)pyrimidin-4-amine | ¹H NMR (400 MHz, Chloroform-d) δ 8.23 (d, J = 1.1 Hz, 1H), 7.46-7.41 (m, 2H), 7.37-7.32 (m, 2H), 7.26-7.21 (m, 2H), 7.20-7.13 (m, 2H), 6.98-6.92 (m, 2H), 6.36 (d, J = 1.1 Hz, 1H), 5.65 (dd, J = 8.6, 4.6 Hz, 1H), 4.09 (td, J = 7.8, 4.5 Hz, 1H), 3.85 (q, J = 7.8 Hz, 1H), 3.20-3.13 (m, 4H), 3.05 (s, 2H), 2.77-2.68 (m, 1H), 2.64 (s, 3H), 2.42 (s, 3H), 2.40-2.33 (m, 1H), 1.72-1.65 (m, 7H); 485.4 [M + H]⁺ |
| 136 | 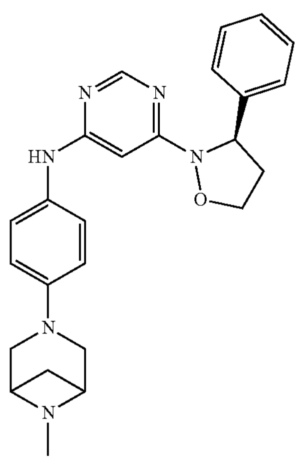 [SMILES: CN1C2CC1CN(c1ccc(Nc3cc(N4OCC[C@@H]4c4ccccc4)ncn3)cc1)C2] | N-(4-(6-methyl-3,6-diazabicyclo[3.1.1]heptan-3-yl)phenyl)-6-((R)-3-phenylisoxazolidin-2-yl)pyrimidin-4-amine | ¹H NMR (400 MHz, Chloroform-d) δ 8.21 (d, J = 1.0 Hz, 1H), 7.54 (s, 1H), 7.46-7.30 (m, 4H), 7.27-7.18 (m, 3H), 6.79-6.72 (m, 2H), 6.33 (d, J = 1.1 Hz, 1H), 5.67 (dd, J = 8.6, 4.6 Hz, 1H), 4.14-4.04 (m, 1H), 3.95 (d, J = 6.0 Hz, 2H), 3.90-3.81 (m, 2H), 3.62 (d, J = 11.4 Hz, 2H), 3.47 (d, J = 11.3 Hz 2H), 2.80 (q, J = 6.5 Hz, 1H), 2.78-2.66 (m, 1H), 2.37 (dt, J = 7.9, 4.5 Hz, 1H), 2.25 (s, 2H), 1.71 (d, J = 9.0 Hz, 1H); 429.3 [M + H]⁺ |
| 137 | 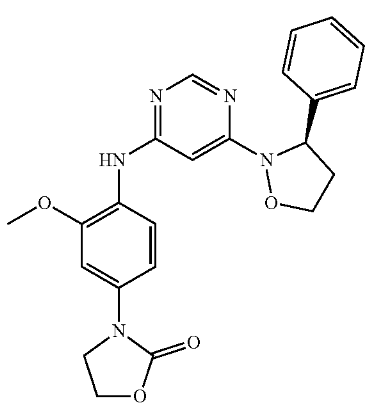 [SMILES: COc1cc(N2CCOC2=O)ccc1Nc1cc(N2OCC[C@@H]2c2ccccc2)ncn1] | (R)-3-(3-methoxy-4-((6-(3-phenylisoxazolidin-2-yl)pyrimidin-4-yl)amino)phenyl)oxazolidin-2-one | ¹H NMR (400 MHz, Chloroform-d) δ 8.36 (d, J = 1.0 Hz, 1H), 7.91 (d, J = 8.7 Hz, 1H), 7.66 (d, J = 2.4 Hz, 1H), 7.48-7.43 (m, 2H), 7.38-7.32 (m, 2H), 7.25-7.21 (m, 1H), 6.97 (s, 1H), 6.73 (dd, J = 8.7, 2.5 Hz, 1H), 6.50 (d, J = 1.0 Hz, 1H), 5.68 (dd, J = 8.6, 4.6 Hz, 1H), 4.56-4.46 (m, 2H), 4.20-4.05 (m, 3H), 3.96-3.87 (m, 4H), 2.80-2.69 (m, 1H), 2.47-2.35 (m, 1H); 434.2 [M + H]⁺ |

TABLE 1-continued

| Example Compound | Structure | Compound Name | ¹H NMR; MS [M + H]⁺ |
|---|---|---|---|
| 138 | 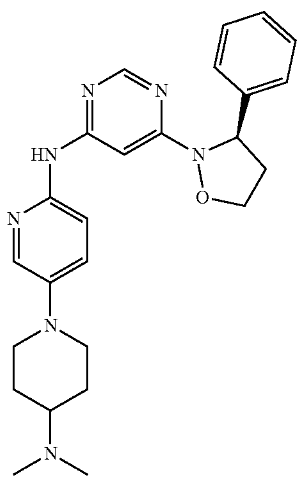 [SMILES: CN(C)C1CCN(c2ccc(Nc3cc(N4OCC[C@@H]4c4ccccc4)ncn3)nc2)CC1] | (R)-N-(5-(4-(dimethylamino)piperidin-1-yl)pyridin-2-yl)-6-(3-phenylisoxazolidin-2-yl)pyrimidin-4-amine | |
| 139 | 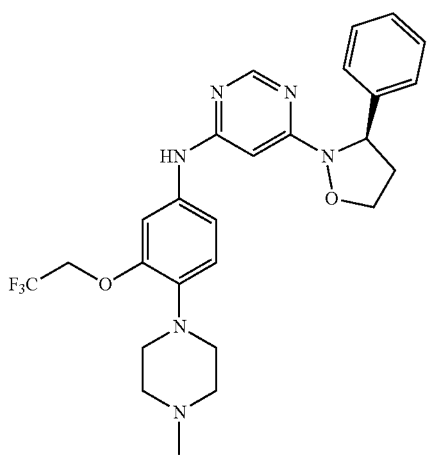 [SMILES: CN1CCN(c2ccc(Nc3cc(N4OCC[C@@H]4c4ccccc4)ncn3)cc2OCC(F)(F)F)CC1] | (R)-N-(4-(4-methylpiperazin-1-yl)-3-(2,2,2-trifluoroethoxy)phenyl)-6-(3-phenylisoxazolidin-2-yl)pyrimidin-4-amine | ¹H NMR (400 MHz, Chloroform-d) δ 13.44 (s, 1H), 11.75 (s, 1H), 8.01 (d, J = 0.8 Hz, 1H), 7.41-7.26 (m, 4H), 7.07-6.94 (m, 2H), 6.78 (d, J = 2.0 Hz, 1H), 6.11-6.03 (m, 1H), 5.59 (dd, J = 8.6, 4.4 Hz, 1H), 4.40 (q, J = 8.0 Hz, 2H), 4.36-4.29 (m, 1H), 4.17-4.10 (m, 1H), 3.67 (d, J = 11.5 Hz, 2H), 3.57-3.46 (m, 2H), 3.39-3.25 (m, 2H), 3.06 (t, J = 11.4 Hz, 2H), 2.96-2.85 (m, 4H), 2.52-2.42 (m, 1H); 515.3 [M + H]⁺ |
| 140 | 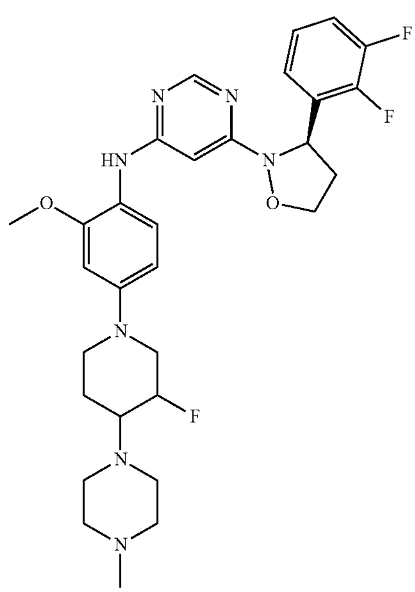 [SMILES: COc1cc(N2CCC(N3CCN(C)CC3)C(F)C2)ccc1Nc1cc(N2OCC[C@@H]2c2cccc(F)c2F)ncn1] | 6-((R)-3-(2,3-difluorophenyl)isoxazolidin-2-yl)-N-(4-(3-fluoro-4-(4-methylpiperazin-1-yl)piperidin-1-yl)-2-methoxyphenyl)pyrimidin-4-amine | ¹H NMR (400 MHz, Chloroform-d) δ 10.84 (s, 1H), 8.05 (s, 1H), 7.18-6.98 (m, 4H), 6.56-6.47 (m, 2H), 5.83-5.75 (m, 2H), 4.28-4.19 (m, 1H), 4.11-3.96 (m, 2H), 3.89 (d, J = 12.8 Hz, 1H), 3.81 (s, 3H), 3.75-3.28 (m, 8H), 3.17-2.99 (m, 2H), 2.98-2.89 (m, 2H), 2.85 (s, 3H), 2.46-2.34 (m, 1H), 2.32-2.19 (m, 1H), 2.05 (s, 1H), 2.00 (d, J = 12.5 Hz, 1H); 584.4 [M + H]⁺ |

TABLE 1-continued

| Example Compound | Structure | Compound Name | ¹H NMR; MS [M + H]⁺ |
|---|---|---|---|
| 141 | 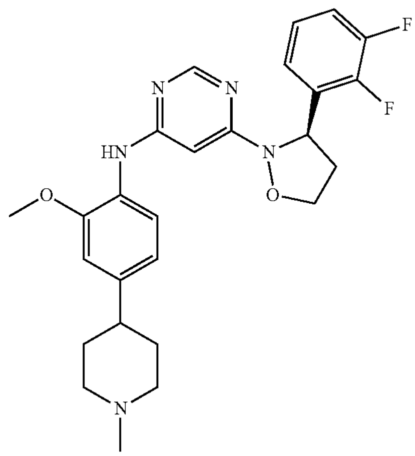 [SMILES: COc1cc(C2CCN(C)CC2)ccc1Nc1cc(N2OCC[C@@H]2c2cccc(F)c2F)ncn1] | (R)-6-(3-(2,3-difluorophenyl)isoxazolidin-2-yl)-N-(2-methoxy-4-(1-methylpiperidin-4-yl)phenyl)pyrimidin-4-amine | ¹H NMR (400 MHz, Chloroform-d) δ 11.01 (s, 1H), 8.07 (s, 1H), 7.21 (d, J = 7.9 Hz, 1H), 7.17-6.98 (m, 3H), 6.89-6.82 (m, 2H), 5.86 (s, 1H), 5.80 (dd, J = 8.7, 5.0 Hz, 1H), 4.27 (td, J = 7.6, 5.0 Hz, 1H), 4.06 (q, J = 7.6 Hz, 1H), 3.84 (s, 3H), 3.74-3.66 (m, 2H), 3.01-2.83 (m, 6H), 2.81-2.72 (m, 1H), 2.47-2.37 (m, 1H), 2.28 (q, J = 12.3 Hz, 2H), 2.12-2.03 (m, 2H); 482.3 [M + H]⁺ |
| 142 | 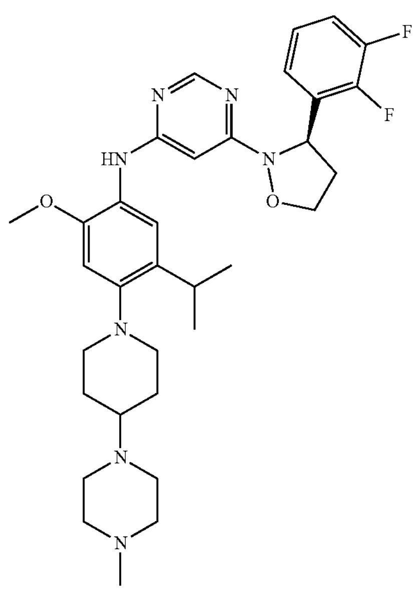 [SMILES: COc1cc(N2CCC(N3CCN(C)CC3)CC2)c(C(C)C)cc1Nc1cc(N2OCC[C@@H]2c2cccc(F)c2F)ncn1] | (R)-6-(3-(2,3-difluorophenyl)isoxazolidin-2-yl)-N-(5-isopropyl-2-methoxy-4-(4-(4-methylpiperazin-1-yl)piperidin-1-yl)phenyl)pyrimidin-4-amine | ¹H NMR (400 MHz, Chloroform-d) δ 11.18 (s, 1H), 8.07 (s, 1H), 7.17-7.01 (m, 4H), 6.67 (s, 1H), 5.93 (s, 1H), 5.81 (dd, J = 8.7, 5.0 Hz, 1H), 4.23 (td, J = 7.6, 4.7 Hz, 1H), 4.01 (q, J = 7.6 Hz, 1H), 3.81 (s, 3H), 3.67 (s, 7H), 3.34-3.18 (m, 4H), 3.01-2.91 (m, 1H), 2.89 (s, 3H), 2.81 (t, J = 11.8 Hz, 2H), 2.40 (td, J = 12.7, 7.4 Hz, 1H), 2.18 (d, J = 11.9 Hz, 2H), 2.09 (s, 1H), 2.06-1.92 (m, 2H), 1.18 (dd, J = 6.9, 2.2 Hz, 6H); 608.4 [M + H]⁺ |

TABLE 1-continued

| Example Compound | Structure | Compound Name | ¹H NMR; MS [M + H]⁺ |
|---|---|---|---|
| 143 | 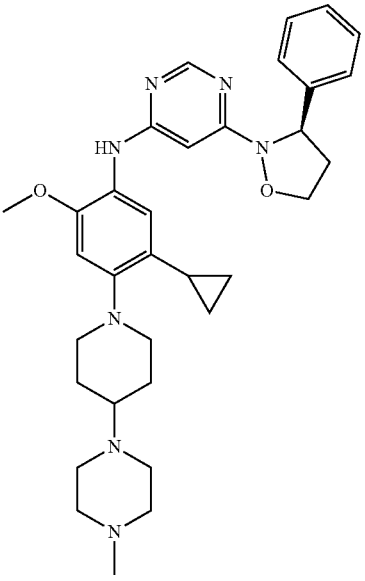 [SMILES: COc1cc(N2CCC(N3CCN(C)CC3)CC2)c(C2CC2)cc1Nc1cc(N2OCC[C@@H]2c2ccccc2)ncn1] | (R)-N-(5-cyclopropyl-2-methoxy-4-(4-(4-methylpiperazin-1-yl)piperidin-1-yl)phenyl)-6-(3-phenylisoxazolidin-2-yl)pyrimidin-4-amine | ¹H NMR (400 MHz, Chloroform-d) δ 10.86 (s, 1H), 8.04 (s, 1H), 7.41-7.26 (m, 5H), 6.68 (s, 1H), 6.59 (s, 1H), 5.74 (s, 1H), 5.58 (dd, J = 8.6, 4.6 Hz, 1H), 4.25 (td, J = 7.6, 5.5 Hz, 1H), 4.03 (q, J = 7.5 Hz, 1H), 3.97-3.91 (m, 1H), 3.79 (s, 3H), 3.78-3.64 (m, 7H), 3.56 (d, J = 11.6 Hz, 2H), 3.30 (t, J = 12.2 Hz, 1H), 2.91 (s, 3H), 2.89-2.85 (m, 1H), 2.84-2.75 (m, 2H), 2.50-2.40 (m, 1H), 2.22 (d, J = 11.4 Hz, 2H), 2.09-1.97 (m, 3H), 1.03-0.97 (m, 2H), 0.66-0.60 (m, 2H); 570.5 [M + H]⁺ |
| 144 | 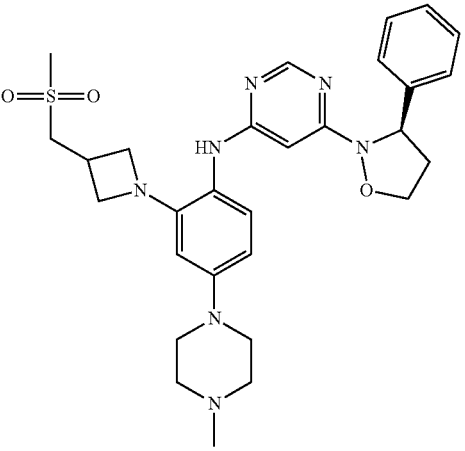 [SMILES: CN1CCN(c2ccc(Nc3cc(N4OCC[C@@H]4c4ccccc4)ncn3)c(N3CC(CS(C)(=O)=O)C3)c2)CC1] | (R)-N-(4-(4-methylpiperazin-1-yl)-2-(3-((methylsulfonyl)methyl)azetidin-1-yl)phenyl)-6-(3-phenylisoxazolidin-2-yl)pyrimidin-4-amine | ¹H NMR (400 MHz, Chloroform-d) δ 8.18 (d, J = 1.0 Hz, 1H), 7.45-7.40 (m, 2H), 7.37-7.31 (m, 2H), 7.25-7.22 (m, 1H), 7.00 (d, J = 8.6 Hz, 1H), 6.95 (s, 1H), 6.42 (dd, J = 8.6, 2.6 Hz, 1H), 6.05 (d, J = 2.7 Hz, 1H), 6.03 (d, J = 1.1 Hz, 1H), 5.63 (dd, J = 8.7, 4.7 Hz, 1H), 4.14-4.08 (m, 3H), 3.84 (q, J = 7.9 Hz, 1H), 3.73-3.65 (m, 2H), 3.29 (d, J = 7.4 Hz, 2H), 3.24 (t, J = 5.1 Hz, 3H), 3.19-3.10 (m, 1H), 2.88 (s, 3H), 2.77-2.70 (m, 2H), 2.65 (t, J = 5.0 Hz, 4H), 2.39 (s, 3H), 2.38-2.33 (m, 1H); 564.4 [M + H]⁺ |

TABLE 1-continued

| Example Compound | Structure | Compound Name | ¹H NMR; MS [M + H]⁺ |
|---|---|---|---|
| 145 | 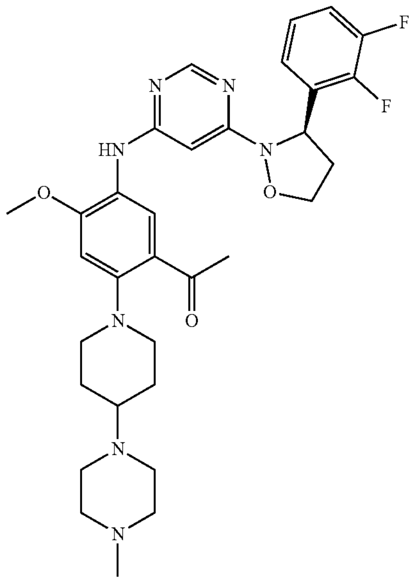 [SMILES: COc1cc(N2CCC(N3CCN(C)CC3)CC2)c(C(C)=O)cc1Nc1cc(N2OCC[C@@H]2c2cccc(F)c2F)ncn1] | (R)-1-(5-((6-(3-(2,3-difluorophenyl)isoxazolidin-2-yl)pyrimidin-4-yl)amino)-4-methoxy-2-(4-(4-methylpiperazin-1-yl)piperidin-1-yl)phenyl)ethan-1-one | ¹H NMR (400 MHz, Chloroform-d) δ 8.34 (s, 1H), 8.04 (s, 1H), 7.36-7.30 (m, 1H), 7.11-7.02 (m, 2H), 6.76 (s, 1H), 6.62 (s, 1H), 6.48 (s, 1H), 5.91 (dd, J = 8.8, 4.7 Hz, 1H), 4.13 (td, J = 7.9, 4.2 Hz, 1H), 3.98-3.93 (m, 1H), 3.91 (s, 3H), 3.33-3.24 (m, 2H), 2.89-2.73 (m, 4H), 2.67 (s, 6H), 2.58-2.40 (m, 4H), 2.37-2.25 (m, 5H), 2.00 (d, J = 12.4 Hz, 2H), 1.81-1.68 (m, 2H); 608.4 [M + H]⁺ |
| 146 | 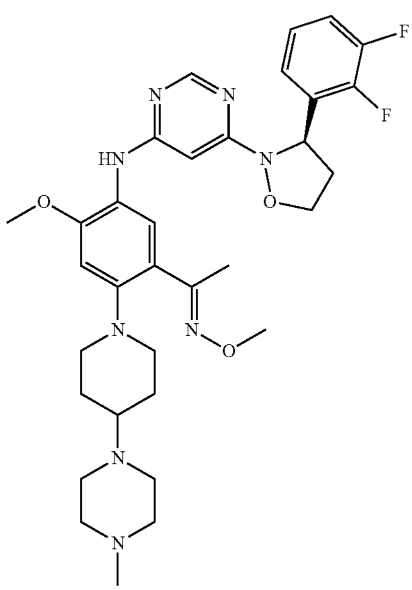 [SMILES: CO/N=C(\C)c1cc(Nc2cc(N3OCC[C@@H]3c3cccc(F)c3F)ncn2)c(OC)cc1N1CCC(N2CCN(C)CC2)CC1] | (R,E)-1-(5-((6-(3-(2,3-difluorophenyl)isoxazolidin-2-yl)pyrimidin-4-yl)amino)-4-methoxy-2-(4-(4-methylpiperazin-1-yl)piperidin-1-yl)phenyl)ethan-1-one O-methyl oxime | ¹H NMR (400 MHz, Chloroform-d) δ 9.46-9.18 (m, 1H), 8.11 (s, 1H), 7.33 (s, 1H), 7.18-6.98 (m, 3H), 6.61 (s, 1H), 5.99 (s, 1H), 5.89-5.74 (m, 1H), 4.31-4.22 (m, 1H), 4.12-4.02 (m, 1H), 3.96 (s, 3H), 3.91-3.71 (m, 6H), 3.61-3.34 (m, 6H), 3.01-2.69 (m, 7H), 2.50-2.37 (m, 2H), 2.36-2.24 (m, 2H), 2.23-2.14 (m, 3H), 2.04-1.87 (m, 2H); 637.4 [M + H]⁺ |

TABLE 1-continued

| Example Compound | Structure | Compound Name | ¹H NMR; MS [M + H]⁺ |
|---|---|---|---|
| 147 | 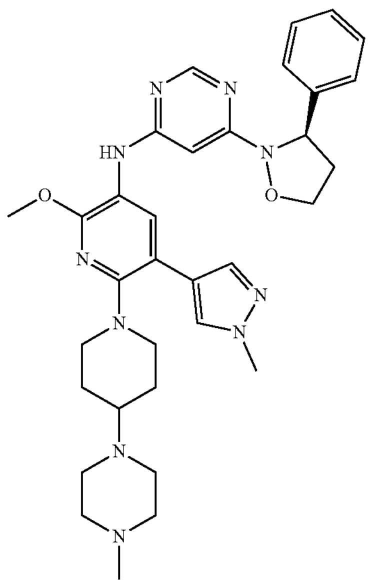 [SMILES: COc1nc(N2CCC(N3CCN(C)CC3)CC2)c(-c2cnn(C)c2)cc1Nc1cc(N2OCC[C@@H]2c2ccccc2)ncn1] | (R)-N-(2-methoxy-5-(1-methyl-1H-pyrazol-4-yl)-6-(4-(4-methylpiperazin-1-yl)piperidin-1-yl)pyridin-3-yl)-6-(3-phenylisoxazolidin-2-yl)pyrimidin-4-amine | ¹H NMR (400 MHz, Chloroform-d) δ 8.32 (d, J = 1.0 Hz, 1H), 8.07 (s, 1H), 7.82 (d, J = 0.7 Hz, 1H), 7.75 (s, 1H), 7.47-7.42 (m, 2H), 7.38-7.31 (m, 2H), 7.25-7.20 (m, 1H), 6.85 (s, 1H), 6.37 (d, J = 1.1 Hz, 1H), 5.68 (dd, J = 8.7, 4.6 Hz, 1H), 4.15 (td, J = 7.9, 4.6 Hz, 1H), 3.99-3.88 (m, 6H), 3.55 (d, J = 12.4 Hz, 2H), 2.78-2.62 (m, 9H), 2.46-2.38 (m, 1H), 2.35 (s, 4H), 2.06 (s, 3H), 1.92 (d, J = 12.4 Hz, 2H), 1.64-1.54 (m, 2H); 611.5 [M + H]⁺ |
| 148 | 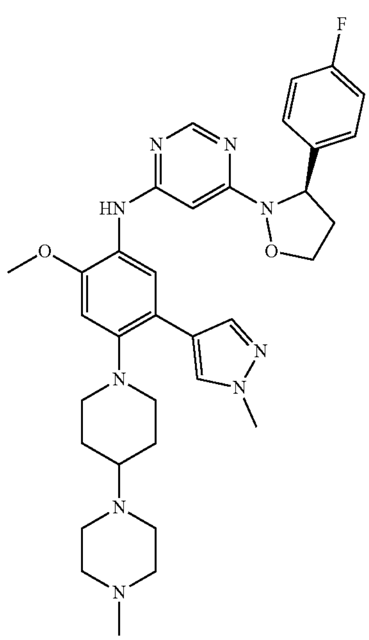 [SMILES: COc1cc(N2CCC(N3CCN(C)CC3)CC2)c(-c2cnn(C)c2)cc1Nc1cc(N2OCC[C@@H]2c2ccc(F)cc2)ncn1] | (R)-6-(3-(4-fluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine | ¹H NMR (400 MHz, Chloroform-d) δ 8.33 (d, J = 1.0 Hz, 1H), 7.90-7.84 (m, 2H), 7.78 (s, 1H), 7.46-7.37 (m, 2H), 7.08-6.97 (m, 2H), 6.84 (s, 1H), 6.70 (s, 1H), 6.51 (d, J = 1.1 Hz, 1H), 5.66 (dd, J = 8.6, 4.6 Hz, 1H), 4.13 (td, J = 7.8, 4.3 Hz, 1H), 3.95 (s, 3H), 3.94-3.89 (m, 1H), 3.87 (s, 3H), 3.23 (d, J = 10.9 Hz, 2H), 2.84-2.42 (m, 11H), 2.40-2.45 (m, 1H), 2.31 (s, 3H), 2.28-2.20 (m, 1H), 1.99-1.92 (m, 2H), 1.61 (dt, J = 11.9, 3.8 Hz, 2H); 628.4 [M + H]⁺ |

TABLE 1-continued

| Example Compound | Structure | Compound Name | ¹H NMR; MS [M + H]⁺ |
|---|---|---|---|
| 149 | 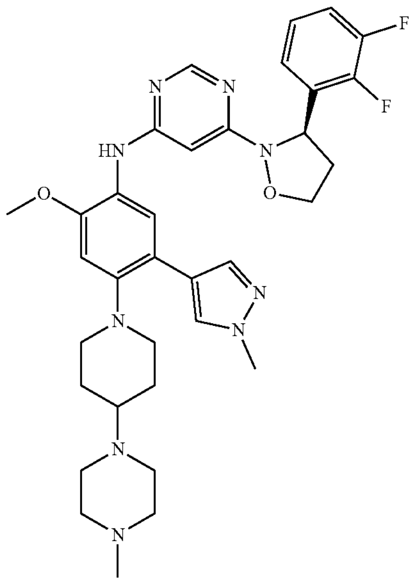 [SMILES: COc1cc(N2CCC(N3CCN(C)CC3)CC2)c(-c2cnn(C)c2)cc1Nc1cc(N2OCC[C@@H]2c2cccc(F)c2F)ncn1] | (R)-6-(3-(2,3-difluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine | ¹H NMR (400 MHz, Chloroform-d) δ 8.33 (d, J = 1.0 Hz, 1H), 7.88 (s, 1H), 7.87 (s, 1H), 7.78 (s, 1H), 7.38-7.29 (m, 1H), 7.13-6.99 (m, 2H), 6.90 (s, 1H), 6.71 (s, 1H), 6.53 (d, J = 1.1 Hz, 1H), 5.92 (dd, J = 8.8, 4.7 Hz, 1H), 4.11 (td, J = 7.9, 4.2 Hz, 1H), 3.95 (s, 3H), 3.93-3.89 (m, 1H), 3.88 (s, 3H), 3.24 (dt, J = 11.0, 3.5 Hz, 2H), 2.87-2.36 (m, 11H), 2.32 (s, 3H), 2.30-2.20 (m, 2H), 2.00-1.92 (m, 2H), 1.68-1.53 (m, 2H); 646.3 [M + H]⁺ |
| 150 | 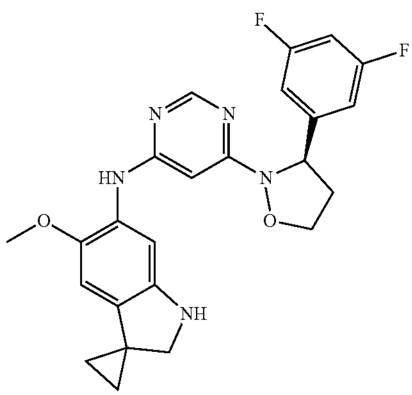 [SMILES: COc1cc2c(cc1Nc1cc(N3OCC[C@@H]3c3cc(F)cc(F)c3)ncn1)NCC21CC1] | (R)-N-(6-(3-(3,5-difluorophenyl)isoxazolidin-2-yl)pyrimidin-4-yl)-5'-methoxyspiro[cyclopropane-1,3'-indoline]-6'-amine | 452.1 [M + H]⁺ |
| 151 | 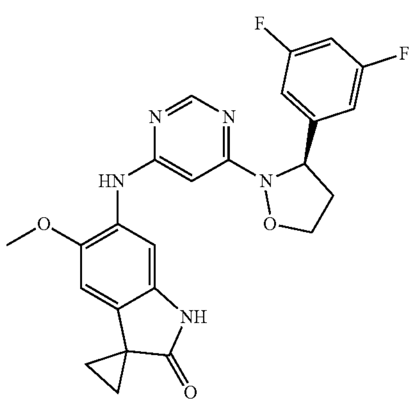 [SMILES: COc1cc2c(cc1Nc1cc(N3OCC[C@@H]3c3cc(F)cc(F)c3)ncn1)NC(=O)C21CC1] | (R)-6'-((6-(3-(3,5-difluorophenyl)isoxazolidin-2-yl)pyrimidin-4-yl)amino)-5'-methoxyspiro[cyclopropane-1,3'-indolin]-2'-one | ¹H NMR (400 MHz, DMSO-d₆) δ 10.35 (s, 1H), 8.68 (s, 1H), 8.27-8.20 (m, 1H), 7.57 (s, 1H), 7.13 (ddd, J = 6.7, 5.3, 2.9 Hz, 2H), 6.81 (s, 1H), 6.54 (s, 1H), 5.55 (dd, J = 8.7, 5.0 Hz, 1H), 4.16 (td, J = 7.9, 3.9 Hz, 1H), 3.76 (s, 3H), 3.39 (dt, J = 10.9, 6.4 Hz, 2H), 2.76 (ddd, J = 12.2, 8.3, 4.4 Hz, 1H), 2.26 (ddt, J = 11.8, 7.7, 4.0 Hz, 1H), 1.55 (q, J = 3.6, 3.2 Hz, 2H), 1.42 (q, J = 3.5 Hz, 2H); 466.3 [M + H]⁺ |

TABLE 1-continued

| Example Compound | Structure | Compound Name | ¹H NMR; MS [M + H]⁺ |
|---|---|---|---|
| 152 | 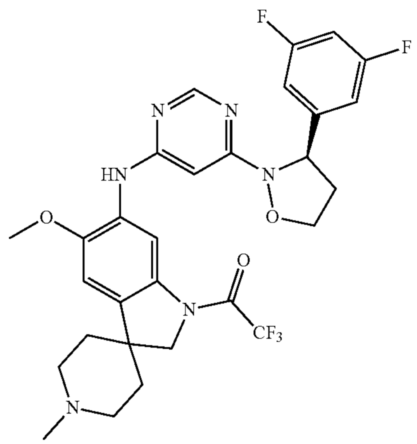 [SMILES: COc1cc2c(cc1Nc1cc(N3OCC[C@@H]3c3cc(F)cc(F)c3)ncn1)N(C(=O)C(F)(F)F)CC21CCN(C)CC1] | (R)-1-(6-((6-(3-(3,5-difluorophenyl)isoxazolidin-2-yl)pyrimidin-4-yl)amino)-5-methoxy-1'-methylspiro[indolin-3,4'-piperidin]-1-yl)-2,2,2-trifluoroethan-1-one | ¹H NMR (400 MHz, DMSO-d₆) δ 8.78 (s, 1H), 8.56 (s, 1H), 8.21 (d, J = 1.0 Hz, 1H), 7.13 (dtd, J = 9.6, 5.2, 2.1 Hz, 3H), 6.53 (s, 1H), 4.18-4.13 (m, 2H), 3.86 (s, 3H), 3.84-3.78 (m, 2H), 2.93 (s, 2H), 2.82-2.74 (m, 2H), 2.40-2.32 (m, 4H), 2.30-2.22 (m, 2H), 2.02 (d, J = 12.3 Hz, 3H), 1.71 (s, 2H); 605.4 [M + H]⁺ |
| 153 | 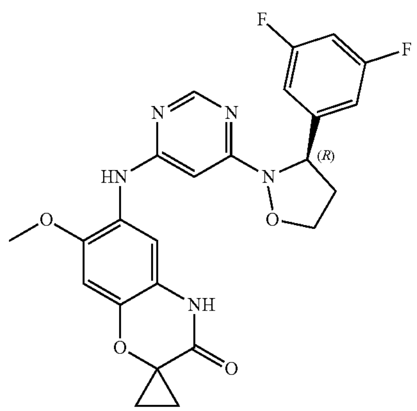 | (R)-6-((6-(3-(3,5-difluorophenyl)isoxazolidin-2-yl)pyrimidin-4-yl)amino)-7-methoxyspiro[benzo[b][1,4]oxazin-2,1'-cyclopropane]-3(4H)-one | ¹H NMR (400 MHz, DMSO-d₆) δ 10.58 (s, 1H), 8.64 (s, 1H), 7.31 (s, 1H), 7.16-7.08 (m, 3H), 6.69 (s, 1H), 6.38 (s, 1H), 5.55 (dd, J = 8.8, 5.1 Hz, 1H), 4.15 (td, J = 7.9, 3.9 Hz, 1H), 3.83 (q, J = 7.9 Hz, 1H), 3.73 (s, 3H), 2.78-2.71 (m, 2H), 2.26 (ddd, J = 12.7, 8.4, 5.0 Hz, 1H), 1.25 (q, J = 4.1, 3.2 Hz, 2H), 1.16-1.12 (m, 2H); 482.3 [M + H]⁺ |
| 154 | 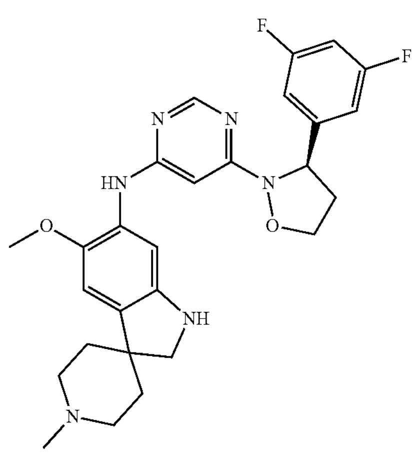 [SMILES: COc1cc2c(cc1Nc1cc(N3OCC[C@@H]3c3cc(F)cc(F)c3)ncn1)NCC21CCN(C)CC1] | (R)-N-(6-(3-(3,5-difluorophenyl)isoxazolidin-2-yl)pyrimidin-4-yl)-5-methoxy-1'-methylspiro[indolin-3,4'-piperidin]-6-amine | ¹H NMR (400 MHz, DMSO-d₆) δ 8.48 (s, 1H), 8.18 (d, J = 1.0 Hz, 1H), 7.13 (td, J = 7.4, 2.9 Hz, 3H), 7.01 (s, 1H), 6.79 (s, 1H), 6.43 (s, 1H), 4.14 (td, J = 7.8, 3.8 Hz, 1H), 3.72 (s, 3H), 3.28 (s, 3H), 2.88-2.69 (m, 4H), 2.30 (s, 3H), 2.24 (ddd, J = 12.9, 8.4, 5.1 Hz, 2H), 2.17 (d, J = 6.9 Hz, 2H), 1.91-1.80 (m, 2H), 1.60 (d, J = 12.9 Hz, 2H); 509.3 [M + H]⁺ |

TABLE 1-continued

| Example Compound | Structure | Compound Name | ¹H NMR; MS [M + H]⁺ |
|---|---|---|---|
| 155 | 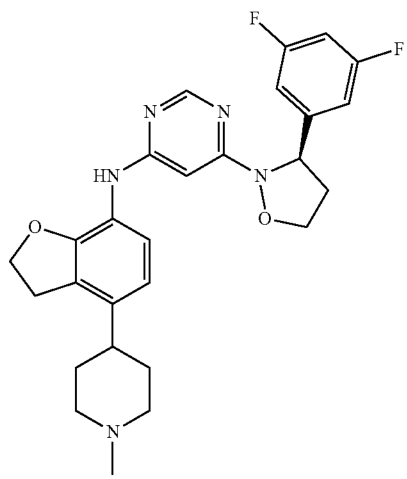 [SMILES: CN1CCC(c2ccc(Nc3cc(N4OCC[C@@H]4c4cc(F)cc(F)c4)ncn3)c3c2CCO3)CC1] | (R)-6-(3-(3,5-difluorophenyl)isoxazolidin-2-yl)-N-(4-(1-methylpiperidin-4-yl)-2,3-dihydrobenzofuran-7-yl)pyrimidin-4-amine | ¹H NMR (400 MHz, DMSO-d₆) δ 8.82 (s, 1H), 8.16 (d, J = 1.0 Hz, 1H), 7.29 (d, J = 8.3 Hz, 1H), 7.11 (dd, J = 7.6, 2.9 Hz, 3H), 6.70 (d, J = 8.3 Hz, 1H), 6.28 (s, 1H), 4.55 (t, J = 9.0 Hz, 2H), 4.14 (td, J = 7.9, 3.8 Hz, 2H), 3.81 (q, J = 7.9 Hz, 2H), 3.22 (t, J = 8.7 Hz, 2H), 2.87 (dt, J = 11.7, 3.2 Hz, 2H), 2.76 (dt, J = 8.4, 4.5 Hz, 2H), 2.47-2.37 (m, 1H), 2.30-2.21 (m, 1H), 2.19 (s, 3H), 1.96 (td, J = 11.0, 4.4 Hz, 2H), 1.68 (td, J = 9.5, 3.1 Hz, 2H); 494.4 [M + H]⁺ |
| 156 | 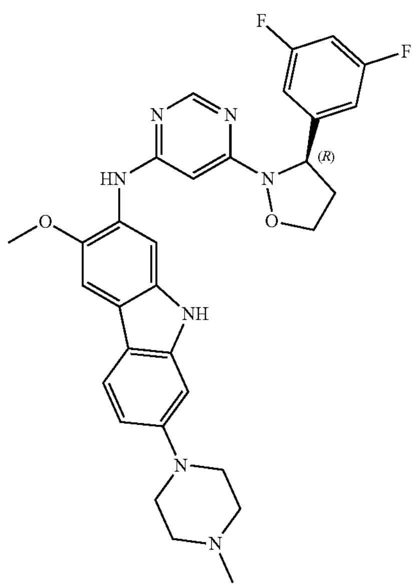 | (R)-N-(6-(3-(3,5-difluorophenyl)isoxazolidin-2-yl)pyrimidin-4-yl)-3-methoxy-7-(4-methylpiperazin-1-yl)-9H-carbazol-2-amine | 572.3 [M + H]⁺ |
| 157 | 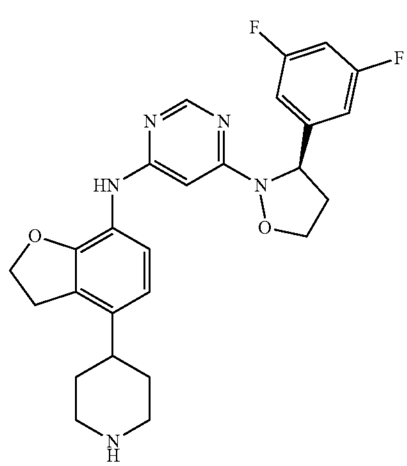 [SMILES: Fc1cc(F)cc([C@H]2CCON2c2cc(Nc3ccc(C4CCNCC4)c4c3OCC4)ncn2)c1] | (R)-6-(3-(3,5-difluorophenyl)isoxazolidin-2-yl)-N-(4-(piperidin-4-yl)-2,3-dihydrobenzofuran-7-yl)pyrimidin-4-amine | ¹H NMR (400 MHz, DMSO-d₆) δ 8.82 (s, 1H), 8.17 (d, J = 0.9 Hz, 1H), 7.30 (d, J = 8.2 Hz, 1H), 7.12 (qd, J = 6.9, 3.0 Hz, 3H), 6.69 (d, J = 8.3 Hz, 1H), 6.28 (s, 1H), 4.55 (t, J = 9.1 Hz, 2H), 4.14 (td, J = 7.8, 3.8 Hz, 2H), 3.81 (q, J = 7.9 Hz, 2H), 3.22 (t, J = 8.7 Hz, 2H), 3.06 (d, J = 11.8 Hz, 2H), 2.76 (ddp, J = 12.1, 7.6, 3.8 Hz, 1H), 2.68-2.54 (m, 3H), 2.24 (dtd, J = 16.2, 8.2, 4.1 Hz, 1H), 1.68 (d, J = 12.3 Hz, 2H), 1.63-1.49 (m, 2H); 480.4 [M + H]⁺ |

TABLE 1-continued

| Example Compound | Structure | Compound Name | ¹H NMR; MS [M + H]⁺ |
|---|---|---|---|
| 158 | 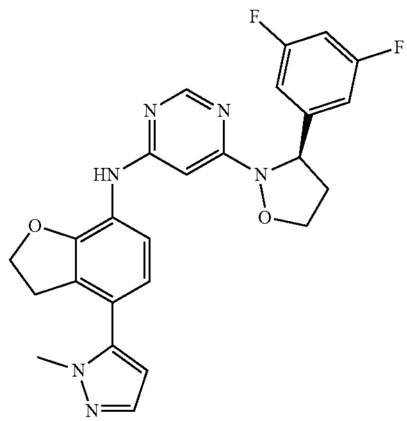 [SMILES: Cn1nccc1-c1ccc(Nc2cc(N3OCC[C@@H]3c3cc(F)cc(F)c3)ncn2)c2c1CCO2] | (R)-6-(3-(3,5-difluorophenyl)isoxazolidin-2-yl)-N-(4-(1-methyl-1H-pyrazol-5-yl)-2,3-dihydrobenzofuran-7-yl)pyrimidin-4-amine | ¹H NMR (400 MHz, DMSO-d₆) δ 9.06 (s, 1H), 8.25 (d, J = 0.9 Hz, 1H), 7.73 (d, J = 8.3 Hz, 1H), 7.49 (d, J = 1.9 Hz, 1H), 7.13 (dtd, J = 7.6, 4.2, 2.2 Hz, 3H), 6.91 (d, J = 8.3 Hz, 1H), 6.53 (s, 1H), 6.39 (d, J = 1.9 Hz, 1H), 5.57 (dd, J = 8.7, 5.0 Hz, 1H), 4.61 (t, J = 8.7 Hz, 2H), 4.18 (td, J = 7.9, 3.9 Hz, 1H), 3.85 (q, J = 7.9 Hz, 1H), 3.79 (s, 3H), 3.21 (t, J = 8.7 Hz, 2H), 2.78 (dq, J = 8.2, 4.2, 3.6 Hz, 1H), 2.27 (dt, J = 12.6, 3.9 Hz, 1H); 477.3 [M + H]⁺ |
| 159 | 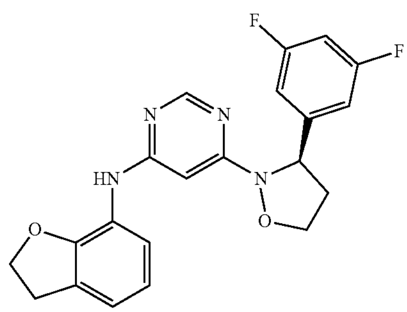 [SMILES: Fc1cc(F)cc([C@H]2CCON2c2cc(Nc3cccc4c3OCC4)ncn2)c1] | (R)-6-(3-(3,5-difluorophenyl)isoxazolidin-2-yl)-N-(2,3-dihydrobenzofuran-7-yl)pyrimidin-4-amine | ¹H NMR (400 MHz, DMSO-d₆) δ 8.92 (s, 1H), 8.20 (d, J = 0.9 Hz, 1H), 7.41 (d, J = 8.0 Hz, 1H), 7.12 (dq, J = 9.5, 3.2 Hz, 3H), 7.03 (dd, J = 7.4, 1.2 Hz, 1H), 6.82 (t, J = 7.6 Hz, 1H), 6.35 (s, 1H), 5.56 (dd, J = 8.7, 5.0 Hz, 1H), 4.56 (t, J = 8.8 Hz, 2H), 4.15 (td, J = 7.9, 3.8 Hz, 1H), 3.86-3.76 (m, 1H), 3.24 (t, J = 8.7 Hz, 2H), 2.81-2.72 (m, 1H), 2.25 (ddt, J = 11.8, 7.8, 4.0 Hz, 1H); 397.2 [M + H]⁺ |
| 160 | 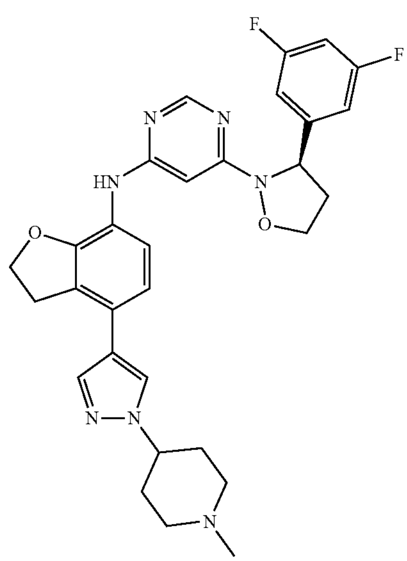 [SMILES: CN1CCC(n2cc(-c3ccc(Nc4cc(N5OCC[C@@H]5c5cc(F)cc(F)c5)ncn4)c4c3CCO4)cn2)CC1] | (R)-6-(3-(3,5-difluorophenyl)isoxazolidin-2-yl)-N-(4-(1-(1-methylpiperidin-4-yl)-1H-pyrazol-4-yl)-2,3-dihydrobenzofuran-7-yl)pyrimidin-4-amine | ¹H NMR (400 MHz, DMSO-d₆) δ 8.92 s, 1H), 8.22 (d, J = 1.0 Hz, 1H), 8.14 (s, 1H), 7.88 (s, 1H), 7.46 (d, J = 8.3 Hz, 1H), 7.18-7.04 (m, 4H), 6.37 (s, 1H), 5.57 (dd, J = 8.7, 5.0 Hz, 1H), 4.63 (t, J = 8.8 Hz, 2H), 4.48 (t, J = 7.5 Hz, 1H), 4.20-4.09 (m, 1H), 3.83 (d, J = 8.1 Hz, 1H), 3.48-3.36 (m, 4H), 3.11-3.00 (m, 2H), 2.76 (s, 2H), 2.26 (dt, J = 9.1, 4.7 Hz, 4H), 1.92 (s, 3H); 560.4 [M + H]⁺ |

TABLE 1-continued

| Example Compound | Structure | Compound Name | ¹H NMR; MS [M + H]⁺ |
|---|---|---|---|
| 161 | 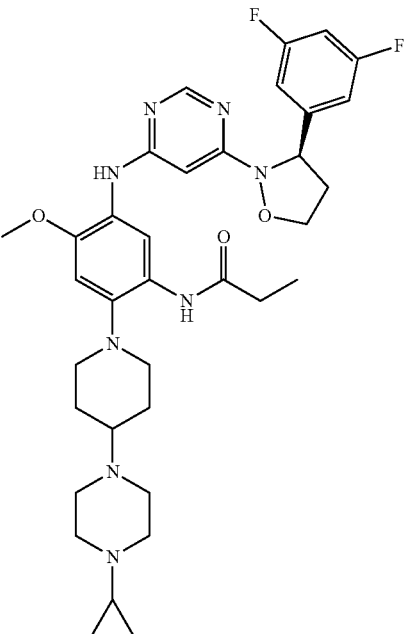 [SMILES: CCC(=O)Nc1cc(Nc2cc(N3OCC[C@@H]3c3cc(F)cc(F)c3)ncn2)c(OC)cc1N1CCC(N2CCN(C3CC3)CC2)CC1] | (R)-N-(2-(4-(4-cyclopropylpiperazin-1-yl)piperidin-1-yl)-5-((6-(3-(3,5-difluorophenyl)isoxazolidin-2-yl)pyrimidin-4-yl)amino)-4-methoxyphenyl)propionamide | ¹H NMR (400 MHz, DMSO-d₆) δ 8.68 (s, 1H), 8.62 (s, 1H), 8.04 (s, 1H), 7.15-7.07 (m, 3H), 6.81 (s, 1H), 6.33 (s, 1H), 5.55 (dd, J = 8.7, 5.0 Hz, 1H), 4.13 (dt, J = 8.6, 4.2 Hz, 1H), 3.82 (q, J = 6.9, 5.7 Hz, 1H), 3.78 (s, 3H), 3.08 (s, 2H), 2.77 (ddd, J = 12.3, 8.2, 4.1 Hz, 2H), 2.70 (d, J = 13.7 Hz, 4H), 2.50 (d, J = 1.9 Hz, 6H), 2.38 (q, J = 7.6 Hz, 2H), 2.30-2.17 (m, 2H), 1.99 (q, J = 6.0, 5.5 Hz, 1H), 1.89 (d, J = 17.8 Hz, 2H), 1.70 (s, 2H), 1.10 (t, J = 7.5 Hz, 3H), 0.45 (s, 2H), 0.32 (s, 2H); 663.4 [M + H]⁺ |
| 162 | 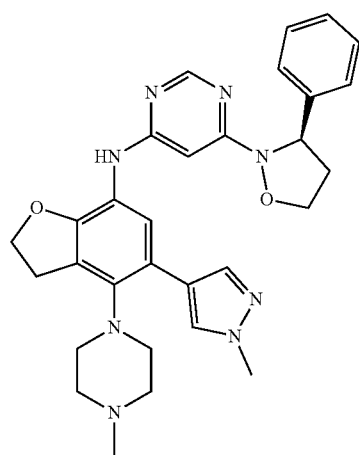 [SMILES: CN1CCN(c2c(-c3cnn(C)c3)cc(Nc3cc(N4OCC[C@@H]4c4ccccc4)ncn3)c3c2CCO3)CC1] | (R)-N-(5-(1-methyl-1H-pyrazol-4-yl)-4-(4-methylpiperazin-1-yl)-2,3-dihydrobenzofuran-7-yl)-6-(3-phenylisoxazolidin-2-yl)pyrimidin-4-amine | ¹H NMR (400 MHz, DMSO-d₆) δ 8.80 (s, 1H), 8.17 (s, 1H), 7.97 (d, J = 6.5 Hz, 1H), 7.73 (s, 1H), 7.40 (d, J = 7.1 Hz, 3H), 7.35 (t, J = 7.5 Hz, 3H), 7.29-7.22 (m, 1H), 6.31 (s, 1H), 5.53 (dd, J = 8.6, 5.0 Hz, 1H), 4.56 (t, J = 8.9 Hz, 2H), 4.15 (td, J = 7.8, 3.9 Hz, 1H), 3.88 (s, 3H), 3.82 (q, J = 7.9 Hz, 1H), 3.40 (t, J = 8.6 Hz, 2H), 3.10 (d, J = 11.1 Hz, 7H), 2.74 (s, 4H), 2.24 (dtd, J = 12.8, 8.1, 5.0 Hz, 1H); 539.4 [M + H]⁺ |

| Example Compound | Structure | Compound Name | ¹H NMR; MS [M + H]⁺ |
|---|---|---|---|
| 163 | 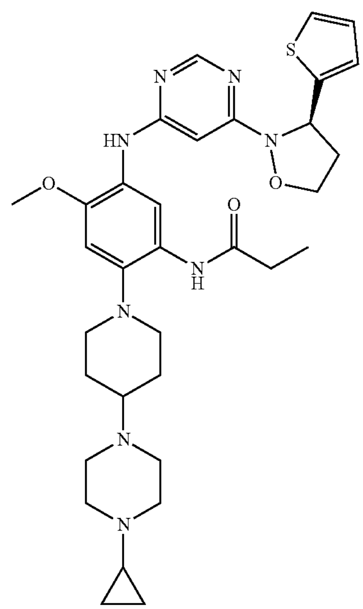 [SMILES: CCC(=O)Nc1cc(Nc2cc(N3OCC[C@@H]3c3cccs3)ncn2)c(OC)cc1N1CCC(N2CCN(C3CC3)CC2)CC1] | (R)-N-(2-(4-(4-cyclopropylpiperazin-1-yl)piperidin-1-yl)-4-methoxy-5-((6-(3-(thiophene)-2-yl)isoxazolidin-2-yl)pyrimidin-4-yl)amino)phenyl)propionamide | ¹H NMR (400 MHz, DMSO-$d_6$) δ 8.66 (s, 1H), 8.61 (s, 1H), 8.04 (s, 1H), 7.40 (dd, J = 5.1, 1.3 Hz, 1H), 7.08 (dt, J = 3.5, 1.2 Hz, 1H), 6.98 (dd, J = 5.1, 3.5 Hz, 1H), 6.81 (s, 1H), 6.28 (s, 1H), 5.81 (dd, J = 8.3, 3.9 Hz, 1H), 4.14 (td, J = 7.9, 4.7 Hz, 1H), 3.86 (q, J = 7.9 Hz, 1H), 3.77 (s, 3H), 3.04 (s, 2H), 2.65 (dd, J = 12.2, 3.6 Hz, 4H), 2.53 (d, J = 6.6 Hz, 8H), 2.43-2.32 (m, 4H), 1.85 (s, 2H), 1.67 (s, 2H), 1.58 (s, 1H), 1.10 (t, J = 7.6 Hz, 3H), 0.40 (s, 2H), 0.28 (s, 2H); 633.4 [M + H]⁺ |
| 164 | 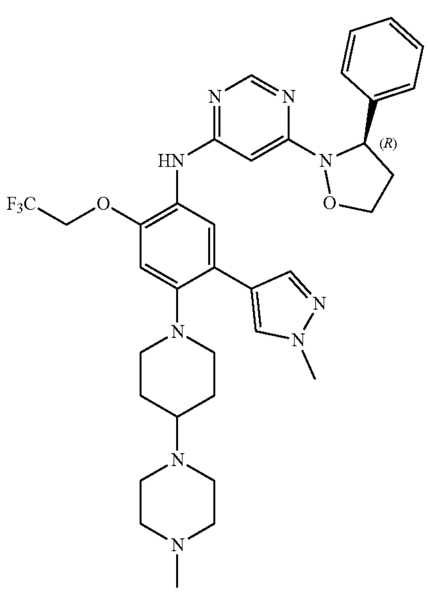 | (R)-N-(5-(1-methyl-1H-pyrazol-4-yl)-4-(4-(4-methylpiperazin-1-yl)piperidin-1-yl)-2-(2,2,2-trifluoroethoxy)phenyl)-6-(3-phenylisoxazolidin-2-yl)pyrimidin-4-amine | ¹H NMR (400 MHz, DMSO-$d_6$) δ 8.58 (s, 1H), 8.08 (s, 1H), 7.87 (s, 1H), 7.48 (s, 1H), 7.43-7.37 (m, 2H), 7.34 (dd, J = 8.5, 6.7 Hz, 2H), 7.28-7.23 (m, 1H), 6.90 (s, 1H), 6.23 (s, 1H), 5.53 (dd, J = 8.6, 4.9 Hz, 1H), 4.74 (q, J = 8.9 Hz, 2H), 4.12 (td, J = 7.9, 4.1 Hz, 1H), 3.87 (s, 3H), 3.80 (q, J = 7.9 Hz, 1H), 3.12 (d, J = 11.2 Hz, 2H), 2.73 (qt, J = 7.9, 4.1 Hz, 2H), 2.64-2.50 (m, 9H), 2.24 (hept, J = 7.9 Hz, 5H), 1.84 (dd, J = 13.2, 7.5 Hz, 2H), 1.61-1.43 (m, 3H); 678.5 [M + H]⁺ |

TABLE 1-continued

| Example Compound | Structure | Compound Name | ¹H NMR; MS [M + H]⁺ |
|---|---|---|---|
| 165 | 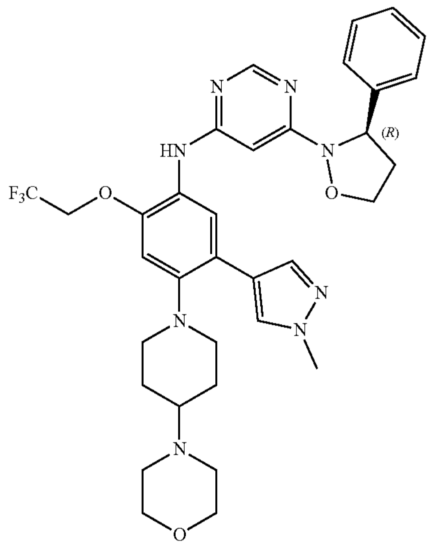 | (R)-N-(5-(1-methyl-1H-pyrazol-4-yl)-4-(4-morpholinopiperidin-1-yl)-2-(2,2,2-trifluoroethoxy)phenyl)-6-(3-phenylisoxazolidin-2-yl)pyrimidin-4-amine | ¹H NMR (400 MHz, DMSO-$d_6$) δ 8.59 (s, 1H), 8.08 (s, 1H), 7.87 (s, 1H), 7.48 (s, 1H), 7.44-7.38 (m, 2H), 7.34 (dd, J = 8.5, 6.8 Hz, 2H), 7.30-7.23 (m, 1H), 6.91 (s, 1H), 6.24 (s, 1H), 5.53 (dd, J = 8.6, 4.9 Hz, 1H), 4.75 (q, J = 9.0 Hz, 2H), 4.11 (tt, J = 9.1, 4.6 Hz, 1H), 3.87 (s, 3H), 3.80 (q, J = 7.9 Hz, 1H), 3.60 (s, 3H), 3.12 (s, 2H), 2.73 (dtd, J = 12.1, 7.9, 4.1 Hz, 1H), 2.57 (t, J = 12.6 Hz, 8H), 2.29-2.13 (m, 2H), 1.85 (s, 2H), 1.53 (s, 2H); 665.4 [M + H]⁺ |
| 166 | 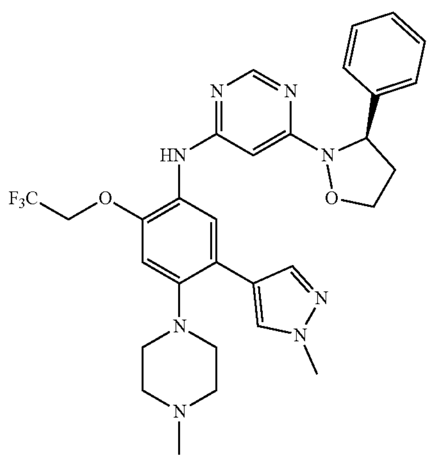 [SMILES: CN1CCN(c2cc(OCC(F)(F)F)c(Nc3cc(N4OCC[C@@H]4c4ccccc4)ncn3)cc2-c2cnn(C)c2)CC1] | (R)-N-(5-(1-methyl-1H-pyrazol-4-yl)-4-(4-methylpiperazin-1-yl)-2-(2,2,2-trifluoroethoxy)phenyl)-6-(3-phenylisoxazolidin-2-yl)pyrimidin-4-amine | ¹H NMR (400 MHz, DMSO-$d_6$) δ 8.66 (s, 1H), 8.15 (t, J = 1.1 Hz, 2H), 7.92 (s, 1H), 7.56 (s, 1H), 7.42-7.38 (m, 2H), 7.37-7.32 (m, 2H), 7.28-7.22 (m, 1H), 6.92 (s, 1H), 6.29 (s, 1H), 5.54 (dd, J = 8.6, 4.9 Hz, 1H), 4.79 (q, J = 9.0 Hz, 2H), 4.13 (d, J = 4.1 Hz, 1H), 3.89 (s, 3H), 3.81 (d, J = 8.0 Hz, 1H), 3.26 (s, 4H), 3.05 (s, 4H), 2.81 (s, 3H), 2.73 (dd, J = 8.2, 4.1 Hz, 1H), 2.25 (dt, J = 8.6, 4.7 Hz, 1H); 595.4 [M + H]⁺ |
| 167 | 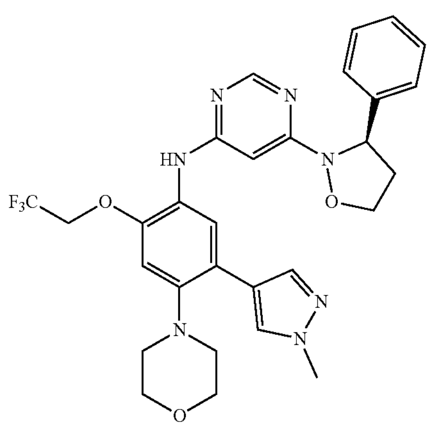 [SMILES: Cn1cc(-c2cc(Nc3cc(N4OCC[C@@H]4c4ccccc4)ncn3)c(OCC(F)(F)F)cc2N2CCOCC2)cn1] | (R)-N-(5-(1-methyl-1H-pyrazol-4-yl)-4-morpholino-2-(2,2,2-trifluoroethoxy)phenyl)-6-(3-phenylisoxazolidin-2-yl)pyrimidin-4-amine | ¹H NMR (400 MHz, DMSO-$d_6$) δ 9.36 (s, 1H), 8.22 (s, 1H), 8.16 (s, 1H), 7.46 (s, 1H), 7.38-7.33 (m, 4H), 7.27 (tt, J = 5.3, 2.4 Hz, 1H), 6.96 (s, 1H), 6.12 (s, 1H), 5.54 (dd, J = 8.5, 5.1 Hz, 1H), 4.79 (dt, J = 8.7, 4.4 Hz, 2H), 4.24-4.18 (m, 1H), 3.93 (d, J = 7.8 Hz, 1H), 3.88 (s, 3H), 3.74 (t, J = 4.5 Hz, 4H), 2.89-2.84 (m, 4H), 2.82 (t, J = 4.6 Hz, 1H), 2.28 (dt, J = 8.0, 4.8 Hz, 1H); 582.4 [M + H]⁺ |

TABLE 1-continued

| Example Compound | Structure | Compound Name | $^1$H NMR; MS [M + H]$^+$ |
|---|---|---|---|
| 168 | 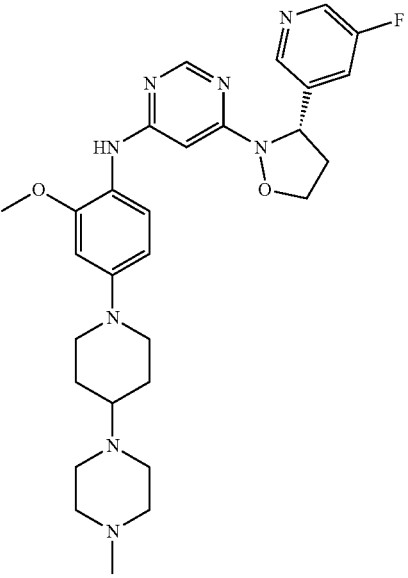 [SMILES: COc1cc(N2CCC(N3CCN(C)CC3)CC2)ccc1Nc1cc(N2OCC[C@H]2c2cncc(F)c2)ncn1] | (S)-6-(3-(5-fluoropyridin-3-yl)isoxazolidin-2-yl)-N-(2-methoxy-4-(4-(4-methylpiperazin-1-yl)piperidin-1-yl)phenyl)pyrimidin-4-amine | $^1$H NMR (400 MHz, Chloroform-d) δ 8.50 (s, 1H), 8.37 (s, 1H), 8.29 (s, 1H), 7.55 (d, J = 9.4 Hz, 1H), 7.49 (d, J = 8.5 Hz, 1H), 6.96 (s, 1H), 6.58-6.51 (m, 2H), 6.41 (s, 1H), 5.76 (dd, J = 8.8, 4.6 Hz, 1H), 4.12 (q, J = 6.9 Hz, 1H), 3.94-3.86 (m, 1H), 3.84 (s, 3H), 3.72 (d, J = 12.0 Hz, 2H), 3.21 (s, 3H), 2.75 (t, J = 12.1 Hz, 4H), 2.68-2.61 (m, 3H), 2.57-2.42 (m, 4H), 2.39-2.34 (m, 2H), 1.96 (d, J = 12.4 Hz, 2H), 1.70 (q, J = 13.0, 12.5 Hz, 2H); 549.3 [M + H]$^+$ |
| 169 | 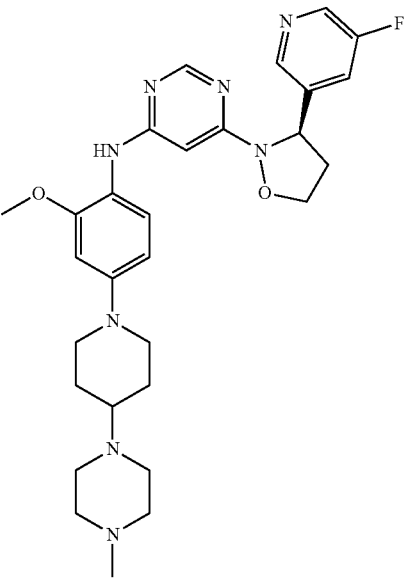 [SMILES: COc1cc(N2CCC(N3CCN(C)CC3)CC2)ccc1Nc1cc(N2OCC[C@@H]2c2cncc(F)c2)ncn1] | (R)-6-(3-(5-fluoropyridin-3-yl)isoxazolidin-2-yl)-N-(2-methoxy-4-(4-(4-methylpiperazin-1-yl)piperidin-1-yl)phenyl)pyrimidin-4-amine | $^1$H NMR (400 MHz, Chloroform-d) δ 8.50 (d, J = 1.8 Hz, 1H), 8.37 (d, J = 2.8 Hz, 1H), 8.29 (s, 1H), 7.55 (dt, J = 9.4, 2.3 Hz, 1H), 7.50 (d, J = 8.8 Hz, 1H), 6.85 (s, 1H), 6.58-6.51 (m, 2H), 6.44-6.39 (m, 1H), 5.76 (dd, J = 8.8, 4.6 Hz, 1H), 4.14-4.10 (m, 1H), 3.93-3.86 (m, 1H), 3.84 (s, 3H), 3.72 (dt, J = 12.1, 3.4 Hz, 2H), 2.84-2.34 (m, 13H), 2.31 (s, 3H), 1.96 (d, J = 11.6 Hz, 2H), 1.70 (qd, J = 12.1, 3.9 Hz, 2H); 549.3 [M + H]$^+$ |

TABLE 1-continued

| Example Compound | Structure | Compound Name | ¹H NMR; MS [M + H]⁺ |
|---|---|---|---|
| 170 | 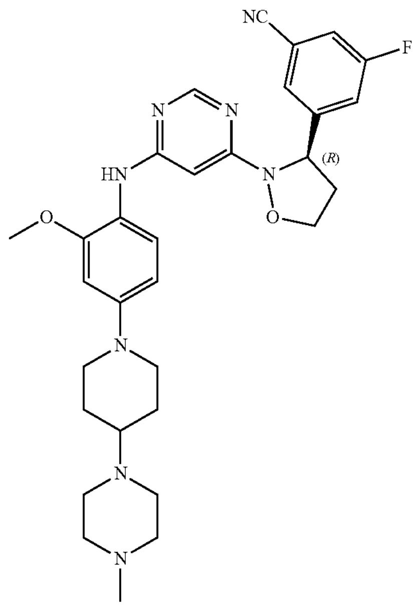 | (R)-3-fluoro-5-(2-(6-((2-methoxy-4-(4-(4-methylpiperazin-1-yl)piperidin-1-yl)phenyl)amino)pyrimidin-4-yl)isoxazolidin-3-yl)benzonitrile | ¹H NMR (400 MHz, Chloroform-d) δ 8.29 (s, 1H), 7.56 (s, 1H), 7.50 (d, J = 9.1 Hz, 1H), 7.44 (dt, J = 9.4, 2.1 Hz, 1H), 7.26-7.23 (m, 1H), 6.79 (s, 1H), 6.58-6.51 (m, 2H), 6.41 (d, J = 0.9 Hz, 1H), 5.70 (dd, J = 8.8, 4.8 Hz, 1H), 4.12 (td, J = 8.0, 3.9 Hz, 1H), 3.90-3.85 (m, 4H), 3.73 (dd, J = 9.5, 6.3 Hz, 2H), 2.84-2.33 (m, 12H), 2.31 (s, 3H), 2.30-2.23 (m, 1H), 1.97 (d, J = 11.5 Hz, 2H), 1.70 (qd, J = 12.0, 3.8 Hz, 2H); 573.3 [M + H]⁺ |
| 171 | 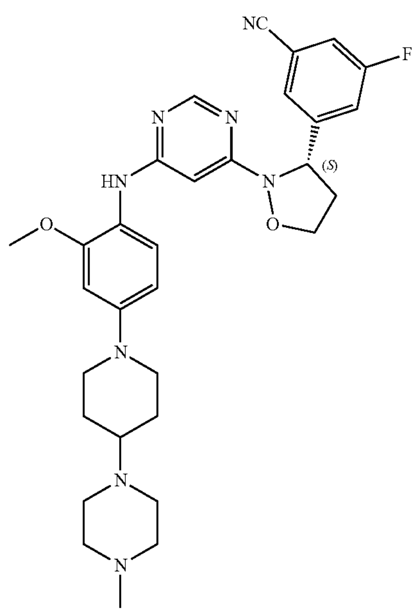 | (S)-3-fluoro-5-(2-(6-((2-methoxy-4-(4-(4-methylpiperazin-1-yl)piperidin-1-yl)phenyl)amino)pyrimidin-4-yl)isoxazolidin-3-yl)benzonitrile | ¹H NMR (400 MHz, Chloroform-d) δ 8.29 (s, 1H), 7.56 (s, 1H), 7.51 (d, J = 9.1 Hz, 1H), 7.44 (dt, J = 9.4, 2.0 Hz, 1H), 7.26-7.23 (m, 1H), 6.77 (s, 1H), 6.58-6.51 (m, 2H), 6.41 (s, 1H), 5.70 (dd, J = 8.8, 4.8 Hz, 1H), 4.12 (td, J = 8.1, 3.9 Hz, 1H), 3.92-3.85 (m, 4H), 3.72 (d, J = 12.5 Hz, 2H), 2.84-2.32 (m, 13H), 2.31 (s, 3H), 1.96 (d, J = 11.0 Hz, 2H), 1.70 (qd, J = 12.2, 4.1 Hz, 2H); 573.3 [M + H]⁺ |

TABLE 1-continued

| Example Compound | Structure | Compound Name | $^1$H NMR; MS [M + H]$^+$ |
|---|---|---|---|
| 172 | 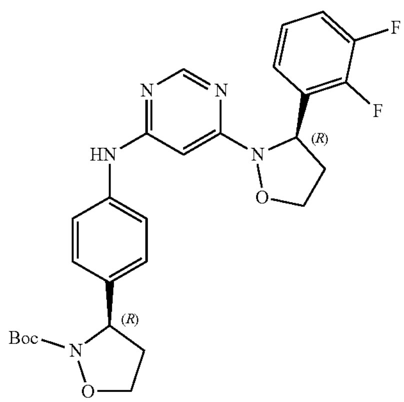 | tert-butyl (R)-3-(4-((6-((R)-3-(2,3-difluorophenyl)isoxazolidin-2-yl)pyrimidin-4-yl)amino)phenyl)isoxazolidin-2-carboxylate | $^1$H NMR (400 MHz, Chloroform-d) δ 8.32 (d, J = 1.0 Hz, 1H), 7.40-7.36 (m, 2H), 7.34-7.27 (m, 3H), 7.10-7.03 (m, 2H), 6.73 (s, 1H), 6.55 (d, J = 1.1 Hz, 1H), 5.91 (dd, J = 8.7, 4.8 Hz, 1H), 5.22 (dd, J = 8.7, 5.5 Hz, 1H), 4.20 (qd, J = 8.1, 3.8 Hz, 1H), 4.12 (td, J = 8.0, 4.2 Hz, 1H), 3.94-3.84 (m, 2H), 2.88-2.73 (m, 2H), 2.37-2.26 (m, 2H), 1.48 (s, 9H); 526.25 [M + H]$^+$ |
| 173 | 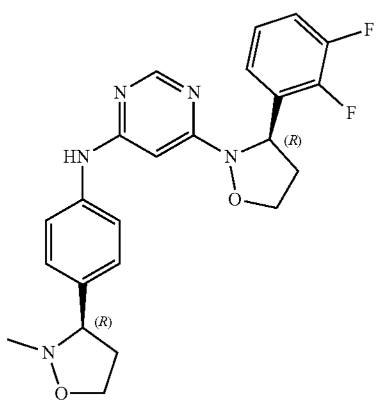 | 6-((R)-3-(2,3-difluorophenyl)isoxazolidin-2-yl)-N-(4-((R)-2-methylisoxazolidin-3-yl)phenyl)pyrimidin-4-amine | $^1$H NMR (400 MHz, Chloroform-d) δ 8.32 (d, J = 1.1 Hz, 1H), 7.43-7.37 (m, 2H), 7.34-7.28 (m, 3H), 7.11-7.02 (m, 2H), 6.85 (s, 1H), 6.56 (d, J = 1.0 Hz, 1H), 5.91 (dd, J = 8.7, 4.8 Hz, 1H), 4.16-4.06 (m, 3H), 3.89 (q, J = 8.0 Hz, 1H), 3.55 (s, 1H), 2.89-2.79 (m, 1H), 2.76-2.67 (m, 1H), 2.64 (s, 3H), 2.37-2.26 (m, 2H); 440.16 [M + H]$^+$ |
| 174 | 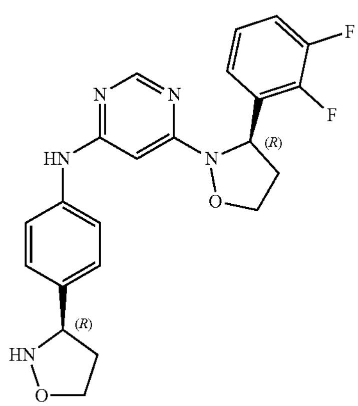 | 6-((R)-3-(2,3-difluorophenyl)isoxazolidin-2-yl)-N-(4-((R)-isoxazolidin-3-yl)phenyl)pyrimidin-4-amine | $^1$H NMR (400 MHz, Chloroform-d) δ 8.30 (d, J = 1.1 Hz, 1H), 7.43-7.39 (m, 2H), 7.33-7.29 (m, 3H), 7.10-7.01 (m, 4H), 6.55 (d, J = 1.1 Hz, 1H), 5.90 (dd, J = 8.8, 4.8 Hz, 1H), 4.50 (t, J = 10.0 Hz, 1H), 4.16-4.09 (m, 2H), 3.88 (q, J = 8.2 Hz, 1H), 3.35 (t, J = 10.1 Hz, 1H), 2.88-2.80 (m, 1H), 2.74-2.64 (m, 1H), 2.36-2.27 (m, 2H); 426.22 [M + H]$^+$ |

TABLE 1-continued

| Example Compound | Structure | Compound Name | ¹H NMR; MS [M + H]⁺ |
|---|---|---|---|
| 175 | 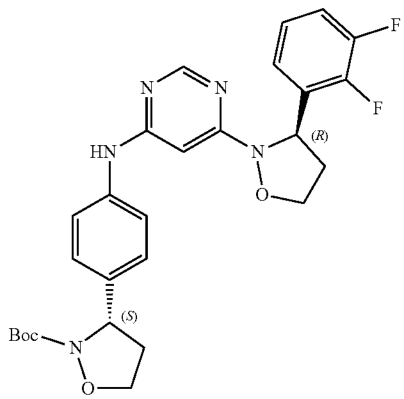 | tert-butyl (S)-3-(4-((6-((R)-3-(2,3-difluorophenyl)isoxazolidin-2-yl)pyrimidin-4-yl)amino)phenyl)isoxazolidin-2-carboxylate | ¹H NMR (400 MHz, Chloroform-d) δ 8.31 (d, J = 1.1 Hz, 1H), 7.40-7.27 (m, 5H), 7.09-7.03 (m, 2H), 6.78 (s, 1H), 6.55 (d, J = 1.1 Hz, 1H), 5.91 (dd, J = 8.9, 4.8 Hz, 1H), 5.22 (dd, J = 8.7, 5.4 Hz, 1H), 4.23-4.16 (m, 1H), 4.12 (td, J = 7.8, 5.6 Hz, 1H), 3.94-3.84 (m, 2H), 2.88-2.75 (m, 2H), 2.37-2.26 (m, 2H), 1.48 (s, 9H); 526.20 [M + H]⁺ |
| 176 | 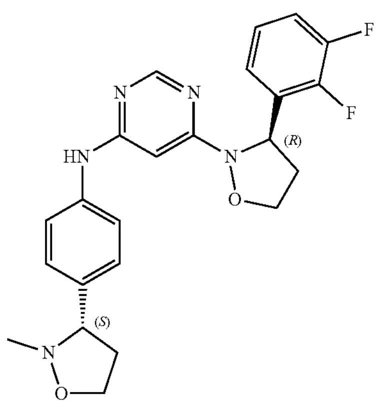 | 6-((R)-3-(2,3-difluorophenyl)isoxazolidin-2-yl)-N-(4-((S)-2-methylisoxazolidin-3-yl)phenyl)pyrimidin-4-amine | ¹H NMR (400 MHz, Chloroform-d) δ 8.31 (d, J = 1.0 Hz, 1H), 7.42-7.36 (m, 2H), 7.35-7.27 (m, 3H), 7.12-6.99 (m, 2H), 6.94 (s, 1H), 6.57 (d, J = 1.1 Hz, 1H), 5.91 (dd, J = 8.8, 4.8 Hz, 1H), 4.17-4.04 (m, 3H), 3.89 (q, J = 8.0 Hz, 1H), 3.56 (s, 1H), 2.84 (dtd, J = 12.3, 8.1, 4.1 Hz, 1H), 2.77-2.66 (m, 1H), 2.64 (s, 3H), 2.37-2.26 (m, 2H); 440.16 [M + H]⁺ |
| 177 | 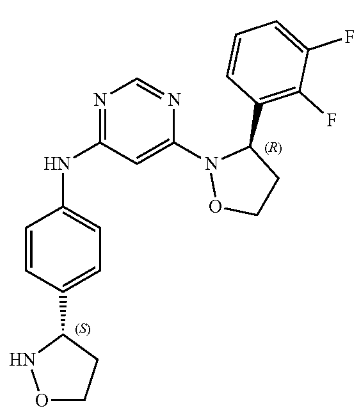 | 6-((R)-3-(2,3-difluorophenyl)isoxazolidin-2-yl)-N-(4-((S)-isoxazolidin-3-yl)phenyl)pyrimidin-4-amine | ¹H NMR (400 MHz, Chloroform-d) δ 8.31 (d, J = 1.1 Hz, 1H), 7.44-7.39 (m, 2H), 7.34-7.29 (m, 3H), 7.13-7.02 (m, 3H), 6.87 (s, 1H), 6.55 (d, J = 1.1 Hz, 1H), 5.90 (dd, J = 8.8, 4.9 Hz, 1H), 4.50 (t, J = 10.1 Hz, 1H), 4.17-4.09 (m, 2H), 3.88 (q, J = 8.2 Hz, 1H), 3.35 (t, J = 10.1 Hz, 1H), 2.88-2.79 (m, 1H), 2.69 (ddd, J = 14.1, 12.3, 8.1 Hz, 1H), 2.33 (ddd, J = 12.7, 8.4, 5.4 Hz, 2H); 426.22 [M + H]⁺ |

TABLE 1-continued

| Example Compound | Structure | Compound Name | ¹H NMR; MS [M + H]⁺ |
|---|---|---|---|
| 178 | 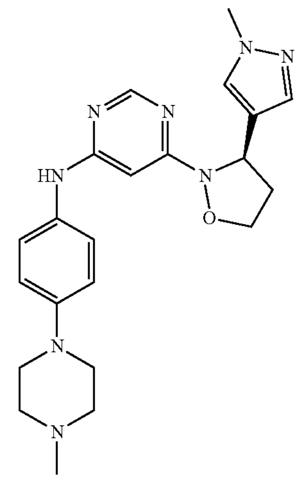 [SMILES: CN1CCN(c2ccc(Nc3cc(N4OCC[C@@H]4c4cnn(C)c4)ncn3)cc2)CC1] | (R)-6-(3-(1-methyl-1H-pyrazol-4-yl)isoxazolidin-2-yl)-N-(4-(4-methylpiperazin-1-yl)phenyl)pyrimidin-4-amine | ¹H NMR (400 MHz, MeOD) δ 8.18 (s, 1H), 7.61 (s, 1H), 7.49 (s, 1H), 7.34 (d, J = 8.9 Hz, 2H), 7.09-6.97 (m, 2H), 6.34 (d, J = 0.6 Hz, 1H), 5.54 (dd, J = 8.1, 3.3 Hz, 1H), 4.14 (tt, J = 8.8, 4.4 Hz, 1H), 4.05-3.95 (m, 1H), 3.86 (d, J = 5.6 Hz, 3H), 3.35 (dd, J = 8.5, 3.7 Hz, 4H), 3.13-3.03 (m, 4H), 2.69 (s, 3H), 2.60 (dtd, J = 12.2, 8.4, 5.8 Hz, 1H), 2.38 (tdd, J = 7.9, 6.7, 3.4 Hz, 1H); 421.19 [M + H]⁺ |
| 179 | 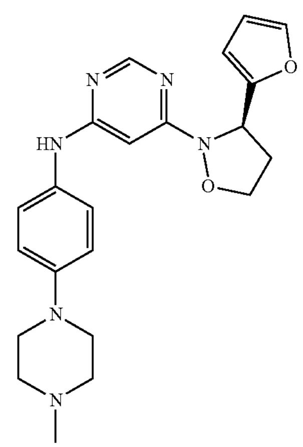 [SMILES: CN1CCN(c2ccc(Nc3cc(N4OCC[C@@H]4c4ccco4)ncn3)cc2)CC1] | (R)-6-(3-(furan-2-yl)isoxazolidin-2-yl)-N-(4-(4-methylpiperazin-1-yl)phenyl)pyrimidin-4-amine | ¹H NMR (400 MHz, MeOD) δ 8.19 (s, 1H), 7.47 (dd, J = 1.6, 0.7 Hz, 1H), 7.33 (d, J = 8.8 Hz, 2H), 7.03 (d, J = 8.9 Hz, 2H), 6.42-6.31 (m, 3H), 5.64 (t, J = 6.1 Hz, 1H), 4.19 (dt, J = 13.6, 6.7 Hz, 1H), 3.96 (q, J = 7.8 Hz, 1H), 3.32 (d, J = 1.6 Hz, 4H), 3.08-2.99 (m, 4H), 2.65 (s, 3H), 2.57 (dt, J = 12.9, 6.5 Hz, 2H); 407.20 [M + H]⁺ |
| 180 | 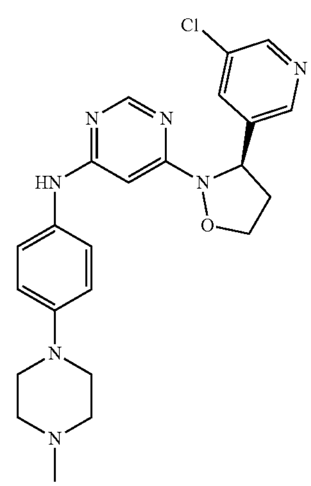 [SMILES: CN1CCN(c2ccc(Nc3cc(N4OCC[C@@H]4c4cncc(Cl)c4)ncn3)cc2)CC1] | (R)-6-(3-(5-chloropyridin-3-yl)isoxazolidin-2-yl)-N-(4-(4-methylpiperazin-1-yl)phenyl)pyrimidin-4-amine | ¹H NMR (400 MHz, DMSO-d₆) δ 9.20 (s, 1H), 8.60 (d, J = 1.9 Hz, 1H), 8.55 (d, J = 2.4 Hz, 1H), 8.22 (d, J = 0.9 Hz, 1H), 7.91-7.90 (m, 1H), 7.38 (d, J = 8.5 Hz, 2H), 6.94-6.89 (m, 2H), 6.36 (d, J = 1.1 Hz, 1H), 3.87 (q, J = 7.9 Hz, 1H), 3.11 (t, J = 5.1 Hz, 4H), 2.79 (dtt, J = 12.2, 7.8, 4.0 Hz, 1H), 2.53 (t, J = 5.5 Hz, 4H), 2.33 (ddd, J = 12.6, 8.4, 4.8 Hz, 2H), 2.27 (s, 2H), 1.91 (s, 3H); 452.1 [M + H]⁺ |

TABLE 1-continued

| Example Compound | Structure | Compound Name | ¹H NMR; MS [M + H]⁺ |
|---|---|---|---|
| 181 | 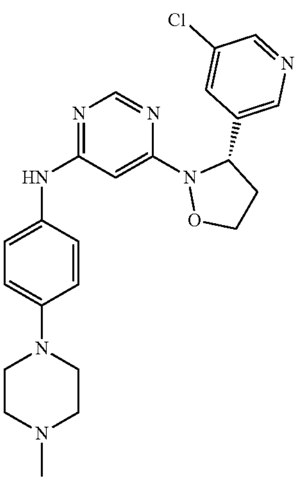 [SMILES: CN1CCN(c2ccc(Nc3cc(N4OCC[C@H]4c4cncc(Cl)c4)ncn3)cc2)CC1] | (S)-6-(3-(5-chloropyridin-3-yl)isoxazolidin-2-yl)-N-(4-(4-methylpiperazin-1-yl)phenyl)pyrimidin-4-amine | ¹H NMR (400 MHz, DMSO-$d_6$) δ 8.60 (d, J = 1.9 Hz, 1H), 8.55 (d, J = 2.4 Hz, 1H), 8.22 (s, 1H), 7.90 (t, J = 2.2 Hz, 1H), 7.37 (d, J = 8.5 Hz, 2H), 6.93-6.89 (m, 2H), 6.36 (s, 1H), 5.63-5.59 (m, 1H), 3.87 (q, J = 8.0 Hz, 2H), 3.08 (t, J = 5.0 Hz, 4H), 2.78 (dtd, J = 12.2, 7.9, 3.9 Hz, 2H), 2.45 (t, J = 5.0 Hz, 4H), 2.37-2.28 (m, 2H), 2.22 (s, 3H), 1.90 (s, 2H); 452.1 [M + H]⁺ |
| 182 | 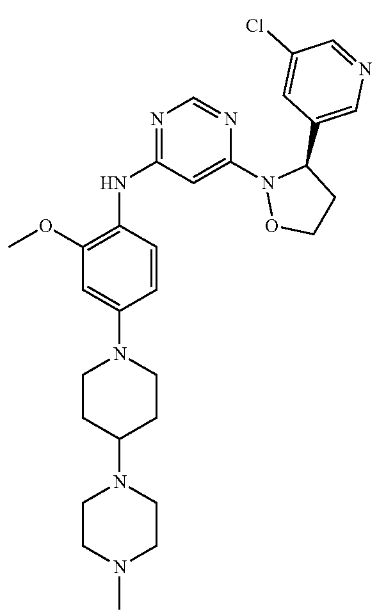 [SMILES: COc1cc(N2CCC(N3CCN(C)CC3)CC2)ccc1Nc1cc(N2OCC[C@@H]2c2cncc(Cl)c2)ncn1] | (R)-6-(3-(5-chloropyridin-3-yl)isoxazolidin-2-yl)-N-(2-methoxy-4-(4-(4-methylpiperazin-1-yl)piperidin-1-yl)phenyl)pyrimidin-4-amine | ¹H NMR (400 MHz, DMSO-$d_6$) δ 8.59 (d, J = 1.9 Hz, 1H), 8.54 (d, J = 2.3 Hz, 1H), 8.47 (s, 1H), 8.13 (d, J = 1.0 Hz, 1H), 7.89-7.88 (m, 1H), 7.30 (d, J = 8.5 Hz, 1H), 6.62 (d, J = 2.5 Hz, 1H), 6.49 (dd, J = 8.8, 2.5 Hz, 1H), 5.59 (dd, J = 8.7, 5.0 Hz, 1H), 4.15 (td, J = 7.8, 3.9 Hz, 1H), 3.82 (t, J = 8.0 Hz, 1H), 3.77 (s, 3H), 3.72 (d, J = 12.4 Hz, 2H), 2.77 (qt, J = 7.9, 3.9 Hz, 2H), 2.67 (td, J = 12.2, 2.4 Hz, 3H), 2.53 (s, 2H), 2.35-2.25 (m, 4H), 2.17 (s, 3H), 1.91 (s, 5H), 1.85 (d, J = 12.5 Hz, 2H), 1.51 (qd, J = 12.1, 3.9 Hz, 3H); 565.2 [M + H]⁺ |

TABLE 1-continued

| Example Compound | Structure | Compound Name | ¹H NMR; MS [M + H]⁺ |
|---|---|---|---|
| 183 | 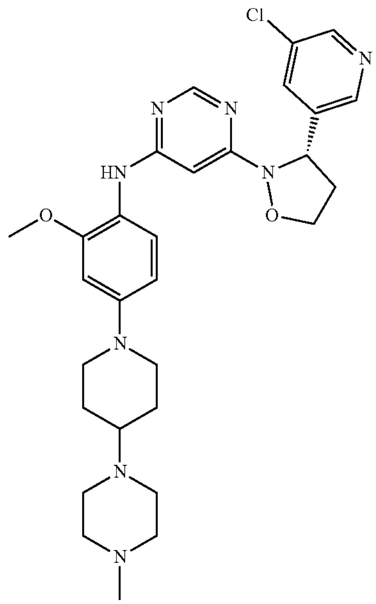 [SMILES: COc1cc(N2CCC(N3CCN(C)CC3)CC2)ccc1Nc1cc(N2OCC[C@H]2c2cncc(Cl)c2)ncn1] | (S)-6-(3-(5-chloropyridin-3-yl)isoxazolidin-2-yl)-N-(2-methoxy-4-(4-(4-methylpiperazin-1-yl)piperidin-1-yl)phenyl)pyrimidin-4-amine | 565.3 [M + H]⁺ |
| 184 | 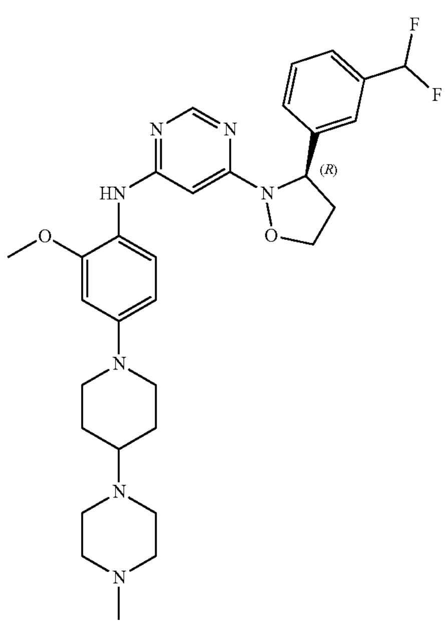 | (R)-6-(3-(3-(difluoromethyl)phenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, MeOD) δ 8.11 (d, J = 0.6 Hz, 1H), 7.66-7.55 (m, 2H), 7.50-7.43 (m, 2H), 7.32 (d, J = 8.6 Hz, 1H), 6.77 (d, J = 3.1 Hz, 1H), 6.70 (d, J = 2.4 Hz, 1H), 6.63-6.58 (m, 1H), 6.24 (s, 1H), 5.58 (dd, J = 8.5, 4.8 Hz, 1H), 4.13 (tt, J = 10.5, 5.3 Hz, 1H), 3.97-3.88 (m, 1H), 3.83 (d, J = 6.4 Hz, 3H), 3.80 (d, J = 12.7 Hz, 2H), 2.98 (d, J = 22.3 Hz, 7H), 2.87-2.71 (m, 4H), 2.68-2.65 (m, 4H), 2.39-2.29 (m, 1H), 2.05 (d, J = 11.9 Hz, 2H), 1.78-1.65 (m, 2H); 580.25 [M + H]⁺ |

TABLE 1-continued

| Example Compound | Structure | Compound Name | ¹H NMR; MS [M + H]⁺ |
|---|---|---|---|
| 185 | 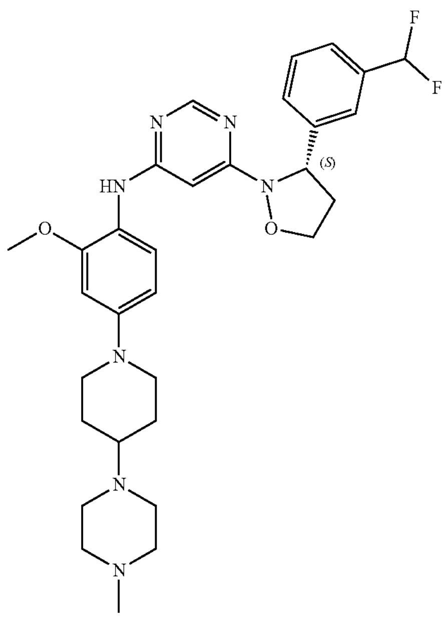 | (S)-6-(3-(3-(difluoromethyl)phenyl)isoxazolidin-2-yl)-N-(2-methoxy-4-(4-(4-methylpiperazin-1-yl)piperidin-1-yl)phenyl)pyrimidin-4-amine | ¹H NMR (400 MHz, MeOD) δ 8.11 (s, 1H), 7.65-7.56 (m, 2H), 7.51-7.43 (m, 2H), 7.32 (d, J = 8.6 Hz, 1H), 6.77 (d, J = 3.2 Hz, 1H), 6.70 (d, J = 2.5 Hz, 1H), 6.66-6.57 (m, 1H), 6.24 (s, 1H), 5.58 (dd, J = 8.5, 4.8 Hz, 1H), 4.13 (td, J = 7.8, 4.3 Hz, 1H), 3.91 (q, J = 7.9 Hz, 1H), 3.85 (d, J = 6.4 Hz, 3H), 3.80 (d, J = 12.6 Hz, 2H), 2.99 (d, J = 29.1 Hz, 7H), 2.79 (dqd, J = 10.1, 7.5, 4.4 Hz, 4H), 2.68-2.63 (m, 4H), 2.40-2.26 (m, 1H), 2.04 (d, J = 12.2 Hz, 2H), 1.73 (tt, J = 11.9, 6.1 Hz, 2H); 580.30 [M + H]⁺ |
| 186 | 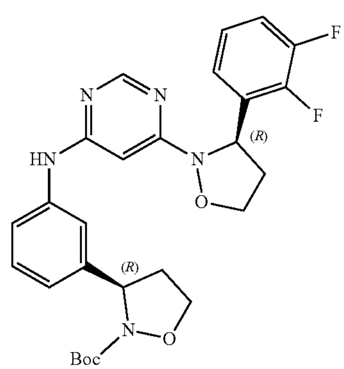 | tert-butyl (R)-3-(3-((6-((R)-3-(2,3-difluorophenyl)isoxazolidin-2-yl)pyrimidin-4-yl)amino)phenyl)isoxazolidin-2-carboxylate | ¹H NMR (400 MHz, Chloroform-d) δ 8.29 (d, J = 1.1 Hz, 1H), 7.35 (t, J = 7.8 Hz, 1H), 7.33-7.29 (m, 2H), 7.26-7.20 (m, 2H), 7.16-7.12 (m, 1H), 7.09-7.03 (m, 2H), 6.59 (d, J = 1.0 Hz, 1H), 5.90 (dd, J = 8.8, 4.8 Hz, 1H), 5.23 (dd, J = 8.7, 5.4 Hz, 1H), 4.19 (td, J = 7.9, 3.7 Hz, 1H), 4.12 (td, J = 8.0, 4.3 Hz, 1H), 3.89 (qd, J = 8.1, 7.7, 1.9 Hz, 2H), 2.89-2.74 (m, 2H), 2.37-2.25 (m, 2H), 1.48 (s, 9H); 526.25 [M + H]⁺ |
| 187 | 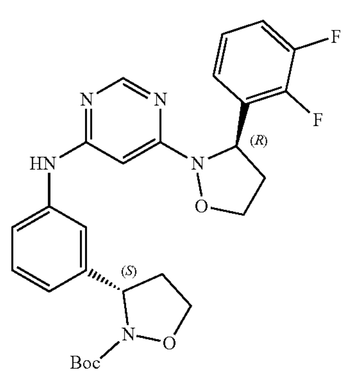 | tert-butyl (S)-3-(3-((6-((R)-3-(2,3-difluorophenyl)isoxazolidin-2-yl)pyrimidin-4-yl)amino)phenyl)isoxazolidin-2-carboxylate | ¹H NMR (400 MHz, Chloroform-d) δ 8.29 (d, J = 1.0 Hz, 1H), 7.36 (t, J = 7.8 Hz, 1H), 7.32 (p, J = 2.7 Hz, 2H), 7.26-7.22 (m, 2H), 7.16-7.12 (m, 1H), 7.06 (qt, J = 8.4, 5.8 Hz, 2H), 6.60 (d, J = 1.0 Hz, 1H), 5.91 (dd, J = 8.8, 4.8 Hz, 1H), 5.24 (dd, J = 8.7, 5.3 Hz, 1H), 4.18 (dt, J = 7.9, 4.0 Hz, 1H), 4.12 (td, J = 8.0, 4.2 Hz, 1H), 3.95-3.85 (m, 2H), 2.89-2.75 (m, 2H), 2.38-2.26 (m, 2H), 1.47 (s, 9H); 526.20 [M + H]⁺ |

TABLE 1-continued

| Example Compound | Compound Name | ¹H NMR; MS [M + H]⁺ |
|---|---|---|
| 188 | (R)-N-(6-(3-(2,3-difluorophenyl)isoxazolidin-2-yl)pyrimidin-4-yl)cyclopropanecarboxamide | ¹H NMR (400 MHz, Chloroform-d) δ 8.38 (d, J = 1.1 Hz, 1H), 8.26 (s, 1H), 7.91 (d, J = 1.1 Hz, 1H), 7.31-7.27 (m, 1H), 7.12-6.98 (m, 2H), 5.86 (dd, J = 8.8, 5.1 Hz, 1H), 4.18 (td, J = 7.9, 3.9 Hz, 1H), 3.93 (td, J = 8.4, 7.3 Hz, 1H), 2.92-2.83 (m, 1H), 2.38-2.28 (m, 1H), 1.55 (dt, J = 7.8, 4.7 Hz, 1H), 1.18-1.10 (m, 2H), 0.97-0.90 (m, 2H); 347.19 [M + H]⁺ |
| 189 | (R)-N-(6-(3-(2,3-difluorophenyl)isoxazolidin-2-yl)pyrimidin-4-yl)benzamide | ¹H NMR (400 MHz, Chloroform-d) δ 8.51 (s, 1H), 8.42 (d, J = 1.1 Hz, 1H), 8.12 (d, J = 1.1 Hz, 1H), 7.95-7.90 (m, 2H), 7.64-7.59 (m, 1H), 7.56-7.50 (m, 2H), 7.34-7.29 (m, 1H), 7.13-7.03 (m, 2H), 5.91 (dd, J = 8.8, 5.1 Hz, 1H), 4.24 (td, J = 8.0, 4.0 Hz, 1H), 3.99 (td, J = 8.4, 7.4 Hz, 1H), 2.96-2.85 (m, 1H), 2.43-2.32 (m, 1H); 383.20 [M + H]⁺ |
| 190 | (R)-N-(cyclopentylmethyl)-6-(3-(2,3-difluorophenyl)isoxazolidin-2-yl)pyrimidin-4-amine | ¹H NMR (400 MHz, Chloroform-d) δ 8.19 (s, 1H), 7.34 (qd, J = 4.8, 1.9 Hz, 1H), 7.12-6.97 (m, 2H), 6.13 (d, J = 1.0 Hz, 1H), 5.92 (dd, J = 8.8, 4.7 Hz, 1H), 5.00-4.84 (m, 1H), 4.14 (ddd, J = 8.3, 7.5, 4.3 Hz, 1H), 3.93 (q, J = 8.0 Hz, 1H), 3.19 (s, 2H), 2.88-2.79 (m, 1H), 2.32 (tdd, J = 12.5, 6.5, 3.0 Hz, 1H), 2.16 (hept, J = 7.6 Hz, 1H), 1.89-1.77 (m, 2H), 1.71-1.59 (m, 3H), 1.32-1.20 (m, 3H); 361.22 [M + H]⁺ |
| 191 | (R)-6-(3-(2,3-difluorophenyl)isoxazolidin-2-yl)-N-(4-fluorobenzyl)pyrimidin-4-amine | ¹H NMR (400 MHz, Chloroform-d) δ 8.24 (d, J = 1.0 Hz, 1H), 7.35-7.28 (m, 3H), 7.08-7.00 (m, 4H), 6.14 (d, J = 1.1 Hz, 1H), 5.89 (dd, J = 8.8, 4.7 Hz, 1H), 5.21 (s, 1H), 4.50 (d, J = 5.9 Hz, 2H), 4.10 (tt, J = 7.8, 3.5 Hz, 1H), 3.84 (q, J = 7.9 Hz, 1H), 2.87-2.76 (m, 1H), 2.36-2.24 (m, 1H); 387.17 [M + H]⁺ |
| 192 | (R)-6-(3-(2,3-difluorophenyl)isoxazolidin-2-yl)-N-(1-(methylsulfonyl)piperidin-4-yl)pyrimidin-4-amine | ¹H NMR (400 MHz, Chloroform-d) δ 8.22 (s, 1H), 7.36-7.27 (m, 1H), 7.12-6.99 (m, 3H), 6.13 (d, J = 1.0 Hz, 1H), 5.89 (dd, J = 8.8, 4.8 Hz, 1H), 4.14 (td, J = 7.9, 4.4 Hz, 1H), 3.92 (q, J = 7.9 Hz, 1H), 3.77 (d, J = 12.8 Hz, 2H), 2.94 (t, J = 12.0 Hz, 2H), 2.88-2.78 (m, 5H), 2.37-2.27 (m, 1H), 2.21-2.11 (m, 2H), 1.68-1.61 (m, 2H); 440.21 [M + H]⁺ |

TABLE 1-continued

| Example Compound | Structure | Compound Name | ¹H NMR; MS [M + H]⁺ |
|---|---|---|---|
| 193 | 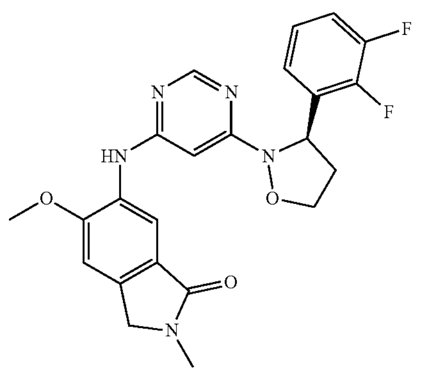 [SMILES: COc1cc2c(cc1Nc1cc(N3OCC[C@@H]3c3cccc(F)c3F)ncn1)C(=O)N(C)C2] | (R)-6-((6-(3-(2,3-difluorophenyl)isoxazolidin-2-yl)pyrimidin-4-yl)amino)-5-methoxy-2-methylisoindolin-1-one | ¹H NMR (400 MHz, Chloroform-d) δ 8.38 (d, J = 1.0 Hz, 1H), 8.37 (s, 1H), 7.35-7.27 (m, 2H), 7.12-7.02 (m, 2H), 6.97 (s, 1H), 6.58 (d, J = 1.0 Hz, 1H), 5.92 (dd, J = 8.9, 4.8 Hz, 1H), 4.33 (s, 2H), 4.13 (ddd, J = 8.3, 7.5, 4.2 Hz, 1H), 3.96 (s, 3H), 3.92 (q, J = 8.0 Hz, 1H), 3.20 (s, 3H), 2.89-2.79 (m, 1H), 2.37-2.26 (m, 1H); 454.13 [M + H]⁺ |
| 194 | 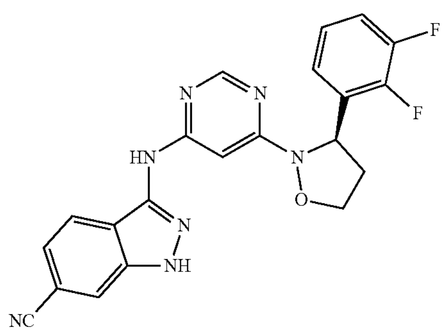 [SMILES: N#Cc1ccc2c(Nc3cc(N4OCC[C@@H]4c4cccc(F)c4F)ncn3)n[nH]c2c1] | (R)-3-((6-(3-(2,3-difluorophenyl)isoxazolidin-2-yl)pyrimidin-4-yl)amino)-1H-indazol-6-carbonitrile | ¹H NMR (400 MHz, Chloroform-d) δ 9.26 (t, J = 1.1 Hz, 1H), 8.59 (d, J = 1.0 Hz, 1H), 7.65 (dd, J = 8.2, 0.8 Hz, 1H), 7.49 (d, J = 1.1 Hz, 1H), 7.46 (dd, J = 8.2, 1.3 Hz, 1H), 7.33 (td, J = 7.0, 6.2, 3.7 Hz, 1H), 7.15-6.98 (m, 2H), 5.95 (dd, J = 8.8, 5.1 Hz, 1H), 4.48 (s, 2H), 4.25 (td, J = 7.9, 4.0 Hz, 1H), 4.00 (q, J = 8.2 Hz, 1H), 2.97-2.87 (m, 1H), 2.45-2.33 (m, 1H); 420.15 [M + H]⁺ |
| 195 | 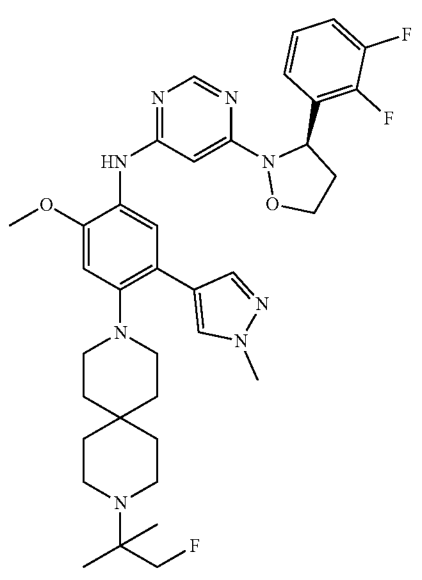 [SMILES: COc1cc(N2CCC3(CC2)CCN(C(C)(C)CF)CC3)c(-c2cnn(C)c2)cc1Nc1cc(N2OCC[C@@H]2c2cccc(F)c2F)ncn1] | (R)-6-(3-(2,3-difluorophenyl)isoxazolidin-2-yl)-N-(4-(9-(1-(fluoro-2-methylpropan-2-yl)-3,9-diazaspiro[5.5]undecan-3-yl)-2-methoxy-5-(1-methyl-1H-pyrazol-4-yl)phenyl)pyrimidin-4-amine | ¹H NMR (400 MHz, DMSO-d6) δ 8.60 (s, 1H), 8.15 (d, J = 1.0 Hz, 1H), 8.05 (s, 1H), 7.85 (s, 1H), 7.57 (s, 1H), 7.35 (q, J = 8.7 Hz, 2H), 7.27 (q, J = 6.8, 6.2 Hz, 2H), 7.20 (dd, J = 8.3, 5.2 Hz, 1H), 6.84 (s, 1H), 6.28 (s, 1H), 4.16 (td, J = 8.0, 3.8 Hz, 1H), 3.94 (q, J = 8.0 Hz, 1H), 3.85 (s, 3H), 3.81 (s, 3H), 2.80 (t, J = 5.7 Hz, 4H), 2.45 (d, J = 6.5 Hz, 4H), 2.38 (s, 1H), 2.21 (tt, J = 8.7, 4.3 Hz, 2H), 1.91 (s, 2H), 1.53 (s, 8H), 1.32 (s, 3H), 1.27 (s, 3H); 691.3 [M + H]⁺ |

TABLE 1-continued

| Example Compound | Structure | Compound Name | ¹H NMR; MS [M + H]⁺ |
|---|---|---|---|
| 196 | 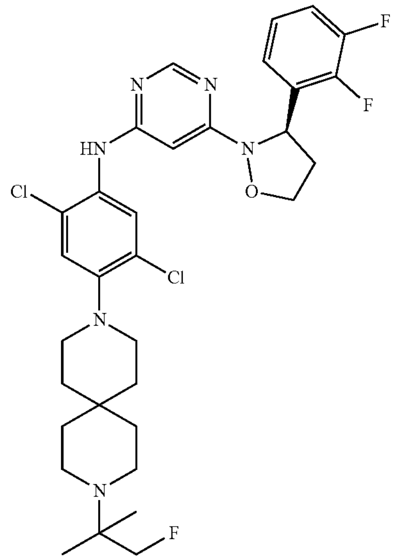 [SMILES: CC(C)(CF)N1CCC2(CCN(c3cc(Cl)c(Nc4cc(N5OCC[C@@H]5c5cccc(F)c5F)ncn4)cc3Cl)CC2)CC1] | (R)-N-(2,5-dichloro-4-(9-(1-fluoro-2-methylpropan-2-yl)-3,9-diazaspiro[5.5]undecan-3-yl)phenyl)-6-(3-(2,3-difluorophenyl)isoxazolidin-2-yl)pyrimidin-4-amine | 649.3 [M + H]⁺ |
| 197 | 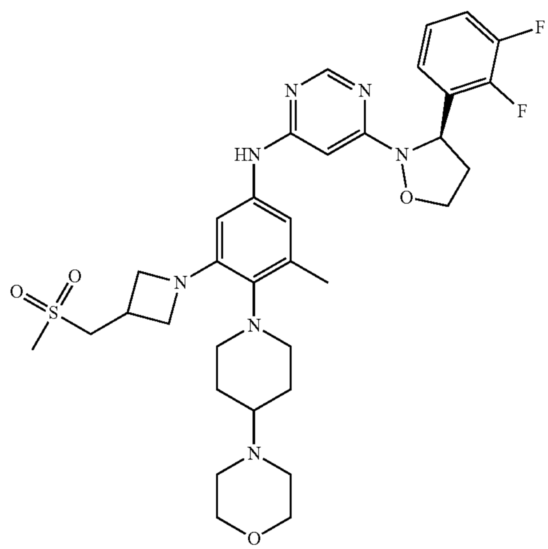 [SMILES: Cc1cc(Nc2cc(N3OCC[C@@H]3c3cccc(F)c3F)ncn2)cc(N2CC(CS(C)(=O)=O)C2)c1N1CCC(N2CCOCC2)CC1] | (R)-6-(3-(2,3-difluorophenyl)isoxazolidin-2-yl)-N-(3-methyl-5-(3-((methylsulfonyl)methyl)azetidin-1-yl)-4-(4-morpholinopiperidin-1-yl)phenyl)pyrimidin-4-amine | 684.3 [M + H]⁺ |
| 198 | 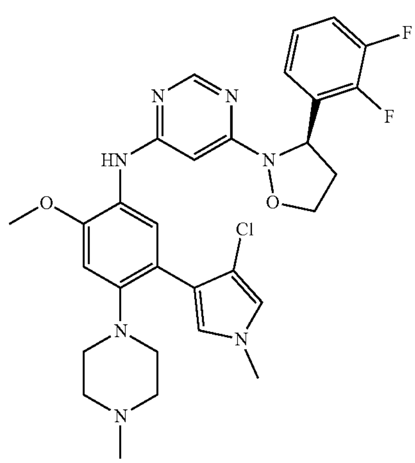 [SMILES: COc1cc(N2CCN(C)CC2)c(-c2cn(C)cc2Cl)cc1Nc1cc(N2OCC[C@@H]2c2cccc(F)c2F)ncn1] | (R)-N-(5-(3-chloro-1-methyl-1H-pyrazol-4-yl)-2-methoxy-4-(4-methylpiperazin-1-yl)phenyl)-6-(3-(2,3-difluorophenyl)isoxazolidin-2-yl)pyrimidin-4-amine | 597.3 [M + H]⁺ |

TABLE 1-continued

| Example Compound | Structure | Compound Name | ¹H NMR; MS [M + H]⁺ |
|---|---|---|---|
| 199 | 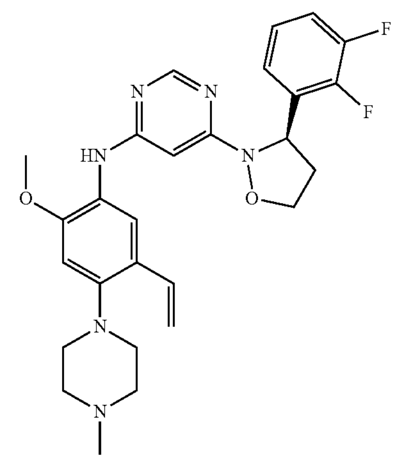 [SMILES: C=Cc1cc(Nc2cc(N3OCC[C@@H]3c3cccc(F)c3F)ncn2)c(OC)cc1N1CCN(C)CC1] | (R)-6-(3-(2,3-difluorophenyl)isoxazolidin-2-yl)-N-(2-methoxy-4-(4-methylpiperazin-1-yl)-5-vinylphenyl)pyrimidin-4-amine | ¹H NMR (400 MHz, DMSO-d6) δ 8.62 (s, 1H), 8.17 (d, J = 1.0 Hz, 1H), 7.76 (s, 1H), 7.39-7.30 (m, 2H), 6.90 (dd, J = 17.8, 11.0 Hz, 1H), 6.73 (s, 1H), 6.32 (s, 1H), 5.75 (dd, J = 8.9, 5.1 Hz, 1H), 5.57 (dd, J = 17.7, 1.6 Hz, 1H), 5.15 (dd, J = 10.9, 1.5 Hz, 1H), 4.17 (td, J = 8.0, 3.8 Hz, 2H), 3.82 (s, 3H), 2.94 (s, 4H), 2.86-2.76 (m, 2H), 2.59 (s, 2H), 2.32 (s, 3H), 2.26-2.16 (m, 3H), 1.91 (s, 2H); 509.3 [M + H]⁺ |
| 200 | 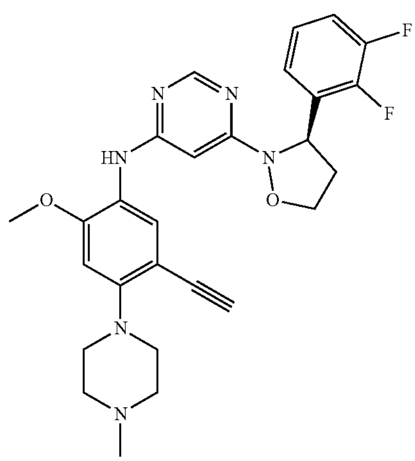 [SMILES: C#Cc1cc(Nc2cc(N3OCC[C@@H]3c3cccc(F)c3F)ncn2)c(OC)cc1N1CCN(C)CC1] | (R)-6-(3-(2,3-difluorophenyl)isoxazolidin-2-yl)-N-(5-ethynyl-2-methoxy-4-(4-methylpiperazine)-1-yl)phenyl)pyrimidin-4-amine | ¹H NMR (400 MHz, DMSO-d6) δ 8.64 (d, J = 1.2 Hz, 1H), 7.38 (dtd, J = 10.3, 8.0, 1.9 Hz, 2H), 7.28 (t, J = 6.9 Hz, 1H), 7.23 (dd, J = 8.1, 5.1 Hz, 1H), 7.14 (d, J = 1.2 Hz, 1H), 6.80 (s, 1H), 6.56 (s, 1H), 5.74 (dd, J = 8.8, 5.8 Hz, 1H), 4.31 (td, J = 7.8, 3.2 Hz, 1H), 3.94 (q, J = 8.0 Hz, 1H), 3.83 (s, 3H), 3.06 (s, 4H), 2.98-2.89 (m, 2H), 2.53 (d, J = 5.5 Hz, 2H), 2.25 (s, 3H), 1.91 (s, 4H); 507.3 [M + H]⁺ |
| 201 | 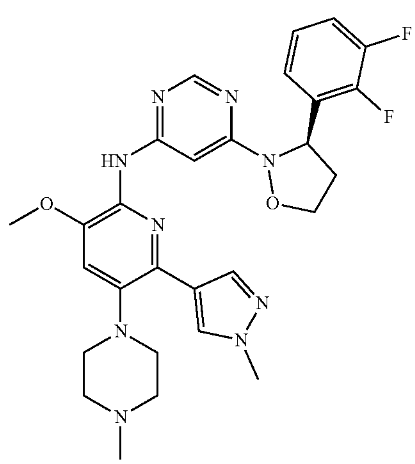 [SMILES: COc1cc(N2CCN(C)CC2)c(-c2cnn(C)c2)nc1Nc1cc(N2OCC[C@@H]2c2cccc(F)c2F)ncn1] | (R)-6-(3-(2,3-difluorophenyl)isoxazolidin-2-yl)-N-(3-methoxy-6-(1-methyl-1H-pyrazol-4-yl)-5-(4-methylpiperazin-1-yl)pyridin-2-yl)pyrimidin-4-amine | ¹H NMR (400 MHz, DMSO-d6) δ 8.31 (t, J = 1.3 Hz, 2H), 8.29 (d, J = 1.1 Hz, 1H), 8.22 (s, 1H), 8.17 (s, 1H), 7.41-7.35 (m, 1H), 7.34-7.31 (m, 1H), 7.25-7.19 (m, 1H), 5.80 (dd, J = 8.7, 5.4 Hz, 1H), 4.01 (q, J = 7.9 Hz, 1H), 3.94 (s, 3H), 3.93 (s, 3H), 2.97-2.93 (m, 4H), 2.89 (dd, J = 12.3, 3.9 Hz, 2H), 2.74 (s, 2H), 2.42 (s, 3H), 2.35-2.26 (m, 2H), 1.91 (s, 2H); 564.3 [M + H]⁺ |

TABLE 1-continued

| Example Compound | Structure | Compound Name | ¹H NMR; MS [M + H]⁺ |
|---|---|---|---|
| 202 | 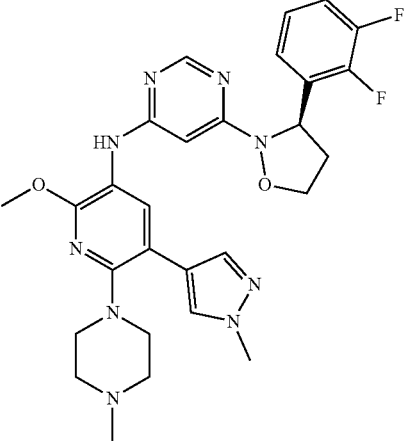 [SMILES: COc1nc(N2CCN(C)CC2)c(-c2cnn(C)c2)cc1Nc1cc(N2OCC[C@@H]2c2cccc(F)c2F)ncn1] | (R)-6-(3-(2,3-difluorophenyl)isoxazolidin-2-yl)-N-(2-methoxy-5-(1-methyl-1H-pyrazol-4-yl)-6-(4-methylpiperazin-1-yl)pyridin-3-yl)pyrimidin-4-amine | ¹H NMR (400 MHz, DMSO-d6) δ 8.76 (s, 1H), 8.18 (d, J = 1.0 Hz, 1H), 8.04 (s, 1H), 7.83 (s, 1H), 7.39-7.31 (m, 2H), 7.28 (d, J = 6.8 Hz, 1H), 7.23-7.19 (m, 1H), 6.42 (s, 1H), 5.75 (dd, J = 8.8, 5.1 Hz, 1H), 4.20 (td, J = 7.9, 3.7 Hz, 1H), 3.90 (s, 3H), 3.87 (s, 3H), 3.15 (s, 5H), 2.81 (dtd, J = 12.0, 8.1, 3.7 Hz, 4H), 2.27-2.16 (m, 2H), 1.91 (s, 3H); 564.3 [M + H]⁺ |
| 203 | 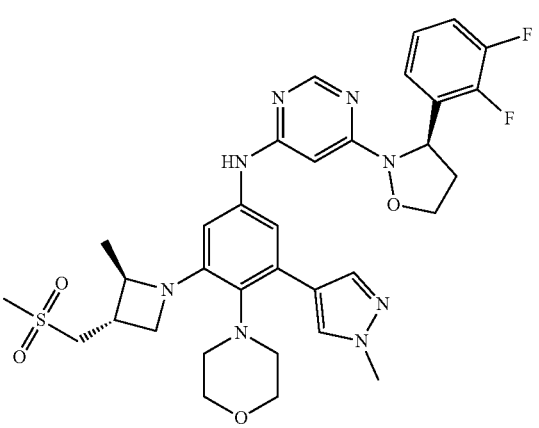 [SMILES: C[C@@H]1[C@@H](CS(C)(=O)=O)CN1c1cc(Nc2cc(N3OCC[C@@H]3c3cccc(F)c3F)ncn2)cc(-c2cnn(C)c2)c1N1CCOCC1] | 6-((R)-3-(2,3-difluorophenyl)isoxazolidin-2-yl)-N-(3-(1-methyl-1H-pyrazol-4-yl)-5-((2R,3S)-2-methyl-3-((methylsulfonyl)methyl)azetidin-1-yl)-4-morpholinophenyl)pyrimidin-4-amine | ¹H NMR (400 MHz, DMSO-d6) δ 9.30 (s, 1H), 8.23 (d, J = 0.9 Hz, 1H), 7.72 (s, 1H), 7.40 (s, 1H), 7.29 (d, J = 7.0 Hz, 1H), 7.23-7.19 (m, 2H), 6.87 (s, 1H), 6.81 (d, J = 2.5 Hz, 1H), 6.49 (d, J = 1.0 Hz, 1H), 4.60 (t, J = 7.8 Hz, 1H), 4.22 (d, J = 3.8 Hz, 1H), 3.89 (s, 3H), 2.99 (s, 4H), 2.74-2.70 (m, 2H), 2.68-2.66 (m, 1H), 2.33 (t, J = 1.9 Hz, 1H), 2.26-2.19 (m, 3H), 1.78 (s, 6H), 1.38 (d, J = 6.0 Hz, 3H), 1.24 (s, 3H); 681.3 [M + H]⁺ |
| 204 | 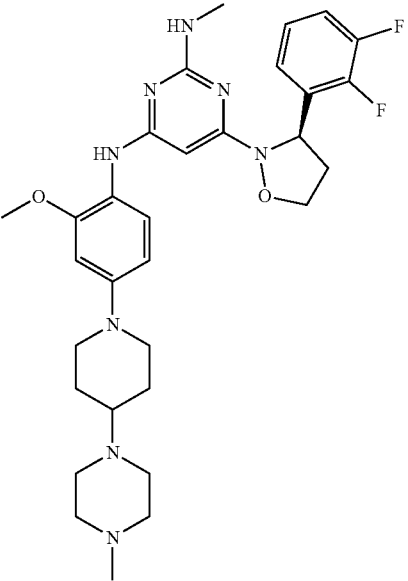 [SMILES: CNc1nc(Nc2ccc(N3CCC(N4CCN(C)CC4)CC3)cc2OC)cc(N2OCC[C@@H]2c2cccc(F)c2F)n1] | (R)-6-(3-(2,3-difluorophenyl)isoxazolidin-2-yl)-N4-(2-methoxy-4-(4-(4-methylpiperazin-1-yl)piperidin-1-yl)phenyl)-N2-methylpyrimidin-2,4-diamine | 595.3 [M + H]⁺ |

TABLE 1-continued

| Example Compound | Structure | Compound Name | ¹H NMR; MS [M + H]⁺ |
|---|---|---|---|
| 205 | 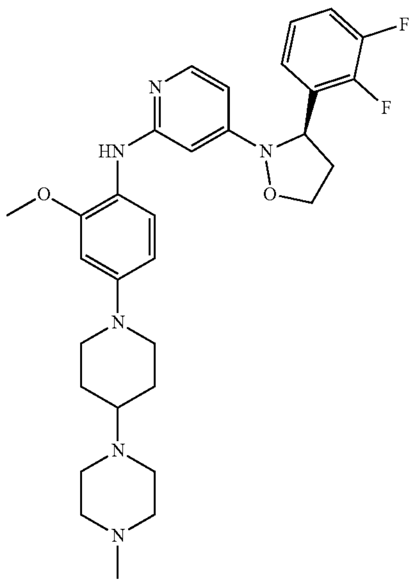 [SMILES: COc1cc(N2CCC(N3CCN(C)CC3)CC2)ccc1Nc1cc(N2OCC[C@@H]2c2cccc(F)c2F)ccn1] | (R)-4-(3-(2,3-difluorophenyl)isoxazolidin-2-yl)-N-(2-methoxy-4-(4-(4-methylpiperazin-1-yl)piperidin-1-yl)phenyl)pyridin-2-amine | 565.3 [M + H]⁺ |
| 206 | 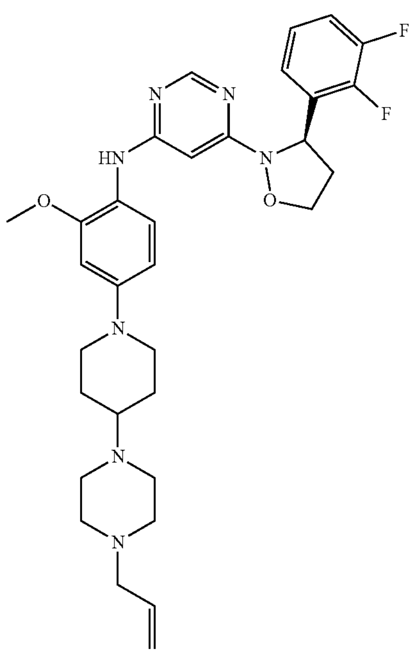 [SMILES: C=CCN1CCN(C2CCN(c3ccc(Nc4cc(N5OCC[C@@H]5c5cccc(F)c5F)ncn4)c(OC)c3)CC2)CC1] | (R)-N-(4-(4-(4-allylpiperazin-1-yl)piperidin-1-yl)-2-methoxyphenyl)-6-(3-(2,3-difluorophenyl)isoxazolidin-2-yl)pyrimidin-4-amine | ¹H NMR (400 MHz, Chloroform-d) δ 8.31 (s, 1H), 7.58 (d, J = 8.7 Hz, 1H), 7.36-7.29 (m, 1H), 7.11-6.98 (m, 2H), 6.79 (s, 1H), 6.59-6.48 (m, 2H), 6.44 (d, J = 1.0 Hz, 1H), 5.91 (dd, J = 8.8, 4.7 Hz, 1H), 5.30 (d, J = 12.9 Hz, 2H), 4.10 (td, J = 7.9, 4.2 Hz, 1H), 3.92-3.82 (m, 4H), 3.73 (d, J = 12.2 Hz, 2H), 3.32-2.69 (m, 13H), 2.35-2.25 (m, 1H), 2.22-1.63 (m, 6H); 592.4 [M + H]⁺ |

TABLE 1-continued

| Example Compound | Structure | Compound Name | $^1$H NMR; MS [M + H]$^+$ |
|---|---|---|---|
| 207 | 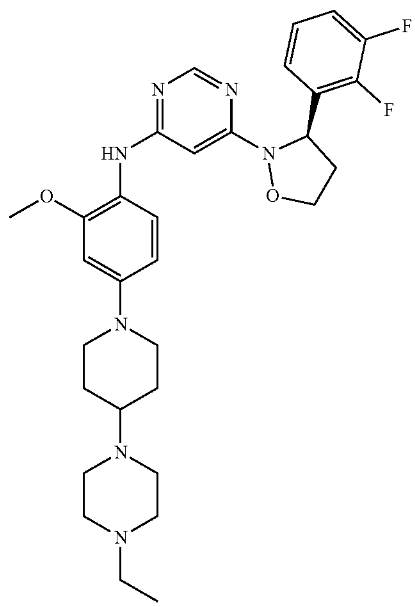 [SMILES: CCN1CCN(C2CCN(c3ccc(Nc4cc(N5OCC[C@@H]5c5cccc(F)c5F)ncn4)c(OC)c3)CC2)CC1] | (R)-6-(3-(2,3-difluorophenyl)isoxazolidin-2-yl)-N-(4-(4-(4-ethylpiperazin-1-yl)piperidin-1-yl)-2-methoxyphenyl)pyrimidin-4-amine | $^1$H NMR (400 MHz, Chloroform-d) δ 8.31 (s, 1H), 7.56 (d, J = 9.1 Hz, 1H), 7.36-7.29 (m, 1H), 7.11-6.99 (m, 2H), 6.76 (s, 1H), 6.54 (dq, J = 5.9, 2.6 Hz, 2H), 6.43 (d, J = 1.0 Hz, 1H), 5.91 (dd, J = 8.9, 4.7 Hz, 1H), 4.10 (td, J = 7.9, 4.2 Hz, 1H), 3.91-3.82 (m, 4H), 3.71 (d, J = 12.3 Hz, 2H), 2.99 (s, 6H), 2.89-2.69 (m, 6H), 2.62-2.49 (m, 1H), 2.30 (dtd, J = 12.7, 8.2, 4.6 Hz, 1H), 2.06-1.93 (m, 2H), 1.79-1.66 (m, 2H), 1.44-1.23 (m, 4H); 580.43 [M + H]$^+$ |
| 208 | 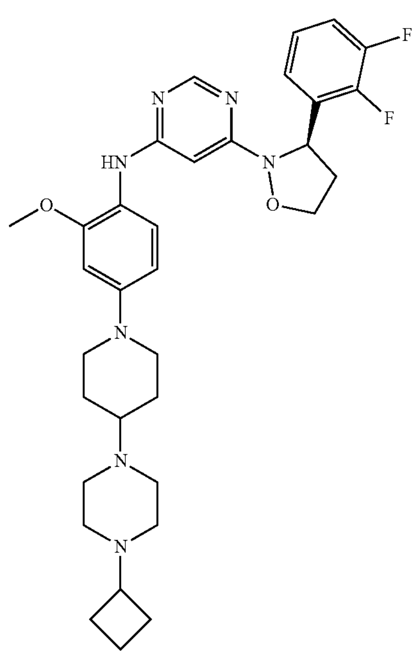 [SMILES: COc1cc(N2CCC(N3CCN(C4CCC4)CC3)CC2)ccc1Nc1cc(N2OCC[C@@H]2c2cccc(F)c2F)ncn1] | (R)-N-(4-(4-(4-cyclobutylpiperazin-1-yl)piperidin-1-yl)-2-methoxyphenyl)-6-(3-(2,3-difluorophenyl)isoxazolidin-2-yl)pyrimidin-4-amine | $^1$H NMR (400 MHz, Methanol-d$_4$) δ 8.11 (d, J = 1.0 Hz, 1H), 7.36-7.30 (m, 2H), 7.16 (dddd, J = 16.0, 12.9, 8.6, 7.1 Hz, 2H), 6.71 (d, J = 2.6 Hz, 1H), 6.62 (dd, J = 8.7, 2.5 Hz, 1H), 6.27 (d, J = 1.1 Hz, 1H), 5.79 (dd, J = 8.8, 4.8 Hz, 1H), 4.14 (td, J = 7.9, 4.1 Hz, 1H), 3.92 (q, J = 8.0 Hz, 1H), 3.85 (s, 3H), 3.81 (d, J = 12.3 Hz, 2H), 3.02 (p, J = 8.2 Hz, 1H), 2.92-2.74 (m, 7H), 2.64 (s, 2H), 2.59-2.51 (m, 2H), 2.33-2.22 (m, 1H), 2.20-2.09 (m, 2H), 2.08-1.97 (m, 4H), 1.83-1.64 (m, 5H); 606.42 [M + H]$^+$ |

TABLE 1-continued

| Example Compound | Structure | Compound Name | ¹H NMR; MS [M + H]⁺ |
|---|---|---|---|
| 209 | 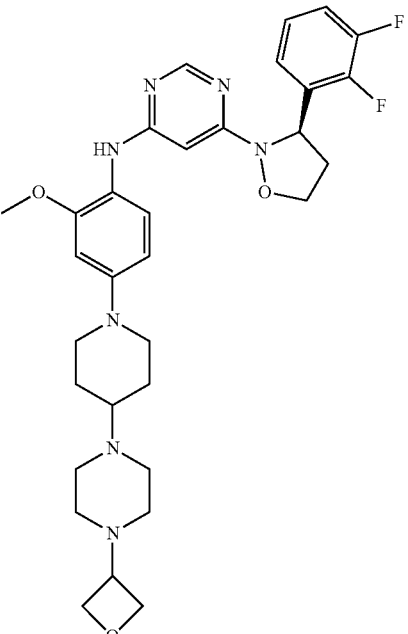 | (R)-6-(3-(2,3-difluorophenyl)isoxazolidin-2-yl)-N-(2-methoxy-4-(4-(4-(oxetan-3-yl)piperazin-1-yl)piperidin-1-yl)phenyl)pyrimidin-4-amine | ¹H NMR (400 MHz, Chloroform-d) δ 8.30 (s, 1H), 7.54 (d, J = 8.9, Hz, 1H), 7.35-7.31 (m, 1H), 7.11-6.99 (m, 2H), 6.76 (s, 1H), 6.58-6.52 (m, 2H), 6.46-6.40 (m, 1H), 5.91 (dd, J = 8.8, 4.7 Hz, 1H), 4.68 (t, J = 6.6 Hz, 2H), 4.62 (t, J = 6.1 Hz, 2H), 4.09 (td, J = 7.9, 4.2 Hz, 1H), 3.91-3.83 (m, 4H), 3.72 (d, J = 12.2 Hz, 2H), 3.53 (t, J = 6.5 Hz, 1H), 2.87-2.63 (m, 7H), 2.45 (s, 4H), 2.30 (dtd, J = 12.6, 8.0, 4.7 Hz, 2H), 2.03-1.92 (m, 2H), 1.80-1.69 (m, 2H); 608.37 [M + H]⁺ |
| 210 | 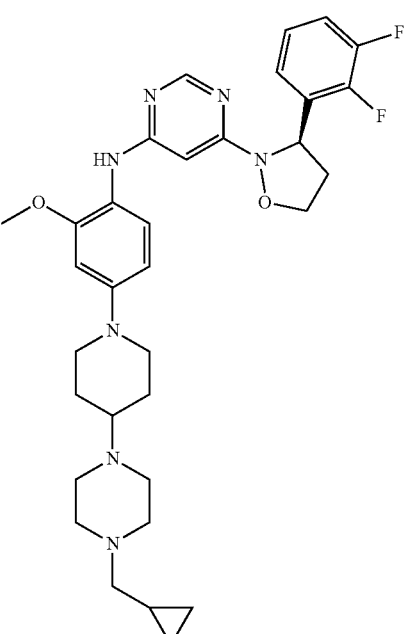 | (R)-N-(4-(4-(4-(cyclopropylmethyl)piperazin-1-yl)piperidin-1-yl)-2-methoxyphenyl)-6-(3-(2,3-difluorophenyl)isoxazolidin-2-yl)pyrimidin-4-amine | ¹H NMR (400 MHz, Chloroform-d) δ 8.30 (s, 1H), 7.55 (d, J = 9.1 Hz, 1H), 7.35-7.30 (m, 1H), 7.10-6.99 (m, 2H), 6.80 (s, 1H), 6.57-6.51 (m, 2H), 6.43 (s, 1H), 5.91 (dd, J = 8.9, 4.7 Hz, 1H), 4.10 (td, J = 7.9, 4.2 Hz, 1H), 3.92-3.80 (m, 4H), 3.71 (d, J = 12.0 Hz, 2H), 3.01 (s, 6H), 2.86-2.49 (m, 8H), 2.31 (ddd, J = 15.3, 8.0, 4.2 Hz, 1H), 2.07-1.95 (m, 2H), 1.80-1.68 (m, 2H), 1.14 (s, 1H), 0.68 (s, 2H), 0.30 (s, 2H); 606.33 [M + H]⁺ |

TABLE 1-continued

| Example Compound | Structure | Compound Name | ¹H NMR; MS [M + H]⁺ |
|---|---|---|---|
| 211 | 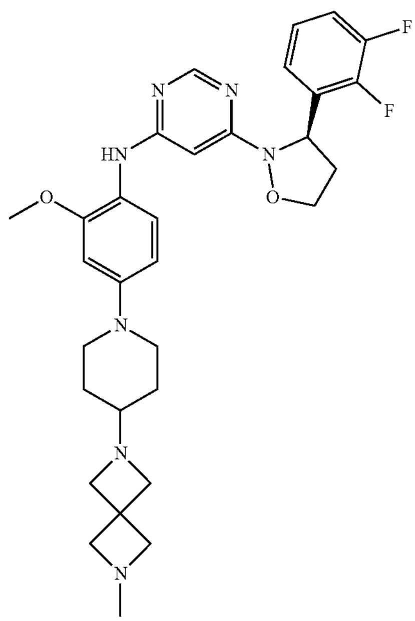 [SMILES: COc1cc(N2CCC(N3CC4(CN(C)C4)C3)CC2)ccc1Nc1cc(N2OCC[C@@H]2c2cccc(F)c2F)ncn1] | (R)-6-(3-(2,3-difluorophenyl)isoxazolidin-2-yl)-N-(2-methoxy-4-(4-(6-methyl-2,6-diazaspiro[3.3]heptan-2-yl)piperidin-1-yl)phenyl)pyrimidin-4-amine | ¹H NMR (400 MHz, Chloroform-d) δ 8.28 (s, 1H), 7.47 (d, J = 8.3 Hz, 1H), 7.32 (t, J = 7.2 Hz, 1H), 7.12-6.99 (m, 2H), 6.93 (s, 1H), 6.57-6.48 (m, 2H), 6.44-6.37 (m, 1H), 5.90 (dd, J = 8.8, 4.7 Hz, 1H), 4.09 (td, J = 7.9, 4.1 Hz, 1H), 3.92-3.86 (m, 1H), 3.84 (s, 3H), 3.68-3.64 (m, 2H), 3.07-2.88 (m, 5H), 2.84-2.67 (m, 4H), 2.31 (tt, J = 12.3, 8.0 Hz, 2H), 2.21-2.10 (m, 2H), 2.05 (s, 3H), 1.79 (d, J = 13.0 Hz, 2H), 1.52-1.41 (m, 2H); 578.4 [M + H]⁺ |
| 212 | 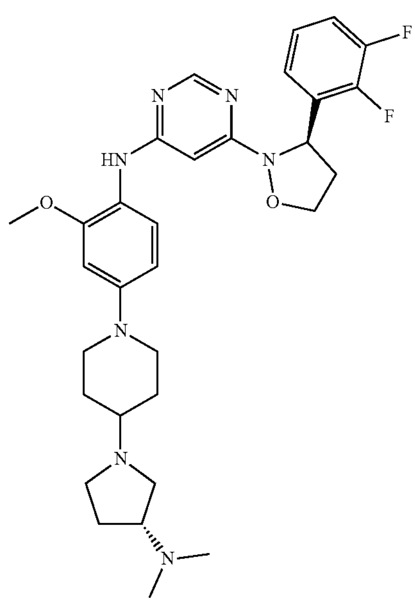 [SMILES: COc1cc(N2CCC(N3CC[C@@H](N(C)C)C3)CC2)ccc1Nc1cc(N2OCC[C@@H]2c2cccc(F)c2F)ncn1] | 6-((R)-3-(2,3-difluorophenyl)isoxazolidin-2-yl)-N-(4-(4-((R)-3-(dimethylamino)pyrrolidin-1-yl)piperidin-1-yl)-2-methoxyphenyl)pyrimidin-4-amine | ¹H NMR (400 MHz, Chloroform-d) δ 8.30 (s, 1H), 7.57 (d, J = 8.3 Hz, 1H), 7.34-7.30 (m, 1H), 7.12-7.01 (m, 2H), 6.84 (s, 1H), 6.57-6.50 (m, 2H), 6.43 (s, 1H), 5.91 (dd, J = 8.5, 4.5 Hz, 1H), 4.11 (td, J = 7.9, 4.1 Hz, 1H), 3.93-3.83 (m, 4H), 3.64 (d, J = 10.9 Hz, 2H), 3.15 (s, 2H), 2.86-2.74 (m, 4H), 2.63 (s, 6H), 2.30 (ddd, J = 16.3, 7.7, 4.0 Hz, 2H), 2.17-1.99 (m, 4H), 1.97-1.70 (m, 4H); 580.33 [M + H]⁺ |

TABLE 1-continued

| Example Compound | Structure | Compound Name | ¹H NMR; MS [M + H]⁺ |
|---|---|---|---|
| 213 | 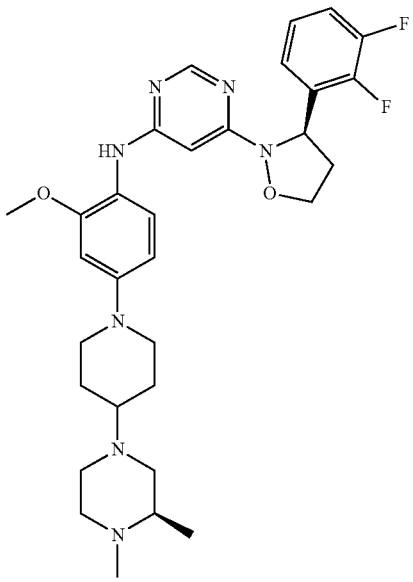 [SMILES: COc1cc(N2CCC(N3CCN(C)[C@H](C)C3)CC2)ccc1Nc1cc(N2OCC[C@@H]2c2cccc(F)c2F)ncn1] | 6-((R)-3-(2,3-difluorophenyl)isoxazolidin-2-yl)-N-(4-(4-((R)-3,4-dimethylpiperazin-1-yl)piperidin-1-yl)-2-methoxyphenyl)pyrimidin-4-amine | ¹H NMR (400 MHz, Methanol-$d_4$) δ 8.12 (s, 1H), 7.34-7.11 (m, 4H), 6.74 (s, 1H), 6.67 (s, 1H), 6.16 (s, 1H), 5.83-5.75 (m, 1H), 4.29 (td, J = 7.7, 4.0 Hz, 1H), 4.06 (q, J = 7.8 Hz, 1H), 3.85 (s, 4H), 3.46 (d, J = 15.1 Hz, 1H), 3.32-3.22 (m, 3H), 3.17-3.03 (m, 2H), 3.02-2.66 (m, 8H), 2.55-2.44 (m, 1H), 2.37 (td, J = 13.2, 7.6 Hz, 1H), 2.10-1.99 (m, 2H), 1.82-1.70 (m, 2H), 1.37 (d, J = 6.5 Hz, 3H); 580.38 [M + H]⁺ |
| 214 | 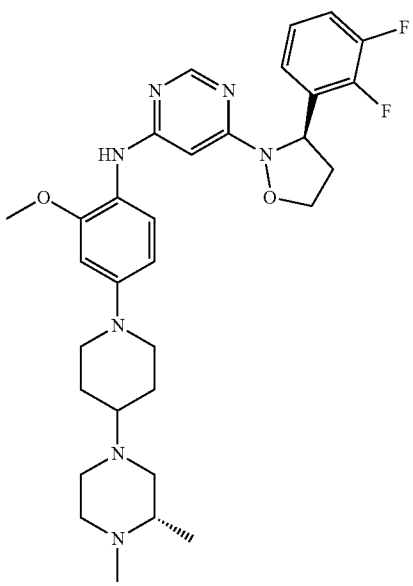 | 6-((R)-3-(2,3-difluorophenyl)isoxazolidin-2-yl)-N-(4-(4-((S)-3,4-dimethylpiperazin-1-yl)piperidin-1-yl)-2-methoxyphenyl)pyrimidin-4-amine | ¹H NMR (400 MHz, Methanol-$d_4$) δ 7.99 (d, J = 1.0 Hz, 1H), 7.24-7.18 (m, 2H), 7.11-6.97 (m, 2H), 6.59 (d, J = 2.5 Hz, 1H), 6.49 (dd, J = 8.7, 2.5 Hz, 1H), 6.15 (d, J = 1.0 Hz, 1H), 5.67 (dd, J = 8.8, 4.8 Hz, 1H), 4.02 (td, J = 7.9, 4.1 Hz, 1H), 3.80 (q, J = 8.0 Hz, 1H), 3.73 (s, 3H), 3.69 (d, J = 12.3 Hz, 2H), 2.98 (t, J = 12.9 Hz, 3H), 2.75 (dtd, J = 12.1, 8.0, 4.1 Hz, 1H), 2.71-2.61 (m, 2H), 2.60-2.38 (m, 7H), 2.21-2.10 (m, 2H), 1.92 (d, J = 12.4 Hz, 2H), 1.58 (q, J = 12.1, 11.4 Hz, 2H), 1.11 (d, J = 6.3 Hz, 3H); 580.38 [M + H]⁺ |

TABLE 1-continued

| Example Compound | Structure | Compound Name | ¹H NMR; MS [M + H]⁺ |
|---|---|---|---|
| 215 | 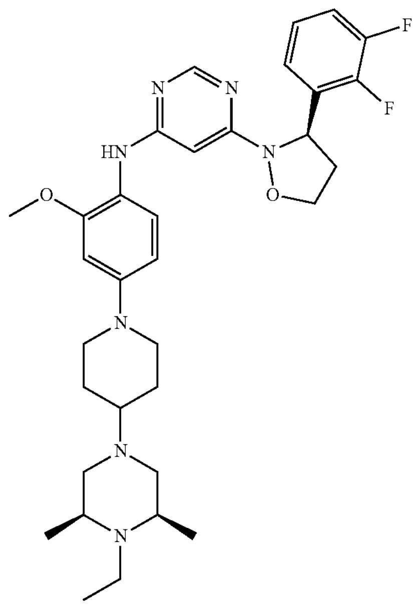 [SMILES: CCN1[C@H](C)CN(C2CCN(c3ccc(Nc4cc(N5OCC[C@@H]5c5cccc(F)c5F)ncn4)c(OC)c3)CC2)C[C@@H]1C] | 6-((R)-3-(2,3-difluorophenyl)isoxazolidin-2-yl)-N-(4-(4-((3S,5R)-4-ethyl-3,5-dimethylpiperazin-1-yl)piperidin-1-yl)-2-methoxyphenyl)pyrimidin-4-amine | ¹H NMR (400 MHz, Chloroform-d) δ 8.31 (s, 1H), 7.55 (d, J = 7.4 Hz, 1H), 7.35-7.30 (m, 1H), 7.10-7.01 (m, 2H), 6.72 (s, 1H), 6.54 (dd, J = 4.6, 2.3 Hz, 2H), 6.44 (s, 1H), 5.92 (dd, J = 8.8, 4.7 Hz, 1H), 4.10 (td, J = 7.9, 4.2 Hz, 1H), 3.92-3.80 (m, 4H), 3.70 (d, J = 11.9 Hz, 2H), 3.44-3.33 (m, 1H), 3.28-3.20 (m, 1H), 3.11-3.03 (m, 1H), 2.98-2.89 (m, 2H), 2.86-2.77 (m, 2H), 2.74 (t, J = 12.4 Hz, 2H), 2.54-2.43 (m, 1H), 2.37-2.25 (m, 2H), 1.97-1.89 (m, 2H), 1.71-1.64 (m, 2H), 1.61-1.44 (m, 10H); 608.41 [M + H]⁺ |
| 216 | 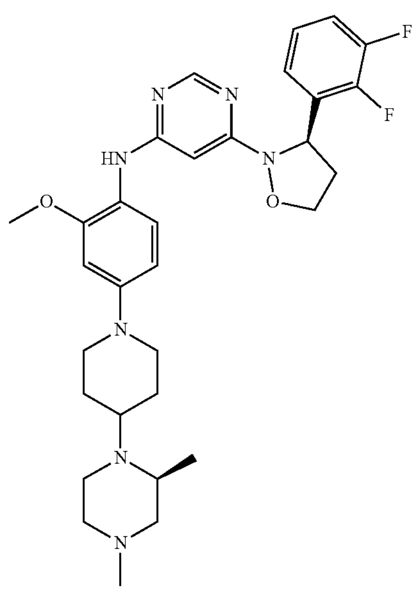 [SMILES: COc1cc(N2CCC(N3CCN(C)C[C@@H]3C)CC2)ccc1Nc1cc(N2OCC[C@@H]2c2cccc(F)c2F)ncn1] | 6-((R)-3-(2,3-difluorophenyl)isoxazolidin-2-yl)-N-(4-(4-((S)-2,4-dimethylpiperazin-1-yl)piperidin-1-yl)-2-methoxyphenyl)pyrimidin-4-amine | ¹H NMR (400 MHz, Chloroform-d) δ 8.30 (s, 1H), 7.59 (s, 1H), 7.31 (t, J = 7.1 Hz, 1H), 7.11-7.01 (m, 2H), 6.89 (s, 1H), 6.58-6.50 (m, 2H), 6.42 (s, 1H), 5.91 (dd, J = 8.8, 4.7 Hz, 1H), 4.11 (td, J = 7.9, 4.2 Hz, 1H), 3.90 (t, J = 8.0 Hz, 1H), 3.86 (s, 3H), 3.74 (d, J = 6.3 Hz, 2H), 3.46-3.36 (m, 1H), 3.11-2.94 (m, 3H), 2.91-2.65 (m, 6H), 2.36-2.26 (m, 1H), 1.99-1.79 (m, 3H), 1.75-1.46 (m, 6H), 1.31-1.12 (m, 2H); 580.43 [M + H]⁺ |

| Example Compound | Structure | Compound Name | ¹H NMR; MS [M + H]⁺ |
|---|---|---|---|
| 217 | 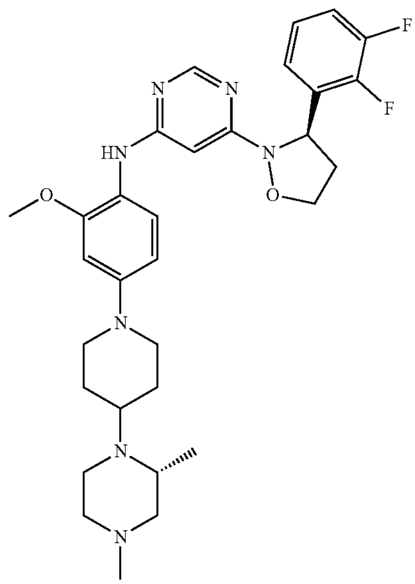 [SMILES: COc1cc(N2CCC(N3CCN(C)C[C@H]3C)CC2)ccc1Nc1cc(N2OCC[C@@H]2c2cccc(F)c2F)ncn1] | 6-((R)-3-(2,3-difluorophenyl)isoxazolidin-2-yl)-N-(4-(4-((R)-2,4-dimethylpiperazin-1-yl)piperidin-1-yl)-2-methoxyphenyl)pyrimidin-4-amine | ¹H NMR (400 MHz, Chloroform-d) δ 8.31 (s, 1H), 7.59 (s, 1H), 7.36-7.29 (m, 1H), 7.12-7.01 (m, 2H), 6.75 (s, 1H), 6.58-6.50 (m, 2H), 6.44 (s, 1H), 5.91 (dd, J = 8.8, 4.7 Hz, 1H), 4.14-4.05 (m, 1H), 3.89 (q, 1H), 3.86 (s, 3H), 3.73 (d, J = 14.1 Hz, 2H), 3.38-3.31 (m, 1H), 3.07-2.90 (m, 3H), 2.86-2.70 (m, 6H), 2.31 (ddt, J = 16.1, 7.7, 4.2 Hz, 1H), 1.93-1.81 (m, 3H), 1.73-1.50 (m, 6H), 1.32-1.26 (m, 1H), 1.18-1.12 (m, 1H); 580.38 [M + H]⁺ |
| 218 | 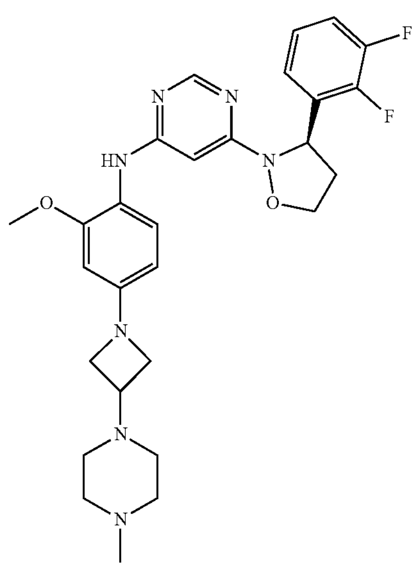 | (R)-6-(3-(2,3-difluorophenyl)isoxazolidin-2-yl)-N-(2-methoxy-4-(3-(4-methylpiperazin-1-yl)azetidin-1-yl)phenyl)pyrimidin-4-amine | ¹H NMR (400 MHz, Chloroform-d) δ 8.28 (s, 1H), 7.38 (d, J = 8.4 Hz, 1H), 7.36-7.30 (m, 1H), 7.12-6.99 (m, 2H), 6.62 (s, 1H), 6.33 (s, 1H), 6.07 (dd, J = 8.4, 2.4 Hz, 1H), 6.04 (d, J = 2.4 Hz, 1H), 5.90 (dd, J = 8.9, 4.7 Hz, 1H), 4.08 (td, J = 8.0, 4.2 Hz, 1H), 4.01 (t, J = 7.0 Hz, 2H), 3.91-3.84 (m, 1H), 3.82 (s, 3H), 3.72 (dd, J = 7.1, 5.4 Hz, 2H), 3.41 (p, J = 6.1 Hz, 1H), 2.89-2.55 (m, 9H), 2.46 (s, 3H), 2.29 (dtd, J = 12.6, 8.1, 4.8 Hz, 1H); 502.3 [M + H]⁺ |

| Example Compound | Structure | Compound Name | ¹H NMR; MS [M + H]⁺ |
|---|---|---|---|
| 219 | 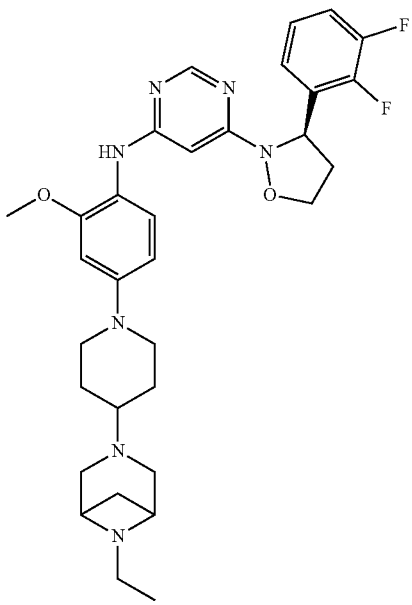 [SMILES: CCN1C2CC1CN(C1CCN(c3ccc(Nc4cc(N5OCC[C@@H]5c5cccc(F)c5F)ncn4)c(OC)c3)CC1)C2] | 6-((R)-3-(2,3-difluorophenyl)isoxazolidin-2-yl)-N-(4-(4-(6-ethyl-3,6-diazabicyclo[3.1.1]heptan-3-yl)piperidin-1-yl)-2-methoxyphenyl)pyrimidin-4-amine | ¹H NMR (400 MHz, Chloroform-d) δ 8.31 (d, J = 3.6 Hz, 1H), 7.64 (d, J = 8.6 Hz, 1H), 7.33 (d, J = 7.6 Hz, 1H), 7.12-6.99 (m, 2H), 6.86 (s, 1H), 6.55 (d, J = 5.0 Hz, 1H), 6.49 (d, J = 8.9 Hz, 1H), 6.44 (s, 1H), 5.94-5.87 (m, 1H), 4.10 (tt, J = 16.2, 12.4, 5.5 Hz, 2H), 3.94-3.87 (m, 2H), 3.85 (s, 3H), 3.76-3.53 (m, 4H), 3.44-3.32 (m, 1H), 3.30-3.16 (m, 1H), 2.97-2.77 (m, 4H), 2.74 (d, J = 11.2 Hz, 1H), 2.69-2.53 (m, 1H), 2.48 (d, J = 12.0 Hz, 1H), 2.30 (dtd, J = 20.7, 14.5, 12.9, 6.0 Hz, 2H), 2.19 (d, J = 13.2 Hz, 1H), 2.09-1.95 (m, 2H), 1.85-1.71 (m, 1H), 1.38 (t, J = 7.3 Hz, 3H); 592.4 [M + H]⁺ |
| 220 | 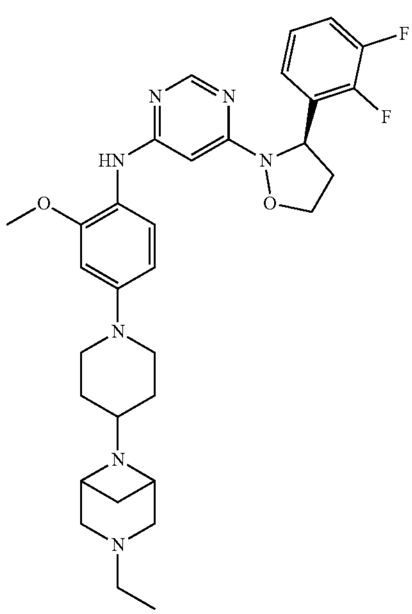 [SMILES: CCN1CC2CC(C1)N2C1CCN(c2ccc(Nc3cc(N4OCC[C@@H]4c4cccc(F)c4F)ncn3)c(OC)c2)CC1] | 6-((R)-3-(2,3-difluorophenyl)isoxazolidin-2-yl)-N-(4-(4-(3-ethyl-3,6-diazabicyclo[3.1.1]heptan-6-yl)piperidin-1-yl)-2-methoxyphenyl)pyrimidin-4-amine | ¹H NMR (400 MHz, Chloroform-d) δ 8.25 (s, 1H), 7.52 (s, 1H), 7.32 (t, J = 10.5 Hz, 1H), 7.07 (d, J = 6.3 Hz, 2H), 6.53 (s, 2H), 6.50 (d, J = 8.3 Hz, 1H), 6.32 (s, 1H), 5.89-5.84 (m, 1H), 4.30-4.10 (m, 4H), 3.94 (p, J = 8.0 Hz, 3H), 3.86-3.83 (m, 3H), 3.75-3.73 (m, 1H), 3.35-3.31 (m, 1H), 3.14-3.10 (m, 1H), 2.96-2.80 (m, 6H), 2.68-2.59 (m, 1H), 2.39-2.30 (m, 3H), 2.18 (d, J = 2.8 Hz, 1H), 2.05-1.95 (m, 2H), 1.41 (t, J = 8.5 Hz, 3H); 592.4 [M + H]⁺ |

TABLE 1-continued

| Example Compound | Structure | Compound Name | ¹H NMR; MS [M + H]⁺ |
|---|---|---|---|
| 221 | 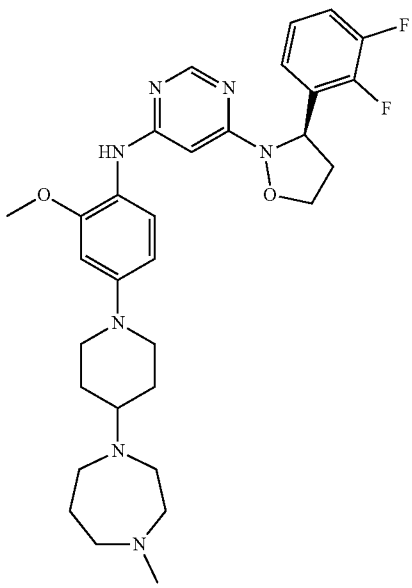 [SMILES: COc1cc(N2CCC(N3CCCN(C)CC3)CC2)ccc1Nc1cc(N2OCC[C@@H]2c2cccc(F)c2F)ncn1] | (R)-6-(3-(2,3-difluorophenyl)isoxazolidin-2-yl)-N-(2-methoxy-4-(4-(4-methyl-1,4-diazepan-1-yl)piperidin-1-yl)phenyl)pyrimidin-4-amine | ¹H NMR (400 MHz, Chloroform-d) δ 8.31 (s, 1H), 7.59 (d, J = 8.6 Hz, 1H), 7.34-7.29 (m, 1H), 7.11-6.99 (m, 2H), 6.83 (s, 1H), 6.54 (d, J = 7.1 Hz, 2H), 6.43 (s, 1H), 5.91 (dd, J = 8.6, 4.3 Hz, 1H), 4.11 (td, J = 7.9, 4.2 Hz, 1H), 3.93-3.83 (m, 4H), 3.72 (d, J = 12.5 Hz, 2H), 3.30 (s, 2H), 3.07 (s, 2H), 2.87-2.71 (m, 7H), 2.32 (ddd, J = 15.2, 7.8, 3.9 Hz, 2H), 2.05-1.96 (m, 2H), 1.81-1.69 (m, 2H), 1.34-1.23 (m, 3H), 0.91-0.83 (m, 2H); 580.43 [M + H]⁺ |
| 222 | 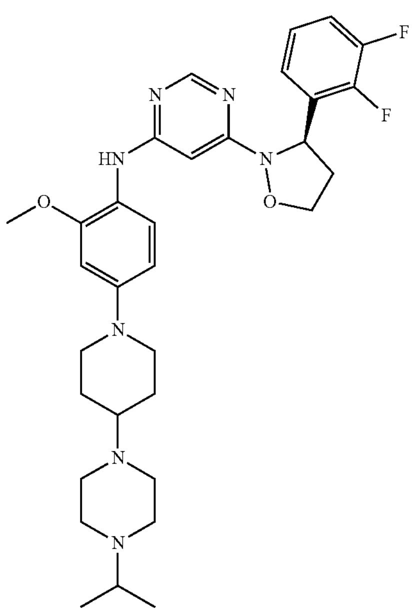 [SMILES: COc1cc(N2CCC(N3CCN(C(C)C)CC3)CC2)ccc1Nc1cc(N2OCC[C@@H]2c2cccc(F)c2F)ncn1] | (R)-6-(3-(2,3-difluorophenyl)isoxazolidin-2-yl)-N-(4-(4-(4-isopropylpiperazin-1-yl)piperidin-1-yl)-2-methoxyphenyl)pyrimidin-4-amine | ¹H NMR (400 MHz, Chloroform-d) δ 8.31 (s, 1H), 7.55 (d, J = 8.9 Hz, 1H), 7.36-7.30 (m, 1H), 7.11-6.99 (m, 2H), 6.74 (s, 1H), 6.54 (dq, J = 5.9, 2.6 Hz, 2H), 6.45-6.41 (m, 1H), 5.91 (dd, J = 8.8, 4.7 Hz, 1H), 4.10 (td, J = 7.9, 4.2 Hz, 1H), 3.92-3.83 (m, 4H), 3.71 (d, J = 12.3 Hz, 2H), 3.10-2.71 (m, 9H), 2.55-2.45 (m, 1H), 2.30 (ddt, J = 16.5, 8.2, 4.8 Hz, 1H), 1.97 (s, 2H), 1.91-1.82 (m, 1H), 1.78-1.64 (m, 3H), 1.56-1.47 (m, 1H), 1.45-1.23 (m, 6H); 594.44 [M + H]⁺ |

| Example Compound | Structure | Compound Name | ¹H NMR; MS [M + H]⁺ |
|---|---|---|---|
| 223 | 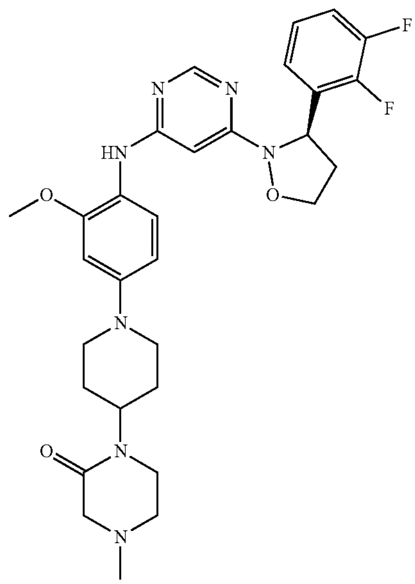 [SMILES: COc1cc(N2CCC(N3CCN(C)CC3=O)CC2)ccc1Nc1cc(N2OCC[C@@H]2c2cccc(F)c2F)ncn1] | (R)-1-(1-(4-((6-(3-(2,3-difluorophenyl)isoxazolidin-2-yl)pyrimidin-4-yl)amino)-3-methoxyphenyl)piperidin-4-yl)-4-methylpiperazin-2-one | 580.3 [M + H]⁺ |
| 224 | 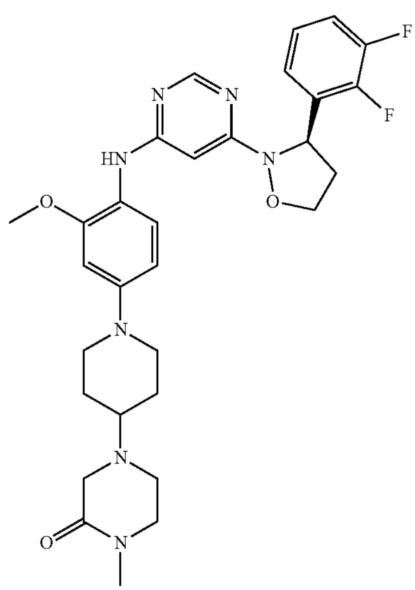 [SMILES: COc1cc(N2CCC(N3CCN(C)C(=O)C3)CC2)ccc1Nc1cc(N2OCC[C@@H]2c2cccc(F)c2F)ncn1] | (R)-4-(1-(4-((6-(3-(2,3-difluorophenyl)isoxazolidin-2-yl)pyrimidin-4-yl)amino)-3-methoxyphenyl)piperidin-4-yl)-1-methylpiperazin-2-one | ¹H NMR (400 MHz, Chloroform-d) δ 8.30 (s, 1H), 7.54 (d, J = 8.4 Hz, 1H), 7.36-7.29 (m, 1H), 7.12-7.00 (m, 2H), 6.85 (s, 1H), 6.59-6.50 (m, 2H), 6.42 (d, 1H), 5.91 (dd, J = 8.8, 4.7 Hz, 1H), 4.10 (td, J = 8.4, 7.9, 4.6 Hz, 1H), 3.89 (q, 1H), 3.85 (s, 3H), 3.69 (d, J = 11.2 Hz, 2H), 3.34 (t, J = 5.4 Hz, 2H), 3.31 (s, 2H), 2.97 (s, 3H), 2.78 (ddd, J = 23.8, 11.4, 3.9 Hz, 5H), 2.43 (tt, J = 11.1, 3.7 Hz, 1H), 2.30 (dtd, J = 12.6, 8.1, 4.7 Hz, 1H), 1.96 (d, J = 12.5 Hz, 2H), 1.70 (qd, J = 1.19, 4.0 Hz, 2H); 580.33 [M + H]⁺ |

TABLE 1-continued

| Example Compound | Structure | Compound Name | ¹H NMR; MS [M + H]⁺ |
|---|---|---|---|
| 225 | 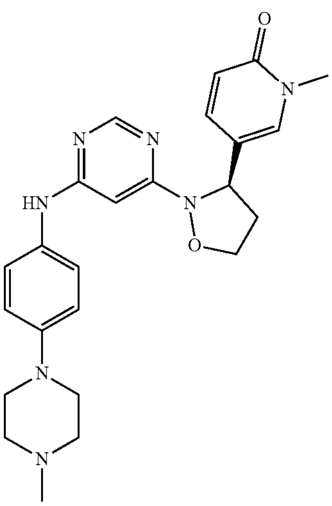 [SMILES: CN1CCN(c2ccc(Nc3cc(N4OCC[C@@H]4c4ccc(=O)n(C)c4)ncn3)cc2)CC1] | (R)-1-methyl-5-(2-(6-((4-(4-methylpiperazin-1-yl)phenyl)amino)pyrimidin-4-yl)isoxazolidin-3-yl)pyridin-2(1H)-one | 448.19 [M + H]⁺ |
| 226 | 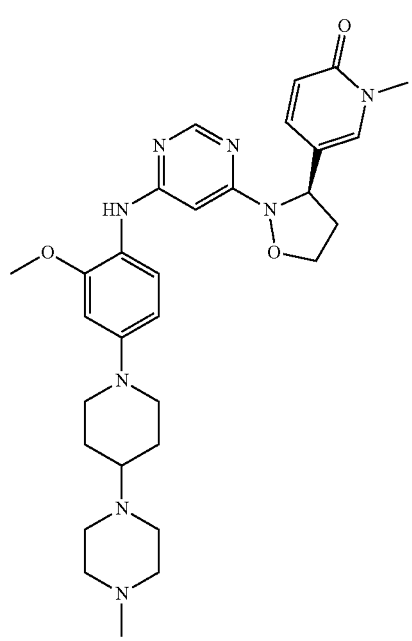 | (R)-5-(2-(6-((2-methoxy-4-(4-(4-methylpiperazin-1-yl)piperidin-1-yl)phenyl)amino)pyrimidin-4-yl)isoxazolidin-3-yl)-1-methylpyridin-2(1H)-one | 561.33 [M + H]⁺ |

TABLE 1-continued

| Example Compound | Structure | Compound Name | ¹H NMR; MS [M + H]⁺ |
|---|---|---|---|
| 227 | 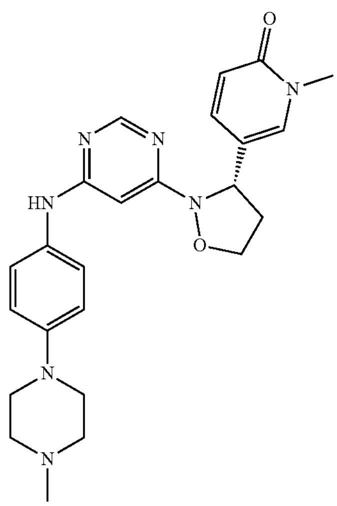 [SMILES: CN1CCN(c2ccc(Nc3cc(N4OCC[C@H]4c4ccc(=O)n(C)c4)ncn3)cc2)CC1] | (S)-1-methyl-5-(2-(6-((4-(4-methylpiperazin-1-yl)phenyl)amino)pyrimidin-4-yl)isoxazolidin-3-yl)pyridin-2(1H)-one | 448.19 [M + H]⁺ |
| 228 | 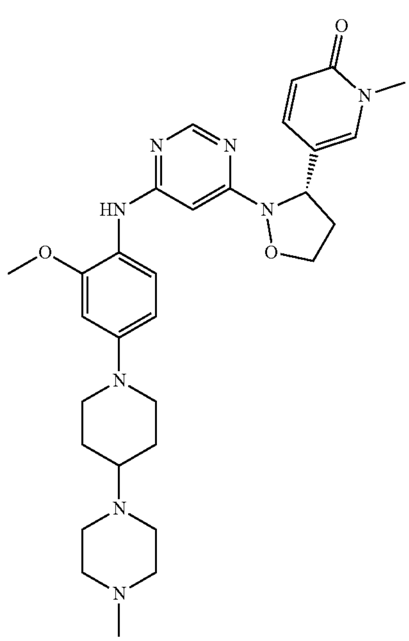 | (S)-5-(2-(6-((2-methoxy-4-(4-(4-methylpiperazin-1-yl)piperidin-1-yl)phenyl)amino)pyrimidin-4-yl)isoxazolidin-3-yl)-1-methylpyridin-2(1H)-one | 561.33 [M + H]⁺ |

TABLE 1-continued

| Example Compound | Structure | Compound Name | ¹H NMR; MS [M + H]⁺ |
|---|---|---|---|
| 229 | 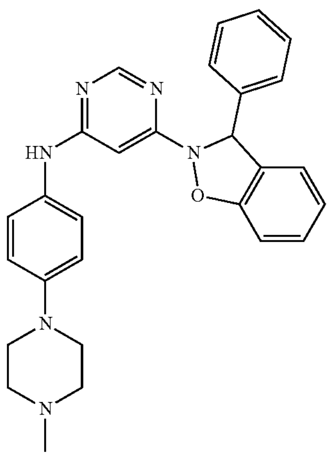 [SMILES: CN1CCN(c2ccc(Nc3cc(N4Oc5ccccc5C4c4ccccc4)ncn3)cc2)CC1] | N-(4-(4-methylpiperazin-1-yl)phenyl)-6-(3-phenylbenzo[d]isoxazol-2(3H)-yl)pyrimidin-4-amine | ¹H NMR (400 MHz, Chloroform-d) δ 8.36 (s, 1H), 8.01 (dd, J = 7.2, 1.9 Hz, 1H), 7.39 (p, J = 4.4 Hz, 5H), 6.98-6.75 (m, 9H), 5.64 (s, 1H), 3.22 (d, J = 4.3 Hz, 4H), 2.63 (t, J = 5.0 Hz, 4H), 2.39 (s, 3H); 465.2 [M + H]⁺ |
| 230 | 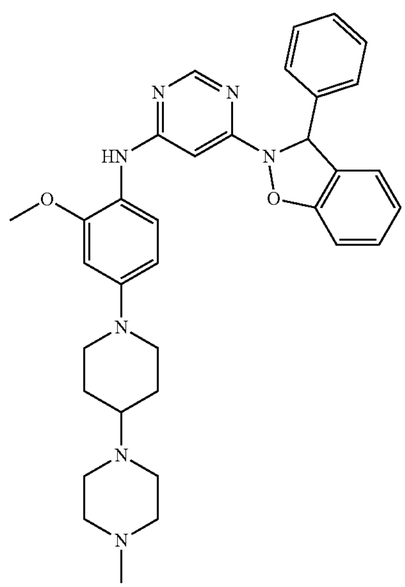 [SMILES: COc1cc(N2CCC(N3CCN(C)CC3)CC2)ccc1Nc1cc(N2Oc3ccccc3C2c2ccccc2)ncn1] | N-(2-methoxy-4-(4-(4-methylpiperazin-1-yl)piperidin-1-yl)phenyl)-6-(3-phenylbenzo[d]oxazol-2(3H)-yl)pyrimidin-4-amine | ¹H NMR (400 MHz, Chloroform-d) δ 8.38 (s, 1H), 8.01 (dd, J = 7.6, 1.6 Hz, 1H), 7.46-7.37 (m, 5H), 6.99-6.86 (m, 4H), 6.79 (dd, J = 7.6, 1.5 Hz, 1H), 6.60 (s, 1H), 6.50 (d, J = 2.5 Hz, 1H), 6.39 (dd, J = 8.7, 2.5 Hz, 1H), 5.70 (s, 1H), 3.75 (s, 3H), 3.71 (d, J = 12.0 Hz, 2H), 2.80-2.64 (m, 6H), 2.59-2.37 (m, 5H), 2.32 (s, 3H), 1.98 (d, J = 12.4 Hz, 2H), 1.73 (tt, J = 13.0, 6.6 Hz, 2H); 578.3 [M + H]⁺ |
| 231 | 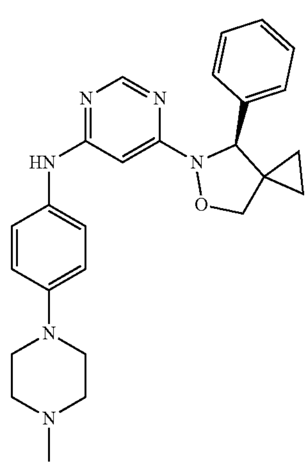 [SMILES: CN1CCN(c2ccc(Nc3cc(N4OCC5(CC5)[C@@H]4c4ccccc4)ncn3)cc2)CC1] | (S)-N-(4-(4-methylpiperazin-1-yl)phenyl)-6-(7-phenyl-5-oxa-6-azaspiro[2.4]heptan-6-yl)pyrimidin-4-amine | ¹H NMR (400 MHz, MeOD) δ 8.13 (d, J = 0.8 Hz, 1H), 7.43-7.25 (m, 7H), 7.07-7.00 (m, 2H), 6.37 (d, J = 0.8 Hz, 1H), 5.13 (s, 1H), 4.07-3.97 (m, 2H), 3.37-3.33 (m, 4H), 3.10-2.99 (m, 4H), 2.67 (s, 3H), 0.85 (ddd, J = 9.9, 5.8, 4.5 Hz, 1H), 0.72 (dtd, J = 15.7, 9.8, 6.1 Hz, 2H), 0.38 (dt, J = 10.7, 5.4 Hz, 1H); 443.25 [M + H]⁺ |

| Example Compound | Structure | Compound Name | ¹H NMR; MS [M + H]⁺ |
|---|---|---|---|
| 232 | 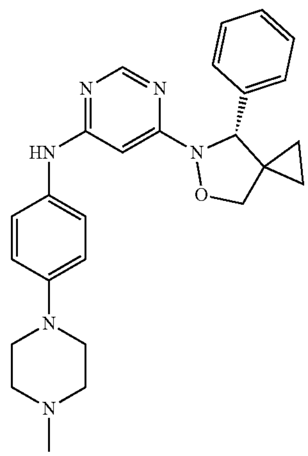 [SMILES: CN1CCN(c2ccc(Nc3cc(N4OCC5(CC5)[C@H]4c4ccccc4)ncn3)cc2)CC1] | (R)-N-(4-(4-methylpiperazin-1-yl)phenyl)-6-(7-phenyl-5-oxa-6-azaspiro[2.4]heptan-6-yl)pyrimidin-4-amine | ¹H NMR (400 MHz, MeOD) δ 8.13 (d, J = 0.9 Hz, 1H), 7.46-7.21 (m, 7H), 7.08-6.95 (m, 2H), 6.37 (d, J = 0.8 Hz, 1H), 5.13 (s, 1H), 4.09-3.96 (m, 2H), 3.35 (dd, J = 9.6, 4.2 Hz, 4H), 3.14-3.02 (m, 4H), 2.69 (s, 3H), 0.88-0.81 (m, 1H), 0.72 (dtd, J = 15.8, 9.8, 6.1 Hz, 2H), 0.38 (dt, J = 10.7, 5.4 Hz, 1H); 443.21 [M + H]⁺ |
| 233 | 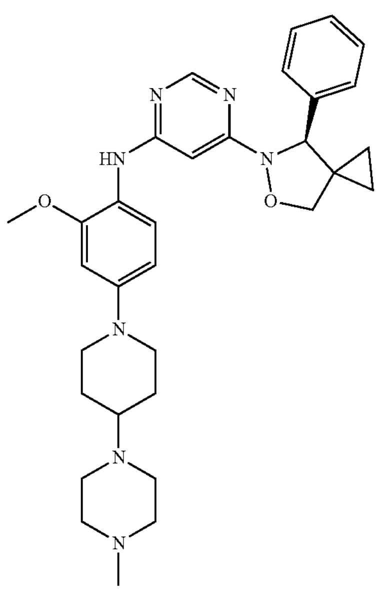 [SMILES: COc1cc(N2CCC(N3CCN(C)CC3)CC2)ccc1Nc1cc(N2OCC3(CC3)[C@@H]2c2ccccc2)ncn1] | (S)-N-(2-methoxy-4-(4-(4-methylpiperazin-1-yl)piperidin-1-yl)phenyl)-6-(7-phenyl-5-oxa-6-azaspiro[2.4]heptan-6-yl)pyrimidin-4-amine | ¹H NMR (400 MHz, MeOD) δ 8.10 (d, J = 0.6 Hz, 1H), 7.37-7.28 (m, 6H), 6.68 (d, J = 2.3 Hz, 1H), 6.58 (dd, J = 8.7, 2.5 Hz, 1H), 6.23 (s, 1H), 5.12 (s, 1H), 4.02-3.97 (m, 2H), 3.85-3.75 (m, 5H), 2.72 (dd, J = 29.9, 19.2 Hz, 10H), 2.49-2.42 (m, 1H), 2.39 (s, 3H), 2.02 (d, J = 12.0 Hz, 2H), 1.69-1.64 (m, 2H), 0.86-0.80 (m, 1H), 0.70 (ddd, J = 14.7, 9.6, 3.9 Hz, 2H), 0.36 (dt, J = 10.7, 5.4 Hz, 1H); 556.30 [M +H]⁺ |

TABLE 1-continued

| Example Compound | Structure | Compound Name | ¹H NMR; MS [M + H]⁺ |
|---|---|---|---|
| 234 | 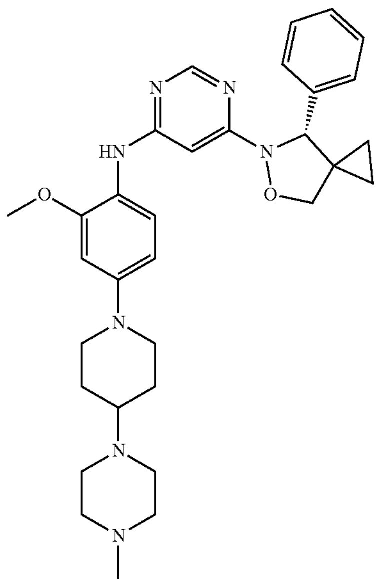 [SMILES: COc1cc(N2CCC(N3CCN(C)CC3)CC2)ccc1Nc1cc(N2OCC3(CC3)[C@H]2c2ccccc2)ncn1] | (R)-N-(2-methoxy-4-(4-(4-ethylpiperazin-1-yl)piperidin-1-yl)phenyl)-6-(7-phenyl-5-oxa-6-azaspiro[2.4]heptan-6-yl)pyrimidin-4-amine | ¹H NMR (400 MHz, MeOD) δ 8.09 (d, J = 0.9 Hz, 1H), 7.43-7.24 (m, 6H), 6.68 (d, J = 2.5 Hz, 1H), 6.59 (dd, J = 8.7, 2.5 Hz, 1H), 6.23 (d, J = 0.5 Hz, 1H), 5.12 (s, 1H), 4.05-3.94 (m, 2H), 3.85-3.73 (m, 5H), 2.95-2.58 (m, 10H), 2.48 (ddd, J = 11.5, 7.9, 3.7 Hz, 1H), 2.43 (d, J = 9.3 Hz, 3H), 2.08-1.98 (m, 2H), 1.72-1.62 (m, 2H), 0.87-0.80 (m, 1H), 0.70 (dtd, J = 15.7, 9.8, 6.1 Hz, 2H), 0.36 (dt, J = 10.7, 5.4 Hz, 1H); 556.30 [M +H]⁺ |
| 235 | 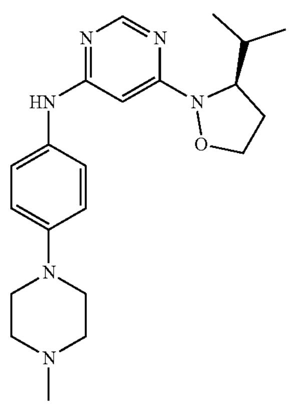 [SMILES: CC(C)[C@H]1CCON1c1cc(Nc2ccc(N3CCN(C)CC3)cc2)ncn1] | (R)-6-(3-isopropylisoxazolidin-2-yl)-N-(4-(4-methylpiperazin-1-yl)phenyl)pyrimidin-4-amine | ¹H NMR (400 MHz, MeOD) δ 8.04 (s, 1H), 7.23-7.17 (m, 2H), 6.95-6.88 (m, 2H), 6.19 (d, J = 0.4 Hz, 1H), 4.12 (td, J = 7.9, 4.7 Hz, 1H), 3.93 (td, J = 8.1, 3.5 Hz, 1H), 3.59 (dt, J = 15.4, 7.7 Hz, 1H), 2.96-2.90 (m, 4H), 2.56-2.51 (m, 7H), 2.19-2.00 (m, 2H), 1.77 (dq, J = 13.6, 6.8 Hz, 1H), 0.90 (dd, J = 11.4, 6.7 Hz, 6H); 383.30 [M + H]⁺ |
| 236 | 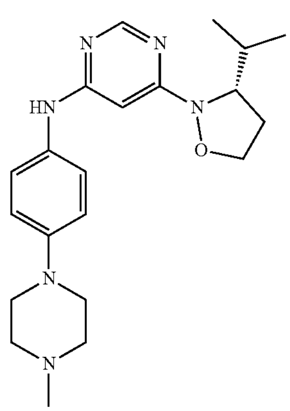 [SMILES: CC(C)[C@@H]1CCON1c1cc(Nc2ccc(N3CCN(C)CC3)cc2)ncn1] | (S)-6-(3-isopropylisoxazolidin-2-yl)-N-(4-(4-methylpiperazin-1-yl)phenyl)pyrimidin-4-amine | ¹H NMR (400 MHz, MeOD) δ 8.16 (s, 1H), 7.36-7.29 (m, 2H), 7.07-7.00 (m, 2H), 6.31 (s, 1H), 4.24 (td, J = 7.9, 4.7 Hz, 1H), 4.05 (td, J = 8.1, 3.4 Hz, 1H), 3.70 (dt, J = 15.6, 7.8 Hz, 1H), 3.09-3.02 (m, 4H), 2.66 (d, J = 7.1 Hz, 7H), 2.31-2.10 (m, 2H), 1.89 (dq, J = 13.6, 6.8 Hz, 1H), 1.01 (dd, J = 11.4, 6.7 Hz, 6H); 383.30 [M + H]⁺ |

TABLE 1-continued

| Example Compound | Structure | Compound Name | $^1$H NMR; MS [M + H]$^+$ |
|---|---|---|---|
| 237 | 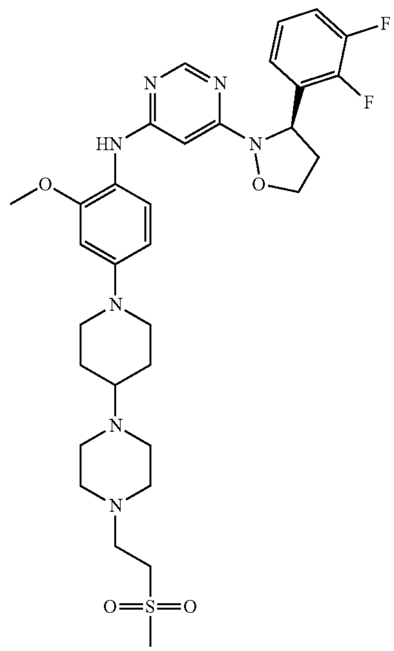 [SMILES: COc1cc(N2CCC(N3CCN(CCS(C)(=O)=O)CC3)CC2)ccc1Nc1cc(N2OCC[C@@H]2c2cccc(F)c2F)ncn1] | (R)-6-(3-(2,3-difluorophenyl)isoxazolidin-2-yl)-N-(2-methoxy-4-(4-(4-(2-(methylsulfonyl)ethyl)piperazin-1-yl)piperidin-1-yl)phenyl)pyrimidin-4-amine | $^1$H NMR (400 MHz, Chloroform-d) δ 8.30 (s, 1H), 7.55-7.49 (m, 1H), 7.36-7.28 (m, 1H), 7.10-7.01 (m, 2H), 6.82 (s, 1H), 6.58-6.51 (m, 2H), 6.42 (s, 1H), 5.91 (dd, J = 8.8, 4.7 Hz, 1H), 4.09 (td, J = 7.9, 4.3 Hz, 1H), 3.88 (q, J = 8.0 Hz, 1H), 3.85 (s, 3H), 3.71 (d, J = 12.1 Hz, 2H), 3.15 (t, J = 6.4 Hz, 2H), 3.04 (s, 3H), 2.89 (t, J = 6.5 Hz, 2H), 2.86-2.70 (m, 3H), 2.64 (s, 3H), 2.58 (s, 3H), 2.43-2.36 (m, 1H), 2.34-2.26 (m, 1H), 1.95 (d, J = 12.5 Hz, 3H), 1.69 (ddd, J = 23.8, 11.7, 3.3 Hz, 3H); 658.35 [M + H]$^+$ |

<Experimental Example 1> Evaluation of Proliferation Inhibitory Activity of EGFR Mutant Overexpression Ba/F3 Cell The following experiments were performed to evaluate the inhibitory activity of the compounds according to the present disclosure on Ba/F3 proliferation expressing EGFR C797S, L861Q, G719A, S768I, L718Q, and/or G724S mutations.

For Ba/F3 cells, RPMI-1640 containing 10% FBS and 5 ng/ml IL-3 (R&D Systems) was used. Transduced Ba/F3 cells were cultured after adding 1 μg/ml puromycin (Invitrogen) to the same medium.

At 24 hours before treatment with the compounds, 3000 to 5000 cells were aliquoted into each well of a white clear bottom 96 well plate (Corning). The compounds were diluted in dimethyl sulfoxide (3 times dilution, 12 concentrations in total), and injected in an amount of 1 μl so that the final concentration was 0.2 nM to 5 uM. For measurement of living cells, after 72 hours of compound treatment, the cells were stored at room temperature for 10 min using CellTiter-Glo luminescent cell-viability reagent (Promega), and then luminescence intensity was measured using a reader (SynergyNeo, Biotek). Each test was repeated three times. Result values were calculated as the cell growth rate (%) compared to the control. The graphs were created using GraphPad Prism version 8.3.0 program and the GI$_{50}$ values were calculated.

Table 2 below shows the evaluation results of the proliferation inhibitory activity of Ba/F3 cells expressing EGFR Del19/C797S (EGFR DC) and EGFR L858R/C797S (EGFR LC) mutations.

TABLE 2

| Example Compound | Ba/F3 (EGFR DC) | Ba/F3 (EGFR LC) |
|---|---|---|
| 1 | A | A |
| 2 | B | — |
| 3 | A | — |
| 4 | A | A |
| 5 | A | A |
| 6 | B | B |
| 7 | B | B |
| 8 | A | A |
| 10 | B | B |
| 11 | B | B |
| 12 | B | B |
| 13 | B | B |
| 14 | B | — |
| 15 | A | A |
| 17 | B | — |
| 18 | B | — |
| 19 | B | — |
| 20 | A | — |
| 21 | A | — |
| 22 | A | — |
| 23 | B | — |
| 24 | B | — |
| 25 | A | — |
| 26 | A | — |
| 27 | B | — |
| 28 | B | — |
| 29 | A | — |
| 30 | A | — |
| 31 | A | — |
| 32 | A | — |
| 33 | A | — |
| 34 | A | — |
| 35 | A | — |
| 36 | B | — |
| 38 | B | — |
| 41 | B | — |

TABLE 2-continued

| Example Compound | Ba/F3 (EGFR DC) | Ba/F3 (EGFR LC) |
|---|---|---|
| 48 | A | — |
| 49 | A | — |
| 52 | A | — |
| 53 | A | — |
| 54 | A | — |
| 56 | A | — |
| 57 | A | — |
| 59 | A | — |
| 61 | A | — |
| 62 | A | — |
| 63 | A | — |
| 64 | A | — |
| 65 | A | — |
| 66 | A | — |
| 67 | A | — |
| 68 | A | — |
| 69 | A | — |
| 72 | B | — |
| 73 | B | — |
| 74 | A | — |
| 75 | A | — |
| 76 | A | — |
| 77 | A | — |
| 78 | A | — |
| 79 | A | — |
| 80 | B | — |
| 81 | B | — |
| 83 | A | — |
| 84 | A | A |
| 85 | A | — |
| 86 | A | — |
| 87 | A | — |
| 88 | A | — |
| 89 | B | — |
| 90 | A | — |
| 91 | A | — |
| 92 | A | — |
| 93 | A | — |
| 94 | A | — |
| 95 | A | — |
| 96 | A | — |
| 97 | A | — |
| 98 | A | — |
| 99 | A | — |
| 100 | B | — |
| 101 | A | — |
| 102 | A | A |
| 103 | A | — |
| 104 | A | A |
| 105 | A | — |
| 106 | A | — |
| 107 | A | — |
| 108 | A | — |
| 109 | A | — |
| 110 | A | — |
| 111 | B | — |
| 112 | B | — |
| 113 | A | — |
| 114 | A | — |
| 115 | A | — |
| 116 | A | — |
| 117 | A | — |
| 118 | A | — |
| 119 | A | — |
| 120 | A | — |
| 121 | A | — |
| 122 | A | — |
| 123 | A | — |
| 124 | A | — |
| 125 | A | — |
| 126 | A | — |
| 127 | A | — |
| 128 | A | A |
| 129 | A | A |
| 130 | B | — |
| 131 | B | — |
| 132 | A | A |
| 133 | B | — |
| 134 | A | — |
| 135 | A | — |
| 136 | A | — |
| 138 | A | — |
| 139 | A | — |
| 140 | A | — |
| 141 | A | — |
| 142 | A | — |
| 143 | A | — |
| 145 | A | — |
| 146 | A | — |
| 147 | A | — |
| 152 | A | — |
| 154 | A | — |
| 155 | A | — |
| 157 | A | — |
| 159 | B | — |
| 160 | B | — |
| 161 | A | — |
| 162 | A | — |
| 163 | A | — |
| 164 | A | — |
| 165 | A | — |
| 166 | A | — |
| 167 | A | — |
| 169 | B | — |
| 170 | B | — |
| 174 | B | — |
| 176 | B | — |
| 177 | B | — |
| 180 | B | — |
| 182 | A | — |
| 184 | B | — |
| 193 | B | — |
| 195 | A | — |
| 199 | A | — |
| 200 | A | — |
| 201 | A | — |
| 202 | A | — |
| 203 | A | — |
| 206 | A | — |
| 207 | A | — |
| 208 | A | — |
| 209 | A | — |
| 210 | A | — |
| 211 | A | — |
| 212 | A | — |
| 213 | A | — |
| 214 | A | — |
| 215 | A | — |
| 216 | A | — |
| 217 | A | — |
| 218 | A | — |
| 219 | A | — |
| 220 | A | — |
| 221 | A | — |
| 222 | A | — |
| 224 | A | — |
| 229 | B | — |
| 230 | B | — |
| 231 | B | — |
| 233 | A | — |
| 234 | B | — |
| 235 | A | — |
| 237 | A | — |

A: $GI_{50} < 50$ nM; B: $50$ nM $\leq GI_{50} < 500$ nM; C: $500$ nM $\leq GI_{50} < 5000$ nM; D: $5000$ nM $\leq GI_{50}$;

Table 3 below shows the evaluation results of the proliferation inhibitory activity of Ba/F3 cells such as L861Q, G719A, S768I, L718Q, G724S, and the like, expressing EGFR rare (or uncommon) and drug-resistant mutations.

TABLE 3

| Example Compound | Ba/F3 G719A | Ba/F3 L861Q | Ba/F3 S768I | Ba/F3 L718Q | Ba/F3 G724S |
|---|---|---|---|---|---|
| 4 | A | A | B | — | — |
| 34 | A | B | B | B | A |

A: $GI_{50} < 50$ nM;
B: 50 nM ≤ $GI_{50}$ < 500 nM;
C: 500 nM ≤ $GI_{50}$ < 5000 nM;
D: 5000 nM ≤ $GI_{50}$;

Table 4 below shows the activity values for EGFR-family mutant enzymes obtained by requesting on external entrusted organization, Reaction Biology (https://www.reactionbiology.com/).

TABLE 4

| EGFR Mutant Enzyme | Compound 34 ($IC_{50}$; nM) |
|---|---|
| EGFR (d746-750) | 8.0 |
| EGFR (d746-750/C797A) | 3.5 |
| EGFR (d746-750/C797S) | <0.5 |
| EGFR (d746-750/T790M/C797S) | 60.5 |
| EGFR (D761Y) | <0.5 |
| EGFR (G719C) | 0.5 |
| EGFR (G719D) | <0.5 |
| EGFR (G719S) | 2.7 |
| EGFR (L718Q) | 49.8 |
| EGFR (L747S) | <0.5 |
| EGFR (L792F) | 8.7 |
| EGFR (L792F/L858R) | 78.1 |
| EGFR (L861Q) | <0.5 |
| ERBB2/HER2 | 5.3 |
| ERBB4/HER4 | 41.7 |

As shown in Tables 2 to 4 above, it could be appreciated that the Example compounds of the present disclosure exhibited high inhibitory ability against overexpressing cell lines or enzymes including EGFR C797S mutations, rare mutations, and the like.

As described above, although the present disclosure has been described in detail through preferred Preparation Examples, Examples and Experimental Examples, the scope of the present disclosure is not limited to specific Example compounds, and should be interpreted by the appended claims. In addition, those skilled in the art will understand that many modifications and variations can be made without departing from the scope of the present disclosure.

The invention claimed is:
1. A compound represented by the following Chemical Formula 1, an optical isomer thereof, or a pharmaceutically acceptable salt thereof:

[Chemical Formula 1]

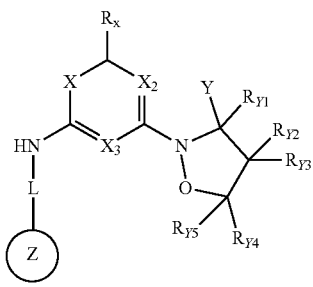

in the Chemical Formula 1,
$X_1$ to $X_3$ are each independently CH or N;
$R_X$ is —H, —$C_{1-6}$alkyl, —$C_{1-6}$aminoalkyl, —$NH_2$, —NH(—$C_{1-6}$alkyl), or —N(—$C_{1-6}$alkyl)(—$C_{1-6}$alkyl);
Y is —$C_{1-6}$alkyl, —$(CH_2)_n$aryl, —$(CH_2)_n$hydroaryl, —$(CH_2)_n$heteroaryl, or —$(CH_2)_n$hydroheteroaryl in which at least one H of the —$(CH_2)_n$aryl, —$(CH_2)_n$hydroaryl, —$(CH_2)_n$heteroaryl, or —$(CH_2)_n$hydroheteroaryl ring may be substituted with —$C_{1-6}$alkyl, —$C_{1-6}$aminoalkyl, —$C_{1-6}$hydroxyalkyl, —$C_{1-6}$haloalkyl, —$C_{1-6}$alkyl-O—$C_{1-6}$alkyl, —$C_{1-6}$alkenyl, —$C_{1-6}$alkynyl, —CN, —C(=O)$NR_1R_2$, —C(=O)$OR_3$, —$NR_4R_5$, —$OR_6$, -halo, =O, cycloalkyl, heterocycloalkyl, aryl, or heteroaryl, wherein at least one H of the cycloalkyl, heterocycloalkyl, aryl, or heteroaryl may be substituted with —$C_{1-6}$alkyl, —$C_{1-6}$haloalkyl, or -halo;
n is 0, 1, 2, 3, or 4;
$R_1$ to $R_3$ are each independently —H, —$C_{1-6}$alkyl, or cycloalkyl;
$R_4$ and $R_5$ are each independently —H or —$C_{1-6}$alkyl;
$R_6$ is —H, —$C_{1-6}$alkyl, or phenyl in which at least one H of the phenyl ring may be substituted with —$C_{1-6}$alkyl, —$C_{1-6}$haloalkyl, or halo;
$R_{Y1}$ to $R_{Y5}$ are each independently —H or —$C_{1-6}$alkyl, or $R_{Y2}$ and $R_{Y3}$ may be linked to each other to form cycloalkyl or heterocycloalkyl, $R_{Y4}$ and $R_{Y5}$ may be linked to each other to form cycloalkyl or heterocycloalkyl, and $R_{Y3}$ and $R_{Y4}$ may be linked to each other to form aryl or heteroaryl;
L is —$(CH_2)m$-, —C(=O)—, or null;
m is 0, 1, 2, 3, or 4;
a ring Z is phenyl, 5- to 6-membered heteroaryl, 9- to 10-membered hydroheteroaryl, 3- to 5-membered cycloalkyl, or 6-membered heterocycloalkyl in which at least one H of the phenyl, 5- to 6-membered heteroaryl, 9- to 10-membered hydroheteroaryl, 3- to 5-membered cycloalkyl, or 6-membered heterocycloalkyl ring may be substituted with —$C_{1-6}$alkyl, —$C_{1-6}$cyanoalkyl, $C_{1-6}$haloalkyl, —$C_{1-6}$alkenyl, —$C_{1-6}$alkynyl, —CN, —OH, —O—$C_{1-6}$alkyl, —O—$C_{1-6}$haloalkyl, —S—$C_{1-6}$alkyl, —C(=O)—$C_{1-6}$alkyl, —C(=O)—$C_{1-6}$haloalkyl, —C(=O)O—$C_{1-6}$alkyl, —S(=O)$_2$—$C_{1-6}$alkyl, —C(=N—O—$C_{1-6}$alkyl)($C_{1-6}$alkyl), =O, -halo, or $Z_1$, wherein at least one H of the phenyl in the meta position relative to the L is unsubstituted or substituted with at least one selected from the group consisting of —$C_{1-6}$alkyl, —$C_{1-6}$cyanoalkyl, —$C_{1-6}$haloalkyl, —$C_{1-6}$alkenyl, —$C_{1-6}$alkynyl, —O—$C_{1-6}$alkyl, —O—$C_{1-6}$haloalkyl, —C(=O)—$C_{1-6}$alkyl, —S(=O)$_2$—$C_{1-6}$alkyl, —C(=N—O—$C_{1-6}$alkyl)($C_{1-6}$alkyl), -halo, and $Z_1$ when the ring Z is phenyl, or two or more substituents of the phenyl, 5- to 6-membered heteroaryl, 9- to 10-membered hydroheteroaryl, 3- to 5-membered cycloalkyl, or 6-membered heterocycloalkyl ring may be linked to each other to form a fused ring or a spiro ring, wherein at least one H of the fused ring or spiro ring may be substituted with —$C_{1-6}$alkyl or $Z_1$;
$Z_1$ is cycloalkyl, heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl in which the heterocycloalkyl, heterobicycloalkyl, heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —$C_{1-6}$alkyl-heterocycloalkyl, —(C=O)-heterocycloalkyl, —NH-heterocycloalkyl, aryl, or heteroaryl ring may be substituted with —C$_{1-6}$alkyl, —C$_{1-6}$aminoalkyl, —C$_{1-6}$haloalkyl, —C$_{1-6}$alkyl-NH—C$_{1-6}$alkyl, —C$_{1-6}$alkyl-N(C$_{1-6}$alkyl)(C$_{1-6}$alkyl), —C$_{1-6}$alkenyl, —C$_{1-6}$alkynyl, —C(=O)—C$_{1-6}$alkyl, —C$_{1-6}$alkyl-C(=O)—C$_{1-6}$alkyl, —S(=O)$_2$—C$_{1-6}$alkyl, —C$_{1-6}$alkyl-S(=O)$_2$—C$_{1-6}$alkyl, =O, —NR$_9$R$_{10}$, -halo, cycloalkyl, or Z$_2$;

R$_9$ and R$_{10}$ are each independently —H or —C$_{1-6}$alkyl;

Z$_2$ is heterocycloalkyl, heterobicycloalkyl, heterospiroalkyl, —C$_{1-6}$alkyl-heterocycloalkyl, —(C=O)-heterocycloalkyl, —NH-heterocycloalkyl, aryl, or heteroaryl in which the heterocycloalkyl, heterobicycloalkyl, heterospiroalkyl, —C$_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —C$_{1-6}$alkyl-heterocycloalkyl, —(C=O)-heterocycloalkyl, —NH-heterocycloalkyl, aryl, or heteroaryl ring may be substituted with —C$_{1-6}$alkyl, —C$_{1-6}$aminoalkyl, —C$_{1-6}$hydroxyalkyl, —C$_{1-6}$haloalkyl, —C$_{1-6}$alkenyl, —C$_{1-6}$alkynyl, —C(=O)—C$_{1-6}$alkyl, —C$_{1-6}$alkyl-S(=O)$_2$—C$_{1-6}$alkyl, =O, —NR$_{11}$R$_{12}$, cycloalkyl, or Z$_3$;

R$_{11}$ and R$_{12}$ are each independently —H or —C$_{1-6}$alkyl; and

Z$_3$ is heterocycloalkyl, heterobicycloalkyl, heterospiroalkyl, —C$_{1-6}$alkyl-heterocycloalkyl, —(C=O)-heterocycloalkyl, or —NH-heterocycloalkyl in which the heterocycloalkyl, heterobicycloalkyl, heterospiroalkyl, —C$_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —C$_{1-6}$alkyl-heterocycloalkyl, —(C=O)-heterocycloalkyl, or —NH-heterocycloalkyl ring may be substituted with —C$_{1-6}$alkyl or cycloalkyl.

2. The compound represented by Chemical Formula I, the optical isomer thereof, or the pharmaceutically acceptable salt thereof of claim 1, wherein X$_1$ to X$_3$ are each independently CH or N;

R$_X$ is —H, —NH$_2$, —NH(—C$_{1-6}$alkyl), or —N(—C$_{1-6}$alkyl)(—C$_{1-6}$alkyl);

Y is —C$_{1-6}$alkyl, —(CH$_2$)$_n$aryl, —(CH$_2$)$_n$heteroaryl, or —(CH$_2$)$_n$hydroheteroaryl in which at least one H of the —(CH$_2$)$_n$aryl, —(CH$_2$)$_n$heteroaryl, or —(CH$_2$)$_n$hydroheteroaryl ring may be substituted with —C$_{1-6}$alkyl, —C$_{1-6}$haloalkyl, —C$_{1-6}$alkenyl, —C$_{1-6}$alkynyl, —CN, —(C=O)NR$_1$R$_2$, —(C=O)OR$_3$, —NR$_4$R$_5$, —OR$_6$, -halo, =O, heterocycloalkyl, aryl, or heteroaryl, wherein at least one H of the heterocycloalkyl, aryl, or heteroaryl may be substituted with -halo;

n is 0, 1, or 2;

R$_1$ to R$_3$ are each independently —H, —C$_{1-6}$alkyl, or cycloalkyl;

R$_4$ and R$_5$ are each independently —H or —C$_{1-6}$alkyl;

R$_6$ is —C$_{1-6}$alkyl or phenyl in which at least one H of the phenyl ring may be substituted with —C$_{1-6}$alkyl, —C$_{1-6}$ haloalkyl, or halo;

R$_{Y1}$ to R$_{Y5}$ are each independently —H or —C$_{1-6}$alkyl, or R$_{Y2}$ and R$_{Y3}$ may be linked to each other to form cycloalkyl, and R$_{Y3}$ and R$_{Y4}$ may be linked to each other to form aryl;

L is —(CH$_2$)m-, —C(=O)—, or null;

m is 0, 1, or 2;

Z$_1$ is cycloalkyl, heterocycloalkyl, heterobicycloalkyl, heterospiroalkyl, —C$_{1-6}$alkyl-heterocycloalkyl, —(C=O)-heterocycloalkyl, —NH-heterocycloalkyl, or heteroaryl in which the heterocycloalkyl, heterobicycloalkyl, heterospiroalkyl, —C$_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the heterocycloalkyl, heterobicycloalkyl, heterospiroalkyl, —C$_{1-6}$alkyl-heterocycloalkyl, —(C=O)-heterocycloalkyl, —NH-heterocycloalkyl, or heteroaryl ring may be substituted with —C$_{1-6}$alkyl, —C$_{1-6}$aminoalkyl, —C$_{1-6}$haloalkyl, —C$_{1-6}$alkenyl, —C$_{1-6}$alkynyl, —C(=O)—C$_{1-6}$alkyl, —C$_{1-6}$alkyl-S(=O)$_2$—C$_{1-6}$alkyl, =O, —NR$_9$R$_{10}$, -halo, cycloalkyl, or Z$_2$;

R$_9$ and R$_{10}$ are each independently —H or —C$_{1-6}$alkyl;

Z$_2$ is heterocycloalkyl, heterobicycloalkyl, or —NH-heterocycloalkyl in which the heterocycloalkyl, heterobicycloalkyl, or —NH-heterocycloalkyl contains, in the ring, at least one selected from the group consisting of N, O, P, P(=O) and S, and at least one H of the heterocycloalkyl, heterobicycloalkyl, or —NH-heterocycloalkyl ring may be substituted with —C$_{1-6}$alkyl, —C$_{1-6}$hydroxyalkyl, —C$_{1-6}$alkenyl, —C$_{1-6}$alkynyl, —C(=O)—C$_{1-6}$alkyl, —C$_{1-6}$alkyl-S(=O)$_2$—C$_{1-6}$alkyl, =O, —NR$_{11}$R$_{12}$, cycloalkyl, or Z$_3$;

R$_{11}$ and R$_{12}$ are each independently —H or —C$_{1-6}$alkyl; and

Z$_3$ is heterocycloalkyl, heterobicycloalkyl, or —C$_{1-6}$alkyl-heterocycloalkyl in which the heterocycloalkyl, heterobicycloalkyl, or —C$_{1-6}$alkyl-heterocycloalkyl contains, in the ring, at least one selected from the group consisting of N, O, P, P(=O) and S, and at least one H of the heterocycloalkyl, heterobicycloalkyl, or —C$_{1-6}$alkyl-heterocycloalkyl ring may be substituted with —C$_{1-6}$alkyl or cycloalkyl.

3. The compound represented by Chemical Formula I, the optical isomer thereof, or the pharmaceutically acceptable salt thereof of claim 1, wherein X$_1$ is N;

X$_2$ and X$_3$ are each independently CH or N; and

R$_X$ is —H, —NH$_2$, or —NH(—C$_{1-6}$alkyl).

4. The compound represented by Chemical Formula I, the optical isomer thereof, or the pharmaceutically acceptable salt thereof of claim 1, wherein Y is —C$_{1-6}$alkyl, —(CH$_2$)$_n$aryl, —(CH$_2$)$_n$heteroaryl, or —(CH$_2$)$_n$hydroheteroaryl in which at least one H of the —(CH$_2$)$_n$aryl, —(CH$_2$)$_n$heteroaryl, or —(CH$_2$)$_n$hydroheteroaryl ring may be substituted with —C$_{1-6}$alkyl, —C$_{1-6}$haloalkyl, —C$_{1-6}$alkynyl, —CN, —(C=O)NH-cycloalkyl, —(C=O)O—C$_{1-6}$alkyl, —N(C$_{1-6}$alkyl)(C$_{1-6}$alkyl), —O(C$_{1-6}$alkyl), —O-phenyl, -halo, =O, heterocycloalkyl, aryl, or heteroaryl, wherein at least one H of the heterocycloalkyl, aryl, or heteroaryl may be substituted with -halo;

n is 0 or 1; and

R$_{Y1}$ to R$_{Y5}$ are each independently —H or —C$_{1-6}$alkyl, or R$_{Y2}$ and R$_{Y3}$ may be linked to each other to form 3- to 6-membered cycloalkyl, and R$_{Y3}$ and R$_{Y4}$ may be linked to each other to form phenyl.

5. The compound represented by Chemical Formula I, the optical isomer thereof, or the pharmaceutically acceptable salt thereof of claim 1, wherein L is —(CH$_2$)m-, —C(=O)—, or null;

m is 0 or 1;

a ring Z is phenyl, 5- to 6-membered heteroaryl, 9- to 10-membered hydroheteroaryl, 3- to 5-membered cycloalkyl, or 6-membered heterocycloalkyl in which at least one H of the phenyl, 5- to 6-membered heteroaryl, 9- to 10-membered hydroheteroaryl, 3- to 5-membered cycloalkyl, or 6-membered heterocycloalkyl ring may be substituted with —$C_{1-6}$alkyl, —$C_{1-6}$cyanoalkyl, —$C_{1-6}$haloalkyl, —$C_{1-6}$alkenyl, —$C_{1-6}$alkynyl, —CN, —O—$C_{1-6}$alkyl, —O—$C_{1-6}$haloalkyl, —S—$C_{1-6}$alkyl, —C(=O)—$C_{1-6}$alkyl, —C(=O)—$C_{1-6}$haloalkyl, —C(=O)O—$C_{1-6}$alkyl, —S(=O)$_2$-$C_{1-6}$ alkyl, —C(=N—O—$C_{1-6}$alkyl)($C_{1-6}$alkyl), =O, -halo, or $Z_1$, wherein at least one H of the phenyl in the meta position relative to the L is unsubstituted or substituted with at least one selected from the group consisting of —$C_{1-6}$alkyl, —$C_{1-6}$cyanoalkyl, —$C_{1-6}$haloalkyl, —$C_{1-6}$alkenyl, —$C_{1-6}$alkynyl, —O—$C_{1-6}$alkyl, —O—$C_{1-6}$haloalkyl, —C(=O)—$C_{1-6}$alkyl, —S(=O)$_2$—$C_{1-6}$alkyl, —C(=N—O—$C_{1-6}$alkyl)($C_{1-6}$alkyl), -halo, and $Z_1$ when the ring Z is phenyl, or two or more substituents of the phenyl, 5- to 6-membered heteroaryl, 9- to 10-membered hydroheteroaryl, 3- to 5-membered cycloalkyl, or 6-membered heterocycloalkyl ring may be linked to each other to form a fused ring or a spiro ring, wherein at least one H of the fused ring or spiro ring may be substituted with —$C_{1-6}$alkyl or $Z_1$;

$Z_1$ is 3- to 7-membered cycloalkyl, 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, —NH-heterocycloalkyl, or heteroaryl in which the 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, or —NH-heterocycloalkyl contains, in the ring, at least one selected from the group consisting of N, O, P, P(=O) and S, and at least one H of the 5- to 7-membered heterocycloalkyl, 6- to 10-membered heterobicycloalkyl, 6- to 10-membered heterospiroalkyl, —$C_{1-6}$alkyl-heterocycloalkyl, —(C=O)-heterocycloalkyl, —NH-heterocycloalkyl, or heteroaryl ring may be substituted with —$C_{1-6}$alkyl, —$C_{1-6}$aminoalkyl, —$C_{1-6}$haloalkyl, —$C_{1-6}$alkenyl, —C(=O)—$C_{1-6}$alkyl, —$C_{1-6}$alkyl-S(=O)$_2$—$C_{1-6}$alkyl, =O, —N($C_{1-6}$alkyl)($C_{1-6}$alkyl), -halo, cycloalkyl, or $Z_2$;

$Z_2$ is 5- to 7-membered heterocycloalkyl, 6- to 10-membered heterobicycloalkyl, or —NH-heterocycloalkyl in which the 5- to 7-membered heterocycloalkyl, 6- to 10-membered heterobicycloalkyl, or —NH-heterocycloalkyl contains, in the ring, at least one selected from the group consisting of N, O, and S, and at least one H of the 5- to 7-membered heterocycloalkyl, 6- to 10-membered heterobicycloalkyl, or —NH-heterocycloalkyl ring may be substituted with —$C_{1-6}$alkyl, —$C_{1-6}$hydroxyalkyl, —$C_{1-6}$alkenyl, —$C_{1-6}$alkynyl, —C(=O)—$C_{1-6}$alkyl, —$C_{1-6}$alkyl-S(=O)$_2$—$C_{1-6}$alkyl, =O, —N($C_{1-6}$alkyl)($C_{1-6}$alkyl), 3- to 7-membered cycloalkyl, or $Z_3$; and $Z_3$ is 5- to 7-membered heterocycloalkyl, 6- to 10-membered heterobicycloalkyl, or —$C_{1-6}$alkyl-heterocycloalkyl in which the 5- to 7-membered heterocycloalkyl, 6- to 10-membered heterobicycloalkyl, or —$C_{1-6}$alkyl-heterocycloalkyl contains, in the ring, at least one selected from the group consisting of N, O, and S, and at least one H of the 5- to 7-membered heterocycloalkyl, 6- to 10-membered heterobicycloalkyl, or —$C_{1-6}$alkyl-heterocycloalkyl ring may be substituted with —$C_{1-6}$alkyl or 3- to 7-membered cycloalkyl.

6. A compound, an optical isomer thereof, or a pharmaceutically acceptable salt thereof selected from the group consisting of the following compounds:

(1) (R)—N-(4-(4-methylpiperazin-1-yl)phenyl)-6-(3-phenylisoxazolidin-2-yl)pyrimidin-4-amine;

(2) (S)—N-(4-(4-methylpiperazin-1-yl)phenyl)-6-(3-phenylisoxazolidin-2-yl)pyrimidin-4-amine;

(3) (S)-6-(3-benzylisoxazolidin-2-yl)-N-(4-(4-methylpiperazin-1-yl)phenyl)pyrimidin-4-amine;

(4) (R)—N-(3-methoxy-4-(4-(4-methylpiperazin-1-yl)piperidin-1-yl)phenyl)-6-(3-phenylisoxazolidin-2-yl)pyrimidin-4-amine;

(5) (R)—N-(2-methoxy-4-(4-(4-methylpiperazin-1-yl)piperidin-1-yl)phenyl)-6-(3-phenylisoxazolidin-2-yl)pyrimidin-4-amine;

(6) (R)—N-(4-(4-(4-cyclopropylpiperazin-1-yl)piperidin-1-yl)-2-methoxyphenyl)-6-(3-(3,5-difluorophenyl)isoxazolidin-2-yl)pyrimidin-4-amine;

(7) (R)-6-(3-(3,5-difluorophenyl)isoxazolidin-2-yl)-N-(2-methoxy-5-(1-methyl-1H-pyrazol-4-yl)-4-morpholinophenyl)pyrimidin-4-amine;

(8) (R)-6-(3-(3,5-difluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine;

(9) (R)-6-(3-(3,5-difluorophenyl)isoxazolidin-2-yl)-N-(2-methoxy-5-(1-methyl-1H-pyrazol-5-yl)-4-morpholinophenyl)pyrimidin-4-amine;

(10) (R)-1'-(4-((6-(3-(3,5-difluorophenyl)isoxazolidin-2-yl)pyrimidin-4-yl)amino)-5-methoxy-2-(1-methyl-1H-pyrazol-4-yl)phenyl)-N,N-dimethyl-[1,4'-bipiperidin]-4-amine;

(11) (R)-6-(3-(3,5-difluorophenyl)isoxazolidin-2-yl)-N-(3-(4-(4-methylpiperazin-1-yl)piperidin-1-yl)-5-(methylsulfonyl)phenyl)pyrimidin-4-amine;

(12) (R)-6-(3-(3,5-difluorophenyl)isoxazolidin-2-yl)-N-(3-(methylsulfonyl)-5-(4-morpholinopiperidin-1-yl)phenyl)pyrimidin-4-amine;

(13) (R)-6-(3-(3,5-difluorophenyl)isoxazolidin-2-yl)-N-(3-(4-methylpiperazin-1-yl)-5-(methylsulfonyl)phenyl)pyrimidin-4-amine;

(14) (R)-2-(3-((6-(3-(3,5-difluorophenyl)isoxazolidin-2-yl)pyrimidin-4-yl)amino)-5-((4-methylpiperazin-1-yl)methyl)phenyl)-2-methylpropanenitrile;

(15) (R)-2-(3-((6-(3-(3,5-difluorophenyl)isoxazolidin-2-yl)pyrimidin-4-yl)amino)-5-(4-methylpiperazin-1-yl)phenyl)-2-methylpropanenitrile;

(16) (R)—N-(4-(4-methylpiperazin-1-yl)phenyl)-6-(3-(3-phenoxyphenyl)isoxazolidin-2-yl)pyrimidin-4-amine;

(17) (R)-6-(3-(3,5-difluorophenyl)isoxazolidin-2-yl)-N-(4-(4-(4-methylpiperazin-1-yl)piperidin-1-yl)phenyl)pyrimidin-4-amine;

(18) (R)-6-(3-(3,5-difluorophenyl)isoxazolidin-2-yl)-N-(4-(4-methylpiperazin-1-yl)phenyl)pyrimidin-4-amine;

(19) (R)—$N^1$-(6-(3-(3,5-difluorophenyl)isoxazolidin-2-yl)pyrimidin-4-yl)-$N^4$-(2-(dimethylamino)ethyl)-$N^4$-methylbenzene-1,4-diamine;

(20) (R)-6-(3-(3,5-difluorophenyl)isoxazolidin-2-yl)-N-(2-methoxy-5-methyl-4-(4-(4-methylpiperazin-1-yl)piperidin-1-yl)phenyl)pyrimidin-4-amine;

(21) (R)-6-(3-(3,5-difluorophenyl)isoxazolidin-2-yl)-N-(2-methoxy-4-(4-(4-methylpiperazin-1-yl)piperidin-1-yl)phenyl)pyrimidin-4-amine;

(22) (R)-6-(3-(3,5-difluorophenyl)isoxazolidin-2-yl)-N-(4-(4-(dimethylamino)piperidin-1-yl)-2-methoxyphenyl)pyrimidin-4-amine;
(23) (R)-6-(3-(3,5-difluorophenyl)isoxazolidin-2-yl)-N-(4-(4-(4-methylpiperazin-1-yl)piperidin-1-yl)-3-(trifluoromethyl)phenyl)pyrimidin-4-amine;
(24) (R)-6-(3-(3,5-difluorophenyl)isoxazolidin-2-yl)-N-(4-(4-(4-methylpiperazin-1-yl)piperidin-1-yl)-3-(methylsulfonyl)phenyl)pyrimidin-4-amine;
(25) (R)-6-(3-(3,5-difluorophenyl)isoxazolidin-2-yl)-N-(5-ethyl-2-methoxy-4-(4-(4-methylpiperazin-1-yl)piperidin-1-yl)phenyl)pyrimidin-4-amine;
(26) (R)-6-(3-(3,5-difluorophenyl)isoxazolidin-2-yl)-N-(3-methoxy-4-(4-(4-methylpiperazin-1)-yl)piperidin-1-yl)phenyl)pyrimidin-4-amine;
(27) (R)—N-(2-methoxy-4-(4-(4-methylpiperazin-1-yl)piperidin-1-yl)phenyl)-6-(3-(3-(trifluoromethyl)phenyl)isoxazolidin-2-yl)pyrimidin-4-amine;
(28) (R)-6-(3-(2-fluoro-3-(trifluoromethyl)phenyl)isoxazolidin-2-yl)-N-(2-methoxy-4-(4-(4-methylpiperazin-1-yl)piperidin-1-yl)phenyl)pyrimidin-4-amine;
(29) (R)-6-(3-(3-fluorophenyl)isoxazolidin-2-yl)-N-(2-methoxy-4-(4-(4-methylpiperazin-1-yl)piperidin-1-yl)phenyl)pyrimidin-4-amine;
(30) (R)-6-(3-(2,5-difluorophenyl)isoxazolidin-2-yl)-N-(2-methoxy-4-(4-(4-methylpiperazin-1-yl)piperidin-1-yl)phenyl)pyrimidin-4-amine;
(31) (R)-6-(3-(3-chloro-4-fluorophenyl)isoxazolidin-2-yl)-N-(2-methoxy-4-(4-(4-methylpiperazin-1-yl)piperidin-1-yl)phenyl) pyrimidin-4-amine;
(32) (R)-6-(3-(2,3-difluorophenyl)isoxazolidin-2-yl)-N-(2-methoxy-4-(4-(4-methylpiperazin-1-yl)piperidin-1-yl)phenyl)pyrimidin-4-amine;
(33) (R)-6-(3-(4-fluorophenyl)isoxazolidin-2-yl)-N-(2-methoxy-4-(4-(4-methylpiperazin-1-yl)piperidin-1-yl)phenyl)pyrimidin-4-amine;
(34) (R)-6-(3-(2,4-difluorophenyl)isoxazolidin-2-yl)-N-(2-methoxy-4-(4-(4-methylpiperazin-1-yl)piperidin-1-yl)phenyl)pyrimidin-4-amine;
(35) (R)—N-(2-methoxy-4-(4-(4-methylpiperazin-1-yl)piperidin-1-yl)phenyl)-6-(3-(thiophen-2-yl)isoxazolidin-2-yl)pyrimidin-4-amine;
(36) (R)—N-(2-methoxy-4-(4-(4-methylpiperazin-1-yl)piperidin-1-yl)phenyl)-6-(3-(naphthalen-1-yl)isoxazolidin-2-yl)pyrimidin-4-amine;
(37) (R)-6-(3-(3-ethynylphenyl)isoxazolidin-2-yl)-N-(2-methoxy-4-(4-(4-methylpiperazin-1-yl)piperidin-1-yl)phenyl)pyrimidin-4-amine;
(38) (R)—N-(2-methoxy-4-(4-(4-methylpiperazin-1-yl)piperidin-1-yl)phenyl)-6-(3-(6-methylpyridin-3-yl)isoxazolidin-2-yl)pyrimidin-4-amine;
(39) (R)-6-(3-(3-([1,2,4]triazolo[1,5-a]pyridin-7-yl)phenyl)isoxazolidin-2-yl)-N-(4-(4-methylpiperazin-1-yl)phenyl)pyrimidin-4-amine;
(40) (R)-6-(3-(3-fluoro-5-thiomorpholinophenyl)isoxazolidin-2-yl)-N-(4-(4-methylpiperazin-1-yl)phenyl)pyrimidin-4-amine;
(41) (R)—N-(2-methoxy-4-(4-(4-methylpiperazin-1-yl)piperidin-1-yl)phenyl)-6-(3-(3-methoxyphenyl)isoxazolidin-2-yl)pyrimidin-4-amine;
(42) (R)-6-(3-methyl-3-phenylisoxazolidin-2-yl)-N-(4-(4-methylpiperazin-1-yl)phenyl)pyrimidin-4-amine;
(43) isopropyl (R)-3-(2-(6-((4-(4-methylpiperazin-1-yl)phenyl)amino)pyrimidin-4-yl)isoxazolidin-3-yl)benzoate;
(44) (R)—N-cyclohexyl-3-(2-(6-((4-(4-methylpiperazin-1-yl)phenyl)amino)pyrimidin-4-yl)isoxazolidin-3-yl)benzamide;
(45) (R)-6-(3-(3',5-difluoro-[1,1'-biphenyl]-3-yl)isoxazolidin-2-yl)-N-(4-(4-methylpiperazin-1-yl)phenyl)pyrimidin-4-amine;
(46) (R)—N,N-dimethyl-7-(2-methyl-4-((6-(3-phenylisoxazolidin-2-yl)pyrimidin-4-yl)amino)phenyl)-7-azaspiro[3.5]nonan-2-amine;
(47) (R)—N,N-dimethyl-2-(2-methyl-4-((6-(3-phenylisoxazolidin-2-yl)pyrimidin-4-yl)amino)phenyl)-2-azaspiro[3.5]nonan-7-amine;
(48) (R)-3-(1-methylpiperidin-4-yl)-N-(6-((R)-3-phenylisoxazolidin-2-yl)pyrimidin-4-yl)-1,2,3,4,4a,5-hexahydrobenzo[b]pyrazino[1,2-d][1,4]oxazin-8-amine;
(49) (6aR,8S)-8-(4-cyclopropylpiperazin-1-yl)-2-methoxy-N-(6-((R)-3-phenylisoxazolidin-2-yl)pyrimidin-4-yl)-6,6a,7,8,9,10-hexahydrobenzo[b]pyrido[1,2-d][1,4]oxazin-3-amine;
(50) N-(4-(4-(5-ethylhexahydropyrrolo[3,4-c]pyrrol-2(1H)-yl)piperidin-1-yl)-2-methoxyphenyl)-6-((R)-3-phenylisoxazolidin-2-yl)pyrimidin-4-amine;
(51) (R)—N-(2-methoxy-4-(4-((1-methylpiperidin-4-yl)amino)piperidin-1-yl)phenyl)-6-(3-phenylisoxazolidin-2-yl)pyrimidin-4-amine;
(52) (R)—N-(2-methyl-4-(4-(4-methylpiperazin-1-yl)piperidin-1-yl)phenyl)-6-(3-phenylisoxazolidin-2-yl)pyrimidin-4-amine;
(53) (R)—N-(3-methyl-4-(4-(4-methylpiperazin-1-yl)piperidin-1-yl)phenyl)-6-(3-phenylisoxazolidin-2-yl)pyrimidin-4-amine;
(54) (R)—N-(4-(4-(4-methylpiperazin-1-yl)piperidin-1-yl)phenyl)-6-(3-phenylisoxazolidin-2-yl)pyrimidin-4-amine;
(55) (R)—N-(2-ethoxy-4-(4-(4-methylpiperazin-1-yl)piperidin-1-yl)phenyl)-6-(3-phenylisoxazolidin-2-yl)pyrimidin-4-amine;
(56) N-(4-(4-(4-methylpiperazin-1-yl)piperidin-1-yl)-2-(((R)-1,1,1-trifluoropropan-2-yl)oxy)phenyl)-6-((R)-3-phenylisoxazolidin-2-yl)pyrimidin-4-amine;
(57) N-(2-methoxy-4-(4-((1R,4R)-5-methyl-2,5-diazabicyclo[2.2.1]heptan-2-yl)piperidin-1-yl)phenyl)-6-((R)-3-phenylisoxazolidin-2-yl)pyrimidin-4-amine;
(58) (R)—N-(2-methoxy-4-(4-(oxetan-3-yl)piperazin-1-yl)phenyl)-6-(3-phenylisoxazolidin-2-yl)pyrimidin-4-amine;
(59) N-(4-((1R,4R)-2-oxa-5-azabicyclo[2.2.1]heptan-5-yl)-2-methoxyphenyl)-6-((R)-3-phenylisoxazolidin-2-yl)pyrimidin-4-amine;
(60) (R)-1-(4-(1-(3-methoxy-4-((6-(3-phenylisoxazolidin-2-yl)pyrimidin-4-yl)amino)phenyl)piperidin-4-yl)piperazin-1-yl)ethan-1-one;
(61) (R)—N-(4-(4-(4-cyclopropyl-3,3-dimethylpiperazin-1-yl)piperidin-1-yl)-2-methoxyphenyl)-6-(3-phenylisoxazolidin-2-yl)pyrimidin-4-amine;
(62) (R)—N-(2-methoxy-4-(4-(pyrrolidin-1-yl)piperidin-1-yl)phenyl)-6-(3-phenylisoxazolidin-2-yl)pyrimidin-4-amine;
(63) (R)—N-(4-(4-(4-cyclopropylpiperazin-1-yl)-[1,4'-bipiperidin]-1'-yl)-2-methoxyphenyl)-6-(3-phenylisoxazolidin-2-yl)pyrimidin-4-amine;
(64) (R)—N-(4-(2-(dimethylamino)ethoxy)-2-methoxyphenyl)-6-(3-phenylisoxazolidin-2-yl)pyrimidin-4-amine;

(65) (R)—N-(4-((2-(dimethylamino)ethyl)thio)-2-methoxyphenyl)-6-(3-phenylisoxazolidin-2-yl)pyrimidin-4-amine;
(66) (R)—N-(2-methoxy-4-thiomorpholinophenyl)-6-(3-phenylisoxazolidin-2-yl)pyrimidin-4-amine;
(67) (R)—N-(2-methoxy-4-(4-methyl-1,4-diazepan-1-yl)phenyl)-6-(3-phenylisoxazolidin-2-yl)pyrimidin-4-amine;
(68) (R)—N-(4-(4-allylpiperazin-1-yl)phenyl)-6-(3-phenylisoxazolidin-2-yl)pyrimidin-4-amine;
(69) N-(4-((R)-3-(dimethylamino)pyrrolidin-1-yl)phenyl)-6-((R)-3-phenylisoxazolidin-2-yl)pyrimidin-4-amine;
(70) N-(4-((S)-2-((dimethylamino)methyl)pyrrolidin-1-yl)phenyl)-6-((R)-3-phenylisoxazolidin-2-yl)pyrimidin-4-amine;
(71) (R)—N-(1-(1-(2-(dimethylamino)ethyl)piperidin-4-yl)-1H-pyrazol-4-yl)-6-(3-phenylisoxazolidin-2-yl)pyrimidin-4-amine;
(72) (R)-(4-methylpiperazin-1-yl)(4-((6-(3-phenylisoxazolidin-2-yl)pyrimidin-4-yl)amino)phenyl)methanone;
(73) (R)-6-(3-phenylisoxazolidin-2-yl)-N-(3-(trifluoromethyl)phenyl)pyrimidin-4-amine;
(74) N-(5-((1S,4S)-2-oxa-5-azabicyclo[2.2.1]heptan-5-yl)-2-fluoropyridin-3-yl)-6-((R)-3-phenylisoxazolidin-2-yl)pyrimidin-4-amine;
(75) (R)-1-(4-((6-(3-phenylisoxazolidin-2-yl)pyrimidin-4-yl)amino)phenyl)pyrrolidin-2-one;
(76) (R)-2-methyl-5-((6-(3-phenylisoxazolidin-2-yl)pyrimidin-4-yl)amino)isoindolin-1-one;
(77) (R)-6-(3-phenylisoxazolidin-2-yl)-N-(4-(piperazin-1-yl)phenyl)pyrimidin-4-amine;
(78) (R)—N-(6-(3-phenylisoxazolidin-2-yl)pyrimidin-4-yl)-1,2,3,4-tetrahydroisoquinolin-6-amine;
(79) (R)—N-(5-(4-(dimethylamino)piperidin-1-yl)pyridin-2-yl)-6-(3-phenylisoxazolidin-2-yl)pyrimidin-4-amine;
(80) (R)—N-(8-(1-methyl-1H-pyrazol-5-yl)-2,3-dihydrobenzo[b][1,4]dioxin-5-yl)-6-(3-phenylisoxazolidin-2-yl)pyrimidin-4-amine;
(81) (R)-1-cyclopropyl-4-(3-methoxy-4-((6-(3-phenylisoxazolidin-2-yl)pyrimidin-4-yl)amino)phenyl)-1,4-azaphosphinane 4-oxide;
(82) N-(4-((2R,6S)-2,6-dimethylmorpholino)phenyl)-6-((R)-3-phenylisoxazolidin-2-yl)pyrimidin-4-amine;
(83) 6-((R)-3-phenylisoxazolidin-2-yl)-N—((R)-7-(pyrrolidin-1-yl)-6,7,8,9-tetrahydro-5H-benzo[7]annulen-2-yl)pyrimidin-4-amine;
(84) (R)—N,N-dimethyl-1'-(4-((6-(3-phenylisoxazolidin-2-yl)pyrimidin-4-yl)amino)phenyl)-[1,4'-bipiperidin]-4-amine;
(88) (R)-7-(5-methoxy-2-methyl-4-((6-(3-phenylisoxazolidin-2-yl)pyrimidin-4-yl)amino)phenyl)-N,N-dimethyl-7-azaspiro[3.5]nonan-2-amine;
(89) (R)—N-(2-methoxy-4-(4-(4-methylpiperazin-1-yl)piperidin-1-yl)phenyl)-6-(3-(naphthalen-2-yl)isoxazolidin-2-yl)pyrimidin-4-amine;
(90) (R)-6-(3-(3,4-difluorophenyl)isoxazolidin-2-yl)-N-(2-methoxy-4-(4-(4-methylpiperazin-1-yl)piperidin-1-yl)phenyl)pyrimidin-4-amine;
(91) (R)—N-(5-ethyl-2-methoxy-4-(4-(4-methylpiperazin-1-yl)piperidin-1-yl)phenyl)-6-(3-(4-fluorophenyl)isoxazolidin-2-yl)pyrimidin-4-amine;
(92) (R)-6-(3-(2,3-difluorophenyl)isoxazolidin-2-yl)-N-(5-ethyl-2-methoxy-4-(4-(4-methylpiperazin-1-yl)piperidin-1-yl)phenyl)pyrimidin-4-amine;
(93) (R)-6-(3-(2,4-difluorophenyl)isoxazolidin-2-yl)-N-(5-ethyl-2-methoxy-4-(4-(4-methylpiperazin-1-yl)piperidin-1-yl)phenyl)pyrimidin-4-amine;
(94) (R)-6-(3-(2,5-difluorophenyl)isoxazolidin-2-yl)-N-(5-ethyl-2-methoxy-4-(4-(4-methylpiperazin-1-yl)piperidin-1-yl)phenyl)pyrimidin-4-amine;
(95) (R)-6-(3-(2,4-difluorophenyl)isoxazolidin-2-yl)-N-(3-methoxy-4-(4-(4-methylpiperazin-1-yl)piperidin-1-yl)phenyl)pyrimidin-4-amine;
(96) (R)-6-(3-(4-fluorophenyl)isoxazolidin-2-yl)-N-(3-methoxy-4-(4-(4-methylpiperazin-1-yl)piperidin-1-yl)phenyl)pyrimidin-4-amine;
(97) N-(4-(4-((1R,4R)-2-oxa-5-azabicyclo[2.2.1]heptan-5-yl)piperidin-1-yl)-2-methoxyphenyl)-6-((R)-3-phenylisoxazolidin-2-yl)pyrimidin-4-amine;
(98) (R)—N-(4-(4-(diethylamino)piperidin-1-yl)-2-methoxyphenyl)-6-(3-phenylisoxazolidin-2-yl)pyrimidin-4-amine;
(99) N-(2-methoxy-4-((R)-2-methyl-4-(1-methylpiperidin-4-yl)piperazin-1-yl)phenyl)-6-((R)-3-phenylisoxazolidin-2-yl)pyrimidin-4-amine;
(100) isopropyl (R)-3-(2-(6-((2-methoxy-4-(4-(4-methylpiperazin-1-yl)piperidin-1-yl)phenyl)amino)pyrimidin-4-yl)isoxazolidin-3-yl)benzoate;
(101) (R)—N-(2-methoxy-4-(4-(1-methylpiperidin-4-yl)piperazin-1-yl)phenyl)-6-(3-phenylisoxazolidin-2-yl)pyrimidin-4-amine;
(102) (R)—N-(3-methoxy-4-(4-(1-methylpiperidin-4-yl)piperazin-1-yl)phenyl)-6-(3-phenylisoxazolidin-2-yl)pyrimidin-4-amine;
(103) (R)-6-(3-(2,5-difluorophenyl)isoxazolidin-2-yl)-N-(3-methyl-4-(4-(4-methylpiperazin-1-yl)piperidin-1-yl)phenyl)pyrimidin-4-amine;
(104) (R)-6-(3-(2,4-difluorophenyl)isoxazolidin-2-yl)-N-(3-methyl-4-(4-(4-methylpiperazin-1-yl)piperidin-1-yl)phenyl)pyrimidin-4-amine;
(105) (R)-6-(3-(4-chloro-2-fluorophenyl)isoxazolidin-2-yl)-N-(3-methoxy-4-(4-(4-methylpiperazin-1-yl)piperidin-1-yl)phenyl)pyrimidin-4-amine;
(106) (R)-6-(3-(2,5-difluorophenyl)isoxazolidin-2-yl)-N-(3-methoxy-4-(4-(4-methylpiperazin-1-yl)piperidin-1-yl)phenyl)pyrimidin-4-amine;
(107) (R)—N-(3-methyl-4-(4-methylpiperazin-1-yl)phenyl)-6-(3-phenylisoxazolidin-2-yl)pyrimidin-4-amine;
(108) (R)—N-(2-methyl-4-morpholinophenyl)-6-(3-phenylisoxazolidin-2-yl)pyrimidin-4-amine;
(109) (R)—N-(5-ethyl-2-methoxy-4-(4-(4-methylpiperazin-1-yl)piperidin-1-yl)phenyl)-6-(3-phenylisoxazolidin-2-yl)pyrimidin-4-amine;
(110) (R)—N-(2-methoxy-4-morpholinophenyl)-6-(3-phenylisoxazolidin-2-yl)pyrimidin-4-amine;
(111) (R)—N4-(2-methoxy-4-(4-(4-methylpiperazin-1-yl)piperidin-1-yl)phenyl)-6-(3-phenylisoxazolidin-2-yl)pyrimidin-2,4-diamine;
(112) (R)—N-(2-methoxy-4-(4-(4-methylpiperazin-1-yl)piperidin-1-yl)phenyl)-4-(3-phenylisoxazolidin-2-yl)-1,3,5-triazin-2-amine;
(113) (R)-2-methoxy-N4-(1-methylpiperidin-4-yl)-$N^1$-(6-(3-phenylisoxazolidin-2-yl)pyrimidin-4-yl)benzene-1,4-diamine;
(114) (R)—N-(2-methoxy-5-methyl-4-(4-(4-methylpiperazin-1-yl)piperidin-1-yl)phenyl)-6-(3-phenylisoxazolidin-2-yl)pyrimidin-4-amine;
(115) (R)-1'-(3-methoxy-4-((6-(3-phenylisoxazolidin-2-yl)pyrimidin-4-yl)amino)phenyl)-N,N-dimethyl-[1,4'-bipiperidin]-4-amine;

(116) N-(4-(4-(((1R,4R)-5-ethyl-2,5-diazabicyclo[2.2.1]heptan-2-yl)piperidin-1-yl)-2-methoxyphenyl)-6-((R)-3-phenylisoxazolidin-2-yl)pyrimidin-4-amine;

(117) (R)—N-(3-ethyl-4-(4-(4-methylpiperazin-1-yl)piperidin-1-yl)phenyl)-6-(3-phenylisoxazolidin-2-yl)pyrimidin-4-amine;

(118) (R)—N-(4-(4-(4-ethylpiperazin-1-yl)piperidin-1-yl)-2-methoxyphenyl)-6-(3-phenylisoxazolidin-2-yl)pyrimidin-4-amine;

(119) (R)—N-(4-(4-(dimethylamino)piperidin-1-yl)-2-methoxyphenyl)-6-(3-phenylisoxazolidin-2-yl)pyrimidin-4-amine;

(120) (R)—N-(2-methoxy-4-(4-morpholinopiperidin-1-yl)phenyl)-6-(3-phenylisoxazolidin-2-yl)pyrimidin-4-amine;

(121) (R)-2-(4-(1-(2-methoxy-4-((6-(3-phenylisoxazolidin-2-yl)pyrimidin-4-yl)amino)phenyl)piperidin-4-yl)piperazin-1-yl)ethan-1-ol;

(122) (R)-1-(4-(4-((6-(3-phenylisoxazolidin-2-yl)pyrimidin-4-yl)amino)phenyl)piperazin-1-yl)ethan-1-one;

(123) (R)—N-(3,5-difluoro-4-(4-(4-methylpiperazin-1-yl)piperidin-1-yl)phenyl)-6-(3-phenylisoxazolidin-2-yl)pyrimidin-4-amine;

(124) (R)—N-(4-(4-(oxetan-3-yl)piperazin-1-yl)phenyl)-6-(3-phenylisoxazolidin-2-yl)pyrimidin-4-amine;

(125) (R)-6-(3-(3-chloro-2-fluorophenyl)isoxazolidin-2-yl)-N-(3-methoxy-4-(4-(4-methylpiperazin-1-yl)piperidin-1-yl)phenyl)pyrimidin-4-amine;

(126) (R)-6-(3-(2,3-difluorophenyl)isoxazolidin-2-yl)-N-(3-methyl-4-(4-(4-methylpiperazin-1-yl)piperidin-1-yl)phenyl)pyrimidin-4-amine;

(127) (R)—N-(4-(4-(dimethylamino)piperidin-1-yl)phenyl)-6-(3-phenylisoxazolidin-2-yl)pyrimidin-4-amine;

(128) (R)-6-(3-(2,3-difluorophenyl)isoxazolidin-2-yl)-N-(3-methoxy-4-(4-(4-methylpiperazin-1-yl)piperidin-1-yl)phenyl)pyrimidin-4-amine;

(129) (R)-6-(3-(4-chloro-3-fluorophenyl)isoxazolidin-2-yl)-N-(2-methoxy-4-(4-(4-methylpiperazin-1-yl)piperidin-1-yl)phenyl)pyrimidin-4-amine;

(130) (R)-6-(3-(3-chloro-2,4-difluorophenyl)isoxazolidin-2-yl)-N-(2-methoxy-4-(4-(4-methylpiperazin-1-yl)piperidin-1-yl)phenyl)pyrimidin-4-amine;

(131) (R)-6-(3-(3-(dimethylamino)phenyl)isoxazolidin-2-yl)-N-(2-methoxy-4-(4-(4-methylpiperazin-1-yl)piperidin-1-yl)phenyl)pyrimidin-4-amine;

(132) (R)—N-(5-chloro-2-methoxy-4-(4-(4-methylpiperazin-1-yl)piperidin-1-yl)phenyl)-6-(3-phenylisoxazolidin-2-yl)pyrimidin-4-amine;

(133) (R)—N-(1-methyl-1H-pyrazol-4-yl)-6-(3-phenylisoxazolidin-2-yl)pyrimidin-4-amine;

(134) tert-butyl (R)-7-((6-(3-phenylisoxazolidin-2-yl)pyrimidin-4-yl)amino)-3,4-dihydroisoquinoline-2(1H)-carboxylate;

(135) (R)—N-(4-(9-methyl-3,9-diazaspiro[5.5]undecan-3-yl)phenyl)-6-(3-phenylisoxazolidin-2-yl)pyrimidin-4-amine;

(136) N-(4-(6-methyl-3,6-diazabicyclo[3.1.1]heptan-3-yl)phenyl)-6-((R)-3-phenylisoxazolidin-2-yl)pyrimidin-4-amine;

(137) (R)-3-(3-methoxy-4-((6-(3-phenylisoxazolidin-2-yl)pyrimidin-4-yl)amino)phenyl)oxazolidin-2-one;

(139) (R)—N-(4-(4-methylpiperazin-1-yl)-3-(2,2,2-trifluoroethoxy)phenyl)-6-(3-phenylisoxazolidin-2-yl)pyrimidin-4-amine;

(140) 6-((R)-3-(2,3-difluorophenyl)isoxazolidin-2-yl)-N-(4-(3-fluoro-4-methylpiperazin-1-yl)piperidin-1-yl)-2-methoxyphenyl)pyrimidin-4-amine;

(141) (R)-6-(3-(2,3-difluorophenyl)isoxazolidin-2-yl)-N-(2-methoxy-4-(1-methylpiperidin-4-yl)phenyl)pyrimidin-4-amine;

(142) (R)-6-(3-(2,3-difluorophenyl)isoxazolidin-2-yl)-N-(5-isopropyl-2-methoxy-4-(4-(4-methylpiperazin-1-yl)piperidin-1-yl)phenyl)pyrimidin-4-amine;

(143) (R)—N-(5-cyclopropyl-2-methoxy-4-(4-(4-methylpiperazin-1-yl)piperidin-1-yl)phenyl)-6-(3-phenylisoxazolidin-2-yl)pyrimidin-4-amine;

(144) (R)—N-(4-(4-methylpiperazin-1-yl)-2-(3-((methylsulfonyl)methyl)azetidin-1-yl)phenyl)-6-(3-phenylisoxazolidin-2-yl)pyrimidin-4-amine;

(145) (R)-1-(5-((6-(3-(2,3-difluorophenyl)isoxazolidin-2-yl)pyrimidin-4-yl)amino)-4-methoxy-2-(4-(4-methylpiperazin-1-yl)piperidin-1-yl)phenyl)ethan-1-one;

(146) (R,E)-1-(5-((6-(3-(2,3-difluorophenyl)isoxazolidin-2-yl)pyrimidin-4-yl)amino)-4-methoxy-2-(4-(4-methylpiperazin-1-yl)piperidin-1-yl)phenyl)ethan-1-one O-methyl oxime;

(147) (R)—N-(2-methoxy-5-(1-methyl-1H-pyrazol-4-yl)-6-(4-(4-methylpiperazin-1-yl)piperidin-1-yl)pyridin-3-yl)-6-(3-phenylisoxazolidin-2-yl)pyrimidin-4-amine;

(148) (R)-6-(3-(4-fluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine;

(149) (R)-6-(3-(2,3-difluorophenyl)isoxazolidin-2-yl)-N-(2-methoxy-5-(1-methyl-1H-pyrazol-4-yl)-4-(4-(4-methylpiperazin-1-yl)piperidin-1-yl)phenyl)pyrimidin-4-amine;

(150) (R)—N-(6-(3-(3,5-difluorophenyl)isoxazolidin-2-yl)pyrimidin-4-yl)-5'-methoxyspiro[cyclopropane-1,3'-indoline]-6'-amine;

(151) (R)-6'-((6-(3-(3,5-difluorophenyl)isoxazolidin-2-yl)pyrimidin-4-yl)amino)-5'-methoxyspiro[cyclopropane-1,3'-indolin]-2'-one;

(152) (R)-1-(6-((6-(3-(3,5-difluorophenyl)isoxazolidin-2-yl)pyrimidin-4-yl)amino)-5-methoxy-1'-methylspiro[indolin-3,4'-piperidin]-1-yl)-2,2,2-trifluoroethan-1-one;

(153) (R)-6-((6-(3-(3,5-difluorophenyl)isoxazolidin-2-yl)pyrimidin-4-yl)amino)-7-methoxyspiro[benzo[b][1,4]oxazin-2,1'-cyclopropane]-3(4H)-one;

(154) (R)—N-(6-(3-(3,5-difluorophenyl)isoxazolidin-2-yl)pyrimidin-4-yl)-5-methoxy-1'-methylspiro[indolin-3,4'-piperidin]-6-amine;

(155) (R)-6-(3-(3,5-difluorophenyl)isoxazolidin-2-yl)-N-(4-(1-methylpiperidin-4-yl)-2,3-dihydrobenzofuran-7-yl)pyrimidin-4-amine;

(156) (R)—N-(6-(3-(3,5-difluorophenyl)isoxazolidin-2-yl)pyrimidin-4-yl)-3-methoxy-7-(4-methylpiperazin-1-yl)-9H-carbazol-2-amine;

(157) (R)-6-(3-(3,5-difluorophenyl)isoxazolidin-2-yl)-N-(4-(piperidin-4-yl)-2,3-dihydrobenzofuran-7-yl)pyrimidin-4-amine;

(158) (R)-6-(3-(3,5-difluorophenyl)isoxazolidin-2-yl)-N-(4-(1-methyl-1H-pyrazol-5-yl)-2,3-dihydrobenzofuran-7-yl)pyrimidin-4-amine;

(159) (R)-6-(3-(3,5-difluorophenyl)isoxazolidin-2-yl)-N-(2,3-dihydrobenzofuran-7-yl)pyrimidin-4-amine;

(160) (R)-6-(3-(3,5-difluorophenyl)isoxazolidin-2-yl)-N-(4-(1-(1-methylpiperidin-4-yl)-1H-pyrazol-4-yl)-2,3-dihydrobenzofuran-7-yl)pyrimidin-4-amine;

(162) (R)—N-(5-(1-methyl-1H-pyrazol-4-yl)-4-(4-methylpiperazin-1-yl)-2,3-dihydrobenzofuran-7-yl)-6-(3-phenylisoxazolidin-2-yl)pyrimidin-4-amine;

(164) (R)—N-(5-(1-methyl-1H-pyrazol-4-yl)-4-(4-(4-methylpiperazin-1-yl)piperidin-1-yl)-2-(2,2,2-trifluoroethoxy)phenyl)-6-(3-phenylisoxazolidin-2-yl)pyrimidin-4-amine;

(165) (R)—N-(5-(1-methyl-1H-pyrazol-4-yl)-4-(4-morpholinopiperidin-1-yl)-2-(2,2,2-trifluoroethoxy)phenyl)-6-(3-phenylisoxazolidin-2-yl)pyrimidin-4-amine;

(166) (R)—N-(5-(1-methyl-1H-pyrazol-4-yl)-4-(4-methylpiperazin-1-yl)-2-(2,2,2-trifluoroethoxy)phenyl)-6-(3-phenylisoxazolidin-2-yl)pyrimidin-4-amine;

(167) (R)—N-(5-(1-methyl-1H-pyrazol-4-yl)-4-morpholino-2-(2,2,2-trifluoroethoxy)phenyl)-6-(3-phenylisoxazolidin-2-yl)pyrimidin-4-amine;

(168) (S)-6-(3-(5-fluoropyridin-3-yl)isoxazolidin-2-yl)-N-(2-methoxy-4-(4-(4-methylpiperazin-1-yl)piperidin-1-yl)phenyl)pyrimidin-4-amine;

(169) (R)-6-(3-(5-fluoropyridin-3-yl)isoxazolidin-2-yl)-N-(2-methoxy-4-(4-(4-methylpiperazin-1-yl)piperidin-1-yl)phenyl)pyrimidin-4-amine;

(170) (R)-3-fluoro-5-(2-(6-((2-methoxy-4-(4-(4-methylpiperazin-1-yl)piperidin-1-yl)phenyl)amino)pyrimidin-4-yl)isoxazolidin-3-yl)benzonitrile;

(171) (S)-3-fluoro-5-(2-(6-((2-methoxy-4-(4-(4-methylpiperazin-1-yl)piperidin-1-yl)phenyl)amino)pyrimidin-4-yl)isoxazolidin-3-yl)benzonitrile;

(172) tert-butyl (R)-3-(4-((6-((R)-3-(2,3-difluorophenyl)isoxazolidin-2-yl)pyrimidin-4-yl)amino)phenyl)isoxazolidin-2-carboxylate;

(173) 6-((R)-3-(2,3-difluorophenyl)isoxazolidin-2-yl)-N-(4-((R)-2-methylisoxazolidin-3-yl)phenyl)pyrimidin-4-amine;

(174) 6-((R)-3-(2,3-difluorophenyl)isoxazolidin-2-yl)-N-(4-((R)-isoxazolidin-3-yl)phenyl)pyrimidin-4-amine;

(175) tert-butyl (S)-3-(4-((6-((R)-3-(2,3-difluorophenyl)isoxazolidin-2-yl)pyrimidin-4-yl)amino)phenyl)isoxazolidin-2-carboxylate;

(176) 6-((R)-3-(2,3-difluorophenyl)isoxazolidin-2-yl)-N-(4-((S)-2-methylisoxazolidin-3-yl)phenyl)pyrimidin-4-amine;

(177) 6-((R)-3-(2,3-difluorophenyl)isoxazolidin-2-yl)-N-(4-((S)-isoxazolidin-3-yl)phenyl)pyrimidin-4-amine;

(178) (R)-6-(3-(1-methyl-1H-pyrazol-4-yl)isoxazolidin-2-yl)-N-(4-(4-methylpiperazin-1-yl)phenyl)pyrimidin-4-amine;

(179) (R)-6-(3-(furan-2-yl)isoxazolidin-2-yl)-N-(4-(4-methylpiperazin-1-yl)phenyl)pyrimidin-4-amine;

(180) (R)-6-(3-(5-chloropyridin-3-yl)isoxazolidin-2-yl)-N-(4-(4-methylpiperazin-1-yl)phenyl)pyrimidin-4-amine;

(181) (S)-6-(3-(5-chloropyridin-3-yl)isoxazolidin-2-yl)-N-(4-(4-methylpiperazin-1-yl)phenyl)pyrimidin-4-amine;

(182) (R)-6-(3-(5-chloropyridin-3-yl)isoxazolidin-2-yl)-N-(2-methoxy-4-(4-(4-methylpiperazin-1-yl)piperidin-1-yl)phenyl)pyrimidin-4-amine;

(183) (S)-6-(3-(5-chloropyridin-3-yl)isoxazolidin-2-yl)-N-(2-methoxy-4-(4-(4-methylpiperazin-1-yl)piperidin-1-yl)phenyl)pyrimidin-4-amine;

(184) (R)-6-(3-(3-(difluoromethyl)phenyl)isoxazolidin-2-yl)-N-(2-methoxy-4-(4-(4-methylpiperazin-1-yl)piperidin-1-yl)phenyl)pyrimidin-4-amine;

(185) (S)-6-(3-(3-(difluoromethyl)phenyl)isoxazolidin-2-yl)-N-(2-methoxy-4-(4-(4-methylpiperazin-1-yl)piperidin-1-yl)phenyl)pyrimidin-4-amine;

(186) tert-butyl (R)-3-(3-((6-((R)-3-(2,3-difluorophenyl)isoxazolidin-2-yl)pyrimidin-4-yl)amino)phenyl)isoxazolidin-2-carboxylate;

(187) tert-butyl (S)-3-(3-((6-((R)-3-(2,3-difluorophenyl)isoxazolidin-2-yl)pyrimidin-4-yl)amino)phenyl)isoxazolidin-2-carboxylate;

(188) (R)—N-(6-(3-(2,3-difluorophenyl)isoxazolidin-2-yl)pyrimidin-4-yl)cyclopropanecarboxamide;

(189) (R)—N-(6-(3-(2,3-difluorophenyl)isoxazolidin-2-yl)pyrimidin-4-yl)benzamide;

(190) (R)—N-(cyclopentylmethyl)-6-(3-(2,3-difluorophenyl)isoxazolidin-2-yl)pyrimidin-4-amine;

(191) (R)-6-(3-(2,3-difluorophenyl)isoxazolidin-2-yl)-N-(4-fluorobenzyl)pyrimidin-4-amine;

(192) (R)-6-(3-(2,3-difluorophenyl)isoxazolidin-2-yl)-N-(1-(methylsulfonyl)piperidin-4-yl)pyrimidin-4-amine;

(193) (R)-6-((6-(3-(2,3-difluorophenyl)isoxazolidin-2-yl)pyrimidin-4-yl)amino)-5-methoxy-2-methylisoindolin-1-one;

(194) (R)-3-((6-(3-(2,3-difluorophenyl)isoxazolidin-2-yl)pyrimidin-4-yl)amino)-1H-indazol-6-carbonitrile;

(195) (R)-6-(3-(2,3-difluorophenyl)isoxazolidin-2-yl)-N-(4-(9-(1-fluoro-2-methylpropan-2-yl)-3,9-diazaspiro[5.5]undecan-3-yl)-2-methoxy-5-(1-methyl-1H-pyrazol-4-yl)phenyl)pyrimidin-4-amine;

(196) (R)—N-(2,5-dichloro-4-(9-(1-fluoro-2-methylpropan-2-yl)-3,9-diazaspiro[5.5]undecan-3-yl)phenyl)-6-(3-(2,3-difluorophenyl)isoxazolidin-2-yl)pyrimidin-4-amine;

(197) (R)-6-(3-(2,3-difluorophenyl)isoxazolidin-2-yl)-N-(3-methyl-5-(3-((methylsulfonyl)methyl)azetidin-1-yl)-4-(4-morpholinopiperidin-1-yl)phenyl)pyrimidin-4-amine;

(198) (R)—N-(5-(3-chloro-1-methyl-1H-pyrazol-4-yl)-2-methoxy-4-(4-methylpiperazin-1-yl)phenyl)-6-(3-(2,3-difluorophenyl)isoxazolidin-2-yl)pyrimidin-4-amine;

(199) (R)-6-(3-(2,3-difluorophenyl)isoxazolidin-2-yl)-N-(2-methoxy-4-(4-methylpiperazin-1-yl)-5-vinylphenyl)pyrimidin-4-amine;

(200) (R)-6-(3-(2,3-difluorophenyl)isoxazolidin-2-yl)-N-(5-ethynyl-2-methoxy-4-(4-methylpiperazine-1-yl)phenyl)pyrimidin-4-amine;

(201) (R)-6-(3-(2,3-difluorophenyl)isoxazolidin-2-yl)-N-(3-methoxy-6-(1-methyl-1H-pyrazol-4-yl)-5-(4-methylpiperazin-1-yl)pyridin-2-yl)pyrimidin-4-amine;

(202) (R)-6-(3-(2,3-difluorophenyl)isoxazolidin-2-yl)-N-(2-methoxy-5-(1-methyl-1H-pyrazol-4-yl)-6-(4-methylpiperazin-1-yl)pyridin-3-yl)pyrimidin-4-amine;

(203) 6-((R)-3-(2,3-difluorophenyl)isoxazolidin-2-yl)-N-(3-(1-methyl-1H-pyrazol-4-yl)-5-((2R,3S)-2-methyl-3-((methylsulfonyl)methyl)azetidin-1-yl)-4-morpholinophenyl)pyrimidin-4-amine;

(204) (R)-6-(3-(2,3-difluorophenyl)isoxazolidin-2-yl)-N4-(2-methoxy-4-(4-(4-methylpiperazin-1-yl)piperidin-1-yl)phenyl)-N2-methylpyrimidin-2,4-diamine;

(205) (R)-4-(3-(2,3-difluorophenyl)isoxazolidin-2-yl)-N-(2-methoxy-4-(4-(4-methylpiperazin-1-yl)piperidin-1-yl)phenyl)pyridin-2-amine;

(206) (R)—N-(4-(4-(4-allylpiperazin-1-yl)piperidin-1-yl)-2-methoxyphenyl)-6-(3-(2,3-difluorophenyl)isoxazolidin-2-yl)pyrimidin-4-amine;

(207) (R)-6-(3-(2,3-difluorophenyl)isoxazolidin-2-yl)-N-(4-(4-(4-ethylpiperazin-1-yl)piperidin-1-yl)-2-methoxyphenyl)pyrimidin-4-amine;

(208) (R)—N-(4-(4-(4-cyclobutylpiperazin-1-yl)piperidin-1-yl)-2-methoxyphenyl)-6-(3-(2,3-difluorophenyl)isoxazolidin-2-yl)pyrimidin-4-amine;

(209) (R)-6-(3-(2,3-difluorophenyl)isoxazolidin-2-yl)-N-(2-methoxy-4-(4-(4-(oxetan-3-yl)piperazin-1-yl)piperidin-1-yl)phenyl)pyrimidin-4-amine;

(210) (R)—N-(4-(4-(4-(cyclopropylmethyl)piperazin-1-yl)piperidin-1-yl)-2-methoxyphenyl)-6-(3-(2,3-difluorophenyl)isoxazolidin-2-yl)pyrimidin-4-amine;

(211) (R)-6-(3-(2,3-difluorophenyl)isoxazolidin-2-yl)-N-(2-methoxy-4-(4-(6-methyl-2,6-diazaspiro[3.3]heptan-2-yl)piperidin-1-yl)phenyl)pyrimidin-4-amine;

(212) 6-((R)-3-(2,3-difluorophenyl)isoxazolidin-2-yl)-N-(4-(4-((R)-3-(dimethylamino)pyrrolidin-1-yl)piperidin-1-yl)-2-methoxyphenyl)pyrimidin-4-amine;

(213) 6-((R)-3-(2,3-difluorophenyl)isoxazolidin-2-yl)-N-(4-(4-((R)-3,4-dimethylpiperazin-1-yl)piperidin-1-yl)-2-methoxyphenyl)pyrimidin-4-amine;

(214) 6-((R)-3-(2,3-difluorophenyl)isoxazolidin-2-yl)-N-(4-(4-((S)-3,4-dimethylpiperazin-1-yl)piperidin-1-yl)-2-methoxyphenyl)pyrimidin-4-amine;

(215) 6-((R)-3-(2,3-difluorophenyl)isoxazolidin-2-yl)-N-(4-(4-((3S,5R)-4-ethyl-3,5-dimethylpiperazin-1-yl)piperidin-1-yl)-2-methoxyphenyl)pyrimidin-4-amine;

(216) 6-((R)-3-(2,3-difluorophenyl)isoxazolidin-2-yl)-N-(4-(4-((S)-2,4-dimethylpiperazin-1-yl)piperidin-1-yl)-2-methoxyphenyl)pyrimidin-4-amine;

(217) 6-((R)-3-(2,3-difluorophenyl)isoxazolidin-2-yl)-N-(4-(4-((R)-2,4-dimethylpiperazin-1-yl)piperidin-1-yl)-2-methoxyphenyl)pyrimidin-4-amine;

(218) (R)-6-(3-(2,3-difluorophenyl)isoxazolidin-2-yl)-N-(2-methoxy-4-(3-(4-methylpiperazin-1-yl)azetidin-1-yl)phenyl)pyrimidin-4-amine;

(219) 6-((R)-3-(2,3-difluorophenyl)isoxazolidin-2-yl)-N-(4-(4-(6-ethyl-3,6-diazabicyclo[3.1.1]heptan-3-yl)piperidin-1-yl)-2-methoxyphenyl)pyrimidin-4-amine;

(220) 6-((R)-3-(2,3-difluorophenyl)isoxazolidin-2-yl)-N-(4-(4-(3-ethyl-3,6-diazabicyclo[3.1.1]heptan-6-yl)piperidin-1-yl)-2-methoxyphenyl)pyrimidin-4-amine;

(221) (R)-6-(3-(2,3-difluorophenyl)isoxazolidin-2-yl)-N-(2-methoxy-4-(4-(4-methyl-1,4-diazepan-1-yl)piperidin-1-yl)phenyl)pyrimidin-4-amine;

(222) (R)-6-(3-(2,3-difluorophenyl)isoxazolidin-2-yl)-N-(4-(4-(4-isopropylpiperazin-1-yl)piperidin-1-yl)-2-methoxyphenyl)pyrimidin-4-amine;

(223) (R)-1-(1-(4-((6-(3-(2,3-difluorophenyl)isoxazolidin-2-yl)pyrimidin-4-yl)amino)-3-methoxyphenyl)piperidin-4-yl)-4-methylpiperazin-2-one;

(224) (R)-4-(1-(4-((6-(3-(2,3-difluorophenyl)isoxazolidin-2-yl)pyrimidin-4-yl)amino)-3-methoxyphenyl)piperidin-4-yl)-1-methylpiperazin-2-one;

(225) (R)-1-methyl-5-(2-(6-((4-(4-methylpiperazin-1-yl)phenyl)amino)pyrimidin-4-yl)isoxazolidin-3-yl)pyridin-2(1H)-one;

(226) (R)-5-(2-(6-((2-methoxy-4-(4-(4-methylpiperazin-1-yl)piperidin-1-yl)phenyl)amino)pyrimidin-4-yl)isoxazolidin-3-yl)-1-methylpyridin-2(1H)-one;

(227) (S)-1-methyl-5-(2-(6-((4-(4-methylpiperazin-1-yl)phenyl)amino)pyrimidin-4-yl)isoxazolidin-3-yl)pyridin-2(1H)-one;

(228) (S)-5-(2-(6-((2-methoxy-4-(4-(4-methylpiperazin-1-yl)piperidin-1-yl)phenyl)amino)pyrimidin-4-yl)isoxazolidin-3-yl)-1-methylpyridin-2(1H)-one;

(229) N-(4-(4-methylpiperazin-1-yl)phenyl)-6-(3-phenylbenzo[d]isoxazol-2(3H)-yl)pyrimidin-4-amine;

(230) N-(2-methoxy-4-(4-(4-methylpiperazin-1-yl)piperidin-1-yl)phenyl)-6-(3-phenylbenzo[d]isoxazol-2(3H)-yl)pyrimidin-4-amine;

(231) (S)—N-(4-(4-methylpiperazin-1-yl)phenyl)-6-(7-phenyl-5-oxa-6-azaspiro[2.4]heptan-6-yl)pyrimidin-4-amine;

(232) (R)—N-(4-(4-methylpiperazin-1-yl)phenyl)-6-(7-phenyl-5-oxa-6-azaspiro[2.4]heptan-6-yl)pyrimidin-4-amine;

(233) (S)—N-(2-methoxy-4-(4-(4-methylpiperazin-1-yl)piperidin-1-yl)phenyl)-6-(7-phenyl-5-oxa-6-azaspiro[2.4]heptan-6-yl)pyrimidin-4-amine;

(234) (R)—N-(2-methoxy-4-(4-(4-methylpiperazin-1-yl)piperidin-1-yl)phenyl)-6-(7-phenyl-5-oxa-6-azaspiro[2.4]heptan-6-yl)pyrimidin-4-amine;

(235) (R)-6-(3-isopropylisoxazolidin-2-yl)-N-(4-(4-methylpiperazin-1-yl)phenyl)pyrimidin-4-amine;

(236) (S)-6-(3-isopropylisoxazolidin-2-yl)-N-(4-(4-methylpiperazin-1-yl)phenyl)pyrimidin-4-amine; and (237) (R)-6-(3-(2,3-difluorophenyl)isoxazolidin-2-yl)-N-(2-methoxy-4-(4-(4-(2-(methylsulfonyl)ethyl)piperazin-1-yl)piperidin-1-yl)phenyl)pyrimidin-4-amine.

\* \* \* \* \*

UNITED STATES PATENT AND TRADEMARK OFFICE
CERTIFICATE OF CORRECTION

PATENT NO. : 12,037,330 B2  
APPLICATION NO. : 17/927324  
DATED : July 16, 2024  
INVENTOR(S) : Youn Ho Lee et al.

Page 1 of 3

It is certified that error appears in the above-identified patent and that said Letters Patent is hereby corrected as shown below:

In the Specification

Column 3, Line 19, the term '-N(-$C_{1-6}$alkyl) (-$C_{1-6}$alkyl)' should read -- -N(-$C_{1-6}$alkyl)(-$C_{1-6}$alkyl) --.

Column 3, Line 25, the term '-$C_{1-6}$ aminoalkyl' should read -- -$C_{1-6}$aminoalkyl --.

Column 3, Line 39, the term '-$C_{1-6}$ haloalkyl' should read -- -$C_{1-6}$haloalkyl --.

Column 3, Line 46, the term '-$(CH)_2$ m-' should read -- -$(CH)_2$m- --.

Column 3, Lines 58 through 59, the term '-C(=N-O-$C_{1-6}$alkyl) ($C_{1-6}$ alkyl)' should read -- -C(=N-O-$C_{1-6}$alkyl)($C_{1-6}$alkyl) --.

Column 3, Line 67 through Column 4, Line 1, the term '-$C_{1-6}$alkyl-N($C_{1-6}$alkyl) ($C_{1-6}$alkyl)' should read -- -$C_{1-6}$alkyl-N($C_{1-6}$alkyl)($C_{1-6}$alkyl) --.

Column 4, Lines 16 through 17, the term '-$C_{1-6}$alkyl-N($C_{1-6}$alkyl) ($C_{1-6}$alkyl)' should read -- -$C_{1-6}$alkyl-N($C_{1-6}$alkyl)($C_{1-6}$alkyl) --.

Column 4, Lines 57-58, the term '-N(-$C_{1-6}$alkyl) (-$C_{1-6}$alkyl)' should read -- -N(-$C_{1-6}$alkyl)(-$C_{1-6}$alkyl) --.

Column 4, Line 64, the terms '-(C=O) $NR_1R_2$, -(C=O) $OR_3$' should read -- -(C=O)$NR_1R_2$, -(C=O)$OR_3$ --.

Column 5, Line 7, the term '-$C_{1-6}$ haloalkyl' should read -- -$C_{1-6}$haloalkyl --.

Column 5, Lines 20 through 21, the term '-C(=O)-$C_{1-6}$ alkyl' should read -- -C(=O)-$C_{1-6}$alkyl --.

Signed and Sealed this  
Twenty-fourth Day of September, 2024

Katherine Kelly Vidal  
*Director of the United States Patent and Trademark Office*

Column 5, Lines 22 through 23, the term '-C(=N-O-C$_{1-6}$alkyl) (C$_{1-6}$alkyl)' should read
-- -C(=N-O-C$_{1-6}$alkyl)(C$_{1-6}$alkyl) --.

Column 6, Lines 18 through 19, the terms '-(C=O) NH-cycloalkyl, -(C=O) O-C$_{1-6}$alkyl' should read
-- -(C=O)NH-cycloalkyl, -(C=O)O-C$_{1-6}$alkyl --.

Column 6, Line 33, the term '-(CH$_2$) m-' should read -- -(CH$_2$)m- --.

Column 6, Line 45, the term '-C(=N-O-C$_{1-6}$alkyl) (C$_{1-6}$alkyl)' should read
-- -C(=N-O-C$_{1-6}$alkyl)(C$_{1-6}$alkyl) --.

Column 6, Line 56, the term '-C$_{1-6}$alkyl-N(-C$_{1-6}$alkyl) (-C$_{1-6}$alkyl)' should read
-- -C$_{1-6}$alkyl-N(-C$_{1-6}$alkyl)(-C$_{1-6}$alkyl) --.

Column 7, Lines 8 through 9, the term '-N(C$_{1-6}$alkyl) (C$_{1-6}$alkyl)' should read
-- -N(C$_{1-6}$alkyl)(C$_{1-6}$alkyl) --.

Column 7, Line 21, the term '-N(C$_{1-6}$alkyl) (C$_{1-6}$alkyl)' should read -- -N(C$_{1-6}$alkyl)(C$_{1-6}$ealkyl) --.

Column 13, Line 39, the term '2. MM Analysis' should read -- 2. NMR Analysis --.

Column 28, Lines 5-14, the portion of the chemical structural formula reading '*(R)*' should read
-- *(S)* --.

Table 1, Column 201, the chemical structure formula for compound 198

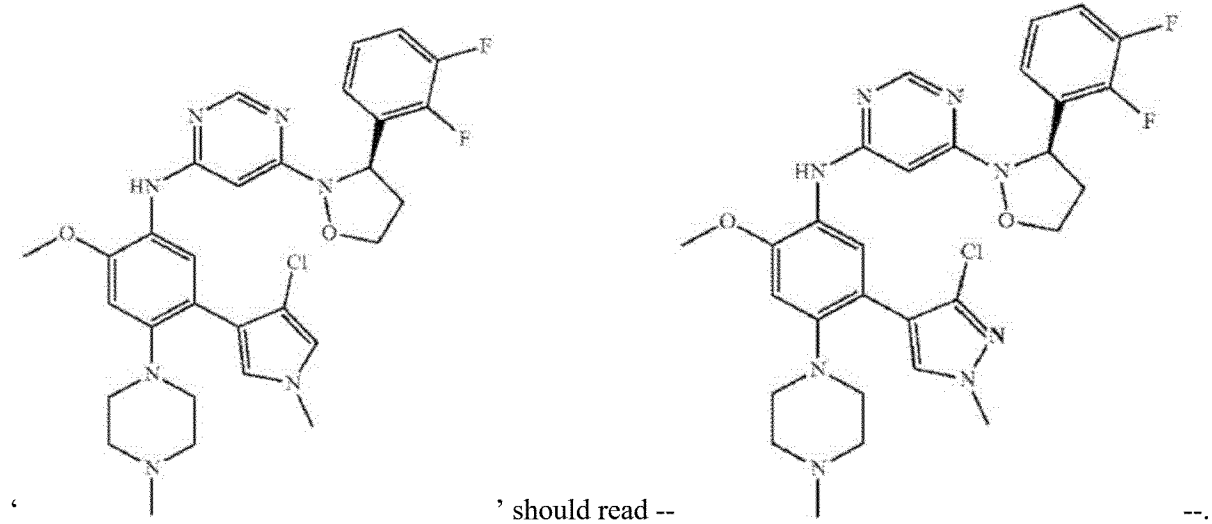

CERTIFICATE OF CORRECTION (continued)
U.S. Pat. No. 12,037,330 B2

In the Claims

In Claim 1, Column 241, Lines 53 through 64, the chemical structural formula for Chemical Formula 1 ' 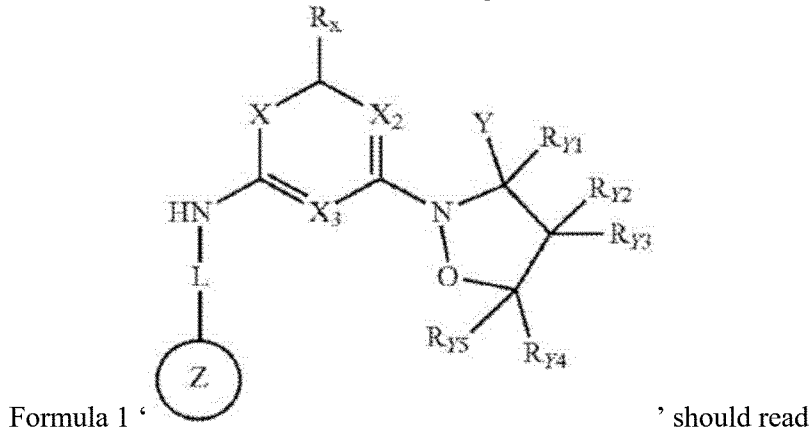 ' should read

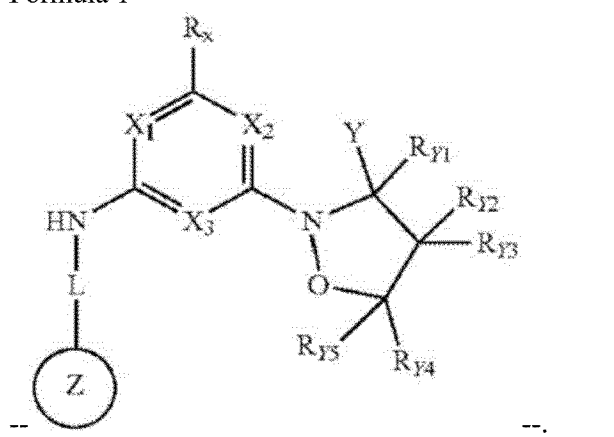

-- --.

In Claim 1, Column 242, Line 3, the term '-(CH$_2$) hydroaryl' should read -- -(CH$_2$)$_n$hydroaryl --.

In Claim 1, Column 242, Lines 5 through 6, the term '-(CH$_2$)hydroaryl' should read -- -(CH$_2$)$_n$hydroaryl --.

In Claim 1, Column 242, Line 8, the term '-C$_{1-6}$ aminoalkyl' should read -- -C$_{1-6}$aminoalkyl --.

In Claim 6, Column 250, Lines 58 through 60, the term '(R)-2-methoxy-N4-(1-methylpiperidin-4-yl)-N$^1$-(6-(3-phenylisoxazolidin-2-yl)pyrimidin-4-yl)benzene-1,4-diamine' should read -- (R)-2-methoxy-N4-(1-methylpiperidin-4-yl)-N1-(6-(3-phenylisoxazolidin-2-yl)pyrimidin-4-yl)benzene-1,4-diamine --.